US011999766B2

(12) United States Patent
Kraemer-Kuehl et al.

(10) Patent No.: US 11,999,766 B2
(45) Date of Patent: Jun. 4, 2024

(54) MODIFIED S1 SUBUNIT OF THE CORONAVIRUS SPIKE PROTEIN

(71) Applicant: Boehringer Ingelheim Vetmedica GmbH, Ingelheim am Rhein (DE)

(72) Inventors: Annika Kraemer-Kuehl, Seesen (DE); Thomas Min Stephan, Hannover (DE); Hans-Christian Philipp, Hemmingen (DE)

(73) Assignee: Boehringer Ingelheim Vetmedia GmbH, Ingelheim am Rhein (DE)

( * ) Notice: Subject to any disclaimer, the term of this patent is extended or adjusted under 35 U.S.C. 154(b) by 0 days.

(21) Appl. No.: 18/059,171

(22) Filed: Nov. 28, 2022

(65) Prior Publication Data

US 2023/0340028 A1    Oct. 26, 2023

Related U.S. Application Data

(63) Continuation of application No. 16/867,650, filed on May 6, 2020, now Pat. No. 11,512,115.

(30) Foreign Application Priority Data

May 10, 2019  (EP) ..................... 19173821
Nov. 29, 2019  (EP) ..................... 19212627

(51) Int. Cl.
| | | |
|---|---|---|
| *A61K 39/215* | (2006.01) | |
| *A61K 9/00* | (2006.01) | |
| *A61K 39/00* | (2006.01) | |
| *A61K 39/12* | (2006.01) | |
| *A61P 31/14* | (2006.01) | |
| *A61P 37/04* | (2006.01) | |
| *C07K 14/005* | (2006.01) | |
| *C12N 7/00* | (2006.01) | |
| *C12N 15/85* | (2006.01) | |

(52) U.S. Cl.
CPC .......... *C07K 14/005* (2013.01); *A61K 39/215* (2013.01); *A61P 31/14* (2018.01); *C12N 7/00* (2013.01); *C12N 15/85* (2013.01); *C12N 2770/20022* (2013.01); *C12N 2770/20023* (2013.01); *C12N 2800/10* (2013.01)

(58) Field of Classification Search
CPC ............... C07K 14/005; C07K 14/165; C07K 2319/74; C12N 2770/20022; C12N 7/00
See application file for complete search history.

(56) References Cited

U.S. PATENT DOCUMENTS

| | | | |
|---|---|---|---|
| 8,828,407 B2 | 9/2014 | Britton et al. | |
| 2006/0257852 A1 | 11/2006 | Rappuoli et al. | |
| 2011/0097353 A1 | 4/2011 | Sellers et al. | |
| 2014/0141043 A1 | 5/2014 | Toro Guzman et al. | |
| 2016/0032253 A1 | 2/2016 | Sellers | |
| 2016/0106828 A1 | 4/2016 | Toro | |
| 2017/0096455 A1 | 4/2017 | Baric et al. | |
| 2018/0216082 A1 | 8/2018 | Jordan et al. | |
| 2019/0046634 A1 | 2/2019 | van Santen et al. | |

FOREIGN PATENT DOCUMENTS

| | | |
|---|---|---|
| CN | 102574897 A | 7/2012 |
| CO | 2019000214 A2 | 1/2019 |
| CO | 2021005066 A2 | 4/2021 |
| CO | 2021005069 A2 | 4/2021 |
| WO | 8605806 A1 | 10/1986 |
| WO | 01009290 A2 | 2/2001 |
| WO | 2004092360 A2 | 10/2004 |
| WO | 2011004146 A1 | 1/2011 |
| WO | 2014177873 A1 | 11/2014 |
| WO | 2019046634 A1 | 3/2019 |

OTHER PUBLICATIONS

Casais, Rosa, et al., Recombinant Avian Infectious Bronchitis Virus Expressing a Heterologous Spike Gene Demonstrates that the Spike Protein Is a Determinant of Cell Tropism, J. Virology, Aug. 2003, vol. 77, No. 16, p. 9084-9089.
Bickerton, Erica, et al., The S2 subunit of Infectious Bronchitis Virus Beaudette Is a determinant of Cellular Tropism, J. Virology ASM, Oct. 2018, vol. 92, Issue 19, e01044-18.
Ellis, Samantha et al., Recombinant Infectious Bronchitis Viruses Expressing Chimeric Spike Glycoproteins Induce Partial Protective Immunity against Homologous Challenge despite Limited Replication In Vivo, J. Virology ASM, Dec. 2018, vol. 92, Issue 23, e01473-18.
Fang, Shou Guo, et al., Selection of and recombination between minor variants lead to the adaptation of an avian coronavirus to primate cells, Biochemical and Biophysical Research Communications, 2005, vol. 336, p. 417-423.
Communication/Extended Search Report, PCT/EP2020/062526, dated Oct. 4, 2019.
International Search Report and Written Opinion, PCT/EP2020/062526, dated Jun. 24, 2020.
Moore, Kristi M., et al. "Sequence comparison of avian infectious bronchitis virus S1 glycoproteins of the Florida serotype and five variant isolates from Georgia and California." Virus Genes 17 (1998): 63-83.
Hulswit, R. J. G., C. A. M. De Haan, and B-J. Bosch. "Coronavirus spike protein and tropism changes." Advances in virus research 96 (2016): 29-57.
English Abstract of WO01009290A2.
English Abstract of CO2019000214A2.
English Abstract of CO2021005066A2.
English Abstract of CO2021005069A2.

Primary Examiner — Barry A Chestnut
(74) Attorney, Agent, or Firm — Steffan Finnegan

(57) ABSTRACT

The present invention relates i.a. to a recombinant avian coronavirus spike protein or fragment thereof comprising a mutation at amino acid position 267 to Cysteine. Further, the present invention relates to an immunogenic composition comprising an avian coronavirus with such spike protein.

18 Claims, 10 Drawing Sheets

Specification includes a Sequence Listing.

| Negative control | H52 wild type | H52-rIBV S F267C |

| Negative control | H52 wild type | H52-rIBV S F267C |

Figure 10

[Graph: CT mean vs hpi (0-48), showing CR88 rIBV S L269C and CR88 rIBV WT]

Figure 11

[Graph: CT values at 0h and 72h for passages P1/P2, P5, P7/P8, comparing CR88 rIBV S L269C and CR88 rIBV WT]

SEQUENCE LISTING

```
Sequence total quantity: 84
SEQ ID NO: 1            moltype = AA   length = 1162
FEATURE                 Location/Qualifiers
source                  1..1162
                        mol_type = protein
                        organism = unidentified
                        note = Avian infectious bronchitis virus
SEQUENCE: 1
MLVTPLLLVT LLCALCSAAL YDSSSYVYYY QSAFRPPDGW HLHGGAYAVV NISSESNNAG   60
SSSGCTVGII HGGRVVNASS IAMTAPSSGM AWSSSQFCTA YCNFSDTTVF VTHCYKHGGC  120
PITGMLQQHS IRVSAMKNGQ LFYNLTVSVA KYPTFKSFQC VNNLTSVYLN GDLVYTSNET  180
TDVTSAGVYF KAGGPITYKV MREVRALAYF VNGTAQDVIL CDGSPRGLLA CQYNTGNFSD  240
GFYPFTNSSL VKQKFIVYRE NSVNTTFTLH NFTFHNETGA NPNPSGVQNI QTYQTQTAQS  300
GYYNFNFSFL SSFVYKESNF MYGSYHPSCN FRLETINNGL WFNSLSVSIA YGPLQGGCKQ  360
SVFSGRATCC YAYSYGGPLL CKGVYSGELD HNFECGLLVY VTKSGGSRIQ TATEPPVITQ  420
HNYNNITLNT CVDYNIYGRT GQGFITNVTD SAVSYNYLAD AGLAILDTSG SIDIFVVQSE  480
YGLNYYKVNP CEDVNQQFVV SGGKLVGILT SRNETGSQLL ENQFYIKITN GTRRFRRSIT  540
ESVENCPYVS YGKFCIKPDG SIATIVPKQL EQFVAPLLNV TENVLIPNSF NLTVTDEYIQ  600
TRMDKVQINC LQYICGNSLE CRNLFQQYGP VCDNILSVVN SVGQKEDMEL LNFYSSTKPA  660
GFNTPVLSNV STGEFNITLF LTTPSSPRRR SFIEDLLFTS VESVGLPTDD AYKNCTAGPL  720
GFLKDLACAR EYNGLLVLPP IITAEMQTLY TSSLVASMAF GGITAAGAIP FATQLQARIN  780
HLGITQSLLL KNQEKIAASF NKAIGHMQEG FRSTSLALQQ IQDVVNKQSA ILTETMASLN  840
KNFGAISSVI QEIYQQLDAI QANAQVDRLI TGRLSSLSVL ASAKQAEYIR VSQQRELATQ  900
KINECVKSQS IRYSFCGNGR HVLTIPQNAP NGIVFIHFSY TPDSFVNVTA IVGFCVKPAN  960
ASQYAIVPAN GRGIFIQVNG SYYITARDMY MPRAITAGDI VTLTSCQANY VSVNKTVITT 1020
FVDNDDFDFN DELSKWWNDT KHELPDFDKF NYTVPILDID SEIDRIQGVI QGLNDSLIDL 1080
EKLSILKTYI KWPWYVWLAI AFATIIFILI LGWVFFMTGC CGCCCGCFGI MPLMSKCGKK 1140
SSYYTTFDND VVTEQYRPKK SV                                          1162

SEQ ID NO: 2            moltype = AA   length = 1162
FEATURE                 Location/Qualifiers
source                  1..1162
                        mol_type = protein
                        organism = unidentified
                        note = Avian infectious bronchitis virus
SEQUENCE: 2
MLVTPLLLVT LLCALCSAAL YDSSSYVYYY QSAFRPPDGW HLHGGAYAVV NISSESNNAG   60
SSSGCTVGII HGGRVVNASS IAMTAPSSGM AWSSSQFCTA YCNFSDTTVF VTHCYKHGGC  120
PITGMLQQHS IRVSAMKNGQ LFYNLTVSVA KYPTFKSFQC VNNLTSVYLN GDLVYTSNET  180
TDVTSAGVYF KAGGPITYKV MREVRALAYF VNGTAQDVIL CDGSPRGLLA CQYNTGNFSD  240
GFYPFTNSSL VKQKFIVYRE NSVNTTCTLH NFTFHNETGA NPNPSGVQNI QTYQTQTAQS  300
GYYNFNFSFL SSFVYKESNF MYGSYHPSCN FRLETINNGL WFNSLSVSIA YGPLQGGCKQ  360
SVFSGRATCC YAYSYGGPLL CKGVYSGELD HNFECGLLVY VTKSGGSRIQ TATEPPVITQ  420
HNYNNITLNT CVDYNIYGRT GQGFITNVTD SAVSYNYLAD AGLAILDTSG SIDIFVVQSE  480
YGLNYYKVNP CEDVNQQFVV SGGKLVGILT SRNETGSQLL ENQFYIKITN GTRRFRRSIT  540
ESVENCPYVS YGKFCIKPDG SIATIVPKQL EQFVAPLLNV TENVLIPNSF NLTVTDEYIQ  600
TRMDKVQINC LQYICGNSLE CRNLFQQYGP VCDNILSVVN SVGQKEDMEL LNFYSSTKPA  660
GFNTPVLSNV STGEFNITLF LTTPSSPRRR SFIEDLLFTS VESVGLPTDD AYKNCTAGPL  720
GFLKDLACAR EYNGLLVLPP IITAEMQTLY TSSLVASMAF GGITAAGAIP FATQLQARIN  780
HLGITQSLLL KNQEKIAASF NKAIGHMQEG FRSTSLALQQ IQDVVNKQSA ILTETMASLN  840
KNFGAISSVI QEIYQQLDAI QANAQVDRLI TGRLSSLSVL ASAKQAEYIR VSQQRELATQ  900
KINECVKSQS IRYSFCGNGR HVLTIPQNAP NGIVFIHFSY TPDSFVNVTA IVGFCVKPAN  960
ASQYAIVPAN GRGIFIQVNG SYYITARDMY MPRAITAGDI VTLTSCQANY VSVNKTVITT 1020
```

```
FVDNDDFDFN DELSKWWNDT KHELPDFDKF NYTVPILDID SEIDRIQGVI QGLNDSLIDL  1080
EKLSILKTYI KWPWYVWLAI AFATIIFILI LGWVFFMTGC CGCCCGCFGI MPLMSKCGKK  1140
SSYYTTFDND VVTEQYRPKK SV                                          1162

SEQ ID NO: 3            moltype = AA  length = 1155
FEATURE                 Location/Qualifiers
source                  1..1155
                        mol_type = protein
                        organism = unidentified
                        note = Avian infectious bronchitis virus
SEQUENCE: 3
MLDKPLLLVT LWYALCSALL YDNNTYVYYY QSAFRPGPGW HLYGGAYAVD RVFNETNNAG  60
SASDCTAGTF YESHNISASS VAMTVPHNGM SWSASQFCTA HCNFSDFTVF VTHCFKNQLG  120
SCPLTGMIPQ NHIRISAMRD GVLFYNLTVS VSKYPRFKSL QCVSNSTSVY VNGDLVFTSN  180
ETSYVTGAGV YFKSGGPVTY KVMKEVKALA YFINGTAQEV ILCDNSPRGL LACQYNTGNF  240
SDGFYPFTNH SLVKDRFIVY RESSTNTTCK LTNFSFTNVS NASPNSGGVD TFQLYQTSTA  300
QDGYYNFNLS FLSSFVYKPS DFMYGSYHPH CKFRPENINN GLWFNSLSVS LTYGPIQGGC  360
KQSVFSNRAT CCYAYSYQGP SRCKGVYRGE LTQYFECGLL VYVTKSDGSR IQTRSEPLVL  420
TQYNYNNITL NKCVEYNIYG RVGQGFITNV TEATANYSYL ADGGLAILDT SGAIDIFVVQ  480
GAYGLNYYKV NPCEDVNQQF VVSGGNLVGI LTSHNETGSE SIENQFYIKL TNGTRRSRRS  540
VTGNVTNCPY VSYGKFCIKP DGSLSIIVPQ ELEQFVAPLF NVTEHVLIPD SFNLTVTDEY  600
IQTRMDKVQI ICLQYVCGNS IECRKLFQQY GPVCDNILSV VNGVQOREDM ELLSFYSSTK  660
PSGYNTPIFN NVSTGDFNIS LLLLTPPNSPT GRSFIEDLLF TSVESVGLPT DEEYKKCTAG  720
PLGFVKDLVC AREYNGLLVL PPIITAEMQT MYTSSLVASM ALGGITAAGA IPFATQLQAR  780
INHLGITNSL LLKNQEKIAA SFNKAIGHMQ EGFKSTSLAL QQIQDVVNKQ SSILTETMQS  840
LNKNFGAISS VIQDIYQQLD AIQADAQVDR LITGRLSSLS VLASAKQAEY HRVSQQRELA  900
TQKINECVKS QSNRYSFCGN GRHVLTIPQN APNGIVFIHF TYTPESFVNV TAIVGFCVNP  960
ANASHYAIVP VNGRGVFIEV NGSYYITARD MYMPRDITAG DIVTLTSCQA NYVNVNKTVI  1020
NTFVEDDDFD FYDELSKWWN DTKHELPDFD EFNYTVPVLN ISNEIDRIQQ VIQGLNDSLI  1080
DLETLSILKT YIKWPWYVWL AIAFLTIIFI LVLCWIFFMT GCCGCCCGCF GIIPLMSKCG  1140
KKSSYYTTFD NDVVT                                                   1155

SEQ ID NO: 4            moltype = AA  length = 1156
FEATURE                 Location/Qualifiers
source                  1..1156
                        mol_type = protein
                        organism = unidentified
                        note = Avian infectious bronchitis virus
SEQUENCE: 4
MLVKSLFLVT ILCALCSANL FDSDNNYVYY YQSAFRPPNG WHLQGGAYAV VSSTNYTNNA  60
GSAHGCTVGV IKDVYNQSVA SIAMTAPLQG MAWSKSQFCS AHCNFSEITV FVTHCYSSGS  120
GSCPITGMIP RDHIRISAMK NGSLFYNLTV SVSKYPNFKS FQCVNNFTSV YLNGDLVFTS  180
NKTTDVTSAG VYFKAGGPVN YSIMKEFKVL AYFVNGTAQD VVLCDNSPKG LLACQYNTGN  240
FSDGFYPFTN STLVREKFIV YRESSVNTTC ALTNFTFSNV SNAQPNSGGV NTFHLYQTQT  300
AQSGYYNFNL SFLSQFVYKA SDFMYGSYHP SCSFRPETIN SGLWFNSLSV SLTYGPLQGG  360
CKQSVFSGKA TCCYAYSYRG PMACKGVYSG ELSTNFECGL LVYVTKSDGS RIQTRTEPLV  420
LTQYNYNNIT LDKCVAYNIY GRVGQGFITN VTDSAANFSY LADGGLAILD TSGAIDVFVV  480
QGIYGLNYYK VNPCEDVNQQ FVVSGGNIVG ILTSRNETGS EQVENQFYVK LTNSSHRRKR  540
SIGQNVTSCP YVSYGRFCIE PDGSLKMIVP EELKQFVAPL LNITESVLIP NSFNLTVTDE  600
YIQTRMDKVQ INCLQYVCGN SLECRKLFQQ YGPVCDNILS VVNSVSQKED MELLSFYSST  660
KPKGYDTPVL SNVSTGEFNI SLLLKPPSSP SGRSFIEELL FTSVETVGLP TDAEYKKCTA  720
GPLGTLKDLI CAREYNGLLV LPPIITADMQ TMYTASLVGA MAFGGITSAA AIPFATQIQA  780
RINHLGITQS LLMKNQEKIA ASFNKAIGHM QEGFRSTSLA LQQIQDVVNK QSAILTETMN  840
SLNKNFGAIT SVIQDIYAQL DAIQADAQVD RLITGRLSSL SVLASAKQSE YIRVSQQREL  900
ATQKINECVK SQSNRYGFCG SGRHVLSIPQ NAPNGIVFIH FTYTPESFVN VTAIVGFCVN  960
PANASQYAIV PANGRGIFIQ VNGTYYITAR DMYMPRDITA GDIVTLTSCQ ANYVNVNKTV  1020
ITTFVEDDDF DFDDELSKWW NDTKHQLPDF DDFNYTVPIL NISGEIDYIQ GVIQGLNDSL  1080
IDLEELSIIK TYIKWPWYVW LAIFFAIIIF ILILGWVFFM TGCCGCCCGC FGIIPLMSKC  1140
GKKSSYYTTF DNDVVT                                                  1156

SEQ ID NO: 5            moltype = AA  length = 1156
FEATURE                 Location/Qualifiers
source                  1..1156
                        mol_type = protein
                        organism = unidentified
                        note = Avian infectious bronchitis virus
SEQUENCE: 5
MLGKSLFVVT LLFALCSAAL FDNNETVYYY QSAFRPADGW HLHGGAYAVV NVSLQTSNAG  60
TVSECIAGAI SWSKEFSASA VAMTAPQLGM TWSTRQFCTA HCNFSDFTVF VTHCFKHGTG  120
LCPLTGFIPS GFIRVSAMRK GSNSLFYNLT SVSVTKYPRF KSLQCVNNYT SVYLNGDLVFT  180
SNETKPVSAA GVSFKAGGPI TYKIMNEVKV LAYFVNGTAQ TVIPCDGSPR GLLACQYNTG  240
NFSDGFYPYT NSSLVKERFI VYRESSVNTI CVLTNFTFSN VSNALPNTGN VHSIVLHQTQ  300
TAQSGYYNLN FSFLSGFRYV ESDFMYGSYH PKCSFRPETI NNGLWFNSLS VSLGYGPLQG  360
GCKQSVFNNK ATCCYAYSYN GPTLCKGVYS GELQKTFECG LLVFVTKSDG SRIQTRNEPL  420
VLTQHNYNNI TLNKCVEYNI YGRVGQGLIT NITDSAANHG YLADGGLAVL DTSGAIDVFV  480
VQGVYGLNYY KVNPCEDVNQ QFVVSGGQLV GILTSRNETG SQPIENRFYV KPSNSRRRTG  540
RSTIANVTNC PYVSYGKFCI KPDGSVLEIV PQEIEHFVAP LLNVTEHVLI PNSFNLTVTD  600
EYIQTRMDKI QINCLQYVCG NSIECRKLFQ QYGPVCDNIL SVVNTVGQRE DMELLSFYSS  660
TKPKDYNVPI FSNVSTGDFN ISLLLTPPNS PTGRSFIEDI LFTSVESVGL PTDEEYKKCT  720
```

```
AGPLGFVKDL VCAREYNGLL VLPPIITADM QTMYTSTLVA SMALGGITAA GAIPFATQLQ    780
ARINHLGITQ SLLLKNQEKI AASFNKAIGH MQEGFRSTSL ALQQIQDVVN KQSSILTETM    840
ASLNKNFGAI SSVLQDIYQQ LDAIQADAQV DRIITGRLSS LSVLASAKQS EYYRVSQQRE    900
LATQKINECV KSQSTRYSFC GNGRHVLTIP QNAPNGIVFI HFTYTPESFV NVTAIVGFCV    960
NPPNASQYAL VPANGRGIFI QVNGSYYITA RDMYMPRDIT AGDIVTLTSC QANYVSVNRT   1020
VITTFVDNDD FDFDDELSKW WNDTKHELPD FDEFNYTIPV LNISNEIDII QEVIRGLNDS   1080
LIDLEALSIL KTYIKWPWYV WLAIAFLTII FILVLCWIFF MTGCCGCCCG CFGIMPLMSK   1140
CGKKSSYYTT FDNDVV                                                  1156

SEQ ID NO: 6            moltype = AA  length = 1156
FEATURE                 Location/Qualifiers
source                  1..1156
                        mol_type = protein
                        organism = unidentified
                        note = Avian infectious bronchitis virus
SEQUENCE: 6
MLVKSLFIVT LLFALCSAAL FDNNQAVYYY QSAFRPSSGW HKHGGAYAVA NVSLEYANAG     60
SSTHCTAGAI YWSKNFTASS VAMTAPGTGM SWSTAQFCTA HCNFSDFTVF VTHCYKSGDV    120
CPLTGLIPSG YIRISAMTKG TTSLFYNLTV PVTKYPKFKS LQCVDNFTSV YLNGDLVFTS    180
NETKDVSAAG VHFKAGGPIT YKVMEKVDVL AYFVNGTAQD VILCDNSPRG LLACQYNTGN    240
FSDGFYPFTN ISLVKEKFIV YRETSVNTTC VLTNFTFTNV SNALPNTGGV NTINIYQTQT    300
AQSGCYNFNF SFLSSFVYKQ SDFMYGSYHP KCDFRPETIN NGLWFNSLSV SLAYGPLQGG    360
CKQSVFSNRA TCCYAYSYNG PRLCKGVYIG ELQQYFECGL LVYVTKSDGS RIQTRNEPLV    420
LTHHNYNNIT LDRCVEYNIY GRSGQGFITN VTAAAANYNY LADGGLAILD TSGAIDIFVV    480
QGEYGPNYYK VNPCEDVNQQ FVVSGGGIVG VLTSHNETGS QQLENLFYVK LTNSTRRTRR    540
STIANVTTCP YVSYGRFCIK PDGLVSEIVP QELDYFVAPL LNVTEHVLIP NSFNLTVTDE    600
YIQTRMEKVQ INCLQYVCGN SIECRNLFQQ YGPVCDNILS IVNSVGQRED MESLTFYSST    660
KPKGYNTPIF SNISTGDFNI SLMLTPPSSP SGRSFIEDLL FTSVETVGLP TDAEYKKCTA    720
GPLGTLKDLI CAREYNGLLV LPPIITADMQ TMYTASLVGA MAFGGITSAA AIPFATQIQA    780
RINHLGITQS LLMKNQEKIA ASFNKAIGHM QEGFRSTSLA LQQIQDVVNK QSAILTETMN    840
SLNKNFGAIT SVIQDIYAQL DAIQADAQVD RLITGRLSSL SVLASAKQSE YIRVSQQREL    900
ATQKINECVK SQSNRYGFCG SGRHVLSIPQ NAPNGIVFIH FTYTPESFVN VTAIVGFCVS    960
PANASQYAIV PANGRGIFIQ VNGTYYITAR DMYMPRDITA GDIVTLTSCQ ANYVNVNKTV   1020
ITTFVEDDDF DFDDELSKWW NETKHEIPDF DEFNYTVPIL NISSEIDRIQ GVIQGLNDSL   1080
INLEELSIIK TYIKWPWYVW LAIGFAIIIF ILILGWVFFM TGCCGCCCGC FGIIPLMSKC   1140
GKKSSYYTTF DNDVVT                                                  1156

SEQ ID NO: 7            moltype = AA  length = 1169
FEATURE                 Location/Qualifiers
source                  1..1169
                        mol_type = protein
                        organism = unidentified
                        note = Avian infectious bronchitis virus
SEQUENCE: 7
MLVQPLLLVT LLCALCSASL YNNDSYVYYY QSAFRPFNGW HLHGGAYAVV NVSQETANAG     60
SSPSCTAGAI YWSKNFTASS VAMTAPLQGM QWSTIQFCTA HCNFTNIVVF VTHCYKSGST    120
VCPLTGLIPQ NHIRISAMKQ GNNGPSGLFY NLTVSPVTKYS KFKSLQCVNN QTSVYLNGDL    180
VFTSNETKDV SGAGVYFKAG GPITYKVMRE VKALAYFVNG TAHDVILCDG SPRGLLACQY    240
NTGKFSDGFY PFTNDTLVKE KFIVYRENSN TTCTLTNFT FYNESNALPN NGGVDTIQLY    300
QTHTAQSGYY NFNFSFLSSF QYVESNFMYG SYHPKCGFRP ESINNGLWFN SLSVSLAYGP    360
LQGGCKQSVF HGRATCCYAY SYNGPTLCKG VYSGELTTRY QCGLLVFVTK SDGSRIQTAQ    420
KPIVLTQHNY NNITLDRCVE YNIYGRVGQG FITNVTESAA AFNYLEDGGL AILDTSGAID    480
IFVVQGEYGF NYYKVNPCED VNQQFVVSGG NLVGILTSIN QTGSQSIENQ FYVKLTNGSR    540
RSRRSVSENV TSCPYVSYGK FCIKPDGSLS TIVPKELEQF VAPLLNVTEH VLIPDSFNLT    600
VTDEYIQTRM DKVQINCLQY VCGNSFECRK LFQQYGPVCD NILSVVNSVG QKEDMELLSF    660
YSSTKPSGIS QPLFNNFSTG DFNISLLLTS PSSPSGRSFI EDLLFTSVES VGLPTDEAYK    720
KCTSGPLGFV KDLVCAREYN GLLVLPPIIT AEMQTMYTSS LVASMALGGI TAAGAIPFAT    780
QLQARINHLG ITQSLLMKNQ EKIAASFNRA IGHMQEGFKS TSLALQQIQD VVNKQSAILT    840
ETMASLNKNF GAISSVLQDI YQQLDVIQAD AQVDRIITGR LSSSLSVLASA KQSEYIAVSQ    900
QRALATQKIN ECVKSQSTRY SFCGNGRHVL TIPQNAPNGI VFIHFTYTPE SFVNVTAIVG    960
FCVKPPNASH YAIVPNGRG IFIQVNGTYY ITSRDMYMPR NITAGDIVTL TSCQANYVSV   1020
NKTVISTFVE DDDFDFDDEL SKWWNDTKHE LPDFDEFNYT IPVLNISNEI DRIQGVIQGL   1080
NDSLIDLETL SILKTYIKWP WYVWLAIFFA IVIFILIIGW VFFMTGCCGC CCGCFGIIPL   1140
MNKCGKKSSY YTTFDNDVVT EQYRPKKSV                                    1169

SEQ ID NO: 8            moltype = AA  length = 1159
FEATURE                 Location/Qualifiers
source                  1..1159
                        mol_type = protein
                        organism = unidentified
                        note = Avian infectious bronchitis virus
SEQUENCE: 8
MLVKSLFLVT ILFALCSANL YDNESFVYYY QSAFRPGHGW HLHGGAYAVV NVSSENNNAG     60
TAPSCTAGAI GYSKNFSAAS VAMTAPLSGM SWSASSFCTA HCNFTSYIVF VTHCFKSGSN    120
SCPLTGLIPS GYIRIAAMKH GSRTPGHLFY NLTVSVTKYP KFRSLQCVNN HTSVYLNGDL    180
VFTSGYTEDV VAAGVHFKSG GPITYKVMRE VKALAYFVNG TAHDVILCDD TPRGLLACQY    240
NTGNFSDGFY PFTNTSIVKD KFIVYRESSN TTCTLTNFT FSNESGAPPN TGGVDSFILY    300
QTQTAQSGYY NFNFSFLSSF VYRESNYMYG SYHPCSFRP ETLNGLWFNS LSVSLTYGPI    360
QGGCKQSVFN GKATCCYAYS YGGPRACKGV YRGELTQHFE CGLLVYVTKS DGSRIQTATQ    420
```

```
PPVLTQNFYN NITLGKCVDY NVYGRTGQGF ITNVTDLATS HNYLADGGLA ILDTSGAIDI    480
FVVQGEYGPN YYKVNLCEDV NQQFVVSGGK LVGILTSRNE TGSQPLENQF YIKITNGTHR    540
SRRSVNENVT NCPYVSYGKF CIKPDGSVSP IVPKELEQFV APLLNVTENV LIPNSFNLTV    600
TDEYIQTHMD KIQINCLQYV CGNSLACRKL FQQYGPVCDN ILSVVNSVGQ KEDMELLSFY    660
SSTKPSGFNT PVFSNLSTGE FNISLLLTTP SSPRGRSFIE DLLFTSVESV GLPTDEAYKK    720
CTAGPLGFLK DLACAREYNG LLVLPPIITA EMQTLYTSSL VVSMAFGGIT SAGAIPFATQ    780
LQARINHLGI TQSLLLKNQE KIAASFNKAI GHMQEGFRST SLALQQIQDV VNKQSAILTE    840
TMASLNKNFG AISSVIQEIY QQLDAIQANA QVDRLITGRL SSLSVLASAK QAEYIRVSQQ    900
RELATQKINE CVKSQSIRYS FCGNGRHVLT IPQNAPNGIV FIHFSYTPDS FVNVTAIVGF    960
CVKPANASQY AIVPANGRGI FIQVNGSYYI TARDMYMPRA ITAGDIVTLT SCQANYVSVN   1020
KTVITTFVDN DDFDFNDELS KWWNDTKHEL PDFDKFNYTV PILDIDSEID RIQGVIQGLN   1080
DSLIDLEKLS ILKTYIKWPW YVWLAIAFAT IIFILILGWV FFMTGCCGCC CGCFGIMPLM   1140
SKCGKKSSYY TTFDNDVVT                                                1159

SEQ ID NO: 9            moltype = DNA   length = 11398
FEATURE                 Location/Qualifiers
misc_feature            1..11398
                        note = Plasmid Sequence
source                  1..11398
                        mol_type = other DNA
                        organism = synthetic construct
SEQUENCE: 9
tcgcgcgttt cggtgatgac ggtgaaaacc tctgacacat gcagctcccg gagacggtca     60
cagcttgtct gtaagcggat gccgggagca gacaagcccg tcaggcgcg tcagcgggtg    120
ttggcgggtg tcgggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt ggagatcggt acttcgcgaa    420
tgcgtcgaga tcggccgccc gggtaatacg actcactata gggacttaag atagatatta    480
atatatatct attgcactag ccttgcgcta gatttcaaac ttaacaaaac ggacttaaat    540
acctacagct ggtccccata ggtgttccat gcagtgcac tttagtgccc tggatggcac     600
ctggccacct gtcaggtttt tgttgttaaa atatcattgt tgctggtatc actgcttgtt    660
ttgccgtgtc tcactttata catccgttgc ttgggctacc tagtatccag cgtcctacgg    720
gcgccgtggt cggttcgagt gcgaaggacc tctggttcat ctagcggtag gcgggtgtag    780
ggaagtagcg cttcagacgt actggttctg ttgcgtgaaa cgcggggtca cctccccca    840
catacctcta agggctttg agcctagcgt gggctacgt tctcgcacaa ggtcggctat     900
acgacgtttg taggggtag tgccaaacaa ccctgaggt gacaggttct ggtggtgttt     960
cgaaaacaac aatgtgtgtg ccgcataata tgccgcgttat gcattttgga gcaggtagtg   1020
ataaaggagt ggcgcctggt agtactgttc ttaaacagtg gctccccgaa ggaacactcc   1080
ttgtcgataa tgatattgta gattatgttt ctgacgcaca cgtttctgtg ctttcagatt   1140
gcaataaata taagacagag cacaagtttg atcttgtgat atctgatatg tatacagaca   1200
atgattcaaa aagaaagcat gaaggcgtga tagccaataa tggcaatgat gacgtcttca   1260
tacccttc aagttttcta cgcaataatt tggctctggg aggcagtttt gctgtaaaat    1320
taacagagac aagttggcat gagagtttat atgacattgc acaggattgt gcatggtgga   1380
caatgttttg tacagcagtg aatgcatctt cttcagaagc attcctgatt ggtgttaatt   1440
acttgggtgc aagtgcaaag gttaaagtta gtggaaaaac actgcacgca aattatatat   1500
tttgaggaa ttgtaattat ttacaaacct ctgcttatag tatatttgat gttgctaagt    1560
ttgattttgag attgaaagca acgcagttg ttaatcttaa gactgaacaa aagacagact   1620
tagtctttaa tttgataaag tgtggtaagt tactggtaag agatgttggt aacacctctt   1680
ttactagtga ctcttttgtg tgcactatgt agtgctgttt tgtatgactc gagttcttac   1740
gtgtactact accaaagtgc cttcagacca cctgatggtt ggcatttaca tgggggtgcg   1800
tatgcggttg ttaatatttc tagtgaatct aataatgcag gctcttcatc tgggtgtact   1860
gttggtatta ttcatggtgg tcgtgttgtt aatgcttctt ctatagctat gacggcaccg   1920
tcatcaggta tggcttggtc tagcagtcag ttttgtatg catactgtaa cttttcagat   1980
actacagtgt ttgttacaca ttgttataaa catggtgggt gtcctataac tggcatgctt   2040
caacagcatt ctatacgtgt ttctgctatg aaaaatggcc agcttttcta atttaaca     2100
gttagtgtag ctaagtaccc tactttaaa tcatttcagt gtgttaataa tttaacatcc    2160
gtatatttaa atggtgatct tgtttacaca tctaatgaga ccacagatgt tacatctgca   2220
ggtgtttatt ttaaagctgg tggacctata acttataaag ttatgagaga agttagagcca  2280
ctggcttatt ttgttaatgg tactgcacaa gatgttattt tgtgtgatgg gtcacctaga   2340
ggcttgttag catgccagta taatactggc aattttcag atggctttta tccttttact   2400
aatagtagtt tagttaagca gaagtttatt gtctatcgtg aaaatagtgt taatactact   2460
tttacgttac acaattcac ttttcataat gagactgcg ccaacccaaa tcctagtagt     2520
gtccagaata ttcaaactta ccaaacacaa acagctcaga gtggttatta aattttaat    2580
ttttcctttc tgagtagttt tgtttataag gagtctaatt ttatgtatgg atcttatcac   2640
ccaagttgta attttagact agaaactatt aataatggtt tgtggtttaa ttcactttca   2700
gttagtattg cttacggtcc tcttcaaggt ggttgcaagc aatctgtctt tagtggtaga   2760
gcaacctgtt gttatgctta ctcatatgga ggtccttgc agttgtaaagg tgttattca    2820
ggtgagttag atcataattt tgaatgtgga ctgttagtttt atgttactaa gagcggtggc   2880
tctcgtatac aaacagccac tgaaccgcca gttataactc aacacaatta taataatatt   2940
actttaaata cttgtgttga ttataatata tatggcagaa ctggccaggg ttttattact   3000
aatgtaaccg actcagctgt tagttataat tatctagcag acgcaggttt ggctatttta   3060
gatacctg gttccataga catctttgtc gtacaaagtg aatctgttat tattat         3120
aaggttaacc cttgcgaaga tgtcaacag cagtttgtag tttctggtgg taaattagta    3180
ggtattctta cttcacgtaa tgagactggt tcccagcttc ttgagaatca gttttacatc   3240
aaaatcacta atggaacacg tcgttttaga cgttctatta ctgaaagtgt tgaaaattgc   3300
ccttatgtta gttatggtaa gttttgtata aaacctgatg gcagtattgc cacaatagta   3360
ccaaaacagt tagaacagtt tgtggcacct ttacttaatg ttactgaaaa tgtgctcata   3420
```

```
cctaacagtt ttaatttaac tgttacagat gagtacatac aaactcggat ggataaggtc 3480
caaattaatt gcctgcagta tatttgtggc aattctctgg agtgcagaaa tttgtttcaa 3540
caatatggtc ctgtttgcga caacatattg tctgtagtaa atagtgttgg tcaaaaagaa 3600
gatatgaac ttttgaattt ctattcttct actaagccgg ctggttttaa tacaccagtt 3660
cttagtaatg ttagcactgg tgagtttaat attactcttt ttttaacaac gcctagtagt 3720
cctagaaggc gttcttttat tgaagaccttc ctatttacaa gtgttgaatc tgttggatta 3780
ccaacagatg acgcatacaa aaattgcact gcaggtcctt taggcttcct gaaagacctt 3840
gcatgtgctc gtgaatataa tggttttgctt gtgttgcctc ctattataac agcagaaatg 3900
caaactttgt atacaagctc tctagtagct tctatgactt ttggtggtat tactgcagct 3960
ggtgctatac cttttgccac acaactgcag gctagaatta atcacttggg tattacccag 4020
tcacttcttt tgaagaatca agaaaaaatt gctgcttcct ttaataaggc catcggtcat 4080
atgcaggaag gttttagaag tacatcttta gcattacaac aaattcaaga tgttgttaat 4140
aagcagagtg ctattcttac tgagactatg gcatcactta ataaaaattt tggtgccatt 4200
tcttctgtga ttcaagaaat ctaccagcaa cttgacgcca tacaagcaaa tgctcaagtg 4260
gatcgtctta taactggtag attgtcatca cttctgtttt tagcatctgc taagcaggcg 4320
gagtatatta gagtgtcaca acagcgtgag ttagctactc agaagattaa tgagtgtgtt 4380
aagtcacagt ccattaggta ctccttttgt ggtaatggac acatgttttt aaccataccg 4440
caaaatgcac ctaatggtat agtgtttata cacttttctt acactccaga tagtttttgtt 4500
aatgttactg caatagtggg ttttttgtgta aagccagcta atgctagtca gtatgcaata 4560
gtacccgcta atggtagggg tatttttata caagttaatg gtagttacta catcactgca 4620
cgagatatgt atatgccaag agctattact gcaggagata tagttacgct tacttcttgt 4680
caagcaaatt atgtaagtgt aaataagacc gtcattacta cattcgtaga caatgatgat 4740
tttgatttta atgacgaatt gtcaaaatgg tggaatacag ctaagcatga gctaccagac 4800
tttgacaaat tcaattacac agtacctata cttgacattg atagtgaaat tgatcgtatt 4860
caaggcgtta tacagggtct taatgactct ctaatagacc ttgaaaaact ttcaatactc 4920
aaaacttata ttaagtggcc ttggtatgtg tggctagaaa tcttttgtgc cactattatc 4980
ttcatcttaa tattaggatg ggtttttcttc atgactgggt gttgtggttg ttgttgtgga 5040
tgctttggca ttatgcctct aatgagtaag tgtggtaaga atcttctta ttacacgact 5100
tttgataacg atgtggtaac tgaacaatac agacctaaaa agtctgttta atgatccaaa 5160
gtcccactag tttcttaata gtattaattt tgctttgtg taaacttgta ctaagttgtt 5220
ttagagagtt tattattgcc cttcaacaac taacacaagt tttactccaa attatcgata 5280
gtaatttaca gtctagactg acccctttggc acagtctaga ctaatgttaa acttagaagc 5340
aattattgaa accggtgatc aagtgattca aaaaatcagt ttcaattttac agcatatttc 5400
aagtgtatta aacacagaag tatttgaccc ctttgactat tgttattaca gaggaggtaa 5460
tttttgggaa atagagtcag ctgaagattg ttcaggtgat gatgaattta ttgaataagt 5520
cgctagagga gaatgaagt tttctaacgg cactttacat atttgtagga tttttagcat 5580
tttatcttct aggtagagca cttcaagcat ttgtacaggc tgctgatgct tgttgtttat 5640
tttggtacac gtgttagta attccaggag ttaagggtac agccttttgta tacaagtata 5700
catatgtag aaaacttaac aattcggaat tagaagcagt tgttgttaac gagtttccta 5760
agaacggttg gaataataaa aatccagcaa attttcaaga tgtccaacga aacaaattgt 5820
actcttgact ttgaacagtc agttgagctt tttaaagagt ataatttatt tataactgca 5880
ttcttgttgt tcttaaccat aatacttcag tatggttatg caacgcgtag taagtttatt 5940
tatatactta aaatgatagt gttatgtgc ttttggcccc ttaacattgc agtaggtgta 6000
atttcatgta tatacccacc aaacacagga ggtcttgtcg cagcgataat acttactgtg 6060
tttgcgtgtc tttctttgt aggttattgg atccagagta ttagactctt taagcggtgt 6120
agatcttggt ggtcatttaa cccagaatct aacgccgtag gttcaatact cctaactaat 6180
ggtcaacaat gtaattttgc tatagaagat gtgccgatgg tgcttttctcc tattataaag 6240
aatggtgttc tttattgtga gggtcagtgg cttgctaaat gtgaaccaga ccacttgcct 6300
aaagacatat ttgtatgcac accagataga cgtaatatct atcgtatggt gcagaaatac 6360
actggtgacc aaagcggaaa taagaaaagg tttgctcatt tgtctatgc aaagcagtca 6420
gtagacactg gcgagctaga aagtgtagca acaggtggaa gtagcctta cacataaatg 6480
tgtgtgtgta gagagtattt aaaattattc ttcaatagtg cctctatttt aagagcgcgg 6540
aagagtattt gttttgagga tattaatata aatcctcttt gttttgtact ctctttacaa 6600
gagttattat ttaagcaaca gtttttcctt tcctttgttt ggaagaaagt tgttgttaat 6660
ggtgtagaat tccaagtaga aaatggaaaa gtccactacg aaggaaaccc catttttcaa 6720
aaaggttgtt gtaggttgtg gtcccattat aagaaggatt aaatggatta accaccttac 6780
actacttact tgtaataagg gcgtttggac ttacaagcgc ttaacaaata cagacgatga 6840
aatggctgac tagttttgga agagcagtta tttcttgtta taaagcccta ctattaactc 6900
agttaagagt attagatagg ttaattttag atcacgacc aaagcgagtc ttaacgtgtg 6960
gtaggcgagt gcttttatct caattagatt tagtttatag gttggcatat acgcccaccc 7020
aatcgctggt atgaataata gtaaagataa tccttttcgc ggagcaatag caagaaaagc 7080
gcgaatttat ctgagagaag gattagagtg tgttactttt cttaacaaag caggacaagc 7140
agagccttgt ccgcgtgta cctccctagt atttcagggg aaaacttgtg aggaacacac 7200
agataataat aatcttttgt catggcgagc ggtaagacaa ctgggaagaa agacgcccca 7260
gcgccagtca tcaaactagg agggccaaaa ccacctaaag ttggttcttc tggaaatgct 7320
agctggtttc aagcactaaa agccaagaag ttaaattcac ctcctcctaa gtttgaaggt 7380
agcggcgttc ctgataatga aaatcttaaa ttaagccagc aacatggta ctggagacgt 7440
caagccaggt acaagccagg taaaggcgga agaaaatcca tcccagatgc ttggtacttc 7500
tattacactg gaacaggacc agccgctgac ctgaattggg gtgataccaa agatggtata 7560
gtgtgggttt ctgcaaaggg tgctgatact aaatctagat ctaaccaggg tacaagggat 7620
cctgataagt tgaccaata cccgctacga ttctcagatg gaggacctga tggtaatttc 7680
cgttgggact tcattccaat aaatcgtggt aggagtggaa gatcaacagc ggcttcatca 7740
gcagcatcta gtagagcacc gtcgcgtgat ggctcgcgtg gacgtagaag cggagctgaa 7800
ggttta tagctcgtgc agcaaagatc attcaggatc tgaggttctcgc 7860
attactaaag ctaaggccga tgaaatggct catcgccggt attgtaagcg tactatccca 7920
cctggttata aggttgatca agtatttggt ccccgtacta aagtaaggga gggaaatttt 7980
ggtgatgaca agatgaatga ggagggtatt aaggatggc gcgttacagc aatgctcaac 8040
ctagtcccta gcagccatgc ttgtcttttt ggaagtagag tgacgcccaa acttcaacca 8100
gatgggctgc acttgagatt tgaatttact actgtggttt ctagggatga tccgcagttt 8160
```

```
gataattatg tgaaaatttg tgatcagtgt gtcgatggtg tagggactcg gccaaaagac   8220
gatgaaccga gaccaaagtc acgcccaaat tcaagacctg ctacaagaac aagttctcca   8280
gcgccaagac aacagcgtca aaagaaggag aagaagtcaa agaagcagga tgatgaagta   8340
gataaggcat tgacctcaga tgaggagagg aacaatgcac agctggaatt tgatgatgaa   8400
ccgaaagtga ttaactgggg ggattcagca ctttggagga atgagttgta aagctagatt   8460
tccaacttaa catcatggac gtgcgtatgc tgttttttccc tactatagac ttttttagcat   8520
attattttt gctatttgta tggtttatta caggtgaaga ttgtatgtat ttgttgtaca   8580
ctcgtatgtt ctatattatg ttttctgtag ttgttattag tgttgttctt gttcttactc   8640
tactgttctc ttttctttat tttagagtat caataagaat caaggaagat aggcatgtag   8700
tttgattacc tacatgtcta tcgccaggga aatgtctaat ctgtctactt agtagcctag   8760
aaacgaacgg tagacccctta gatttttaatt tagtttaatt tttagtttag tttaagttag   8820
tttagagtag gtataaagaa gccagtgccg gggccacgcg gagtacgatc gagggtacga   8880
cactaggacg cccactaggg gaagagctaa attttagttt aagttaagtt taattggcta   8940
agtatagtta aaatttatag gctagtatag agttagagca aaaaaaaaa aaaaaaaaa    9000
aaaaaaaaaa aaaaaaaaa aaaaaaaaa aaaaaaaaa aaaaaaaaa aaaaaaaaaa      9060
aaaaaaaaa aaaaaaaaag tttaaactta attaagaatt cccttggctc gagttcgaaa   9120
tcggatgccg ggaccgacga gtgcagaggc gtgcaagcga gcttggcgta atcatggtca   9180
tagctgtttc ctgtgtgaaa ttgttatccg ctcacaattc cacacaacat acgagccgga   9240
agcataaagt gtaaagcctg gggtgcctaa tgagtgagct aactcacatt aattgcgttg   9300
cgctcactgc ccgctttcca gtcgggaaac ctgtcgtgcc agctgcatta atgaatcggc   9360
caacgcgcgg ggagaggcgg tttgcgtatt gggcgctctt ccgcttcctc gctcactgac   9420
tcgctgcgct cggtcgttcg gctgcggcga gcggtatcag ctcactcaaa ggcggtaata   9480
cggttatcca cagaatcagg ggataacgca ggaaagaaca tgtgagcaaa aggccagcaa   9540
aaggccagga accgtaaaaa ggccgcgttg ctggcgtttt tccataggct ccgcccccct   9600
gacgagcatc acaaaaatcg acgctcaagt cagaggtggc gaaacccgac aggactataa   9660
agataccagg cgtttccccc tggaagctcc ctcgtgcgct ctcctgttcc gaccctgccg   9720
cttaccggat acctgtccgc ctttctccct tcgggaagcg tggcgctttc tcatagctca   9780
cgctgtaggt atctcagttc ggtgtaggtc gttcgctcca agctgggctg tgtgcacgaa   9840
ccccccgttc agcccgaccg ctgcgcctta tccggtaact atcgtcttga gtccaacccg   9900
gtaagacacg acttatcgcc actggcagca gccactggta acaggattag cagagcgagg   9960
tatgtaggcg gtgctacaga gttcttgaag tggtggccta actacggcta cactagaaga   10020
acagtatttg gtatctgcgc tctgctgaag ccagttacct tcggaaaaag agttggtagc   10080
tcttgatccg gcaaacaaac caccgctggt agcggtggtt tttttgtttg caagcagcag   10140
attacgcgca gaaaaaaagg atctcaagaa gatcctttga tcttttctac ggggtctgac   10200
gctcagtgga acgaaaactc acgttaaggg attttggtca tgagattatc aaaaaggatc   10260
ttcacctaga tccttttaaa ttaaaaatga agttttaaat caatctaaag tatatatgag   10320
taaacttggt ctgacagtta ccaatgctta atcagtgagg cacctatctc agcgatctgt   10380
ctatttcgtt catccatagt tgcctgactc cccgtcgtgt agataactac gatacgggag   10440
ggcttaccat ctggccccag tgctgcaatg ataccgcgag acccacgctc accggctcca   10500
gatttatcag caataaacca gccagccgga agggccgagc gcagaagtgg tcctgcaact   10560
ttatccgcct ccatccagtc tattaattgt tgccgggaag ctagagtaag tagttcgcca   10620
gttaatagtt tgcgcaacgt tgttgccatt gctacaggca tcgtggtgtc acgctcgtcg   10680
tttggtatgg cttcattcag ctccggttcc caacgatcaa ggcgagttac atgatccccc   10740
atgttgtgca aaaaagcggt tagctccttc ggtcctccga tcgttgtcag aagtaagttg   10800
gccgcagtgt tatcactcat ggttatggca gcactgcata attctcttac tgtcatgcca   10860
tccgtaagat gcttttctgt gactggtgag tactcaacca agtcattctg agaatagtgt   10920
atgcggcgac cgagttgctc ttgcccggcg tcaatacggg ataataccgc gccacatagc   10980
agaactttaa aagtgctcat cattggaaaa cgttcttcgg ggcgaaaact ctcaaggatc   11040
ttaccgctgt tgagatccag ttcgatgtaa cccactcgtg cacccaactg atcttcagca   11100
tcttttactt tcaccagcgt ttctgggtga gcaaaaacag gaaggcaaaa tgccgcaaaa   11160
aagggaataa gggcgacacg gaaatgttga atactcatac tcttcctttt tcaatattat   11220
tgaagcattt atcagggtta ttgtctcatg agcggataca tatttgaatg tatttagaaa   11280
aataaacaaa taggggttcc gcgcacattt ccccgaaaag tgccacctga cgtctaagaa   11340
accattatta tcatgacatt aacctataaa aataggcgta tcacgaggcc ctttcgtc    11398

SEQ ID NO: 10            moltype = DNA   length = 11398
FEATURE                  Location/Qualifiers
misc_feature             1..11398
                         note = Plasmid Sequence
source                   1..11398
                         mol_type = other DNA
                         organism = synthetic construct
SEQUENCE: 10
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt ggagatcggt acttcgcgaa    420
tgcgtcgaga tcgccgcccc gggtaatacg actcactata gggacttaag atagatatta    480
atatatatct attgcactag ccttgcgcta gatttcaaac ttaacaaaac ggacttaaat    540
acctacagct ggtccccata ggtgttccat tgcagtgcac tttagtgccc tggatggcac    600
ctggccacct gtcaggtttt tgttgttaaa atatcattgt tctggtatc actgcttgtt    660
ttgccgtgtc tcactttata catccgttgc ttgggctacc tagtatccag cgtcctacgg    720
gcgccgtggt cggttcgagt gcgaaggacc tctggttcat ctagcggtag cgggtgtgt    780
ggaagtagcg cttcagacgt actggttctg ttgcgtgaaa cgcggggtca cctccccca    840
catacctcta agggctttg agcctagcgt tgggctacgt tctcgcacaa ggtcggctat    900
acgacgtttg taggggtag tgccaaacaa ccccctgagg gacaggttct ggtggtgttt    960
```

```
cgaaaacaac aatgtgtgtg ccgcataata tgcgcgttat gcattttgga gcaggtagtg   1020
ataaaggagt ggcgcctggt agtactgttc ttaaacagtg gctccccgaa ggaacactcc   1080
ttgtcgataa tgatattgta gattatgttt ctgacgcaca cgtttctgtg ctttcagatt   1140
gcaataaata taagacagag cacaagtttg atcttgtgat atctgatatg tatacagaca   1200
atgattcaaa aagaaagcat gaaggcgtga tagccaataa tggcaatgat gacgtcttca   1260
tatacctttc aagttttcta cgcaataatt tggctctggg aggcagtttt gctgtaaaat   1320
taacagagac aagttggcat gagagtttat atgacattgc acaggattgt gcatggtgga   1380
caatgttttg tacagcagtg aatgcatctt cttcagaagc attcctgatt ggtgttaatt   1440
acttgggtgc aagtgcaaag gttaaagtta gtggaaaaac actgcacgca aattatatat   1500
tttggaggaa ttgtaattat ttacaaacct ctgcttatag tatatttgat gttgctaagt   1560
ttgatttgag attgaaagca acgccagttg ttaatcttaa gactgaacaa aagacagact   1620
tagtcttttaa tttgataaag tgtggtaagt tactggtaag atgttggt aacacctctt   1680
ttactagtga ctcttttgtg tgcactatgt agtgctgctt tgtatgactc gagttcttac   1740
gtgtactact accaaagtgc cttcagacca cctgatggtt gacatttaca tgggggtgcg   1800
tatgcggttg ttaatatttc tagtgaatct aataatgcag gctcttcatc tgggtgtact   1860
gttggtatta ttcatggtgg tcgtgttgtt aatgcttctt ctatagctat gacggcaccg   1920
tcatcaggta tggcttggtc tagcagtcag ttttgtactg catactgtaa cttttcagat   1980
actacagtgt ttgttacaca ttgttataaa catggtaggt gtcctataac tggcatgctt   2040
caacagcatt ctatacgtgt ttctgctatg aaaaatggcc agcttttcta aatttaaca   2100
gttagtgtag ctaagtaccc tacttttaaa tcatttcagt gtgttaataa tttaacatcc   2160
gtatatttaa atggtgatct tgtttacacc tctaatgaga ccacagatgt tacatctgca   2220
ggtgtttatt ttaaagctgg tggacctata acttataaag ttatgagaga agttagagcc   2280
ctggcttatt ttgttaatgg tactgcacaa gatgttattt tgtgtgatgg gtcacctaga   2340
ggcttgttag catgccagta taatactggc aattttcag atggctttta tccttttact   2400
aatagtagtt tagttaagca gaagtttatt gtctatcgtg aaaatagtgt taatactact   2460
tgtacgttac acaatttcac ttttcataat gagactgccg ccaacccaaa tcctagtagt   2520
gtccagaata ttcaaactta ccaaacacaa acagctcaga gtggttatta taattttaat   2580
ttttcctttc tgagtagttt tgtttataag gagtctaatt ttatgtatgg atcttatcac   2640
ccaagttgta atttttagact agaaactatt aataatggtt tgtggtttaa ttcactttca   2700
gttagtattg cttacggtcc tcttcaaggt ggttgcaagc aatctgtctt cagtggtaga   2760
gcaacctgtt gttatgctta ctcatatgga ggtcctttgc tgtgtaaagg tgtttattca   2820
ggtgagttag atcataattt tgaatatgga ctgttagttt atgttactaa gagcggtggc   2880
tctcgtatac aaacagccac tgaaccgcca gttataactc aacacaatta taataatatt   2940
actttaaata cttgtgttga ttataatata tatggcagaa ctggccaggg ttttattact   3000
aatgtaaccg actcagctgt tagttataat tatctagcag acgcaggttt ggctatttta   3060
gatacatctg gttccataga catctttgtc gtacaaagtg aatatggtct taattattat   3120
aaggttaacc cttgcgaaga tgtcaaccag cagtttgtag tttctggtgg taaattagta   3180
ggtattctta cttcacgtaa tgagactggt tcccagcttc ttgagaatca gttttacatc   3240
aaaatcacta atggaacacg tcgttttaga cgttctatta ctgaaagtgt tgaaaattgc   3300
ccttatgtta gttatggtaa gttttgtata aaacctgatg gcagtattgc cacaatagta   3360
ccaaaacagt tagaacagtt tgtggcacct ttacttaatg ttactgaaaa tgtgctcata   3420
cctaacagtt ttaatttaac tgttacagat gagtacatac aaactcggat ggataaggtc   3480
caaattaatt gcctgcagta tatttgtggc aattctctgg agtgcagaaa tttgtttcaa   3540
caatatggtc ctgtttgcga caacatattg tctgtagtaa atagtgttgg tcaaaaagaa   3600
gatatggaac ttttgaattt ctattcttct actaagccgg ctggttttaa tacaccagtt   3660
cttagtaatg ttagcactgg tgagtttaat attactcttt ttaacaac gcctagtagt   3720
cctagaaggc gttcttttat tgaagacctt ctatttacaa gtgttgaatc tgttggatta   3780
ccaacagatg acgcatacaa aaattgcact gcaggtcctt taggctttct gaaagaccttt   3840
gcatgtgctc gtgaatataa tggttttgctt gtgttgcctc ctattataac agcagaaatg   3900
caaactttgt atacaagctc tctagtagct tctatggctt ttggtggtat tactgcagct   3960
ggtgctatac cttttgccac acaactgcag ctagaatta atcacttggg tattacccag   4020
tcacttcttt tgaagaatca agaaaaaatt gctgcttcct ttaataaggc catcggtcat   4080
atgcaggaag gttttagaag tacacttta gcattacaac aaattcaaga tgttgttaat   4140
aagcagagtg ctattcttac tgagactatg gcatcactta taaaattt tggtgccatt   4200
tcttctgtga ttcaagaaat ctaccagcaa cttgacgcca tacaagcaaa tgctcaagtg   4260
gatcgtctta taactggtag attgtcatca cttctgtttt tagcatctgc taagcaggcg   4320
gagtatatta gagtgtcaca acagcgtgag ttagctactc agaagattaa tgagtgtgtt   4380
aagtcacagt ccattaggta ctccttttgt ggtaatggac gacatgtttt aaccataccg   4440
caaaatgcac ctaatggtat agtgtttata cactttcttt acactccaga tagttttgtt   4500
aatgttactg caatagtggg ttttgtgta aagccagtca atgctagtca gtatgcaata   4560
gtacccgcta atggtagggg tattttttata caagttaatg gtagtacta catcactgca   4620
cgagatatgt atatgccaag agctattact gcaggagata tagttacgct tacttcttgt   4680
caagcaaatt atgtaagtgt aaataagacc gtcattacta cattcgtaga caatgatgat   4740
tttgatttta atgacgaatt gtcaaaatgg tggaatgata ctaagcatga gctaccagac   4800
tttgacaaat tcaattacac agtacctata cttgacattg atagtgaaat tgatcgtatt   4860
caaggcgtta tacagggtct taatgactct ctaatagacc ttgaaaaact ttcaatactc   4920
aaaacttata ttaagtggcc ttggtatgtg tggctagcca tagcttttgc cactattatc   4980
ttcatcttaa tattaggatg ggttttcttc atgactgggt gttgtggttg ttgttgtgga   5040
tgctttggct ttatgcctct aatgagtaag ttactggcgg aatcttctta ttacacgctt   5100
tttgataacg atgtggtaac tgaacaatac agacctaaaa agtctgttta atgatccaaa   5160
gtcccactag tttcttaata gtattaattt tgctttggtg taaacttgta ctaagttgtt   5220
ttagagagtt tattattgcc cttcaacaac taacacaagt tttactccaa attatcgata   5280
gtaatttaca gtctagactg acccctttgc acagtctaga ctaatgttaa acttagaggc   5340
aattattgaa accggtgatc aagtgattca aaaatcagt acatttttac agcatattc   5400
aagtgtatta aacacagaag tatttgaccc ctttgactat tgttattaca gaggaggtaa   5460
ttttttggga aatagagtcag ctgaagattg ttcaggtgat gatgaattta ttgataagt   5520
cgctagagga gaatgaagt tttctaacgg cactttacat atttgtagga ttttagcat   5580
tttatcttct aggtagagca cttcaagcat ttgtacaggc tgctgatgct tgttgttat   5640
tttggtacac gtggttagta attccaggag ttaagggtac agcctttgta tacaagtata   5700
```

-continued

```
catatggtag aaaacttaac aattcggaat tagaagcagt tgttgttaac gagtttccta   5760
agaacggttg gaataataaa aatccagcaa attttcaaga tgtccaacga aacaaattgt   5820
actcttgact ttgaacagtc agttgagctt tttaaagagt ataatttatt tataactgca   5880
ttcttgttgt tcttaaccat aatacttcag tatggttatg caacgcgtag taagtttatt   5940
tatatactta aaatgatagt gttatggtgc ttttggcccc ttaacattgc agtaggtgta   6000
atttcatgta tatacccacc aaacacagga ggtcttgtcg cagcgataat acttactgtg   6060
tttgcgtgtc tttctttttgt aggttattgg atccagagta ttagactctt taagcggtgt   6120
agatcttggt ggtcatttaa cccagaatct aacgccgtag gttcaatact cctaactaat   6180
ggtcaacaat gtaattttgc tatagagagt gtgccgatgg tgctttctcc tattataaag   6240
aatggtgttc tttattgtga gggtcagtgg cttgctaaat gtgaaccaga ccacttgcct   6300
aaagacatat ttgtatgcac accagataga cgtaatatct atcgtatggt gcagaaatac   6360
actggtgacc aaagcggaaa taagaaaagg tttgctacat ttgtctatgc aaagcagtca   6420
gtagacactg gcgagctaga aagtgtagca acaggtggaa gtagcccttta cacataaatg   6480
tgtgtgtgta gagagtattt aaaattattc ttcaatagtg cctctatttt aagagcgcgg   6540
aagagtattt gttttgagga tattaatata aatcctctt gttttgtact ctctttacaa   6600
gagttattat ttaagcaaca gttttccctt tcctttgttt ggaagaaagt tgttgttaat   6660
ggtgtagaat tccaagtaga aaatggaaaa gtccactacg aaggaaaccc cattttccaa   6720
aaaggttgtt gtaggttgtg gtcccattat aagaaggatt aaatggatta aaccacctac   6780
actacttact tgtaataagg gcgtttggac ttacaagcgc ttaacaaata cagacgatga   6840
aatggctgac tagttttgga agagcagtta tttcttgtta taaagcccta ctattaactc   6900
agttaagagt attagatagg ttaattttag atcacggacc aaagcgagtc ttaacgtgtg   6960
gtaggcgagt gcttttatct caattagatt tagtttatag gttggcatat acgcccaccc   7020
aatcgctggt atgaataata gtaaagataa tcctttcgc ggagcaatag caagaaaagc   7080
gcgaatttat ctgagagaag gattagagtg tgttactttt cttaacaaag caggacaagc   7140
agagcctttg cccgcgtgta cctccctagt atttcagggg aaaacttgtg aggaacacac   7200
agataataat aatcttttgt catggcgagc ggtaagacaa ctgggaagac agacgcccca   7260
gcgccagtca tcaaactagg aggggccaaaa ccacctaaag ttggttcttc tggaaatgct   7320
agctggtttc aagcactaaa agccaagaag ttaaattcac ctcctcctaa gtttgaaggt   7380
agcggcgttc ctgataatga aaatcttaaa ttaagccagc aacatgggta ctggagacgt   7440
caagccaggt acaagccagg taaaggcgga agaaaatcag tcccagatgc ttggtacttc   7500
tattacactg gaacaggacc agccgctgac ctgaattggg gtgatagcca agatggtata   7560
gtgtgggttt ctgcaaaggg tgctgatact aaatctagat ctaaccaggg tacaagggat   7620
cctgataagt ttgaccaata cccgctacga ttctcagatg gaggacctga tggtaatttc   7680
cgttgggact tcattccaat aaatcgtggt aggagtggaa gatcaacagc ggcttcatca   7740
gcagcatcta gtagagcacc gtcgcgtgat ggctcgcgtg gacgtagaag cggagctgaa   7800
gatgatctta tagctcgtgc agcaaagatc attcaggatc agcagaagaa gggttctcgc   7860
attactaaag ctaaggccga tgaaatggct catcgccggt attgtaagcg tactatccca   7920
cctggttata aggttgatca agtatttggt ccccgtacta aagtaaggaa gggaaatttt   7980
ggtgatgaca agataagtaa tgagggtatt aaggatggc gcgttacgac aatgctcaac   8040
ctagtccccta gcagccatgc ttgtctttttt ggaagtagag tgacgcccaa acttcaacca   8100
gatgggctgc acttgagatt tgaatttact actgtggttt ctagggatga tccgcagttt   8160
gataattatg tgaaaatttg tgatcagtgt gtcgatggtg tagggactcg gccaaaaagac   8220
gatgaaccga gaccaaagtc acgcccaaat tcaagacctg ctacaagaac aagttctcca   8280
gcgccaagac aacagcgtca aaagaaggag aagaagtcaa agaagcagga tgatgaagta   8340
gataaggcat tgacctcaga tgaggagagg aacaatgcac agctggaatt tgatgatgaa   8400
ccgaaagtga ttaactgggg ggattcagca cttgagagaa atgagttgta aagctagatt   8460
tccaacttaa catcatggac gtgcgtatgc tgttttttccc tactatagac tttttagcat   8520
attattttt gctatttgta tggtttatta caggtgaaga ttgtatgtat ttgttgtaca   8580
ctcgtatgtt ctatattatg ttttctgtag ttgttattag tgttgttctt gttcttactc   8640
tactgttctc ttttctttat tttagagtat caataagaat caaggaagat aggcatgtag   8700
tttgattacc tacatgtcta tcgccaggga aatgtctaat ctgtctactt agtagcctgg   8760
aaacgaacgg tagaccctta gattttaatt tagtttaatt tttagtttag tttaagttag   8820
tttagagtag gtataaagaa gccagtgccg gggccacgcg gagtacgatc gagggtacag   8880
cactaggacg cccactaggg gaagagctaa attttagttt aagttaagtt taattggcta   8940
agtatagtta aaatttatag gctagtatag agttagagca aaaaaaaaaa aaaaaaaaaa   9000
aaaaaaaaaa aaaaaaaaaa aaaaaaaaaa aaaaaaaaaa aaaaaaaaaa aaaaaaaaaa   9060
aaaaaaaaaa aaaaaaaaag tttaaactta attaagaatt cccttggctc gagttcgaaa   9120
tcggatgccg ggaccgacga gtgcagaggc gtgcaagcga gcttggcgta atcatggtca   9180
tagctgtttc ctgtgtgaaa ttgttatccg ctcacaattc cacacaacat acgagccgga   9240
agcataaagt gtaaagcctg gggtgcctaa tgagtgagct aactcacatt aattgcgttg   9300
cgctcactgc ccgctttcca gtcgggaaac ctgtcgtgcc agctgcatta atgaatcggc   9360
caacgcgcgg ggagaggcgg tttgcgtatt gggcgctctt ccgcttcctc gctcactgac   9420
tcgctgcgct cggtcgttcg gctgcggcga gcggtatcag ctcactcaaa ggcggtaata   9480
cggttatcca cagaatcagg ggataacgca ggaaagaaca tgtgagcaaa aggccagcaa   9540
aaggccagga accgtaaaaa ggccgcgttg ctggcgtttt tccataggct ccgcccccct   9600
gacgagcatc acaaaaatcg acgctcaagt cagaggtggc gaaacccgac aggactataa   9660
agataccagg cgtttccccc tggaagctcc ctcgtgcgct ctcctgttcc gaccctgccg   9720
cttaccggat acctgtccgc ctttctccct tcgggaagcg tggcgctttc tcatagctca   9780
cgctgtaggt atctcagttc ggtgtaggtc gttcgctcca agctgggctg tgtgcacgaa   9840
ccccccgttc agcccgaccg ctgcgcctta tccggtaact atcgtcttga gtccaacccg   9900
gtaagacacg acttatcgcc actggcagca gccactggta acaggattag cagagcgagg   9960
tatgtaggcg gtgctacaga gttcttgaag tggtggccta actacggcta cactagaaga  10020
acagtatttg gtatctgcgc tctgctgaag ccagttacct tcggaaaaag agttggtagc  10080
tcttgatccg gcaaacaaac caccgctggt agcggtggtt tttttgttttg caagcagcag  10140
attacgcgca gaaaaaaagg atctcaagaa gatcctttga tcttttctac ggggtctgac  10200
gctcagtgga acgaaaactc acgttaaggg attttggtca tgagattatc aaaaaggatc  10260
ttcacctaga tccttttaaa ttaaaaatga agttttaaat caatctaaag tatatatgag  10320
taaacttggt ctgacagtta ccaatgctta atcagtgagg cacctatctc agcgatctgt  10380
ctatttcgtt catccatagt tgcctgactc cccgtcgtgt agataactac gatacgggag  10440
```

-continued

```
ggcttaccat ctggcccccag tgctgcaatg ataccgcgag acccacgctc accggctcca  10500
gatttatcag caataaaacca gccagccgga agggccgagc gcagaagtgg tcctgcaact  10560
ttatccgcct ccatccagtc tattaattgt tgccggaaag ctagagtaag tagttcgcca  10620
gttaatagtt tgcgcaacgt tgttgccatt gctacaggca tcgtggtgtc acgctcgtcg  10680
tttggtatgg cttcattcag ctccggttcc caacgatcaa ggcagttac atgatcccca  10740
atgttgtgca aaaagcggt tagctccttc ggtcctccga tcgttgtcag aagtaagttg  10800
gccgcagtgt tatcactcat ggttatggca gcactgcata attctcttac tgtcatgcca  10860
tccgtaagat gcttttctgt gactggtgag tactcaacca agtcattctg agaatagtgt  10920
atgcggcgac cgagttgctc ttgccccggcg tcaataacgg ataataccgc gccacatagc  10980
agaactttaa aagtgctcat cattggaaaa cgttcttcgg ggcgaaaact ctcaaggatc  11040
ttaccgctgt tgagatccag ttcgatgtaa cccactcgtg cacccaactg atcttcagca  11100
tcttttactt tcaccagcgt ttctgggtga gcaaaaacag gaaggcaaaa tgccgcaaaa  11160
aagggaataa gggcgacacg gaaatgttga atactcatac tcttcctttt tcaatattat  11220
tgaagcattt atcagggtta ttgtctcatg agcggataca tatttgaatg tatttagaaa  11280
aataaacaaa taggggttcc gcgcacattt ccccgaaaag tgccacctga cgtctaagaa  11340
accattatta tcatgacatt aacctataaa aataggcgta tcacgaggcc ctttcgtc   11398
```

SEQ ID NO: 11            moltype = AA   length = 1155
FEATURE                  Location/Qualifiers
source                   1..1155
                         mol_type = protein
                         organism = unidentified
                         note = Avian infectious bronchitis virus
SEQUENCE: 11
MLDKPLLLVT LWYALCSALL YDNNTYVYYY QSAFRPGPGW HLYGGAYAVD RVFNETNNAG    60
SASDCTAGTF YESHNISASS VAMTVPHNGM SWSASQFCTA HCNFSDFTVF VTHCFKNQLG   120
SCPLTGMIPQ NHIRISAMRD GVLFYNLTVS VSKYPRFKSL QCVSNSTSVY VNGDLVFTSN   180
ETSYVTGAGV YFKSGGPVTY KVMKEVKALA YFINGTAQEV ILCDNSPRGL LACQYNTGNF   240
SDGFYPFTNH SLVKDRFIVY RESSTNTTLK LTNFSFTNVS NASPNSGGVD TFQLYQTSTA   300
QDGYYNFNLS FLSSFVYKPS DFMYGSYHPH CKFRPENINN GLWFNSLSVS LTYGPIQGGC   360
KQSVFSNRAT CCYAYSYQGP SRCKGVYRGE LTQYFECGLL VYVTKSDGSR IQTRSEPLVL   420
TQYNYNNITL NKCVEYNIYG RVGQGFITNV TEATANYSYL ADGGLAILDT SGAIDIFVVQ   480
GAYGLNYYKV NPCEDVNQQF VVSGGNLVGI LTSHNETGSE SIENQFYIKL TNGTRRSRRS   540
VTGNVTNCPY VSYGKFCIKP DGSLSIIVPQ ELEQFVAPLF NVTEHVLIPD SFNLTVTDEY   600
IQTRMDKVQI ICLQYVCGNS IECRKLFQQY GPVCDNILSV VNGVGQREDM ELLSFYSSTK   660
PSGYNTPIFN NVSTGDFNIS LLLTPPNSPT GRSFIEDLLF TSVESVGLPT DEEYKKCTAG   720
PLGFVKDLVC AREYNGLLVL PPIITAEMQT MYTSSLVASM ALGGITAAGA IPFATQLQAR   780
INHLGITNSL LLKNQEKIAA SFNKAIGHMQ EGFKSTSLAL QQIQDVVNKQ SSILTETMQS   840
LNKNFGAISS VIQDIYQQLD AIQADAQVDR LITGRLSSLS VLASAKQAEY HRVSQQRELA   900
TQKINECVKS QSNRYSFCGN GRHVLTIPQN APNGIVFIHF TYTPESFVNV TAIVGFCVNP   960
ANASHYAIVP VNGRGVFIEV NGSYYITARD MYMPRDITAG DIVTLTSCQA NYVNVNKTVI  1020
NTFVEDDDFD FYDELSKWWN DTKHELPDFD EFNYTVPVLN ISNEIDRIQQ VIQGLNDSLI  1080
DLETLSILKT YIKWPWYVWL AIAFLTIIFI LVLCWIFFMT GCCGCCCGCF GIIPLMSKCG  1140
KKSSYYTTFD NDVVT                                                  1155

SEQ ID NO: 12            moltype = DNA   length = 11860
FEATURE                  Location/Qualifiers
misc_feature             1..11860
                         note = Plasmid Sequence
source                   1..11860
                         mol_type = other DNA
                         organism = synthetic construct
SEQUENCE: 12
```

```
tcgcgcgttt cggtgatgac ggtgaaaacc tctgacacat gcagctcccg gagacggtca    60
cagcttgtct gtaagcggat gccgggagca gacaagcccg tcagcgggtg ttggcgggtg   120
tcggggctgg cttaactatg cggcatcaga gcagattgta ctgagagtgc accatatgcg   180
gtgtgaaata ccgcacagat gcgtaaggag aaaataccgc atcaggcgcc attgccatt   240
caggctgcgc aactgttggg aagggcgatc ggtgcgggcc tcttcgctat tacgccagct   300
ggcgaaaggg ggatgtgctg caaggcgatt aagttgggta acgccagggt tttcccagtc   360
acgacgttgt aaaacgacgg ccagtgaatt ggagatcgtt acttcgtgaa   420
tgcgtcgaga tgagctctaa tacgactcac tataggact taagtgtgat ataaatatat    480
atcatacata ctagccttgt gctagatttc aacttaaca aaacgagcatt aaatacctac   540
agttggtccc tataggtgtt ccattgcagt gcactttagt gccctggatg gcacctggcc   600
acctgtcagg tttttgttat taaaataata tgttgctcg tatcactgct tgttttgacg   660
tgtctcactt tatacatccg ttgcttgggc tacctagtac ccagcgtcct actggcgttg   720
tggtcggttc gagtgcgaag aacctctggt tcatctagcg gtacgcgggt gtgtggaagt   780
agcgcttcag acgtaccggt tctgttgcgt gaaatacggg gtcacctccc ccacatacc   840
tctaagggct tttgagccta gcgttgggct acgttctcgc acaaggtcgg ctatacggcg   900
tttgtagggg gtagtgccaa acaacccctg aggtagtcag ttctggtgtc gtttcgaaa   960
caacaatgtg tgtgccgcat aatatgcgag taatgcattt tggagcagga agtgacaaag  1020
gagtggcccc aggtagcgct gttccttagc agtggcttcc cgaaggtaca ctccttgtcg  1080
ataatgatat tgtagattat gtatctgatg cacatgtctc tgtgctttca gattgcaata  1140
aatgtaaaac agagcacaag tttgatcttg tgatatctga tatgtataca gataatgatt  1200
caaagagaaa gcatgaaggc gttgtagcca ataacggcag tgatgacgtc ttcatatacc  1260
tttcaaactt tcttccgtaac aatttagctc tgggaggcag ttttgccgta aaagtaacag  1320
agacaagttg gcatgagagt ttatatgaca ttgcacagga ttgtcatgg tggacaatgt  1380
tttgtacagc agtgaatgct tcttcgtcag agcattctt gattggtgtt aattatttgg  1440
gtgcaagtga aaaggttaga gttagtggta aaaccctgca cgcaaattat atattttgga  1500
ggaattgtaa ttatttacaa acttcagcct atagtatatt tgacgttgct aagtttgatt  1560
```

-continued

```
tgaaattaaa agcaacgcca gttgtgaatt tgaaaactga acaaaagaca gacttagtct  1620
ttaatttaat taagtgtggt aagttactgg taagagatgt tggacaaacc gcttttacta  1680
gtgactcttt ggtatgcact atgtagtgct ttgctctatg ataataatta tattggtgat  1740
tttagatgta tccagcttgt gaactcaaac ggtgctaatg ttagtgctcc aagcattagc  1800
actgagaccg ttgaagtttc acaaggcctg gggacatatt atgtgttaga tcgagtttat  1860
ttaaatgcca cattattgct tactggttac taccccggtcg atggttctaa gtttagaaac  1920
ctcgctctta cgggaactaa ctcagttagc ttgtcgtggt ttcaaccacc ctatttaagt  1980
cagtttaatg atggcatatt tgcgaaggtg cagaaccttta agacaagtac gccatcaggt  2040
gcaactgcat atttttcctac tatagttata ggtagtttgt ttggctatac ttcctatacc  2100
gttgtaatag agccatataa tggtgttata atggcctcag tgtgccagta taccatttgt  2160
cagttacctt acactgattg taagcctaac actaatggta ataagcttat agggttttgg  2220
cacacggatg taaaacccccc aatttgtgtg ttaaagcgaa atttcacgct taatgttaat  2280
gctgatgcat tttattttca tttttaccaa catggtggta cttttttatgc gtactatgcg  2340
gataaaccct ccgctactac gtttttgttt agtgtatata ttggcgatat tttaacacag  2400
tattatgtgt tacctttcat ctgcaaccca acagctggta gcactttttgc tccgcgctat  2460
tgggttacac ctttggttaa cgccaatat ttgtttaatt tcaaccagaa gggtgtcatt  2520
actagtgctg ttgattgtgc tagtagttat accagtgaaa taaaatgtaa gacccagagc  2580
atgttaccta gcactggtgt ctatgagtta tccggttata cggtccaacc agttggagtt  2640
gtataccggc gtgttgctaa cctcccagct tgtaatatag aggagtggct tactgctagg  2700
tcagtcccct cccctctcaa ctgggagcgt aagactttttc agaattgtaa ttttaattta  2760
agcagcctgt tacgttatgt tcaggctgag agtttgtttt gtaataatat cgatgcttcc  2820
aaagtgtatg gcaggtgctt tggtagtatt tcagttgata agtttgctgt accccgaagt  2880
aggcaagttg atttacagct tggtaactct ggatttctgc agactgctaa ttataagatt  2940
gatacagctg ccactctgtg tcagctgcat tacaccttgc ctaagaataa tgtcaccata  3000
aacaaccata accccctcgtc ttggaatagg aggtatggct ttaatgatgc tggcgtcttt  3060
ggcaaaaacc aacatgacgt tgtttacgct cagcaatgtt ttactgtaag atctagttat  3120
tgcccgtgtg ctcaaccgga catagttagc ccttgcacta ctcagactaa gcctaagtct  3180
gcttttgtta atgtgggtga ccattgtgaa ggctaggtg ttttagaaga taattgtggc  3240
aatgctgatc cacataaggg ttgtatctgt gccaacaatt catttattgg atggtcacat  3300
gatacctgcc ttgttaatga tcgctgccaa atttttgcta atatattgtt aaatggcatt  3360
aatagtggta ccacatgttc cacagatttg cagttgccta atactgaagt ggttactggc  3420
atttgtgtca aatatgacct ctacggtatt actggacaag gtgttttttaa agaggttaag  3480
gctgactatt ataatagctg gcaaaacctt ctgtatgatg ttaatggtaa tttgaatggt  3540
tttcgtgatc ttaccactaa caagacttat acgataagga gctgttatag tggccgtgtt  3600
tctgctgcat ttcataaaga tgcacccgaa ccggctctgc tctatcgtaa tataaattgt  3660
agctatgttt ttagcaataa tatttcccgt gaggagaacc cacttaatta ctttgatagt  3720
tatttgggtt gtgttgttaa tgctgataac cgcacggatg aggcgcttcc taattgtgat  3780
ctccgtatgg gtgctggctt atgcgttgat tattcaaaat cacgcagggc tcaccgatca  3840
gtttctactg gctatcggtt aactacattt gagccatca ctccgatgtt agttaatgat  3900
agtgtccaat ccgttgatgg attatatgag atgcaaatac caaccaattt tactattggg  3960
caccatgagg agttcattca aactagatct ccaaaggtga ctatagattg tgctgcattt  4020
gtctgtggtg ataacactgc atgcaggcag cagttggttg agtatggctc tttctgtgtt  4080
aatgttaatg ccattcttaa tgaggttaat aacctcttag ataatatgca actacaagtt  4140
gctagtgcat taatgcaggg tgttactata agttcgagac tgccagacgg catctcaggc  4200
cctatagatg acattaattt tagtcctcta cttggatgca taggttcaac atgtgctgaa  4260
gacggcaatg gacctagtgc aatccgaggg cgttctgcta tagaggattt gttatttgac  4320
aaggtcaaat tatctgatgt tggctttgtc gaggcttata ataattgcac cggtggtcaa  4380
gaagttcgtg acctccttttg tgtacaatct tttaatggca tcaaagtatt acctcctgtg  4440
ttgtcagaga gtcagatctc tggctacaca accggtgcta ctgcggcagc tatgttccca  4500
ccgtggtcag cagctgccgg tgtgccattt agtttaagtg ttcaatatag aattaatggt  4560
ttaggtgtca ctatgaatgt gcttagtgag aaccaaaaga tgattgctag tgcttttttaac  4620
aatgcgctgg gtgctatcca ggatgggttt gatgcaacca attctgcttt aggtaagatc  4680
cagtccgttg ttaatgcaaa tgctgaagca ctcaataact tactaaatca acttttctaac  4740
aggtttggtg ctattagtgc ttcttttacaa gaaattctaa ctcggcttga ggctgtagaa  4800
gcaaaagccc agatagatcg tcttattaat ggcaggttaa ctgcacttaa tgcgtatata  4860
tccaagcaac ttagtgatag tacgcttatt aaagttagtg ctgctcaggc catagaaaag  4920
gtcaatgagt gcgttaagag ccaaaccacg cgtattaatt tctgtggcaa tggtaatcat  4980
atattatctc ttgtccagaa tgcgccttat ggcttatatt ttatacactt cagctatgtg  5040
ccaatatcct ttacaaccgc aaatgtgagt cctggacttt gcatttctgg tgatagagga  5100
ttagcaccta aagctggata ttttgttcaa gatgatggag aatggaagtt cacaggcagt  5160
tcatattact acccctgaacc cattacagat aaaaacagtg tcattatgag tagttgcgca  5220
gtaaactaca caaaggcacc tgaagttttc ttgaacactt caatacctaa tccacccgac  5280
tttaaggagg agttagataa atggtttaag aatcagacgt ctattgcgcc tgatttatct  5340
ctcgatttcg agaagttaaa tgttactttg tctggacctga cgtatgagt gaacaggatt  5400
caggatgcaa ttaagaagtt aaatgagagc tacatcaacc tcaaggaagt tggcacatat  5460
gaaatgtatg tgaaatggcc ttggtatgtg tggcttgcca ttgcattcct taccattatt  5520
tttattctgg tactttgttg gatattttc atgaccggtt gttgcggttg ttgttgtgga  5580
tgctttggta tcataccgtt aatgagtaag tgtggtaaga aatcttctta ctacacgact  5640
tttgataatg atgtggtaac ttaacaatac agacctaaaca agtctgttta atgattaaaa  5700
gtcccacatc ttttctaata ttattaattc ttctttggtg taaacttgca ttaagttgtt  5760
ttaaagagtg tgttataaca ctccagcaac tagtacaaat tttactccaa attattaata  5820
gtaacttaca atctagactt ctgctttggc acagtctaga ctaatgttag attttgaagc  5880
aattattgaa actggtcagc aaataactca acaaattagt ttcatttttac agcatatttc  5940
aagggtgcta agtactgaat tatttgaccc ctttgaagtt tgtgtttaca gaggaggtaa  6000
ttgtgggag ttagagtcag ctgacgagtt ttcaggtgat gacgaatata ttgagtagat  6060
cgctcgagga gaacggaagt tttctaacag cggtttacgt gttttttagga tttttagcac  6120
tttatctact aggtagagcg cttcaagctt ttgtacaagc ggctgacgct tgttgtcttt  6180
tttggtatac atgggtagta gttcctggag ccaagggcac agcctttgtt tataatcata  6240
catatggtaa aaaacttaac aaaccggagt tagaaacggt tattgttaac gaatttccaa  6300
```

```
aaaacggttg gaaatatgga taataccatc aattgtactc ttggtactga acaagcagtt    6360
cagcttttta aggaatataa tctgtttgta actgcattcc tgttgttttt aaccatacta    6420
cttcagtatg gatacgcaac taggagcaag gttatttaca tactgaaaat gatagtgtta    6480
tggtgctttt ggcccttaa cattgcagta ggtgtaatct catgtatata cccaccaaac     6540
acaggaggtc ttgtcgcagc gataattctt acagtgtttg cgtgtctttc tttataggt    6600
tattggatcc agagtattag acttttaag cggtgcaggt catggtggtc atttaacccc     6660
gaatctaatg ccgtaggttc aatactccta actaatggtc aacaatgtaa ttttgctata    6720
gagagtgtgc cgatggtgct ttctcctatt ataaagaatg gtgctcttta ttgcgagggt    6780
cagtggcttg ctaaatgtga accagaccac ttgcctagag atatatttgt atgcacaccg    6840
gatagacgta atatctatcg tatggtgcaa aaatatactg gtgaccaaag cggaagtaag    6900
aaaaggtttg ccacatttgt ctatgcaaag cagtcagtag atactggcga gctagaaagt    6960
gtgtcagcag taggaggtag tctttacaca taaatgtgtg tgtgtagaga gtatttaaaa    7020
ttattctttg acagtgcctc cgttttaaga gcgcggaaga gtattatttt tgaggatatt    7080
aatataaatc ctctttgttt catactctcc tttcaggagt tattatttaa aaaacagttt    7140
ttccactctt ttgtgccaaa aacaattgtt gttaatggtg taaccttca ggtagacaat     7200
ggaaaagtct actacgaagg aagaccaatt ttccaaaaag gttgttgtag tttgtggtcc    7260
aattataaga aagattagaa taattaaacc acctacaaca cttattttta caaatggcgt    7320
tttaggttac aaacgcttaa caaatacgga tgatgaaatg gctgactagt tttggaagag    7380
ctttcatctc ctgttataaa tccctattac taactcaatt aagagtatta gataggttaa    7440
ttttagatca cggacccaag cgcacattaa cgtgtgctag gcgagtgctt ttagttcaat    7500
tagatttagt ttataggttg gcttatacgc ccacccaatc gctggtatga ataatagtaa    7560
agataatcct tttcgcggag caatagcaag aaaagcggta atttatctga gaggaggatt    7620
agattgtgtt tactttctta acaaagcagg acaagcagag ccttgtcccg cgtgtacctc    7680
cctagtattc caagggaaaa cttgtgagga acactattat aataacaatc ttttgtcatg    7740
gcaagcggta aggcaactgg aaagacagac gccccagcgc cagtcatcaa actaggagga    7800
ccaaagccac ctaaagttgg ttcttctgga aatgcatcat ggtttcaacc gataaaggcc    7860
aagaagctaa attcacctgt gcctaaattt gacggtagtg gtgttcctga aaatgaaaat    7920
ctcaagtcaa gccagcaaca tggatactgg agacgcaaac acaggtttaa gcctggcaaa    7980
ggtggaagaa aaccagtccc tgatgcttgg tacttttact acactggaac aggaccggcc    8040
gccgacctga attgggtga aactcaagat ggtatagtgt ggttgctgc aaagggtgct     8100
gatactaaat ctagatcaaa ccagggtaca agggatcctg ataagtttga ccaatacca     8160
ctacgattct cagatggagg accggatggt aatttccgtt gggacttcat accaataaat    8220
cgtggtagga gtgggagatc aacagcagct tcatcagcag catctagtag agcaccatct    8280
cgtgaggggt cacgtggacg tagaagcgga gttgaagatg atcttatagc tcgcgcagca    8340
aagattatac aggaccagca aaagaagggt gcgcgcatta ccaaggctaa ggctgatgaa    8400
atggctcatc gccgcattg caagcgcact atcccacctg gttataaggt tgagcaagta    8460
tttggtcccc gtactaaagg taaggaagga attttggtg atgacaagat gaatgaggaa     8520
ggtgttaagg atgggcgtgt tacggcaatg ctcaacctag tccctagcag tcatgcttgt    8580
cttttggaa gtagggtgac gcccaaactg cagccagatg gtcttcacct gagatttgaa     8640
tttactactg tggtgtcacg tgatgatccg cagtttgata attatgtgaa aatttgtgat    8700
cagtgtgtcg atggtgtagg gacgcgtcca aaggacgatg aatcgagacc aaagtcacgc    8760
ccaaattcaa gacctgcaac tagaggaaat tctccagcgc cgagacaaca gcgcccaaag    8820
aaggagaaaa agcccaagaa gcaggatgat gaagtagata aggcattgac ctcagatgag    8880
gagaggaaca atgcacagct ggaatttgat gatgaaccca aggtgattaa ctgggggac     8940
tctgcactag gtgaaaatga actttgatta acataatgga cttgctgcat ttgctgtcac    9000
attttgttaa atattatttt tgtgtttac tatcaattat tacaggtatt gattgtgatt     9060
atgttcaata cttaagcttc ttctggttgc tttttgcttg ttgtattgtt gctgtgcttt    9120
ttattattgt gattctcatt agtttgcttt atcgtagaaa ttcaatagta agagttaagg    9180
aagataggca tgtagcttag cacctacatg tctatcgcca gggaaatgtc taatctgtct    9240
acttagtagc ctgaaacga acggtagacc cttagatttt aatttagttt aatttttagt    9300
ttagtttaag ttagtttaga gtaggtataa agatgccagt gccggggcca cgcgtagtac    9360
gaccgagggt acagcactag gacgcccact aggggaagag ctaaatttta gtttaagtta    9420
agtttaattg gctaaatata gttaaaattt ataggctagt atagagttag agcaaaaaaa    9480
aaaaaaaaaa aaaaaaaaaa aaaaaaaaa aaaaaaaaa aaaaaaaaaa aaaaaaaaaa     9540
aaaaaaaaaa aaaaaaaaaa aaaaaaaaa aaagcggccg catcggatgc cgggaccgac     9600
gagtgcagag gcgtgcaagc gagcttggcg taatcatggt catagctgtt tcctgtgtga    9660
aattgttatc cgctcacaat tccacacaac atacgagccg gaagcataaa gtgtaaagcc    9720
tggggtgcct aatgagtgag ctaactcaca ttaattgcgt tgcgctcact gcccgctttc    9780
cagtcgggca acctgtcgtg ccagctgcat taatgaatcg gccaacgcgc ggggagagc    9840
ggtttgcgta ttgggcgctc ttccgcttcc tcgctcactg actcgctgcg ctcggtcgtt    9900
cggctgcggc gagcggtatc agctcactca aaggcggtaa tacggttatc cacagaatca    9960
ggggataacg caggaaagaa catgtgagca aaaggccagc aaaaggccag gaaccgtaaa   10020
aaggccgcgt tgctggcgtt tttccatagg ctccgccccc ctgacgagca tcacaaaaat   10080
cgacgctcaa gtcagaggtg gcgaaacccg acaggactat aaagataccg gcgtttcccc   10140
cctggaagct ccctcgtgcg ctctcctgtt ccgaccctgc cgcttaccgg atacctgtcc   10200
gcctttctcc cttcgggaag cgtggcgctt tctcatagct cacgctgtag gtatctcagt   10260
tcggtgtagg tcgttcgctc caagctgggc tgtgtgcacg aaccccccgt tcagcccgac   10320
cgctgcgcct tatccggtaa ctatcgtctt gagtccaacc cggtaagaca cgacttatcg   10380
ccactggcag cagccactgg taacaggatt agcagagcga ggtatgtagg cggtgctaca   10440
gagttcttga agtggtggcc taactacggc tacactagaa gaacagtatt tggtatctgc   10500
gctctgctga agccagttac cttcggaaaa agagttggta gctcttgatc cggcaaacaa   10560
accaccgctg gtagcggtgg ttttttttgtt tgcaagcagc agattacgcg cagaaaaaaa   10620
ggatctcaag aagatccttt gatcttttct acggggtctg acgctcagtg gaacgaaaac   10680
tcacgttaag ggattttggt catgagatta tcaaaaagga tcttcaccta gatccttta   10740
aattaaaaat gaagttttaa atcaatctaa agtatatatg agtaaacttg gtctgacagt   10800
taccaatgct taatcagtga ggcacctatc tcagcgatct gtctatttcg ttcatccata   10860
gttgcctgac tccccgtcgt gtagataact acgatacggg agggcttacc atctggcccc   10920
agtgctgcaa tgataccgcg agaccacgcg tcaccggctc cagatttatc agcaataaac   10980
cagccagccg aagggccga gcgcagaagt ggtcctgcaa ctttatccgc ctccatccag    11040
```

```
tctattaatt gttgccggga agctagagta agtagttcgc cagttaatag tttgcgcaac   11100
gttgttgcca ttgctacagg catcgtggtg tcacgctcgt cgtttggtat ggcttcattc   11160
agctccggtt cccaacgatc aaggcgagtt acatgatccc ccatgttgtg caaaaaagcg   11220
gttagctcct tcggtcctcc gatcgttgtc agaagtaagt tggccgcagt gttatcactc   11280
atggttatgg cagcactgca taattctctt actgtcatgc catccgtaag atgcttttct   11340
gtgactggtg agtactcaac caagtcattc tgagaatagt gtatgcggcg accgagttgc   11400
tcttgcccgg cgtcaatacg ggataatacc gcgccacata gcagaacttt aaaagtgctc   11460
atcattggaa aacgttcttc ggggcgaaaa ctctcaagga tcttaccgct gttgagatcc   11520
agttcgatgt aacccactcg tgcacccaac tgatcttcag catcttttac tttcaccagc   11580
gtttctgggt gagcaaaaac aggaaggcaa aatgccgcaa aaaagggaat aagggcgaca   11640
cggaaatgtt gaatactcat actcttcctt tttcaatatt attgaagcat ttatcagggt   11700
tattgtctca tgagcggata catatttgaa tgtatttaga aaaataaaca aatagggggtt   11760
ccgcgcacat ttccccgaaa agtgccacct gacgtctaag aaaccattat tatcatgaca   11820
ttaacctata aaaataggcg tatcacgagg ccctttcgtc                          11860
```

SEQ ID NO: 13        moltype = DNA  length = 6905
FEATURE              Location/Qualifiers
misc_feature       1..6905
                      note = Plasmid Sequence
source              1..6905
                      mol_type = other DNA
                      organism = synthetic construct
SEQUENCE: 13

```
ttaattaagt gtggtaagtt actggtaaga gatgttggac aaaccgcttt tactagtgac     60
tctttggtat gcactatgta gtgctttgct ctatgataat aatacttacg tttactacta    120
ccaaagtgcc tttaggcctg gtccaggttg gcacctatat ggggtgtt atgcagtaga     180
tagggttttt aatgaaacca acaatgcagg cagtgcatct gattgcactg ctggtacttt    240
ttatgaaagc cataatattt ctgcttcttc tgtagccatg acagtaccac ataatggtat    300
gtcttggtca gcttcacaat tttgtacagc tcattgtaac ttctcagact ttacagtgtt    360
cgttacgcat tgttttaaaa atcaactcgg tagttgtccc ttgacaggta tgattcctca    420
gaatcatatt cgtatttctg ctatgagaga tggagttttg ttttataact taacagttag    480
cgtatctaaa tacccctagat ttaaatcgct tcaatgtgtt agcaattcta catctgtcta    540
tgtaaatggt gaccttgttt tcacttctaa tgaaacttct tacgttacgg gtgcaggcgt    600
ttattttaaa agtggtgggc ctgtaactta taaagttatg aaagaagtta aagccctagc    660
ctactttatt aatggtaccg cacaagaggt tattttatgt gataactcac ctagaggttt    720
gcttgcatgt cagtataaca ctggtaattt ttcagatgga ttctacccctt ttactaatca    780
ttctttagtt aaggataggt ttattgtata tcgagaaagt agcactaaca ctactttaaa    840
gttaactaat ttcagtttta ctaatgtaag taatgcttcc cctaattcag gtggcgttga    900
tactttccaa ttatatcaaa caagtactgc tcaggatgct tattataatt ttaatttatc    960
atttctgagt agttttgtgt ataaaccatc tgatttatg tatggtcat accacccaca    1020
ttgtaagttt agaccagaga atattaataa tggcttatgg tttaattcat tatctgtgtc    1080
acttacttac ggacccattc aaggtggttg taagcaatcc gttttttagta atagagcaac    1140
ttgttgctat gcttattctt atcaagggcc tagtagatgt aagggtgttt atagagggga    1200
gctaacgcaa tactttgaat gtggacttct agtttacgta actaagagtg atggctctcg    1260
tatacaaact agaagtgaac cactggtgtt aactcaatat aattataaca acattacttt    1320
aaataagtgt gttgagtata atatatatgg tagggttggt caaggtttta ttactaatgt    1380
aactgaagca actgctaatt atagttatct agcagatgtt ggtttagcta ttttagatac    1440
ctcaggagcc atagacatat tgttgttca aggtgcatat ggtcttaatt attataaggt    1500
taatccctgt gaagatgtta accaacagtt tgtagtgtct ggtggcaact agttggcat    1560
tcttacatct cataatgaaa caggttctga atctattgag aaccagtttt acatcaaact    1620
cactaacgga acacgtcgct ctagacgttc tgttactggg aatgttacaa attgccctta    1680
tgttagttat ggcaagtttt gtataaaacc agatgttct ttatctataa tagtaccaca    1740
agaattagaa cagtttgtgg cgcctttatt caatgttact gagcatgtgc tcatacctga    1800
tagttttaat ttaactgtca cagatgagta catacaaact cgtatggata aggttcaaat    1860
tatttgcctt cagtatgttt gtggtaattc tattgaatgc agaaagttgt ttcagcagta    1920
tggaccgtt tgtgataata tattgtctgt tgtaaatgtgt gtaggtcaaa gagaggatat    1980
ggaacttta agtttctatt cttctactaa acctagtggt tacaatacac aattttttaa    2040
taatgttagc actggtgact ttaatatttc gctcctacta acaccaccta atagtcctac    2100
tgggcgctct tttattgaag atcttctctt tacaagtgta gaatctgtg gattaccaac    2160
tgatgaagag tataaaaagt gtacagcagg accttttaaag accttgtttg    2220
tgctagagag tataatggtt tgctcgttct gcctccatt attactgcgg aaatgcaaac    2280
catgtatact agttctttag tagcctctat ggctttaggt ggcattactg cagctggtgc    2340
tataccttt gctacacaac tgcaggccag aattaaccat ttgggtatta ctaattctct    2400
tttgttgaaa aaccaagaaa aaattgctgc ttcctttaat aaggccatcg gtcatatgca    2460
ggaagggttt aaaagtactt ctcagcatt acaacagatt caagatgttg ttaataaaca    2520
gagttctatt cttacagaga ctatgcaatc acttaataaa aattttggtg ctatttcctc    2580
tgtaattcaa gacatttacc agcaactaga tgctattcag gcagatgctc aggttgatcg    2640
tcttattaca ggtagactct cttcactatc tgttttagct tctgctaaac aggcagagta    2700
tcatagagtg tcacaacagc gtgagttggc cactcagaaa attaatgagt gtgttaagtc    2760
tcagtctaat aggtattcat tttggtggtaa tggtagacat gttctaacca taccacagaa    2820
tgcacccaat ggcatagtgt ttatacactt tacatacact ccagagagtt ttgttaatgt    2880
tacggcaata gtagggttt gcgtaaaccc agctaatgct agtcattatg caatagtgcc    2940
tgttaatggc aggggtgttt ttatagaagt taatggtagt tactatatca ctgctcgtga    3000
tatgtatatg ccaagagata ttactgcagg agacataggtc actttgactt cttgtcaagc    3060
aaactatgtt aatgtaaata aaaccgtcat taacactttt gtggaagatg acgattttga    3120
tttttatgat gaattgtcaa aatggtgaa tgatactaag catgagctac cagattttga    3180
tgaattcaat tataccgttc cagttttaaa tattagtaat gaaattgaca gaattcaaca    3240
ggttattcag ggattaaatg attccctaat agaccttgaa acactctcaa ttctcaaaac    3300
ttatattaaa tggccttggt atgtgtggct tgccattgca ttccttacca ttatttttat    3360
```

```
tctggtactt tgttggatat ttttcatgac cggttgttgc ggttgttgtt gtggatgctt   3420
tggtatcata ccgttaatga gtaagtgtgt taagaaatct tcttactaca cgacttttga   3480
taatgatgtg gtaacttaac aatacagacc taaaaagtct gtttaatgat taaaagtccc   3540
acatcttttc taatattatt aattcttctt tggtgtaaac ttgcattaag ttgttttaaa   3600
gagtgtgtta taacactcca gcaactagta caaattttac tccaaattat taatagtaac   3660
ttacaatcta gacttctgct ttggcacagt ctagactaat gttagatttt gaagcaatta   3720
ttgaaactgg tcagcaaata actcaacaaa ttagtttcta tttacagcat atttcaaggg   3780
tgctaagtac tgaattattt gaccccttg aagtttgtgt ttacagagga ggtaattgtt    3840
gggagttaga gtcagctgac gagttttcag gtgatgacga atatattgag tagatcgctc   3900
gagaatcact agtgcggccg cctgcaggtc gaccatatgg gagagctccc aacgcgttgg   3960
atgcatagct tgagtattct atagtgtcac ctaaatagct tggcgtaatc atggtcatag   4020
ctgtttcctg tgtgaaattg ttatccgctc acaattccac acaacatacg agccggaagc   4080
ataaagtgta aagcctgggg tgcctaatga gtgagctaac tcacattaat tgcgttgcgc   4140
tcactgcccg ctttccagtc gggaaacctg tcgtgccagc tgcattaatg aatcggccaa   4200
cgcgcgggga gaggcggttt gcgtattggg cgctcttccg cttcctcgct cactgactcg   4260
ctgcgctcgg tcgttcggct gcggcgagcg gtatcagctc actcaaaggc ggtaatacgg   4320
ttatccacag aatcagggga taacgcagga agaacatgt gagcaaaagg ccagcaaaag    4380
gccaggaacc gtaaaaaggc cgcgttgctg cgttttttcc ataggctccg cccccctgac   4440
gagcatcaca aaaatcgacg ctcaagtcag aggtggcgaa acccgacagg actataaaga   4500
taccaggcgt ttccccctgg aagctccctc gtgcgctctc ctgttccgac cctgccgctt   4560
accggatacc tgtccgcctt tctcccttcg ggaagcgtgg cgctttctca tagctcacgc   4620
tgtaggtatc tcagttcggt gtaggtcgtt cgctccaagc tgggctgtgt gcacgaaccc   4680
cccgttcagc ccgaccgctg cgccttatcc ggtaactatc gtcttgagtc caacccgta    4740
agacacgact tatcgccact ggcagcagcc actggtaaca ggattagcag agcgaggtat   4800
gtaggcggtg ctacagagtt cttgaagtgg tggcctaact acggctacac tagaagaaca   4860
gtattggta tctgcgctct gctgaagcca gttaccttcg gaaaaagagt tggtagctct    4920
tgatccggca aacaaaccac cgctggtagc ggtggttttt ttgtttgcaa gcagcagatt   4980
acgcgcagaa aaaaaggatc tcaagaagat cctttgatct tttctacggg gtctgacgct   5040
cagtggaacg aaaactcacg ttaagggatt ttggtcatga gattatcaaa aaggatcttc   5100
acctagatcc ttttaaatta aaaatgaagt tttaaatcaa tctaaagtat atatgagtaa   5160
acttggtctg acagttacca atgcttaatc agtgaggcac ctatctcagc gatctgtcta   5220
tttcgttcat ccatagttgc ctgactcccc gtcgtgtaga taactacgat acgggagggc   5280
ttaccatctg gccccagtgc tgcaatgata ccgcgagacc cacgctcacc ggctccagat   5340
ttatcagcaa taaaccagcc agccggaagg gccgagcgca gaagtggtcc tgcaacttta   5400
tccgcctcca tccagtctat taattgttgc cgggaagcta gtaagtag ttcgccagtt     5460
aatagtttgc gcaacgttgt tgccattgct acaggcatcg tggtgtcacg ctcgtcgttt   5520
ggtatggctt cattcagctc cggttcccaa cgatcaaggc gagttacatg atcccccatg   5580
ttgtgcaaaa aagcggttag ctccttcggt cctccgatcg ttgtcagaag taagttggcc   5640
gcagtgttat cactcatggt tatggcagca ctgcataatt ctcttactgt catgccatcc   5700
gtaagatgct tttctgtgac tggtgagtac tcaaccaagt cattctgaga atagtgtatg   5760
cggcgaccga gttgctcttg cccggcgtca tacgggata taccgcgcc acatagcaga    5820
actttaaaag tgctcatcat tggaaaacgt tcttcggggc gaaaactctc aaggatctta   5880
ccgctgttga tccagttcg atgtaaccc actcgtgcac ccaactgatc ttcagcatct     5940
tttactttca ccagcgtttc tgggtgagca aaaacaggaa ggcaaaatgc cgcaaaaaag   6000
ggaataaggc gacacggaaa atgttgaata ctcatactct tccttttca atattattga    6060
agcatttatc agggttattg tctcatgagc ggatacatat ttgaatgtat ttagaaaaat   6120
aaacaaatag gggttccgcg cacatttccc cgaaaagtgc cacctgatgc ggtgtgaaat   6180
accgcacaga tgcgtaagga gaaaataccg catcaggaaa ttgtaagcgt taatattttg   6240
ttaaaattcg cgttaaattt tgttaaatc agctcatttt taaccaata ggccgaaatc    6300
ggcaaaatcc cttataaatc aaaagaatag accgagatag ggttgagtgt tgttccagtt   6360
tggaacaaga gtccactatt aaagaacgtg gactccaacg tcaaagggcg aaaaaccgtc   6420
tatcagggcg atgccacact acgtgaacca tcacctaat caagttttt ggggtcgagg     6480
tgccgtaaag cactaaatcg gaaccctaaa gggagccccc gatttagagc ttgacgggga   6540
aagccggcga acgtggcgag aaaggaaggg aagaaagcga aaggagcggg cgctagggcg   6600
ctggcaagtg tagcggtcac gctgcgcgta accaccacac ccgccgcgct taatgcgccg   6660
ctacagggcg cgtccattcg ccattcaggc tgcgcaactg ttgggaaggg cgatcggtgc   6720
gggcctcttc gctattacgc cagctggcga aggggggatg tgctgcaagg cgattaagtt   6780
gggtaacgcc agggttttcc cagtcacgac gttgtaaaac gacggccagt gaattgtaat   6840
acgactcact atagggcgaa ttgggcccga cgtcgcatgc tcccggccgc catggccgcg   6900
ggatt                                                              6905
```

| | | |
|---|---|---|
| SEQ ID NO: 14 | moltype = DNA length = 11320 | |
| FEATURE | Location/Qualifiers | |
| misc_feature | 1..11320 | |
| | note = Plasmid Sequence | |
| source | 1..11320 | |
| | mol_type = other DNA | |
| | organism = synthetic construct | |

SEQUENCE: 14

```
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcgggctgg cttaactatg cggcatcaga gcagattgta ctgagagtgc    180
accatatgcg gtgtgaaata ccgcacagat gcgtaaggag aaaataccgc atcaggcgcc   240
attcgccatt caggctgcgc aactgttggg aagggcgatc ggtgcgggcc tcttcgctat   300
tacgccagct ggcgaaaggg gatgtgctgc aaggcgatt aagtgggta acgccagggt    360
tttcccagtc acgacgttgt aaaacgacgg ccagtgaatt ggagatcggt acttcgcgaa   420
tgcgtcgaga tgagctctaa tacgactcac tatagggact aagtgtgat ataaatatat    480
atcatacata ctagccttgt gctagatttc caacttaaca aaacgactt aaataccac     540
agttggtccc tataggtgtt ccattgcagt gcactttagt gccctggatg gcacctgcc    600
```

```
acctgtcagg ttttttgttat taaaataata ttgttgctgg tatcactgct tgttttgccg    660
tgtctcactt tatacatccg ttgcttgggc tacctagtat ccagcgtcct actggcgttg    720
tggtcggttc gagtgcgaag aacctctggt tcatctagcg gtacgcgggt gtgtggaagt    780
agcgcttcag acgtaccggt tctgttcgt gaaatacggg gtcacctccc cccacatacc    840
tctaagggct tttgagccta gcgttgggct acgttctcgc acaaggtcgg ctatacggcg    900
tttgtagggg gtagtgccaa acaacccctg aggtgacagg ttctggtggt gtttcgaaaa    960
caacaatgtg tgtgccgcat aatatgcgag taatgcattt tggagcagga agtgacaaag   1020
gagtggcccc aggtagcgct gttcttaggc agtggcttcc cgaaggtaca ctccttgtcg   1080
ataatgatat tgtagattat gtatctgatg cacatgtcct tgtgctttca gattgcaata   1140
aatgtaaaac agagcacaag tttgatcttg tgatatctga tatgtataca gataatgatt   1200
caaagagaaa gcatgaaggc gttgtagcca ataacggcaa tgatgacgtc ttcatatacc   1260
tttcaaactt tcttcgtaac aatttagctc tgggaggcag ttttgccgta aaagtaacag   1320
agacaagttg gcatgagagt ttatatgaca ttgcacagga ttgtgcatgg tggacaatgt   1380
tttgtacagc agtgaatgct tcttcgtcag aagcattctt gattggtgtt aattatttgg   1440
gtgcaagtga aaaggttaga gttagtggta aaaccctgca cgcaaattat atattttgga   1500
ggaattgtaa ttatttacaa acttcagcct atagtatatt tgacgttgct aagtttgatt   1560
tgaaattaaa agcaacgcca gttgtgaatt tgaaaactga acaaaagaca gacttagtct   1620
ttaatttaat taagtgtggt aagttactgg taagagatgt tggacaaacc gcttttacta   1680
gtgactcttt ggtatgcact atgtagtgct ttgctctatg ataataatac ttacgtttac   1740
tactaccaaa gtgcctttag gcctggtcca ggttggcacc tatatggggg tgcttatgca   1800
gtagataggt ttttaatga aaccaacaat gcaggcagtg catctgattg cactgctggt   1860
actttttatg aaagccataa tatttctgct tcttctgtag ccatgacagt accacataat   1920
ggtatgtctt ggtcagcttc acaattttgt acagctcatt gtaacttctc agactttaca   1980
gtgttcgtta cgcattgttt taaaaatcaa ctcggtagtt gtcccttgac aggtatgatt   2040
cctcagaatc atattcgtat ttctgctatg agagatggag ttttgtttta aacttaaca   2100
gttagcgtat ctaaataccc tagattaaa tcgcttcaat gtgttagcaa ttctacatct   2160
gtctatgtaa atggtgacct tgttttcact tctaatgaaa cttcttacgt tacgggtgca   2220
ggcgtttatt ttaaaagtgg tgggcctgta acttataaag ttatgaaaga agttaaagcc   2280
ctagcctact ttattaatgg taccgcacaa gaggttattt tatgtgataa ctcacctaga   2340
ggtttgcttg catgtcagta taacactggt aattttttcag atggattcta ccctttacta   2400
aatcattctt tagttaagga taggtttatt gtatatcgag aaagtagcac taacactact   2460
tgtaagttaa ctaatttcag ttttactaat gtaagtaatg cttctcctaa ttcaggtggc   2520
gttgatactt tccaattata tcaaacaagt actgctcagg atggttatta taattttaat   2580
ttatcatttc tgagtagttt tgtgtataaa ccatctgatt ttatgtatgg gtcataccac   2640
ccacattgta gtttagacc agagaatatt aataatgct tatgtttaa ttcattatct   2700
gtgtcactta cttacggacc cattcaaggt ggttgtaagc aatctgttt tagtaataga   2760
gcaacttgtt gctatgctta ttcttatcaa gggcctagta gatgtaaggg tgtttataga   2820
ggggagctaa cgcaatactt tgaatgtgga cttctagttt acgtaactaa gagtgatggc   2880
tctcgtatac aaactagaag tgaaccactg gtgttaactc aatataatta taacaatt    2940
actttaaata agtgtgttga gtataatata tatggtaggg ttggtcaagg ttttattact   3000
aatgtaactg aagcaactgc taattatagt tatcagcag atggtggttt agctatttta   3060
gatacctcag gagccataga catatttgtt gttcaaggtg catatggtct taattattat   3120
aaggttaatc cctgtgaaga tgttaaccaa cagtttgtgt tgtctggtgg caacttagtt   3180
ggcattctta catctcataa tgaaacaggt tctgaatcta ttgagaacca gttttacatc   3240
aaactcacta acgaacacg tcgctctaga cgttctgtta ctgggaatgt tacaaattgc   3300
ccttatgtta gttatggcaa gttttgtata aaaccagatg gttctttatc tataatagta   3360
ccacaagaat tagaacagtt tgtggcgcct ttattcaagta ttactgagca tgtctcata   3420
cctgatagtt ttaatttaac tgtcacagat gagtacatac aaaactcgtat ggataaggtt   3480
caaattattt gccttcagta tgttttgtggt aattctattg aatgcagaaa gttgtttcag   3540
cagtatggac ctgtttgtga taatatattg tctgttgtaa atggtgtagg tcaaagagag   3600
gatatggaac ttttaagttt ctattcttct actaaaccta gtggttacaa taccaatt    3660
tttaataatg ttagcactgg tgactttaat atttcgctcc tactaacacc acctaatagt   3720
cctactgggc gctcttttat tgaagatctc tctcttacaa gtgtagaatc tgttggatta   3780
ccaactgatg aagagtataa aaagtgtaca gcaggacctt taggttttgt taaagacctt   3840
gttgtgcta gagagtataa tggttgctgc gttctgcctc ctattattac tcggaaatg   3900
caaaccatgt atactagttc tttagtagcc tctatggcct taggtggcat tactgcagct   3960
ggtgctatac cttttgctac acaactgcag gccagaatta accatttggg tattactaat   4020
tctcttttgt tgaaaaccaa agaaaaaatt gctgcttcct ttaataaggc catcggtcat   4080
atgcaggaag ggttttaaaag tacttctcta gcattacaac agattcaaga tgttgttaat   4140
aaacagagtt ctattcttac agagactatg caatcactta ataaaaattt tggtgctatt   4200
tcctctgtaa ttcaagacat ttaccagcaa ctagatgcta ttcaggcaga tgctcaggtt   4260
gatcgtctta ttacaggtag actctcttca ctatctgttt tagcttctgc taaacaggca   4320
gagtatcata gagtgtcaca acagcgtgag ttggccactc agaaaattaa tgagtgtgtt   4380
aagtctcagt ctaataggta ttcatttgt ggtaatggta gacatgttct aacatacca   4440
cagaatgcac ccaatggcat agtgtttata cactttacat acactccaga gagttttgta   4500
aatgttacgg caatagtagg gttttgcgta aacccagcta atgctagtca ttatgcaata   4560
gtgcctgtta atggcagggg tgtttttata gaagttaatg gtagttacta tatcactgct   4620
cgtgatatgt atatgccaag agatattact gcaggagaca tagtcactt gacttcttgt   4680
caagcaaact atgttaatgt aaataaacc gtcattaaca cttttgtgga agatgacgat   4740
tttgattttt atgatgaatt gtcaaatgg tggaatgata ctaagcatga gctaccagat   4800
tttgatgaat tcaattata cgttccagtt taaatatta gtaatgaaat tgacagaatt   4860
caacaggtta ttcagggatt aaatgattcc ctaatagacc ttgaaacact ctcaattctc   4920
aaaacttata ttaaatggcc ttggtatgtg tggcttgcca ttgcattcct taccattatt   4980
tttattctgg tactttgttg gatattttttc atgaccggtg gttgcggttg ttgttgtgga   5040
tgctttgtga tcataccgtt aatgagtaag tgtggtaaga atcttctta ctacacgact   5100
tttgataatg atgtggtaac ttaacaatac agacctaaaa agtctgttta atgattaaaa   5160
gtcccacatc ttttctaata ttattaattc tcttggtg taaacttgca ttaagttgtt   5220
ttaaagagtg tgttataaca ctccagcaac tagtacaaat tttactccaa attattaata   5280
gtaacttaca atctagactt ctgctttggc acagtctaga ctaatgttag attttgaagc   5340
```

```
aattattgaa actggtcagc aaataactca acaaattagt ttctatttac agcatatttc   5400
aagggtgcta agtactgaat tatttgaccc ctttgaagtt tgtgtttaca gaggaggtaa   5460
ttgttgggag ttagagtcag ctgacgagtt ttcaggtgat gacgaatata ttgagtagat   5520
cgctcgagga gaacggaagt tttctaacag cggtttacgt gtttttagga tttttagcac   5580
tttatctact aggtagagcg cttcaagctt ttgtacaagg ggctgacgct tgttgtcttt   5640
tttggtatac atgggtagta gttcctggag ccaagggcac agcctttgtt tataatcata   5700
catatggtaa aaaacttaac aaaccggagt tagaaacggt tattgttaac gaatttccaa   5760
aaaacggttg gaaatatgga taataccatc aattgtactc ttggtactga caagcagtt    5820
cagcttttta aggaatataa tctgtttgta actgcattcc tgttgttttt aaccatacta   5880
cttcagtatg gatacgcaac taggagcaag gttatttaca tactgaaaat gatagtgtta   5940
tggtgctttt ggcccttaa cattgcagta ggtgtaatct catgtatata cccaccaaac    6000
acaggaggtc ttgtcgcagc gataattctt acagtgtttg cgtgtctttc ttttataggt   6060
tattggatcc agagtattag actttttaag cggtgcaggt catggtggtc atttaacccc   6120
gaatctaatg ccgtaggttc aatactccta actaatggt aacaatgtaa ttttgctata    6180
gagagtgtgc cgatggtgct ttctcctatt ataaagaatg gtgctcttta ttgcgagggt   6240
cagtggcttg ctaaatgtga accagaccac ttgcctagag atatatttgt atgcacaccg   6300
gatagacgta atatctatcg tatggtgcaa aaatatactg gtgaccaaag cggaagtaag   6360
aaaaggtttg ccacatttgt ctatgcaaag cagtcagtag atactggcga gctagaaagt   6420
gtgtcagcag taggaggtag tctttacaca taaatgtgtg tgtagtagaga gtatttaaaa   6480
ttattctttg acagtgcctc cgttttaaga gcgcggaaga gtattatttt tgaggatatt   6540
aatataaatc ctctttgttt catactctcc tttcaggagt tattatttaa aaaacagttt   6600
ttccactctt ttgtgccaaa aacaattgtt gttaatggtg taaccttttca ggtagacaat   6660
ggaaaagtct actacgaagg aagaccaatt ttccaaaaag gttgttgtag tttgtggtcc   6720
aattataaga aagattagaa taattaaacc acctacaaca cttatttta caaatggcgt    6780
tttaggttac aaacgcttaa caaatacgga tgatgaaatg gctgactagt tttggaagag   6840
ctttcatctc ctgttataaa tccctattac taactcaatt aagagtatta gataggttaa   6900
ttttagatca cggacccaag cgcacattaa cgtgtgctag gcgagtgctt ttagttcaat   6960
tagatttagt ttataggttg gcttatacgc ccacccaatc gctggtatga ataatagtaa   7020
agataatcct tttcgcggag caatagcaag aaaagcgcga atttatctga gaggaggatt   7080
agattgtgtt tactttctta acaaagcagg acaagcaagg ccttgtcccg cgtgtacctc   7140
cctagtattc caaggaaaa cttgtgagga acactattat aataacaatc ttttgtcatg    7200
gcaagcggta aggcaactgg aaagacagac gccccagcgc cagtcatcaa actaggagga   7260
ccaaagccac ctaaagttgg ttcttctgga aatgcatcat ggtttcaacc gataaaggcc    7320
aagaagctaa attcacctgt gcctaaattt gacggtagtg gtgttcctga aaatgaaaat   7380
ctcaagtcaa gccagcaaca tggatactgg agacgccaac acaggtttaa gcctggcaaa   7440
ggtggaagaa aaccagtccc tgatgcttgg tactttact acactggaac aggaccggcc    7500
gccgacctga attggggtga aactcaagat ggtatagtgt gggttgctgc aaagggtgct   7560
gatactaaat ctagatcaaa ccagggtaca agggatcctg ataagtttga ccaataccca   7620
ctacgattct cagatggagg accggatggt aatttccgtt gggacttcat accaataaat   7680
cgtggtagga gtgggagatc aacagcagct tcatcagcag catctagtag agcaccatct   7740
cgtgaggggt cacgtggacg tagaagcgga gttgaagatg atcttatagc tcgcgcagca   7800
aagattatac aggaccagca aaagaagggt gcgcgcatta ccaaggctaa ggctgatgaa   7860
atggctcatc gccgctattg caagcgcact atcccacgcg gttataaggt tgagcaagta   7920
tttggtcccc gtactaaagg taaggaagga aattttggtg atgacaagat gaatgaggaa   7980
ggtgttaagg atgggcgtgt tacggcaatg ctcaacctag tccctagcag tcatgcttgt   8040
cttttggaa gtagggtgac gcccaaactg cagccagatg gtcttcacct gagatttgaa    8100
tttactactg tggtgtcacg tgatgatccg cagtttgata attatgtgaa aatttgtgat   8160
cagtgtgtcg atggtgtagg gacgcgtcca aaggacgatg aatcgagacc aaagtcacgc   8220
ccaaattcaa gacctgcaac tagaggaaat tctccagcgc cgagacaaca gcgcccaaag   8280
aaggagaaaa agcccaagaa gcaggatgat gaagtagata aggcattgac ctcagatgag   8340
gagagaaaca atgcacagct ggaatttgat gatgaaccca aggtgattaa ctgggggggac  8400
tctgcactag gtgaaaatga actttgatta acataatgga cttgctgcat ttgctgtcac   8460
atttgttaa atattatttt tgtgttttac tatcaattat tacaggtatt gattgtgatt    8520
atgttcaata cttaagcttc ttctggttgc ttttttgcttg ttgtattgtt gctgtgctttt 8580
ttattattgt gattctcatt agtttgcttt atcgtagaaa ttcaatagta agagttaagg   8640
aagataggca tgtagcttag cacctacatg tctatcgcca gggaaatgtc taatctgtct   8700
acttagtagc ctgaaacga acggtagacc cttagatttt aatttagttt aatttttagt    8760
ttagtttaag ttagttaga gtaggtataa agatgccagt gccggggcca cgcgtagtac    8820
gaccgagggt acagcactag gacgcccact aggggaagag ctaaattta gtttaagtta    8880
agtttaattg gctaaatata gttaaaattt ataggctagt atagagttag agcaaaaaaa   8940
aaaaaaaaaa aaaaaaaaa aaaaaaaaa aaaaaaaaa aaaaaaaaaa aaaaaaaaa       9000
aaaaaaaaaa aaaaaaaaaa aaaaaaaaa aaagcggccg catcggatgc cgggaccgac    9060
gagtgcagag gcgtgcaagc gagcttggcg taatcatggt catagctgtt tcctgtgtga   9120
aattgttatc cgctcacaat tccacacaac atacgagccg gaagcataaa gtgtaaagcc   9180
tggggtgcct aatgagtgag ctaactcaca ttaattgcgt tgcgtcact gcccgctttc    9240
cagtcgggaa acctgtcgtg ccagctgcat taatgaatcg gccaacgcgc ggggagaggc   9300
ggtttgcgta ttgggcgctc ttccgcttcc tcgctcactg actcgctgcg ctcggtcgtt   9360
cggctgcggc gagcggtatc agctcactca aaggcggtaa tacggttatc cacagaatca   9420
ggggataacg caggaaagaa catgtgagca aaaggccagc aaaaggccag gaaccgtaaa   9480
aaggccgcgt tgctggcgtt tttccatagg ctccgccccc ctgacgagca tcacaaaaat   9540
cgacgctcaa gtcagaggtg gcgaaacccg acaggactat aaagatacca ggcgtttccc   9600
cctggaagct ccctcgtgcg ctctcctgtt ccgaccctgc cgcttaccgg atacctgtcc   9660
gcctttctcc cttcgggaag cgtggcgctt tctcatagct cacgctgtag gtatctcagt   9720
tcggtgtagg tcgttcgctc caagctgggc tgtgtgcacg aaccccccgt tcagcccgac   9780
cgctgcgcct tatccggtaa ctatcgtctt gagtccaacc cggtaagaca cgacttatcg   9840
ccactggcag cagccactgg taacaggatt agcagagcga ggtatgtagg cggtgctaca   9900
gagttcttga agtggtggcc taactacggc tacactagaa gaacagtatt tggtatctgc   9960
gctctgctga agccagttac cttcggaaaa agagttggta gctcttgatc cggcaaacaa   10020
accaccgctg gtagcggtgg tttttttgtt tgcaagcagc agattacgcg cagaaaaaaa   10080
```

```
ggatctcaag aagatccttt gatcttttct acggggtctg acgctcagtg gaacgaaaac   10140
tcacgttaag ggattttggt catgagatta tcaaaaagga tcttcaccta gatccttta    10200
aattaaaaat gaagttttaa atcaatctaa agtatatatg agtaaacttg gtctgacagt   10260
taccaatgct taatcagtga ggcacctatc tcagcgatct gtctatttcg ttcatccata   10320
gttgcctgac tccccgtcgt gtagataact acgatacggg agggcttacc atctggcccc   10380
agtgctgcaa tgataccgcg agacccacgc tcaccggctc cagatttatc agcaataaac   10440
cagccagccg gaagggccga gcgcagaagt ggtcctgcaa ctttatccgc ctccatccag   10500
tctattaatt gttgccggga agctagagta agtagttcgc cagttaatag tttgcgcaac   10560
gttgttgcca ttgctacagg catcgtggtg tcacgctcgt cgtttggtat ggcttcattc   10620
agctccggtt cccaacgatc aaggcgagtt acatgatccc ccatgttgtg caaaaaagcg   10680
gttagctcct tcggtcctcc gatcgttgtc agaagtaagt tggccgcagt gttatcactc   10740
atggttatgg cagcactgca taattctctt actgtcatgc catccgtaag atgcttttct   10800
gtgactggtg agtactcaac caagtcattc tgagaatagt gtatgcggcg accgagttgc   10860
tcttgcccgg cgtcaatacg ggataatacc gcgccacata gcagaactt aaaagtgctc    10920
atcattggaa aacgttcttc ggggcgaaaa ctctcaagga tcttaccgct gttgagatcc   10980
agttcgatgt aacccactcg tgcacccaac tgatcttcag catctttac tttcaccagc    11040
gtttctgggt gagcaaaaac aggaaggcaa aatgccgcaa aaaagggaat aagggcgaca   11100
cggaaatgtt gaatactcat actcttcctt tttcaatatt attgaagcat ttatcagggt   11160
tattgtctca tgagcggata catatttgaa tgtatttaga aaaataaaca aataggggtt   11220
ccgcgcacat ttccccgaaa agtgccacct gacgtctaag aaaccattat tatcatgaca   11280
ttaacctata aaaataggcg tatcacgagg ccctttcgtc                         11320

SEQ ID NO: 15           moltype = DNA   length = 11320
FEATURE                 Location/Qualifiers
misc_feature            1..11320
                        note = Plasmid Sequence
source                  1..11320
                        mol_type = other DNA
                        organism = synthetic construct
SEQUENCE: 15
tcgcgcgttt cggtgatgac ggtgaaaacc tctgacacat gcagctcccg gagacggtca   60
cagcttgtct gtaagcggat gccgggagca gacaagcccg tcagggcgcg tcagcgggtg   120
ttggcgggtg tcgggctgg cttaactatg cggcatcaga gcagattgta ctgagagtgc    180
accatatgcg gtgtgaaata ccgcacagat gcgtaaggag aaaataccgc atcaggcgc    240
attcgccatt caggctgcgc aactgttggg aagggcgatc ggtgcgggcc tcttcgctat   300
tacgccagct ggcgaaaggg ggatgtgctg caaggcgatt aagttgggta acgccagggt   360
tttcccagtc acgacgttgt aaaacgacgg ccagtgaatt ggagatcggt acttcgcgaa   420
tgcgtcgaga tgagctctaa tacgactcac tataggggact taagtgtgat ataaatatat   480
atcatacata ctagccttgt gctagatttc caacttaaca aacggactt aaatacctac    540
agttggtccc tataggtgtt ccattgcagt gcactttagt gccctggatg cacctggcc    600
acctgtcagg ttttttgttat aaaataata ttgttgctgg tatcactgct tgttttgccg    660
tgtctcactt tatacatccg ttgcttggc tacctagtat ccagcgtcct actggcgttg    720
tggtcggttc gagtgcgaag aacctctggt tcatctagcg gtacgcgggt gtgtggaagt   780
agcgcttcag acgtaccggt tctgttgcgt gaaatacggg gtcacctccc ccacatacc    840
tctaagggct tttgagccta gcgttgggct acgttctcgc acaagtcgg ctatacggcg    900
tttgtagggg gtagtgccaa acaacccctg aggtgacagg ttctggtggt gtttcgaaaa   960
caacaatgtg tgtgccgcat aatatgcgag taatgcattt tggagcagga agtgacaaag   1020
gagtggcccc aggtagcgct gttcttaggc agtggcttcc cgaaggtaca ctccttgtcg   1080
ataatgatat tgtagattat gtatctgatg cacatgtctc tgtgctttca gattgcaata   1140
aatgtaaaac agagcacaag tttgatcttg tgatatctga tatgtataca gataatgatt   1200
caaagagaaa gcatgaaggc gttgtagcca ataacgacgtc ttcatatcc              1260
tttcaaactt tcttcgtaac aatttagctc tgggaggcag ttttgccgta aaagtaacag   1320
agacaagttg gcatgagagt ttatatgaca ttgcacagga ttgtgcatgg tggacaatgt   1380
tttgtacagc agtgaatgct tcttcgtcag aagcattctt gattggtgtt aattatttgg   1440
gtgcaagtga aaaggttaga gttagtggta aaacctgca cgcaaattat atattttgga   1500
ggaattgtaa ttatttacaa acttcagcct atagtatatt tgacgttgct aagtttgatt   1560
tgaaattaaa agcaacgcca gttgtgaatt tgaaaactga acaaaagaca gacttagtct   1620
ttaatttaat taagtgtggt aagttactgg taagagatgt tggacaaacc gcttttacta   1680
gtgactcttt ggtatgcact atgtagtgct ttgctctatg ataataatac ttacgtttac   1740
tactaccaaa gtgccttag gcctggtcca ggttggcacc tatatggggg tgcttatgca    1800
gtagataggg ttttttaatga aaccaacaat gcaggcagtg catctgattg cactgctggt   1860
acttttatg aaagccataa tatttctgct tcttctgtag ccatgacagt accacataat    1920
ggtatgtctt ggtcagcttc acaatttgt acagctcatt gtaacttctc agactttaca   1980
gtgttcgtta cgcattgttt taaaaatcaa tcggtagttc gtcccttgac aggtatgatt   2040
cctcagaatc atattcgtat ttctgctatg agagatggag ttttgttta taacttaaca   2100
gttagcgtat ctaaataccc tagatttaaa tcgcttcaat gtgttagcaa ttctacatct   2160
gtctatgtaa atggtgacct tgttttcact tctaatgaaa cttcttacgt tacgggtgca   2220
ggcgttttatt ttaaaagtgg tgggcctgta acttataag ttatgaaaga agttaaagcc    2280
ctagcctact ttattaatgg taccgcacaa gaggttattt tatgtgataa ctcacctaga   2340
ggtttgcttg catgtcagta taacactggt aattttttcag atggattcta ccctttact    2400
aatcattctt tagttaagga taggtttatt gtatatcgag aaagtagcac taacactact   2460
tgtaagttaa ctaatttcag ttttactaat gtaagtaatg cttctcctaa ttcaggtggc   2520
gttgatactt ccaattata tcaaacaagt actgctcagg atggttatta taattttaat   2580
ttatcatttc tgagtagttt tgtgtataaa ccatcgattt tatgtatgtt gtcataccac   2640
ccacattgta gtttagacc agagaatatt aataatggct tatggttaaa ttcattatct    2700
gtgtcactta cttcggacc cattcaaggt ggttgtaagc aatctgtttt tagtaataga    2760
gcaacttgtt gctatgctta ttcttatcaa gggcctagta gatgtaaggg tgtttataga   2820
ggggagctaa cgcaatactt tgaatgtgga cttctagttt acgtaactaa gagtgatggc   2880
tctcgtatac aaactagaag tgaaccactg gtgttaactc aatataatta taacaacatt   2940
```

```
actttaaata agtgtgttga gtataatata tatggtaggg ttggtcaagg ttttattact    3000
aatgtaactg aagcaactgc taattatagt tatctagcag atggtggttt agctatttta    3060
gatacctcag gagccataga catatttgtt gttcaaggtg catatggtct taattattat    3120
aaggttaatc cctgtgaaga tgttaaccaa cagtttgtag tgtctggtgg caacttagtt    3180
ggcattctta catctcataa tgaaacaggt tctgaatcta ttgagaacca gttttacatc    3240
aaactcacta acggaacacg tcgctctaga cgttctgtta ctgggaatgt tacaaattgc    3300
ccttatgtta gttatggcaa gttttgtata aaaccagatg gttctttatc tataatagta    3360
ccacaagaat tagaacagtt tgtggcgcct ttattcaatg ttactgagca tgtgctcata    3420
cctgatagtt ttaatttaac tgtcacagat gagtacatac aaactcgtat ggataaggtt    3480
caaattattt gccttcagta tgttgtggt  aattctattg aatgcagaaa gttgtttcag    3540
cagtatggac ctgtttgtga taatatattg tctgttgtaa atggtgtagg tcaaagagag    3600
gatatggaac ttttaagttt ctattcttct actaaaccta gtggttacaa tacaccaatt    3660
tttaataatg ttagcactgg tgactttaat atttcgctcc tactaacacc acctaatagt    3720
cctactgggc gctctttat  tgaagatctt ctctttacaa gtgtagaatc tgttggatta    3780
ccaactgatg aagagtataa aaagtgtaca gcaggacctt taggttttgt taaagacctt    3840
gtttgtgcta gagagtataa tggtttgctc gttctgcctc ctattattac tgcggaaatg    3900
caaaccatgt atactagttc tttagtagcc tctatggctt taggtggcat tactgcagct    3960
ggtgctatac cttttgctac acaactgcag gccagaatta accatttgtg tattactaat    4020
tctcttttgt tgaaaaacca agaaaaaatt gctgcttcct ttaataaggc catcggtcat    4080
atgcaggaag ggtttaaaag tacttctcta gcattacaac agattcaaga tgttgttaat    4140
aaacagagtt ctattcttac agagactatg caatcactta ataaaatttt tggtgctatt    4200
tcctctgtaa ttcaagacat ttaccagcaa ctagatgcta ttcaggcaga tgctcaggtt    4260
gatcgtctta ttacaggtag actctcttca ctatctgttt tagcttctgc taaacaggca    4320
gagtatcata gagtgtcaca acagcgtgag ttggccactc agaaaattaa tgagtgtgtt    4380
aagtctcagt ctaataggta ttcatttgt  ggtaatggta gacatgttct aaccatacca    4440
cagaatgcac ccaatggcat agtgtttata cactttacat acactccaga gagttttgta    4500
aatgttacgg caatagtagg gttttgcgta aacccagcta atgctagtca ttatgcaata    4560
gtgcctgtta atggcagggg tgtttttata gaagttaatg gtagttacta tatcactgct    4620
cgtgatatgt atatgccaag agatattact gcaggagaca tagtcacttt gacttcttgt    4680
caagcaaact atgttaatgt aaataaaacc gtcattaaca cttttgtgga agatgacgat    4740
tttgattttt atgatgaatt gtcaaaatgg tggaatgata ctaagcatga gctaccagat    4800
tttgatgaat tcaattatac cgttccagtt taaatatta  gtaatgaaat tgacagaatt    4860
caacaggtta ttcagggatt aaatgattcc ctaatagacc ttgaaacact ctcaattctc    4920
aaaacttata ttaaatggcc ttggtatgtg tggcttgcca ttgcattcct taccattatt    4980
tttattctgg tactttgttg gatattttc  atgaccggtt gttgcggttg ttgttgtgga    5040
tgctttggta tcataccgtt aatgagtaag tgtggtaaga atcttcctta ctacacgact    5100
tttgataatg atgtggtaac ttaacaatac agacctaaaa agtctgttta atgattaaaa    5160
gtcccacatc ttttctaata ttattaattc ttctttggtg taaacttgca ttaagttgtt    5220
ttaaagagtg tgttataaca ctccagcaac tagtacaaat tttactccaa attattaata    5280
gtaacttaca atctagactt ctgctttggc acagtctaga ctaatgttag attttgaagc    5340
aattattgaa actggtcagc aaataactca acaaattagt ttctatttac agcatatttc    5400
aagggtgcta agtactgaat tatttgaccc ctttgaagtt tgtgtttaca gaggaggtaa    5460
ttgttgggaa ttagagtcag ctgacgagtt ttcaggtgat gacgaatata ttgagtagat    5520
cgctcgagga gaacggaagt tttctaacag cggtttacgt gttttaggat tttttagcac    5580
tttatctact aggtagagcg cttcaagctt ttgtacaagc ggctgacgct tgttgtcttt    5640
tttggtatac atgggtagta gttcctggag ccaagggcac agccttttgt tataatcata    5700
catatgtaa  aaaacttaac aaaccggagt tagaaacgtt tattgttaac gaatttccaa    5760
aaaacggttg gaaatatgga taataccatc aattgtactc ttggtactga caagcagtt   5820
cagcttttta aggaatataa tctgtttgta actgcattcc tgttgttttt aaccatacta    5880
cttcagtatg gatacgcaac taggagcaag gttatttaca tactgaaaat gatagtgtta    5940
tggtgctttt ggccccttaa cattgcagta ggtgtaatct catgtatata cccaccaaac    6000
acaggaggtc ttgtcgcagc gataattctt acagtgtttg cgtgtctttc ttttataggt    6060
tattggatcc agagtattag acttttaag  cggtgcaggt catggtggtc atttaacccc    6120
gaatctaatc ccgtaggttc aatactccta actaatggtc aacaatgtaa ttttgctata    6180
gagagtgtgc cgatgtgtgt ttctcctatt ataaagatgg gtgctcttta ttgcgagggt    6240
cagtggcttg ctaaatgtga accagaccac ttgcctagaa atatatttgt atgcacaccg    6300
gatagacgta atatctatcg tatggtgcaa aaatatactg gtgaccaaag cggaagtaag    6360
aaaaggtttg ccacatttgt ctatgcaaag cagtcagtag atactggcga gctagaaagt    6420
gtgtcagcag taggaggtag tcttttacac aaatgtgtg  tgtgtagaga gtatttaaaa    6480
ttattctttg acagtgcctc cgttttaaga gcgcggaagg gtattttttt tgaggatatt    6540
aatataaatc ctctttgttt catactctcc tttcaggagt tattatttaa aaaacagttt    6600
ttccactctt ttgtgccaaa aacaattgtt gttaatggtg taacctttca ggtagacaat    6660
ggaaaagtct actacgaagg aagaccaatt tccaaaaag  gttgttgtag tttgtggtcc    6720
aattataaga aagattagaa taattaaacc acctacaaca cttatttta  caaatggcgt    6780
tttaggttac aaacgcttaa caaatacgga tgatgaaatt gctgactagt tttgaagagt    6840
ctttcatctc ctgttataaa tccctattac taactcaatt aagagtatta gataggttaa    6900
ttttagatca cggacccaag cgcacattaa cgtgtgctag cgagtgctt  ttagttcaat    6960
tagatttagt ttataggttg gcttatacgc ccacccaatc gctgattga  ataatagtaa    7020
agataatcct tttcgcggag caatagcaag aaaagcgcga atttatctga gaggaggatt    7080
agattgtgtt tactttctta acaaagcagg acaagcagag ccttgtcccg cgtgtacctc    7140
cctagtattc caagggaaaa cttgtgagga acactattat aataacaatc ttttgtcatg    7200
gcaagcggta aggcaactgg aaagacagac gcccagcgc  cagtcatcaa actaggagga    7260
ccaaagccac ctaagttgg  ttcttctgga aatgcatcat ggtttcaacc gataaaggcc    7320
aagtaa aa   attcacctgt gcctaaattt gacggtagta ttgttcctga aaatgaaaat    7380
ctcaagtcaa gccagcaaca tggatactgg agacgccaac acaggtttaa gcctggcaaa    7440
ggtgaagaa  aaccagtccc tgatgcttgg tactttact  acactggaac aggaccggcc    7500
gccgacctga attggggtga aactcaagat ggtatagtgt gggttgctgc aaagggtgct    7560
gatactaaat ctagatcaaa ccagggtaca agggatcctg ataagtttga ccaatacca    7620
ctacgattct cagatggagg accggatggt aatttccgtt gggacttcat accaataaat    7680
```

```
cgtggtagga gtgggagatc aacagcagct tcatcagcag catctagtag agcaccatct   7740
cgtgagggt cacgtggacg tagaagcgga gttgaagatg atcttatagc tcgcgcagca   7800
aagattatac aggaccagca aaagaagggt gcgcgcatta ccaaggctaa ggctgatgaa   7860
atggctcatc gccgctattg caagcgcact atcccacctg gttataaggt tgagcaagta   7920
tttggtcccc gtactaaagg taaggaagga aattttggtg atgacaagat gaatgaggaa   7980
ggtgttaagg atgggcgtgt tacggcaatg ctcaacctag tccctagcag tcatgccttg   8040
cttttggaa  gtagggtgac gcccaaactg cagccagatg gtcttcacct gagatttgaa   8100
tttactactg tggtgtcacg tgatgatccg cagtttgata attatgtgaa aatttgtgat   8160
cagtgtgtcg atggtgtagg gacgcgtcca aaggacgtga aatcgagacc aaagtcacgc   8220
ccaaattcaa gacctgcaac tagaggaaat tctccagcgc cgagacaaca gcgcccaaag   8280
aaggagaaaa agcccaagaa gcaggatgat gaagtagata aggcattgac ctcagatgag   8340
gagaggaaca atgcacagct ggaatttgat gatgaaccca aggtgattaa ctgggggggac  8400
tctgcactag gtgaaaatga actttgatta acataatgga cttgctgcat ttgctgtcac   8460
attttgttaa atattatttt tgtgttttac tatcaattat tacaggtatt gattgtgatt   8520
atgttcaata cttaagcttc ttctggttgc tttttgcttg ttgtattgtt gctgtgcttt   8580
ttattattgt gattctcatt agtttgcttt atcgtagaaa ttcaatagta agagttaagg   8640
aagataggca tgtagcttag cacctacatg tctatcgcca gggaaatgtc taatctgtct   8700
acttagtagc ctgaaacga acggtagacc cttagatttt aatttagttt aattttttagt  8760
ttagtttaag ttagtttaga gtaggtataa agatgccagt gccggggcca cgcgtagtac   8820
gaccgagggt acagcactag gacgcccact aggggaagag ctaaatttta gtttaagtta   8880
agtttaattg gctaaatata gttaaaattt ataggctagt atagagttag agcaaaaaaa   8940
aaaaaaaaaa aaaaaaaaaa aaaaaaaaaa aaaaaaaaaa aaaaaaaaaa aaaaaaaaaa   9000
aaaaaaaaaa aaaaaaaaaa aaaaaaaaaa aaagcggccg catcggatgc cgggaccgac   9060
gagtgcagag gcgtgcaagc gagcttggcg taatcatggt catagctgtt tcctgtgtga   9120
aattgttatc cgctcacaat tccacacaac atacgagccg gaagcataaa gtgtaaagcc   9180
tggggtgcct aatgagtgag ctaactcaca ttaattgcgt tgcgctcact gcccgctttc   9240
cagtcgggaa acctgtcgtg ccagctgcat taatgaatcg gccaacgcgc ggggagaggc   9300
ggtttgcgta ttgggcgctc ttccgcttcc tcgctcactg actcgctgcg ctcggtcgtt   9360
cggctgcggc gagcggtatc agctcactca aaggcggtaa tacggttatc cacagaatca   9420
ggggataacg caggaaagaa catgtgagca aaaggccagc aaaaggccag gaaccgtaaa   9480
aaggccgcgt tgctggcgtt tttccatagg ctccgccccc ctgacgagca tcacaaaaat   9540
cgacgctcaa gtcagaggtg gcgaaacccg acaggactat aaagatacca ggcgtttccc   9600
cctggaagct ccctcgtgcg ctctcctgtt ccgaccctgc cgcttaccgg atacctgtcc   9660
gcctttctcc cttcgggaag cgtggcgctt tctcatagct cacgctgtag tatctcagt   9720
tcggtgtagg tcgttcgctc caagctgggc tgtgtgcacg aaccccccgt tcagcccgac   9780
cgctgcgcct tatccggtaa ctatcgtctt gagtccaacc cggtaagaca cgacttatcg   9840
ccactgcag cagccactgg taacaggatt agcagagcga ggtatgtagg cggtgctaca   9900
gagttcttga agtggtggcc taactacggc tacactagaa gaacagtatt tggtatctgc   9960
gctctgctga agccagttac cttcggaaaa agagttggta gctcttgatc cggcaaacaa  10020
accaccgctg gtagcggtgg ttttttttgtt tgcaagcagc agattacgcg cagaaaaaaa  10080
ggatctcaag aagatccttt gatcttttct acggggtctg acgctcagtg gaacgaaaac  10140
tcacgttaag ggatttttggt catgagatta tcaaaaagga tcttcaccta gatcctttta  10200
aattaaaaat gaagttttaa atcaatctaa agtatatatg agtaaacttg gtctgacagt  10260
taccaatgct taatcagtga ggcacctatc tcagcgatct gtctatttcg ttcatccata  10320
gttgcctgac tccccgtcgt gtagataact acgatacggg agggcttacc atctggcccc  10380
agtgctgcaa tgataccgcg agaccacgct caccggctc cagatttatc agcaataaac  10440
cagccagccg gaagggccga gcgcagaagt ggtcctgcaa ctttatccgc ctccatccag  10500
tctattaatt gttgccggga agctagagta agtagttcgc cagttaatag tttgcgcaac  10560
gttgttgcca ttgctacagg catcgtggtg tcacgctcgt cgtttggtat ggcttcattc  10620
agctccggtt cccaacgatc aaggcgagtt acatgatccc ccatgttgtg caaaaaagcg  10680
gttagctcct tcggtcctcc gatcgttgtc agaagtaagt tggccgcagt gttatcactc  10740
atggttatgg cagcactgca taattctctt actgtcatgc catccgtaag atgcttttct  10800
gtgactggtg agtactcaac caagtcattc tgagaatagt gtatgcggcg accgagttgc  10860
tcttgcccg cgtcaatacg gataatacc gcgccacata gcagaacttt aaaagtgctc  10920
atcattggaa aacgttcttc ggggcgaaaa ctctcaagga tcttaccgct gttgagatcc  10980
agttcgatgt aacccactcg tgcacccaac tgatcttcag catctttac tttcaccagc  11040
gtttctgggt gagcaaaaac aggaaggcaa aatgccgcaa aaaagggaat aagggcgaca  11100
cggaaatgtt gaatactcat actcttcctt tttcaatatt attgaagcat ttatcagggt  11160
tattgtctca tgagcggata catatttgaa tgtatttaga aaaataaaca aatagggggt  11220
ccgcgcacat ttccccgaaa agtgccacct gacgtctaag aaaccattat tatcatgaca  11280
ttaacctata aaaataggcg tatcacgagg ccctttcgtc                        11320
```

```
SEQ ID NO: 16          moltype = DNA  length = 21
FEATURE                Location/Qualifiers
misc_feature           1..21
                       note = Primer Sequence
source                 1..21
                       mol_type = other DNA
                       organism = synthetic construct
SEQUENCE: 16
cggataacaa tttcacacag g                                             21

SEQ ID NO: 17          moltype = DNA  length = 21
FEATURE                Location/Qualifiers
misc_feature           1..21
                       note = Primer Sequence
source                 1..21
                       mol_type = other DNA
                       organism = synthetic construct
```

```
SEQUENCE: 17
aacactattt tcacgataga c                                              21

SEQ ID NO: 18           moltype = DNA  length = 27
FEATURE                 Location/Qualifiers
misc_feature            1..27
                        note = Primer Sequence
source                  1..27
                        mol_type = other DNA
                        organism = synthetic construct
SEQUENCE: 18
aatactactt gtacgttaca caatttc                                        27

SEQ ID NO: 19           moltype = DNA  length = 18
FEATURE                 Location/Qualifiers
misc_feature            1..18
                        note = Primer Sequence
source                  1..18
                        mol_type = other DNA
                        organism = synthetic construct
SEQUENCE: 19
taaatggtga tcttgttt                                                  18

SEQ ID NO: 20           moltype = DNA  length = 18
FEATURE                 Location/Qualifiers
misc_feature            1..18
                        note = Primer Sequence
source                  1..18
                        mol_type = other DNA
                        organism = synthetic construct
SEQUENCE: 20
gcattcactg ctgtacaa                                                  18

SEQ ID NO: 21           moltype = DNA  length = 19
FEATURE                 Location/Qualifiers
misc_feature            1..19
                        note = Primer Sequence
source                  1..19
                        mol_type = other DNA
                        organism = synthetic construct
SEQUENCE: 21
cgctcttagt aacataaac                                                 19

SEQ ID NO: 22           moltype = DNA  length = 19
FEATURE                 Location/Qualifiers
misc_feature            1..19
                        note = Primer Sequence
source                  1..19
                        mol_type = other DNA
                        organism = synthetic construct
SEQUENCE: 22
ctgaggtcaa tgctttatc                                                 19

SEQ ID NO: 23           moltype = DNA  length = 20
FEATURE                 Location/Qualifiers
misc_feature            1..20
                        note = Primer Sequence
source                  1..20
                        mol_type = other DNA
                        organism = synthetic construct
SEQUENCE: 23
gacagagcac aagtttgatc                                                20

SEQ ID NO: 24           moltype = DNA  length = 20
FEATURE                 Location/Qualifiers
misc_feature            1..20
                        note = Primer Sequence
source                  1..20
                        mol_type = other DNA
                        organism = synthetic construct
SEQUENCE: 24
acttcaagca tttgtacagg                                                20

SEQ ID NO: 25           moltype = DNA  length = 21
FEATURE                 Location/Qualifiers
misc_feature            1..21
                        note = Primer Sequence
source                  1..21
                        mol_type = other DNA
```

```
                        organism = synthetic construct
SEQUENCE: 25
ggtcaacaat gtaattttgc t                                              21

SEQ ID NO: 26           moltype = DNA  length = 20
FEATURE                 Location/Qualifiers
misc_feature            1..20
                        note = Primer Sequence
source                  1..20
                        mol_type = other DNA
                        organism = synthetic construct
SEQUENCE: 26
gcagatgcta aaacagaaag                                                20

SEQ ID NO: 27           moltype = DNA  length = 20
FEATURE                 Location/Qualifiers
misc_feature            1..20
                        note = Primer Sequence
source                  1..20
                        mol_type = other DNA
                        organism = synthetic construct
SEQUENCE: 27
tcacctgaac aatcttcagc                                                20

SEQ ID NO: 28           moltype = DNA  length = 20
FEATURE                 Location/Qualifiers
misc_feature            1..20
                        note = Primer Sequence
source                  1..20
                        mol_type = other DNA
                        organism = synthetic construct
SEQUENCE: 28
ggtcaccagt atatttctgc                                                20

SEQ ID NO: 29           moltype = DNA  length = 20
FEATURE                 Location/Qualifiers
misc_feature            1..20
                        note = Primer Sequence
source                  1..20
                        mol_type = other DNA
                        organism = synthetic construct
SEQUENCE: 29
aaagaagcag gatgatgaag                                                20

SEQ ID NO: 30           moltype = DNA  length = 20
FEATURE                 Location/Qualifiers
misc_feature            1..20
                        note = Primer Sequence
source                  1..20
                        mol_type = other DNA
                        organism = synthetic construct
SEQUENCE: 30
aagagatgtt ggtaacacct                                                20

SEQ ID NO: 31           moltype = DNA  length = 20
FEATURE                 Location/Qualifiers
misc_feature            1..20
                        note = Primer Sequence
source                  1..20
                        mol_type = other DNA
                        organism = synthetic construct
SEQUENCE: 31
ctaaaccggc tggttttaat                                                20

SEQ ID NO: 32           moltype = DNA  length = 20
FEATURE                 Location/Qualifiers
misc_feature            1..20
                        note = Primer Sequence
source                  1..20
                        mol_type = other DNA
                        organism = synthetic construct
SEQUENCE: 32
ccatagcttt tgccactatt                                                20

SEQ ID NO: 33           moltype = DNA  length = 20
FEATURE                 Location/Qualifiers
misc_feature            1..20
                        note = Primer Sequence
source                  1..20
```

```
                        mol_type = other DNA
                        organism = synthetic construct
SEQUENCE: 33
cgcttgtaaa tagaaggtct                                                   20

SEQ ID NO: 34           moltype = DNA   length = 20
FEATURE                 Location/Qualifiers
misc_feature            1..20
                        note = Primer Sequence
source                  1..20
                        mol_type = other DNA
                        organism = synthetic construct
SEQUENCE: 34
acataccaag gccacttaat                                                   20

SEQ ID NO: 35           moltype = DNA   length = 20
FEATURE                 Location/Qualifiers
misc_feature            1..20
                        note = Primer Sequence
source                  1..20
                        mol_type = other DNA
                        organism = synthetic construct
SEQUENCE: 35
ggtcctgttc cagtatagta                                                   20

SEQ ID NO: 36           moltype = DNA   length = 20
FEATURE                 Location/Qualifiers
misc_feature            1..20
                        note = Primer Sequence
source                  1..20
                        mol_type = other DNA
                        organism = synthetic construct
SEQUENCE: 36
cttgtcctgc tttgttaaga                                                   20

SEQ ID NO: 37           moltype = DNA   length = 20
FEATURE                 Location/Qualifiers
misc_feature            1..20
                        note = Primer Sequence
source                  1..20
                        mol_type = other DNA
                        organism = synthetic construct
SEQUENCE: 37
gtggatcgtc ttataactgg                                                   20

SEQ ID NO: 38           moltype = DNA   length = 20
FEATURE                 Location/Qualifiers
misc_feature            1..20
                        note = Primer Sequence
source                  1..20
                        mol_type = other DNA
                        organism = synthetic construct
SEQUENCE: 38
ctcgcattac aaaggctaag                                                   20

SEQ ID NO: 39           moltype = DNA   length = 20
FEATURE                 Location/Qualifiers
misc_feature            1..20
                        note = Primer Sequence
source                  1..20
                        mol_type = other DNA
                        organism = synthetic construct
SEQUENCE: 39
ccagttatag gacacccatc                                                   20

SEQ ID NO: 40           moltype = DNA   length = 20
FEATURE                 Location/Qualifiers
misc_feature            1..20
                        note = Primer Sequence
source                  1..20
                        mol_type = other DNA
                        organism = synthetic construct
SEQUENCE: 40
gttggttctt ctggaaatgt                                                   20

SEQ ID NO: 41           moltype = DNA   length = 20
FEATURE                 Location/Qualifiers
misc_feature            1..20
                        note = Primer Sequence
```

```
source                  1..20
                        mol_type = other DNA
                        organism = synthetic construct
SEQUENCE: 41
tcagcatgga cgtgtggtta                                                  20

SEQ ID NO: 42           moltype = DNA  length = 20
FEATURE                 Location/Qualifiers
misc_feature            1..20
                        note = Primer Sequence
source                  1..20
                        mol_type = other DNA
                        organism = synthetic construct
SEQUENCE: 42
ccccatgtaa atgccaacca                                                  20

SEQ ID NO: 43           moltype = DNA  length = 61
FEATURE                 Location/Qualifiers
misc_feature            1..61
                        note = Primer Sequence
source                  1..61
                        mol_type = other DNA
                        organism = synthetic construct
SEQUENCE: 43
gtatatcgag aaagtagcac taacactact tgtaagttaa ctaatttcag ttttactaat      60
g                                                                     61

SEQ ID NO: 44           moltype = DNA  length = 20
FEATURE                 Location/Qualifiers
misc_feature            1..20
                        note = Primer Sequence
source                  1..20
                        mol_type = other DNA
                        organism = synthetic construct
SEQUENCE: 44
tttgtatacg agagccatca                                                  20

SEQ ID NO: 45           moltype = DNA  length = 20
FEATURE                 Location/Qualifiers
misc_feature            1..20
                        note = Primer Sequence
source                  1..20
                        mol_type = other DNA
                        organism = synthetic construct
SEQUENCE: 45
tcagcgtgga catgtggtta                                                  20

SEQ ID NO: 46           moltype = DNA  length = 20
FEATURE                 Location/Qualifiers
misc_feature            1..20
                        note = Primer Sequence
source                  1..20
                        mol_type = other DNA
                        organism = synthetic construct
SEQUENCE: 46
ccccatatag gtgccaacct                                                  20

SEQ ID NO: 47           moltype = DNA  length = 33
FEATURE                 Location/Qualifiers
misc_feature            1..33
                        note = Primer Sequence
source                  1..33
                        mol_type = other DNA
                        organism = synthetic construct
SEQUENCE: 47
cgcggatccg ccaccatgtt ggtgaagtca ctg                                   33

SEQ ID NO: 48           moltype = DNA  length = 33
FEATURE                 Location/Qualifiers
misc_feature            1..33
                        note = Primer Sequence
source                  1..33
                        mol_type = other DNA
                        organism = synthetic construct
SEQUENCE: 48
gcggcggccg cttaaacaga cttttttaggt ctg                                  33

SEQ ID NO: 49           moltype = DNA  length = 41
FEATURE                 Location/Qualifiers
```

```
                            misc_feature     1..41
                                             note = Primer Sequence
                            source           1..41
                                             mol_type = other DNA
                                             organism = synthetic construct
SEQUENCE: 49
taatactact tgtgcgttaa ctaattttac ttttagtaat g                                    41

SEQ ID NO: 50               moltype = DNA   length = 18
FEATURE                     Location/Qualifiers
misc_feature                1..18
                            note = Primer Sequence
source                      1..18
                            mol_type = other DNA
                            organism = synthetic construct
SEQUENCE: 50
acactactttt cacgatag                                                             18

SEQ ID NO: 51               moltype = DNA   length = 20
FEATURE                     Location/Qualifiers
misc_feature                1..20
                            note = Primer Sequence
source                      1..20
                            mol_type = other DNA
                            organism = synthetic construct
SEQUENCE: 51
aatttaacag ttagcgtatc                                                            20

SEQ ID NO: 52               moltype = DNA   length = 43
FEATURE                     Location/Qualifiers
misc_feature                1..43
                            note = Primer Sequence
source                      1..43
                            mol_type = other DNA
                            organism = synthetic construct
SEQUENCE: 52
aagtgtggta agttactggt aagagatgtt ggtgaagtca ctg                                  43

SEQ ID NO: 53               moltype = DNA   length = 47
FEATURE                     Location/Qualifiers
misc_feature                1..47
                            note = Primer Sequence
source                      1..47
                            mol_type = other DNA
                            organism = synthetic construct
SEQUENCE: 53
agaaaagatg tgggactttt aatcattaaa cagactttt aggtctg                               47

SEQ ID NO: 54               moltype = DNA   length = 47
FEATURE                     Location/Qualifiers
misc_feature                1..47
                            note = Primer Sequence
source                      1..47
                            mol_type = other DNA
                            organism = synthetic construct
SEQUENCE: 54
tgattaaaag tcccacatct tttctaatat tattaattct tctttgg                              47

SEQ ID NO: 55               moltype = DNA   length = 46
FEATURE                     Location/Qualifiers
misc_feature                1..46
                            note = Primer Sequence
source                      1..46
                            mol_type = other DNA
                            organism = synthetic construct
SEQUENCE: 55
ctcttaccag taacttacca cacttaatta aattaaagac taagtc                               46

SEQ ID NO: 56               moltype = DNA   length = 20
FEATURE                     Location/Qualifiers
misc_feature                1..20
                            note = Primer Sequence
source                      1..20
                            mol_type = other DNA
                            organism = synthetic construct
SEQUENCE: 56
caggattgtg catggtggac                                                            20

SEQ ID NO: 57               moltype = DNA   length = 24
```

-continued

```
FEATURE                 Location/Qualifiers
misc_feature            1..24
                        note = Primer Sequence
source                  1..24
                        mol_type = other DNA
                        organism = synthetic construct
SEQUENCE: 57
gaagtgaaya caagatcacc attt                                              24

SEQ ID NO: 58           moltype = DNA  length = 20
FEATURE                 Location/Qualifiers
misc_feature            1..20
                        note = Primer Sequence
source                  1..20
                        mol_type = other DNA
                        organism = synthetic construct
SEQUENCE: 58
tgactgattc tgctgctaaa                                                   20

SEQ ID NO: 59           moltype = DNA  length = 19
FEATURE                 Location/Qualifiers
misc_feature            1..19
                        note = Primer Sequence
source                  1..19
                        mol_type = other DNA
                        organism = synthetic construct
SEQUENCE: 59
tcttgaaacc cccaagtag                                                    19

SEQ ID NO: 60           moltype = DNA  length = 20
FEATURE                 Location/Qualifiers
misc_feature            1..20
                        note = Primer Sequence
source                  1..20
                        mol_type = other DNA
                        organism = synthetic construct
SEQUENCE: 60
tatattcagc atcagttggc                                                   20

SEQ ID NO: 61           moltype = DNA  length = 20
FEATURE                 Location/Qualifiers
misc_feature            1..20
                        note = Primer Sequence
source                  1..20
                        mol_type = other DNA
                        organism = synthetic construct
SEQUENCE: 61
ggattttgtg gtagtggaag                                                   20

SEQ ID NO: 62           moltype = DNA  length = 23
FEATURE                 Location/Qualifiers
misc_feature            1..23
                        note = Primer Sequence
source                  1..23
                        mol_type = other DNA
                        organism = synthetic construct
SEQUENCE: 62
ccactattgc agtaacatta aca                                               23

SEQ ID NO: 63           moltype = DNA  length = 21
FEATURE                 Location/Qualifiers
misc_feature            1..21
                        note = Primer Sequence
source                  1..21
                        mol_type = other DNA
                        organism = synthetic construct
SEQUENCE: 63
ctagactgta agttactatt g                                                 21

SEQ ID NO: 64           moltype = DNA  length = 20
FEATURE                 Location/Qualifiers
misc_feature            1..20
                        note = Primer Sequence
source                  1..20
                        mol_type = other DNA
                        organism = synthetic construct
SEQUENCE: 64
ccagggtttt cccagtcacg                                                   20
```

```
SEQ ID NO: 65           moltype = AA  length = 1156
FEATURE                 Location/Qualifiers
source                  1..1156
                        mol_type = protein
                        organism = unidentified
                        note = Avian infectious bronchitis virus
SEQUENCE: 65
MLVKSLFLVT ILCALCSANL FDSDNNYVYY YQSAFRPPNG WHLQGGAYAV VSSTNYTNNA    60
GSAHGCTVGV IKDVYNQSVA SIAMTAPLQG MAWSKSQFCS AHCNFSEITV FVTHCYSSGS   120
GSCPITGMIP RDHIRISAMK NGSLFYNLTV SVSKYPNFKS FQCVNNFTSV YLNGDLVFTS   180
NKTTDVTSAG VYFKAGGPVN YSIMKEFKVL AYFVNGTAQD VVLCDNSPKG LLACQYNTGN   240
FSDGFYPFTN STLVREKFIV YRESSVNTTL ALTNFTFSNV SNAQPNSGGV NTFHLYQTQT   300
AQSGYYNFNL SFLSQFVYKA SDFMYGSYHP SCSFRPETIN SGLWFNSLSV SLTYGPLQGG   360
CKQSVFSGKA TCCYAYSYRG PMACKGVYSG ELSTNFECGL LVYVTKSDGS RIQTRTEPLV   420
LTQYNYNNIT LDKCVAYNIY GRVGQGFITN VTDSAANFSY LADGGLAILD TSGAIDVFVV   480
QGIYGLNYYK VNPCEDVNQQ FVVSGGNIVG ILTSRNETGS EQVENQFYVK LTNSSHRRKR   540
SIGQNVTSCP YVSYGRFCIE PDGSLKMIVP EELKQFVAPL LNITESVLIP NSFNLTVTDE   600
YIQTRMDKVQ INCLQYVCGN SLECRKLFQQ YGPVCDNILS VVNSVSQKED MELLSFYSST   660
KPKGYDTPVL SNVSTGEFNI SLLLKPPSSP SGRSFIEELL FTSVETVGLP TDAEYKKCTA   720
GPLGTLKDLI CAREYNGLLV LPPIITADMQ TMYTASLVGA MAFGGITSAA AIPFATQIQA   780
RINHLGITQS LLMKNQEKIA ASFNKAIGHM QEGFRSTSLA LQQIQDVVNK QSAILTETMN   840
SLNKNFGAIT SVIQDIYAQL DAIQADAQVD RLITGRLSSL SVLASAKQSE YIRVSQQREL   900
ATQKINECVK SQSNRYGFCG SGRHVLSIPQ NAPNGIVFIH FTYTPESFVN VTAIVGFCVN   960
PANASQYAIV PANGRGIFIQ VNGTYYITAR DMYMPRDITA GDIVTLTSCQ ANYVNVNKTV  1020
ITTFVEDDDF DFDDELSKWW NDTKHQLPDF DDFNYTVPIL NISGEIDYIQ GVIQGLNDSL  1080
IDLEELSIIK TYIKWPWYVW LAIFFAIIIF ILILGWVFFM TGCCGCCCGC FGIIPLMSKC  1140
GKKSSYYTTF DNDVVT                                                 1156

SEQ ID NO: 66           moltype = DNA  length = 6523
FEATURE                 Location/Qualifiers
misc_feature            1..6523
                        note = Plasmid Sequence
source                  1..6523
                        mol_type = other DNA
                        organism = synthetic construct
SEQUENCE: 66
aatcactagt gcggccgcct gcaggtcgac catatgggag agctcccaac gcgttggatg    60
catagcttga gtattctata gtgtcaccta aatagcttgg cgtaatcatg gtcatagctg   120
tttcctgtgt gaaattgtta tccgctcaca attccacaca acatacgagc cggaagcata   180
aagtgtaaag cctggggtgc ctaatgagtg agctaactca cattaattgc gttgcgctca   240
ctgcccgctt tccagtcggg aaacctgtcg tgccagctgc attaatgaat cggccaacgc   300
gcggggagag gcggtttgcg tattgggcgc tcttccgctt cctcgctcac tgactcgctg   360
cgctcggtcg ttcggctgcg gcgagcggta tcagctcact caaaggcggt aatacggtta   420
tccacagaat caggggataa cgcaggaaag aacatgtgag caaaaggcca gcaaaaggcc   480
aggaaccgta aaaaggccgc gttgctggcg tttttccata ggctccgccc cctgacgag    540
catcacaaaa atcgacgctc aagtcagagg tggcgaaacc cgacaggact ataaagatac   600
caggcgtttc ccccctggaag ctccctcgtg cgctctcctg ttccgaccct gccgcttacc   660
ggatacctgt ccgcctttct cccttcggga agcgtggcgc tttctcatag ctcacgctgt   720
aggtatctca gttcggtgta ggtcgttcgc tccaagctgg gctgtgtgca cgaaccccc    780
gttcagcccg accgctgcgc cttatccggt aactatcgtc ttgagtccaa cccggtaaga   840
cacgacttat cgccactggc agcagccact ggtaacagga ttagcagagc gaggtatgta   900
ggcggtgcta cagagttctt gaagtggtgg cctaactacg gctacactag aagaacagta   960
tttggtatct gcgctctgct gaagccagtt accttcggaa aaagagttgg tagctcttga  1020
tccggcaaac aaaccaccgc tggtagcggt ggtttttttg tttgcaagca gcagattacg  1080
cgcagaaaaa aaggatctca agaagatcct ttgatctttt ctacggggtc tgacgctcag  1140
tggaacgaaa actcacgtta agggattttg gtcatgagat tatcaaaaag gatcttcacc  1200
tagatccttt taaattaaaa atgaagtttt aaatcaatct aaagtatata tgagtaaact  1260
tggtctgaca gttaccaatg cttaatcagt gaggcaccta tctcagcgat ctgtctattt  1320
cgttcatcca tagttgcctg actccccgtc gtgtagataa ctacgatacg ggagggctta  1380
ccatctggcc ccagtgctgc aatgataccg cgagacccac gctcaccggc tccagattta  1440
tcagcaataa accagccagc cggaagggcc gagcgcagaa gtggtcctgc aactttatcc  1500
gcctccatcc agtctattaa ttgttgccgg gaagctagag taagtagttc gccagttaat  1560
agtttgcgca acgttgttgc cattgctaca ggcatcgtgg tgtcacgctc gtcgtttggt  1620
atggcttcat tcagctccgg ttcccaacga tcaaggcgag ttacatgatc ccccatgttg  1680
tgcaaaaaag cggttagctc cttcggtcct ccgatcgttg tcagaagtaa gttggccgca  1740
gtgttatcac tcatggttat ggcagcactg cataattctc ttactgtcat gccatccgta  1800
agatgctttt ctgtgactgg tgagtactca accaagtcat tctgagaata gtgtatgcgg  1860
cgaccgagtt gctcttgccc ggcgtcaata cgggataata ccgcgccaca tagcagaact  1920
ttaaaagtgc tcatcattgg aaaacgttct tcggggcgaa aactctcaag gatcttaccg  1980
ctgttgagat ccagttcgat gtaacccact cgtgcaccca actgatcttc agcatctttt  2040
actttcacca gcgtttctgg gtgagcaaaa acaggaaggc aaaatgccgc aaaaaaggga  2100
ataagggcga cacggaaatg ttgaatactc atactcttcc ttttttcaata ttattgaagc  2160
atttatcagg gttattgtct catgagcgga tacatatttg aatgtattta gaaaaataaa  2220
caaataggg ttccgcgcac atttccccga aaagtgccac ctgacgtctaa gaaaccatta  2280
gcacagatgc gtaaggagaa aataccgcat caggaaattg taagcgttaa tattttgtta  2340
aaattcgcgt taaattttttg ttaaatcagc tcatttttta accaataggc cgaaatcggc  2400
aaaatccctt ataaatcaaa agaatagacc gagatagggt tgagtgttgt tccagtttgg  2460
aacaagagtc cactattaaa gaacgtggac tccaacgtca aagggcgaaa aaccgtctat  2520
cagggcgatg gcccactacg tgaaccatca ccctaatcaa gttttttggg gtcgaggtgc  2580
```

```
cgtaaagcac taaatcggaa ccctaaaggg agccccgat ttagagcttg acggggaaag      2640
ccggcgaacg tggcgagaaa ggaagggaag aaagcgaaag gagcgggcgc tagggcgctg      2700
gcaagtgtag cggtcacgct gcgcgtaacc accacacccg ccgcgcttaa tgcgccgcta      2760
cagggcgcgt ccattcgcca ttcaggctgc gcaactgttg ggaagggcga tcggtgcggg      2820
cctcttcgct attacgccag ctggccgaaa ggggatgtgc tgcaaggcga ttaagttggg      2880
taacgccagg gttttcccag tcacgacgtt gtaaaacgac ggccagtgaa ttgtaatacg      2940
actcactata gggcgaattg ggcccgacgt cgcatgctcc cggccgccat ggccgcggga      3000
ttcgcggatc cgccaatgtt ggtgaagtca ctgtttttag tgaccatttt gtgtgcacta      3060
tgtagtgcaa atttgtttga ttctgataat aattatgtgt actactacca aagtgcttttc      3120
agaccgccaa atgggtggca cttacaagga ggtgcttatg cagtagtcag ttctactaat      3180
tatactaata atgccggttc tgcacatggg tgcactgttg gtgttattaa ggatgtttat      3240
aatcaaagtg tggcttccat agctatgaca gcacctcttc agggtatggc ttggtctaag      3300
tcacaattct gtagtgcaca ctgtaatttt tctgaaatta cagttttgt cacacattgt      3360
tatagtagtg gtagtgggtc gtgtcctata acaggcatga ttccacgtga tcatattcgt      3420
atttctgcaa tgaaaaatgg ttccttattt tataatttaa cagttagcgt atctaaatac      3480
cctaattttta aatcttttca atgtgttaac aacttcacat ctgtttattt aaatggtgat      3540
cttgtttta cttccaacaa aactactgat gttacgtcag caggtgtgta ttttaaagca      3600
ggtggacctg taaattatag tattatgaaa gaatttaagg ttcttgctta ttttgttaat      3660
ggtacagcac aagatgtagt tttgtgcgca aattccccca agggtttgct agcttgtcaa      3720
tataacactg gcaatttttc agatggcttt tatcctttta ctaatagtac tttggttagg      3780
gaaaagttca tcgtcgtatcg tgaaagtagt gttaatacta cttgtgcgtt aactaatttt      3840
actttttagta atgtaagtaa tgcacagcct aatagtggt gtgttaatac ttttcattta      3900
tatcaaacac aaacagctca gagtggttat taaaatttta atttgtcatt tctgagtcag      3960
tttgtgtata aggcaagtga ttttatgtat gggtcctacc atcctagttg ttctttttaga      4020
ccagaaacca ttaatagtgg tttatgttt aattccttgt cagtttctct tacctatgga      4080
cccctacagg gaggggtgtaa gcaatctgtt tttagtggta aggcaacgtg ttgtttacgcc      4140
tactcttata gaggcccaat ggcatgtaaa ggtgttttatt caggtgaatt aagcacgaat      4200
tttgaatgtg gattgctggt ttatgtact aagagtgatg gctctcgtat acagactaga      4260
acagagccct tagtattaac gcaatacaat tataataata ttactttaga taagtgtgtt      4320
gcctataata tatatggcag agtgggccaa ggttttatta ctaatgtgac tgattctgct      4380
gctaattttta gttatttagc agatggtgg ttagctattt tagatacgtc gggtgccata      4440
gatgtttttg ttgtacaggg catctatggc cttaattatt acaaggtcaa tccttgtgaa      4500
gatgttaacc aacaatttgt agtgtctggt ggcaatatag ttggcattct tacttctaga      4560
aatgaaacag gttctgaaca ggttgagaac cagttttatg ttaagttaac caatagctca      4620
catcgtcgta agcgttctat tggccaaaac gtaacaagtt gtccttatgt tagctatggc      4680
agattttgta ttgaaccaga tggttcgtta aagatgatag tgccagaaga attgaaacag      4740
tttgtggcac ctttactaa tattactgaa agtgtactca tacctaacag tttttaatctt      4800
actgttacag atgagtacat acaaacacgt atggataagg tccaaatcaa ttgccttcaa      4860
tatgtttgcg gcaattcttt ggagtgtaga aaattgtttc aacaatatgg tccggtttgt      4920
gataatatat tgtctgttgt aaatagtgtt agtcaaaaag aagatatgga acttttaagc      4980
ttctattcct ctactaaacc aaaggggtat gatacaccag ttcttagtaa tgtaagcact      5040
ggtgaattta atatttctct tctcttgaaa ccccaagca gtcctagtgg gcgttctttc      5100
attgaagagc tttttatttac aagtgttgaa acagttggtt gccaactga tgtctgaatat      5160
aaaaaatgca cagcgggacc tttgggtact cttaaagatc ttatctgtgc tagggaatat      5220
aatggtttat tagtgttgcc tccaattatt acggcggata tgcaaacaat gtatactgct      5280
tctttagtgg gtgctatggc ctttggtggt attacatcag ctgcagctat accttttgct      5340
actcagattc aggcaagaat taatcatctt ggtattacaa agtctttgtt aatgaaaaat      5400
caagaaaaga ttgctgcttc ctttaataag gccattggtc atatgcagga aggttttaga      5460
agcacttctc tagcattaca acagattcaa gatgttgtta ataagcagag tgctattctt      5520
actgaaacta tgaattctct taataagaat tttggtgcta ttacatcagt cattcaagat      5580
atttacgcgc aacttgacgc aatccaagca gatgcacaag ttgaccgcct tattactggt      5640
agactttcat cactctcagt gttagcctct gctaaacagt ctgagtatat tagagttttcc      5700
cagcagcgtg aattagccac tcaaaaaatt aatgagtgtg ttaaatcaca atctaatagg      5760
tacgatttt gtggtagtgg aagacatgtt ctttcgatac cacaaaatgc acctaatggt      5820
atagtgttta cactttac ttatacacca gagagttttg ttaatgttac tgcaatagtg      5880
ggttttttgtg taaatcctgc taatgctagt cagtatgcta tagtacctgc taatggaagg      5940
ggtatttta tacaagttaa tggcacgtac tatatcactg cacgtgatat gtatatgcca      6000
cgagacatta ctgcaggaga tatagttact cttacgtctt gtcaagcaaa ttatgttaat      6060
gtaaataaaa ccgtcattac tacatttgta gaagatgacg attttgattt tgatgatgag      6120
ttgtcaaaat ggtggaatga tactaagcat cagctaccag actttgacga cttcaattac      6180
acagtaccca tacttaatat tagccggtgaa attgattata ttcaaggtgt tatacagggc      6240
cttaatgact ccttatag ccttgaagaa ctttcaataa ttaaaactta tattaagtgg      6300
ccttggtatg tttggcttgc catattcttt gccattatta tctttatcct tatattagga      6360
tgggttttct tcatgactgg atgttgtggt tgttgtttgg gtgctttgg cattattcct      6420
ctaatgagta agtgtggtaa gaaatcttcc tactacacta cttttgataa tgatgtggta      6480
acttaacaat acagacctaa aaagtctgtt taacggccgc cgc                        6523

SEQ ID NO: 67          moltype = DNA  length = 11320
FEATURE                Location/Qualifiers
misc_feature           1..11320
                       note = Plasmid Sequence
source                 1..11320
                       mol_type = other DNA
                       organism = synthetic construct
SEQUENCE: 67
tcgcgcgttt cggtgatgac ggtgaaaacc tctgacacat gcagctcccg gagacggtca       60
cagcttgtct gtaagcggat gccgggagca gacaagcccg tcagggcgcg tcagcggtg      120
ttggcggggt tcgggctgg cttaactatg cggcatcaga gcagattgta ctgagagtgc      180
accatatgcg gtgtgaaata ccgcacagat gcgtaaggag aaaataccgc atcaggcgcc      240
```

```
attcgccatt caggctgcgc aactgttggg aagggcgatc ggtgcgggcc tcttcgctat    300
tacgccagct ggcgaaaggg ggatgtgctg caaggcgatt aagttgggta acgccaggt     360
tttcccagtc acgacgttgt aaaacgacgg ccagtgaatt ggagatcggt acttcgcgaa    420
tgcgtcgaga tgagctctaa tacgactcac tatagggact taagtgtgat ataaatatat    480
atcatacata ctagccttgt gctagatttc caacttaaca aaacgactt aaataccttac    540
agttggtccc tataggtgtt ccattgcagt gcactttagt gccctggatg cacctggcc     600
acctgtcagg ttttttgttat taaaataata ttgttgctgg tatcactgct tgttttgccg   660
tgtctcactt tatacatccg ttgcttgggc tacctagtat ccagcgtcct actggcgttg    720
tggtcggttc gagtgcgaag aacctctggt tcatctagcg gtacgcgggt gtgtggaagt    780
agcgcttcag acgtaccggt tctgttgcgt gaaatacggg gtcacctccc cccacatacc    840
tctaagggct tttgagccta gcgttgggct acgttctcgc acaaggtcgg ctatacggcg    900
tttgtagggg gtagtgccaa acaaccctg aggtgacagg ttctggtggt gtttcgaaaa     960
caacaatgtg tgtgccgcat aatatgcgag taatgcattt tggagcagga agtgacaaag   1020
gagtggcccc aggtagcgct gttcttaggc agtggcttcc cgaaggtaca ctccttgtcg   1080
ataatgatat tgtagattat gtatctgatg cacatgtctc tgtgctttca gattgcaata   1140
aatgtaaaac agagcacaag tttgatcttg tgatatctga tatgtataca gataatgatt   1200
caaagagaaa gcatgaaggc gttgtagcca ataacggcaa tgatgacgtc ttcatatacc   1260
tttcaaactt tcttcgtaac aattgctc tgggaggcag ttttgccgta aaagtaacag     1320
agacaagttg gcatgagagt ttatatgaca ttgcacagga ttgtgcatgg tggacaatgt   1380
tttgtacagc agtgaatgct tcttcgtcag aagcattctt gattggtgtt aattatttgg   1440
gtgcaagtga aaggttaga gttagtggta aaaccctgca cgcaaattat atattttgga    1500
ggaattgtaa ttatttacaa acttcagcct atagtatatt tgacgttgct aagtttgatt   1560
tgaaattaaa agcaacgcca gttgtgaatt tgaaaactga acaaaagaca gacttagtct   1620
ttaatttaat taagtgtggt aagttactgg taagagatgt tggacaaacc gcttttacta   1680
gtgactcttt ggtatgcact atgtagtgct ttgctctatg ataataatac ttacgtttac   1740
tactaccaaa gtgcctttag gcctggtcca ggttggcacc tatatggggg tgcttatgca   1800
gtagataggg tttttaatga aaccaacaat gcaggcagtg catctgattg cactgctggt   1860
acttttatg aaagccataa tatttctgct tcttctgtag ccatgacagt accacataat    1920
ggtatgtctt ggtcagcttc acaattttgt acagctcatt gtaacttctc agactttaca   1980
gtgttcgtta cgcattgttt taaaaatcaa ctcggtagtt gtcccttgac aggtatgatt   2040
cctcagaatc atattcgtat ttctgctatg agagatggga ttttgtttta taacttaaca   2100
gttagcgtat ctaaataccc tagatttaaa tcgcttcaat gtgttagcaa ttctacatct   2160
gtctatgtaa atggtgacct tgttttcact tctaatgaaa cttcttacgt tacgggtgca   2220
ggcgttttatt ttaaaagtgg tgggcctgta acttataaag ttattaaaga agttaaagcc  2280
ctagcctact ttattaatgg taccgcacaa gaggttattt tatgtgataa ctcacctaga   2340
ggtttgcttg catgtcagta taacactggt aattttcag atggattcta ccctttttact  2400
aatcattctt tagttaagga taggtttatt gtatatcgag aaagtagcac taacactact   2460
ttaaagttaa ctaatttcag ttttactaat gtaagtaatg cttctcctaa ttcaggtggc   2520
gttgatactt tccaattata tcaaacaagt actgctcagg atggttatta taattttaag   2580
ttatcatttc tgagtagttt tgtgtataaa ccatctgatt ttatgtatgg gtcataccac   2640
ccacattgta agtttagacc agagaatatt aataatggct tatggtttaa ttcattatct   2700
gtgtcactta cttacggacc cattcaaggt ggttgtaagc aatctgtttt tagtaataga   2760
gcaacttgtt gctatgctta ttcttatcaa gggcctgata gatgtaaggt tgttataga   2820
ggggagctaa cgcaatactt tgaatgtgga cttctagttt acgtaactaa gagtgatggc   2880
tctcgtatac aaactagaag tgaaccactg gtgttaactc aatataatta taacaacatt   2940
actttaaata agtgtgttga gtaaatata tatggtaggg ttggtcaagg ttttattact   3000
aatgtaactg aagcaactgc taattatagt tatctagcag atgctggttt agctatttta   3060
gataccctcag gagccataga catatttgtt gttcaaggtg catatggtct taattattat   3120
aaggttaatc cctgtgaaga tgttaaccaa cagtttgtag tgtctggtgg caacttagtt   3180
ggcattctta catctcataa tgaaacaggt tctgaatcta ttgagaacca gttttacatc   3240
aaactcacta acggaaacg tcgctctaga cgttctgtta ctgggaatgt tacaaattgc   3300
ccttatgtta gttatggcaa gttttgtata aaaccagatg gttctttatc tataatagta   3360
ccacaagaat tagaacagtt tgtggcgcct ttattcaatg ttactgagca gtgtgctcata   3420
cctgatagtt ttaatttaac tgtcacagat gagtacatac aaaactcgtat ggataaggtt   3480
caaattattt gccttcagta tttggttggt aattctatta aatgcagaaa gttgtttcag   3540
cagtatggac ctgtttgtga taatatattg tctgttgtaa atggtgtagg tcaagagag    3600
gatatggaac ttttaagttt ctattcttct actaaaccta gtggttacaa tacaccaatt   3660
tttaataatg ttagcactgg tgactttaat atttcgctcc tactaacacc acctaatagt   3720
cctactgggc gctcttttat tgaagatctt ctctttacaa gtgtagaatc tgttggatta   3780
ccaactgatg aagagtataa aaagtgtaca gcaggacctt taggttttgt taaagacctt   3840
gtttgtgcta gagagtataa tggtttgctc gttctgcctc ctattattac tgcggaaatg   3900
caaaccatgt atactagttc tttagtagcc tctatggctt taggtggcat tactgcagct   3960
ggtgctatac ctttgctac acaactgcag gccagaatta ccatttggg tattactaat    4020
tctcttttgt tgaaaaacca agaaaaaatt gctgcttcct ttaataggc catcggtcat   4080
atgcaggaag ggtttaaaag tacttctcta gcattacaac agattcaaga tgttgttaat   4140
aaacagagtt ctattcttac agagactatg caatcactta ataaaaattt tggtgctatt   4200
tcctctgtaa ttcaagacat ttaccagcaa ctagatgcta tcaggcaga tgctcaggtt   4260
gatcgtctta ttacaggtag actctcttca ctatctgttt tagcttctgc taaacaggca   4320
gagtatcata gagtgtcaca acagggtact ttggccactc agaaaattaa tgagtgtgtt   4380
aagtctcagt ctaataggta ttcattttgt ggtaatggta cacatgttct aaccatacca   4440
cagaatgcac ccatggcat agtgtttata cactttacat acactccaga gagttttgtt   4500
aatgttacgg caatagtagg gttttgcgta acccagcta tgctagtca ttatgcaata   4560
gtgcctgtta atgcagggg tgtttttata gaagttaatg gtagttacta tcactgct    4620
agtgt cgtatat atatgccaag agattattact gcaggagaca tagtcacttt gacttcttgt   4680
caagcaaact atgttaatgt aaataaaacc gtcattaaca ctttgtgga agatgacgat   4740
tttgattttt atgatgaatt gtcaaatgg tggaatgata ctaagcatga gctaccagat   4800
tttgatgaat tcaattatac cgttccagtt taaatatta gtaatgaaat tgacagaatt    4860
caacaggtta ttcagggatt aaatgattcc ctaatagacc ttgaaacact ctcaattctc   4920
aaaacttata ttaaatggcc ttggtatgtg tggcttgcca ttgcattcct taccattatt   4980
```

```
tttattctgg tactttgttg gatattttc  atgaccggtt gttgcggttg ttgttgtgga 5040
tgctttggta tcataccgtt aatgagtaag tgtggtaaga aatcttctta ctacacgact 5100
tttgataatg atgtggtaac ttaacaatac agacctaaaa agtctgttta atgattaaaa 5160
gtcccacatc ttttctaata ttattaattc ttctttggtg taaacttgca ttaagttgtt 5220
ttaaagagtg tgttataaca ctccagcaac tagtacaaat tttactccaa attattaata 5280
gtaacttaca atctagactt ctgctttggc acagtctaga ctaatgttag attttgaagc 5340
aattattgaa actggtcagc aaataactca acaaattagt ttctatttac agcatatttc 5400
aagggtgcta agtactgaat tatttgaccc ctttgaagtt tgtgtttaca gaggaggtaa 5460
ttgttgggag ttagagtcag ctgacgagtt ttcaggtgat gacgaatata ttgagtagat 5520
cgctcgagga gaacggaagt tttctaacag cggtttacgt gtttttagga tttttagcac 5580
tttatctact aggtagagcg cttcaagctt ttgtacaagc ggctgacgct tgttgtcttt 5640
tttggtatac atgggtagta gttcctggag ccaagggcac agcctttgtt tataatcata 5700
catatggtaa aaaacttaac aaaccggagt tagaaacggt tattgttaac gaatttccaa 5760
aaaacggttg gaaatatgga taataccatc aattgtactc ttggtactga acaagcagtt 5820
cagctttttta aggaatataa tctgtttgta actgcattcc tgttgttttt aaccatacta 5880
cttcagtatg gatacgcaac taggagcaag gttatttaca tactgaaaat gatagtgtta 5940
tggtgctttt ggcccttaa  cattgcagta ggtgtaatct catgtatata cccaccaaac 6000
acaggaggtc ttgtcgcagc gataattctt acagtgtttg cgtgtctttc ttttataggt 6060
tattggatcc agagtattag actttttaag cggtgcaggt catggtggtc atttaaccc  6120
gaatctaatg ccgtaggttc aatactccta actaatggtc aacaatgtaa ttttgctata 6180
gagagtgtgc cgatggtgct ttctcctatt ataaagaatg gtgctcttta ttgcgagggt 6240
cagtggcttg ctaaatgtga accagaccac ttgcctagga atatttgt  atgcacaccg 6300
gatagacgta atatctatcg tatggtgcaa aaatatactg gtgaccaaag cggaagtaag 6360
aaaaggtttg ccacatttgt ctatgcaaag cagtcagtag atactggcga gctagaaagt 6420
gtgtcagcag taggaggtag tctttacaca taaatgtgtg tgtgtagaga gtatttaaaa 6480
ttattctttg acagtgcctc cgttttaaga gcgcggaaga gtattatttt tgaggatatt 6540
aatataaatc ctctttgttt cataattctcc tttcaggagt tattatttaa aaaacagttt 6600
ttccactctt ttgtgccaaa acaattgtt  gttaatggtg taacctttca ggtagacaat 6660
ggaaaagtct actacgaagg aagaccaatt ttccaaaaag gttgttgtag tttgtggtcc 6720
aattataaga aagattagaa taattaaacc acctacaaca cttatttta  caaatggcgt 6780
tttaggttac aaacgcttaa caaatacgga tgatgaaatg gctgactagt tttgggaagag 6840
ctttcatctc ctgttataaa tcccctattac taactcaatt aagagtatta gataggttaa 6900
ttttagatca cggacccaag cgcacattaa cgtgtgctag gcgagtgctt ttagttcaat 6960
tagatttagt ttataggttg gcttatacgc ccacccaatc gctggtatga ataatagtaa 7020
agataatcct tttcgcggag caatagcaag aaaagcgcga atttatctga gaggaggatt 7080
agattgtgtt tactttctta acaaagcagg acaagcagag ccttgtcccg cgtgtacctc 7140
cctagtattc caagggaaaa cttgtgagga acactattat aataacaatc ttttgtcatg 7200
gcaagcggta aggcaactgg aaagacagac gccccagcgc cagttcatcaa actaggagga 7260
ccaaagccac ctaaagttgg ttcttctgga aatgcatcat ggttcaacc  gataaaggcc 7320
aagaagctaa attcacctgt gcctaaattt gacggtagtg gtgttcctga aaatgaaaat 7380
ctcaagtcaa gccagcaaca tggatactgg agacgcaaac acaggtttaa gcctggcaaa 7440
ggtggaagaa aaccagtccc tgatgcttgg tacttttact acactggaac aggaccggcc 7500
gccgacctga attggggtga aactcaagat ggtatagtgt gggttgctgc aaagggtgct 7560
gatactaaat ctagatcaaa ccagggtaca agggatcctg ataagtttga ccaatacacca 7620
ctacgattct cagatggagg accggatggt aatttccgtt gggacttcat accaataaat 7680
cgtggtagga gtgggagatc aacagcagct tcatcagcag catctagtag agcaccatct 7740
cgtgaggggt cacgtggacg tagaagcgga gttgaagatg atcttatagc tcgcgcagca 7800
aagattatac aggaccagca aaagaaggg  gcgcgcatta ccaaggctaa ggctgatgaa 7860
atggctcatc gccgctattg caagcgcact atcccacctg gttataaggt tgagcaagta 7920
tttggtccc  gtactaaagg taaggaagga aattttggtg atgacaagat gaatgaggaa 7980
ggtgttaagg atgggcgtgt tacggcaatg ctcaacctag tccctagcag tcatgcttgt 8040
cttttttggaa gtagggtgac gcccaaactg cagccagatg gtcttcacct gagatttgaa 8100
tttactactg tggtgtcacg tgatgatccg cagtttgata attatgtgaa aatttgtgat 8160
cagtgtgtcg atggtgtagg gacgcgtcca aggacgatg  aatcgagacc aaagtcacgc 8220
ccaaattcaa gacctgcaac tagaggaaat tctccagcgc cgagacaaca gcgcccaaag 8280
aaggagaaaa agcccaagaa gcaggatgat gaagtagata aggcattgac ctcagatgag 8340
gagaggaaca atgcacagct ggaatttgat gatgaaccca agtgattaa  ctgggggac  8400
tctgcactag gtgaaaatga actttgatta acataatgga cttgctgcat tgctgtcac  8460
attttgttaa atattatttt tgtgtttac  tatcaattat tacaggtatt gattgtgatt 8520
atgttcaata cttaagcttc ttctggttgc ttttttgcttg ttgtattgtt gctgtgcttt 8580
ttattattgt gattctcatt agtttgcttt atcgtagaaa ttcaatagta agagttaagg 8640
aagataggca tgtagcttag cacctacatg tctatcgcca gggaaatgtc taatctgtct 8700
acttagtagc ctggaaacga acggtagacc cttagatttt aatttagttt aattttttagt 8760
ttagtttaag ttagtttaga gtaggtataa agatgccagt gccggggcca cgcgtagtac 8820
gaccgagggt acagcactag gacgcccact aggggaagag ctaaatttta gtttaagtta 8880
agtttaattg gctaaatata gttaaaatt  ataggctagt atagagttag agcaaaaaaa 8940
aaaaaaaaaa aaaaaaaaaa aaaaaaaaaa aaaaaaaaaa aaaaaaaaaa aaaaaaaaaa 9000
aaaaaaaaaa aaaaaaaaaa aaaaaaaaaa aacgcggccg catcggatgc cgggaccgac 9060
gagtgcagag gcgtgcaagc gagcttggcg taatcatggt catgctgtt  tcctgtgtga 9120
aattgttatc cgctcacaat tccacacaac atacgagccg gaagcataaa gtgtaaagcc 9180
tggggtgcct aatgagtgag ctaactcaca ttaattgcgt tgcgctcact gcccgctttc 9240
cagtcgggaa acctgtcgtg ccagctgcat taatgaatcg gccaacgcgc ggggagaggc 9300
ggtttgcgta ttgggcgctc ttccgcttcc tcgctcactg actcgctgcg ctcggtcgtt 9360
cggctgcggc gagcggtatc agctcactca aaggcggtaa tacggttatc cacagaatca 9420
ggggataacg caggaaagaa catgtgagca aaaggccagc aaaaggccag gaaccgtaaa 9480
aaggccgcgt tgctggcgtt tttccatagg ctccgccccc ctgacgagca tcacaaaaat 9540
cgacgctcaa gtcagaggtg gcgaaacccg acaggactat aaagatacca ggcgtttccc 9600
cctggaagct ccctcgtgcg ctctcctgtt ccgaccctgc cgcttaccgg atacctgtcc 9660
gcctttctcc cttcgggaag cgtggcgctt tctcatagct cacgctgtag gtatctcagt 9720
```

```
tcggtgtagg tcgttcgctc caagctgggc tgtgtgcacg aacccccgt tcagcccgac    9780
cgctgcgcct tatccggtaa ctatcgtctt gagtccaacc cggtaagaca cgacttatcg    9840
ccactggcag cagccactgg taacaggatt agcagagcga ggtatgtagg cggtgctaca    9900
gagttcttga agtggtggcc taactacggc tacactagaa gaacagtatt tggtatctgc    9960
gctctgctga agccagttac cttcggaaaa agagttggta gctcttgatc cggcaaacaa   10020
accaccgctg gtagcggtgg ttttttttgtt tgcaagcagc agattacgcg cagaaaaaaa   10080
ggatctcaag aagatccttt gatcttttct acggggtctg acgctcagtg gaacgaaaac   10140
tcacgttaag ggattttggt catgagatta tcaaaaagga tcttcaccta gatccttta   10200
aattaaaaat gaagttttaa atcaatctaa agtatatatg agtaaacttg gtctgacagt   10260
taccaatgct taatcagtga ggcacctatc tcagcgatct gtctatttcg ttcatccata   10320
gttgcctgac tccccgtcgt gtagataact acgatacggg agggcttacc atctggcccc   10380
agtgctgcaa tgataccgcg agacccacgc tcaccggctc cagatttatc agcaataaac   10440
cagccagccg aagggccga cgcagaagt ggtcctgcaa ctttatccgc ctccatccag   10500
tctattaatt gttgccggga agctagagta agtagttcgc cagttaatag tttgcgcaac   10560
gttgttgcca ttgctacagg catcgtggtg tcacgctcgt cgtttggtat ggcttcattc   10620
agctccggtt cccaacgatc aaggcgagtt acatgatccc ccatgttgtg caaaaaagcg   10680
gttagctcct tcggtcctcc gatcgttgtc agaagtaagt tggccgcagt gttatcactc   10740
atggttatgg cagcactgca taattctctt actgtcatgc catccgtaag atgcttttct   10800
gtgactggtg agtactcaac caagtcattc tgagaatagt gtatgcgcg accgagttgc   10860
tcttgcccgg cgtcaatacg ggataatacc gcgccacata gcagaacttt aaaagtgctc   10920
atcattggaa aacgttcttc ggggcgaaaa ctctcaagga tcttaccgct gttgagatcc   10980
agttcgatgt aacccactcg tgcacccaac tgatcttcag catcttttac tttcaccagc   11040
gtttctgggt gagcaaaaac aggaaggcaa aatgccgcaa aaaagggaat aagggcgaca   11100
cggaaatgtt gaatactcat actcttcctt tttcaatatt attgaagcat ttatcagggt   11160
tattgtctca tgagcggata catatttgaa tgtatttaga aaaataaaca aataggggtt   11220
ccgcgcacat ttccccgaaa agtgccacct gacgtctaag aaaccattat tatcatgaca   11280
ttaacctata aaaataggcg tatcacgagg ccctttcgtc                         11320
```

SEQ ID NO: 68        moltype = DNA  length = 11323
FEATURE               Location/Qualifiers
misc_feature       1..11323
                      note = Plasmid Sequence
source              1..11323
                      mol_type = other DNA
                      organism = synthetic construct
SEQUENCE: 68

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt ggagatcgtt acttcgcgaa     420
tgcgtcgaga tgagctctaa tacgactcac tatagggact taagtgtgat ataaatatat     480
atcatacata ctagccttgt gctagatttc caacttaaca aaacggactt aaatacctac     540
agttggtccc tataggtgtt ccattgcagt gcactttagt gccctggatg gcacctggcc     600
acctgtcagg ttttttgttat taaaataata ttgttgctgg tatcactgct tgtttttgccg     660
tgtctcactt tatacatccg ttgcttgggc tacctagtat ccagcgtcct actggcgttg     720
tggtcggttc gagtgcgaag aacctctggt tcatctagcg gtacgcgggt gtgtggaagt     780
agcgcttcag acgtaccggt tctgttgcgt gaaatacggg gtcacctccc ccacatacc     840
tctaagggct tttgagccta gcgttgggct acgttctcgc acaaggtcgg ctatacggcg     900
tttgtagggg gtagtgccaa acaacccctg aggtgacagg ttctggtggt gtttcgaaaa     960
caacaatgtg tgtgccgcat aatatgcgag taatgcattt tggagcagga agtgacaaag    1020
gagtggcccc aggtagcgct gttcttaggc agtggcttcc cgaaggtaca ctccttgtcg    1080
ataatgatat tgtagattat tgatctgatg cacatgtgtc tgtgctttca gattgcaata    1140
aatgtaaaac agagcacaag tttgatcttg tgatatctga tatgtataca gataatgatt    1200
caaagagaaa gcatgaaggc gttgtagcca ataacggcaa tgatgacgtc ttcatatacc    1260
tttcaaactt tcttcgtaac aatttagctc tgggaggcag ttttgccgta aaagtaacag    1320
agacaagttg gcatgagagt ttatatgaca ttgcacagga ttgtcatggg tggacaatgg    1380
tttgtacagc agtgaatgct tcttcgtcag aagcattctt gattggtgta aattatttgg    1440
gtgcaagtga aaaggttaga gttagtggta aaaccctgca cgcaaattat atattttgga    1500
ggaattgtaa ttatttacaa acttcagcct atagtatatt tgacgttgct aagtttgatt    1560
tgaaattaaa agcaacgcca gttgtgaatt tgaaaactga acaaaagaca gacttagtct    1620
ttaatttaat taagtggtgt aagttactgg taagagatgt actgttttcs    1680
gtgaccattt tgtgtgcact atgtagtgca aatttgtttg attctgataa taattatgtg    1740
tactactacc aaaagtgctt tagaccgcca aatgggtggc acttacaagg aggtgcttat    1800
gcagtagtca gttctactaa ttatactaat aatgccggtt ctgcacatgg tgtgcactgtt    1860
ggtgttatta aggatgttta taatcaaagt gtggcttcca tagctatgac agcacctctt    1920
cagggtatgg cttggtctaa gtcacaattc tgtagtgcac actgaaattt ttctgaaatt    1980
acagttttg tcacacattg ttatagtagt ggtagtgggt cgtgtcctat aacaggcatg    2040
attccacgtg atcatattcg tatttctgca atgaaaaatg gttccttatt ttataattta    2100
acagttagcg tatctaaata ccctaatttt aaatcttttc aatgtgttaa caacttcaca    2160
tctgtttatt taaatggtga tcttgttttt acttccaaca aaactactga tgttacgtca    2220
gcaggtgtgt atttaaaagc aggtggaccc gtaattata gtattatgaa agaattaag    2280
gttcttgctt attttgttaa tggtacagca caagatgtag ttttgtgcga caattccccc    2340
aagggtttgc tagcttgtca atataacact ggcaattttt cagatggctt ttatccttt    2400
actaatagta cttggttag ggaaaagttc atcgtctatc gtgaaagtag tgttaatact    2460
acttgtgcgt taactaattt tacttttagt aatgtaagta atgcacagcc taatagtggt    2520
ggtgttaata cttttcattt atatcaaaca caaacagctc agagtggtta ttataattt    2580
```

```
aatttgtcat ttctgagtca gtttgtgtat aaggcaagtg attttatgta tgggtcctac   2640
catcctagtt gttctttag accagaaacc attaatagtg gtttatggtt taattccttg   2700
tcagtttctc ttacctatgg accctacag ggagggtgta agcaatcgt ttttagtggt   2760
aaggcaacgt gttgttacgc ctactcttat agaggcccaa tggcatgtaa aggtgtttat   2820
tcaggtgaat taagcacgaa ttttgaatgt ggattgctgg tttatgttac taagagtgat   2880
ggctctcgta tacagactag aacagagccc ttagtattaa cgcaatacaa ttataataat   2940
attactttag ataagtgtgt tgcctataat atatatggca gagtgggcca aggttttatt   3000
actaatgtga ctgattctgc tgctaatttt agttatttag cagatggtgg gttagctatt   3060
ttagatacgt cgggtgccat agatgttttt gttgtacagg gcatctatgg ccttaattat   3120
tacaaggtca atccttgtga agatgttaac caacaatttg tagtgtctgg tggcaatata   3180
gttggcattc ttacttctag aaatgaaaca ggttctgaac aggttgagaa ccagttttat   3240
gttaagttaa ccaatagctc acatcgtcgt aagcgttcta ttggccaaaa cgtaacaagt   3300
tgtccttatg ttagctatgg cagattttgt attgaaccag atggtcgtt aaagatgata   3360
gtgccagaag aattgaaaca gtttgtggca cctttactta atattactga aagtgtactc   3420
atacctaaca gttttaatct tactgttaca gatgagtaca tacaaacacg tatggataag   3480
gtccaaatca attgccttca atatgtttgc ggcaattctt tggagtgtag aaaattgttt   3540
caacaatatg gtccggtttg tgataatata ttgtctgttg taaatagtgt tagtcaaaaa   3600
gaagatatgg aacttttaag cttctattcc tctactaaac caaagggtta tgatacacca   3660
gttcttagta atgtaagcac tggtgaattt aatatttctc ttctcttgaa acccccaagc   3720
agtcctagtg ggcgttcttt cattgaagag cttttattta caagtgttga aacagttggt   3780
ttgccaactg atgctgaata taaaaaatgc acagcgggac ctttgggtac tcttaaagat   3840
cttatctgtg ctagggaata taatggttta ttagtgttgc ctccaattat tacggcggat   3900
atgcaaacaa tgtatactgc ttctttagtt ggtgctatgg cctttggtgg tattacatca   3960
gctgcagcta taccttttgc tactcagatt caggcaagaa ttaatcatct tggtattaca   4020
cagtctttgt taatgaaaaa tcaagaaaag attgctgctt cctttaataa ggccattggt   4080
catatgcagg aagttttag aagcacttct ctagcattac aacagattca agatgttgtt   4140
aataagcaga gtgctattct tactgaaact atgaattctc ttaataagaa ttttggtgct   4200
attacatcag tcattcaaga tatttacgcg caacttgacg caatccaagc agatgcacaa   4260
gttgaccgcc ttattactgg tagactttca tcactctcag tgttagcctc tgctaaacag   4320
tctgagtata ttagagtttc ccagcagcgt gaattagcca ctcaaaaaat taatgagtgt   4380
gttaaatcac aatctaatag gtacggattt tgtggtagtg gaagacatgt tctttcgata   4440
ccacaaaatg cacctaatgg tatagtgttt atacactttta cttatacacc agagagtttt   4500
gttaatgtta ctgcaatagt gggttttttgt gtaaatcctg ctaatgctag tcagtatgct   4560
atagtacctg ctaatggaag gggtattttt atacaagtta atggcacga ctatatcact   4620
gcacgtgata tgtatatgcc acgagacatt actgcaggag atatagttac tcttacgtct   4680
tgtcaagcaa attatgttaa tgtaaataaa accgtcatta ctacatttgt agaagatgac   4740
gatttttgatt tgatgatga gttgtcaaaa tggtggaatg atactaagca tcagctacca   4800
gactttgacg acttcaatta cacagtaccc atacttaata ttagcggtga aattgattat   4860
attcaaggtg ttatacaggg tcttaatgac tcccttaacta accttgaaga actttcaata   4920
attaaaactt atattaagtg gccttggtat gtttggcttg ccatattctt tgccattatt   4980
atctttatcc ttatattagg atgggttttc ttcatgactg gatgttgtgg ttgttgttgt   5040
gggtgctttg gcattattcc tctaatgagt aagtgtggta agaaatcttc ttactacact   5100
acttttgtata atgatgtggt aacttaacaa tacagaccta aaaagtctgt ttaatgatta   5160
aaagtcccac atcttttcta atattattaa ttcttctttg gtgtaaactt gcattaagtt   5220
gttttaaaga gtgtgttata acactccagc aactagtaca aatttactc caaattatta   5280
atagtaactt acaatctaga cttctgcttt ggcacagtct agactaatgt tagatttga   5340
agcaattatt gaaactggtc agcaaataac tcaacaaatt agtttctatt tacagcatat   5400
ttcaagggtg ctaagtactg aattatttga cccccttgaa gtttgtgttt acagaggagg   5460
taattgttgg gagttagagt cagctgacga gttttcaggt gatgacgaat atattgagta   5520
gatcgctcga ggagaacgga agttttctaa cagcggttta cgtgttttta ggattttag   5580
cactttatct actaggtaga gcgcttcaag ttttgtaca agcggctgac gcttgttgtc   5640
ttttttggta tacatgggta gtagttcctg gagccaaggg cacagccttt gtttataatc   5700
atacatatgg taaaaaactt aacaaaacgg agttagaaac ggtattgtt aacgaatttc   5760
caaaaaacgg ttgaaatat ggataatacc atcaattgta ctcttggtac tgaacaagca   5820
gtcagctttt ttaaggaata taatctgttt gtaactgcat tcctgttgtt tttaaccata   5880
ctacttcagt atggatacgc aactaggagc aaggttattt acatactgaa aatgatagtg   5940
ttatggtgct tttggcccct taacattgca gtaggtgtaa tctcatgtat atacccacca   6000
aacacaggag gtcttgtcgc agcgataatt cttacagtgt ttgcgtgtct ttcttttata   6060
ggttattgga tccagagtat tagacttttt aagcggtgca ggtcatggtg gtcatttaac   6120
cccgaatcta atgccgtagg ttcaatactc ctaactaatg gtcaacaatg taattttgct   6180
atagagagtg tgccgatggt gcttctcct attataaaga atggtgctct ttattgcgag   6240
ggtcagtggc ttgctaaatg tgaaccagac cacttgccta gagatatatt tgtatgcaca   6300
ccggatagac gtaatatcta tcgtatggtg caaaatatata ctggtgacca aagcggaagt   6360
aagaaaaggt ttgccacatt tgtctatgca aagcagtcaa agctagcaga agagcaagaa   6420
agtgtgtcag cagtaggagg tagtcttac acataaatgt gtgtgtgtag agagtattta   6480
aaattattct ttgacagtgc ctccgtttta agagcgcgga agagtattat ttttgaggat   6540
attaataataa atcctcttg tttcatactc tcctttcagg agttattatt taaaaaacag   6600
ttttccact ctttttgtcc aaaaacaatt gttgttaatg gtgtaacctt tcaggtagac   6660
aatggaaaag tctactacga aggaagacca attttccaaa aaggttgttg tagtttgtgg   6720
tccaattata agaagattga gaataattaa accacctaca acacttattt ttacaaatgg   6780
cgttttaggt tacaaacgct taacaaatac ggatgatgaa atggctgact agttttggaa   6840
gagctttcat ctcctgttat aaatccctat tactaactca attaagagta ttagataggt   6900
taattttaga tcacggaccc aagcgcacat taacgtgtgc taggcgagtg cttttagttc   6960
aattagttt agttttatagg ttggcttata cgcccaccca atcgctggta tgaataatag   7020
taaagataat cctttttcgcg gagcaatagc aagaaaagcg cgaatttatc tgagaggagg   7080
attagattgt gtttactttc ttaacaaagc aggacaagca gagccttgtc ccgcgtgtac   7140
ctccctagta ttccaaggga aaacttgtga ggaacactat tataataaca atcttttgtc   7200
atggcaagcg gtaaggcaac tggaaagaca gacgccccag cgccagtcat caaactagga   7260
ggaccaaagc cacctaaagt tggttcttct ggaaatgcat catggtttca accgataaag   7320
```

```
gccaagaagc taaattcacc tgtgcctaaa tttgacggta gtggtgttcc tgaaaatgaa   7380
aatctcaagt caagccagca acatggatac tggagacgcc aacacaggtt taagcctggc   7440
aaaggtggaa gaaaccagt ccctgatgct tggtactttt actacactgg aacaggaccg   7500
gccgccgacc tgaattgggg tgaaactcaa gatggtatag tgtgggttgc tgcaaagggt   7560
gctgatacta aatctagatc aaaccagggt acaagggatc ctgataagtt tgaccaatac   7620
ccactacgat tctcagatgg aggaccggat ggtaatttcc gttgggactt cataccaata   7680
aatcgtggta ggagtgggag atcaacagca gcttcatcag cagcatctag tagagcacca   7740
tctcgtgagg ggtcacgtgg acgtagaagc ggagttgaag atgatcttat agctcgcgca   7800
gcaaagatta tacaggacca gcaaaagaag ggtgcgcgca ttaccaaggc taaggctgat   7860
gaaatggctc atcgccgcta ttgcaagcgc actatcccac ctggttataa ggttgagcaa   7920
gtatttggtc cccgtactaa aggtaaggaa ggaaattttg gtgatgacaa gatgaatgag   7980
gaaggtgtta aggatgggcg tgttacggca atgctcaacc tagtccctag cagtcatgct   8040
tgtctttttg gaagtagggt gacgcccaaa ctgcagccag atggtcttca cctgagattt   8100
gaatttacta ctgtggtgtc acgtgatgat ccgcagtttg ataattatgt gaaaatttgt   8160
gatcagtgtg tcgatggtgt agggacgcgt ccaaaggacg atgaatcgag accaaagtca   8220
cgcccaaatt caagacctgc aactagagga aattctccag cgccgagaca acagcgccca   8280
aagaaggaga aaaagcccaa gaagcaggat gatgaagtag ataaggcatt gacctcagat   8340
gaggagagca acaatgcaca gctggaattt gatgatgaac ccaaggtgat taactggggg   8400
gactctgcac taggtgaaaa tgaactttga ttaacataat ggacttgctg catttgctgt   8460
cacattttgt taaatattat ttttgtgttt tactatcaat tattacaggt attgattgtg   8520
attatgttca atacttaagc ttcttctggt tgcttttttgc ttgttgtatt gttgctgtgc   8580
tttttattat tgtgattctc attagtttgc tttatcgttg aaattcaata gtaagagtta   8640
aggaagatag gcatgtagct tagcacctac atgtctatcg ccaggaaat gtctaatctg   8700
tctacttagt agcctggaaa cgaacggtag acccttagat tttaatttag tttaatttt   8760
agtttagttt aagttagttt agagtaggta taaagatgcc agtgccgggg ccacgcgtag   8820
tacgaccgag ggtacagcac taggacgccc actagggaa gagctaaatt ttagtttaag   8880
ttaagtttaa ttggctaaat atagttaaaa tttataggct agtatagagt tagagcaaaa   8940
aaaaaaaaaa aaaaaaaaaa aaaaaaaaaa aaaaaaaaaa aaaaaaaaaa aaaaaaaaaa   9000
aaaaaaaaaa aaaaaaaaaa aaaaaaaaaa aaaaagcgg ccgcatcgga tgcgggacc    9060
gacgagtgca gaggcgtgca agcgagcttg gcgtaatcat ggtcatagct gtttcctgtg   9120
tgaaattgtt atccgctcac aattccacac aacatacgag ccggaagcat aaagtgtaaa   9180
gcctggggtg cctaatgagt gagctaactc acattaattg cgttgcgctc actgcccgct   9240
ttccagtcgg gaaacctgtc gtgccagctg cattaatgaa tcggccaacg cgcggggaga   9300
ggcggtttgc gtattgggcg ctcttccgct tcctcgctca ctgactcgct gcgctcggtc   9360
gttcggctgc ggcgagcggt atcagctcac tcaaaggcgg taatacggtt atccacagaa   9420
tcaggggata acgcaggaaa gaacatgtga gcaaaaggcc agcaaaaggc caggaaccgt   9480
aaaaaggccg cgttgctggc gtttttccat aggctccgcc ccctgacga gcatcacaaa   9540
aatcgacgct caagtcagag gtggcgaaac ccgacaggac tataaagata ccaggcgttt   9600
ccccctggaa gctccctcgt gcgctctcct gttccgaccc tgccgcttac cggatacctg   9660
tccgcctttc tcccttcggg aagcgtggcg ctttctcata gctcacgctg taggtatctc   9720
agttcggtgt aggtcgttcg ctccaagctg ggctgtgtgc acgaaccccc cgttcagccc   9780
gaccgctgcg ccttatccgg taactatcgt cttgagtcca acccggtaag acacgactta   9840
tcgccactgg cagcagccac tggtaacagg attagcagag cgaggtatgt aggcggtgct   9900
acagagttct tgaagtggtg gcctaactac ggctacacta agaacagt atttggtatc    9960
tgcgctctgc tgaagccagt taccttcgga aaaagagttg gtagctcttg atccggcaaa  10020
caaaccaccg ctggtagcgg tggtttttttt gtttgcaagc agcagattac gcgcagaaaa  10080
aaaggatctc aagaagatcc tttgatcttt tctacggggt ctgacgctca gtggaacgaa  10140
aactcacgtt aagggatttt ggtcatgaga ttatcaaaaa ggatcttcac ctagatcctt  10200
ttaaattaaa aatgaagttt taaatcaatc taaagtatat atgagtaaac ttggtctgac  10260
agttaccaat gcttaatcag tgaggcacct atctcagcga tctgtctatt tcgttcatcc  10320
atagttgcct gactccccgt cgtgtagata actacgatac gggagggctt accatctggc  10380
cccagtgctg caatgatacc gcgagaccca cgctcaccgg ctccagattt atcagcaata  10440
aaccagccag ccggaagggc cgagcgcaga agtggtcctg caactttatc cgcctccatc  10500
cagtctatta attgttgccg ggaagctaga gtaagtagtt cgccagttaa tagtttgcgc  10560
aacgttgttg ccattgctac aggcatcgtg gtgtcacgct cgtcgtttgg tatggcttca  10620
ttcagctccg gttcccaacg atcaaggcga gttacatgat cccccatgtt gtgcaaaaaa  10680
gcggttagct ccttcggtcc tccgatcgtt gtcagaagta agttggccgc agtgttatca  10740
ctcatggtta tggcagcact gcataattct cttactgtca tgccatccgt aagatgcttt  10800
tctgtgactg tgagtactc aaccaagtca ttctgagaat agtgtatgcg gcgaccgagt  10860
tgctcttgcc cggcgtcaat acgggataat accgcgccac atagcagaac tttaaaagtg  10920
ctcatcattg gaaaacgttc ttcggggcga aaactctcaa ggatcttacc gctgttgaga  10980
tccagttcga tgtaacccac tcgtgcaccc aactgatctt cagcatcttt tactttcacc  11040
agcgtttctg ggtgagcaaa aacaggaagg caaaatgccg caaaaaaggg aataagggcg  11100
acacggaaat gttgaatact catactcttc cttttcaat attattgaag catttatcag  11160
ggttattgtc tcatgagcgg atacatattt gaatgtattt agaaaaataa acaaataggg  11220
gttccgcgca catttccccg aaaagtgcca cctgacgtct aagaaaccat tattatcatg  11280
acattaacct ataaaaatag gcgtatcacg aggccctttc gtc                    11323

SEQ ID NO: 69         moltype = DNA  length = 11407
FEATURE               Location/Qualifiers
misc_feature          1..11407
                      note = Vector sequence
source                1..11407
                      mol_type = other DNA
                      organism = synthetic construct
SEQUENCE: 69
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
```

```
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt ggagatcggt acttcgcgaa    420
tgcgtcgaga tcggccgccc gggtaatacg actcactata gggacttaag atagatatta    480
atatatatct attgcactag ccttgcgcta gatttcaaac ttaacaaaac ggacttaaat    540
acctacagct ggtccccata ggtgttccat tgcagtgcac tttagtgccc tggatggcac    600
ctggccacct gtcaggtttt tgttgttaaa atatcattgt tgctggtatc actgcttgtt    660
ttgccgtgtc tcactttata catccgttgc ttgggctacc tagtatccga cgtcctacgg    720
gcgccgtggt cggttcgagt gcgaaggacc tctggttcat ctagcggtag gcgggtgtgt    780
ggaagtagcg cttcagacgt actggttctg ttgcgtgaaa cgcggggtca cctccccca    840
catacctcta agggctttg agcctagcgt tgggctacgt tctcgcacaa ggtcggctat    900
acgacgtttg taggggtag tgccaaacaa cccctgaggt gacaggttct ggtggtgttt    960
cgaaaacaac aatgtgtgtg ccgcataata tgcgcgttat gcattttgga gcaggtagtg   1020
ataaaggagt ggcgcctggt agtactgttc ttaaacagtg gctccccgaa ggaacactcc   1080
ttgtcgataa tgatattgta gattatgttt ctgacgcaca cgtttctgtg ctttcagatt   1140
gcaataaata taagacagag cacaagtttg atcttgtgat atctgatatg tatacagaca   1200
atgattcaaa aagaaagcat gaaggcgtga tagccaataa tggcaatgat gacgtcttca   1260
tataccttc aagttttcta cgcaataatt tggctctggg aggcagtttt gctgtaaaat   1320
taacagagac aagttggcat gagagtttat atgacattgc acaggattgt gcatggtgga   1380
caatgttttg tacagcagtg aatgcatctt cttcagaagc attcctgatt ggtgttaatt   1440
acttgggtgc aagtgcaaag gttaaagtta gtggaaaaac actgcacgca aattatatat   1500
tttgaggaa ttgtaattat ttacaaacct ctgcttatag tatatttgat gttgctaagt   1560
ttgatttgag attgaaagca acgcagttg ttaatcttaa gactgaacaa aagacagact   1620
tagtcttta tttgataaag tgtggtaagt tactggtaag atgttggt gaagtcactg    1680
tttttagtga ccatttttgt tgcactatgt agtgcaaatt tgtttgattc tgataataat   1740
tatgtgtact actaccaaag tgcttttaga ccgccaaatg ggtggcactt acaaggaggt   1800
gcttatgcag tagtcagttc tactaattat actaataatg ccggttctgc acatgggtgc   1860
actgttggtg ttattaagga tgtttataat caaagtgtgg cttccatagc tatgacagca   1920
cctcttcagg gtatggcttg gtctaagtca caattctgta gtgcacactg taatttttct   1980
gaaattacag ttttttgtcac acattgttat agtagtggta gtgggtcgtg tcctataaca   2040
ggcatgattc cacgtgatca tattcgtatt tctgcaatga aaaatggttc cttattttat   2100
aatttaacag ttagcgtatc taaataccct aattttaaat cttttcaatg tgttaacaac   2160
ttcacatctg tttatttaaa tggtgatctt gttttttactt ccaacaaaac tactgatgtt   2220
acgtcagcag gtgtgtattt taaagcaggt ggacctgtaa attatagtat tatgaaagaa   2280
tttaaggttc ttgcttattt tgttaatggt acagcacaag atgtagtttt gtgcgacaat   2340
tcccccaagg gtttgctagc ttgtcaatat aacactggca atttttcaga tggcttttat   2400
ccttttacta atagtacttt ggttagggaa aagttcatcg tctatcgtga aagtagtgtt   2460
aatactactt gtgcgttaac taattttact tttagtaatg taagtaatgc acagcctaat   2520
agtggtggtg ttaatacttt tcatttatat caaacacaaa cagctcagag tggttattat   2580
aatttttaatt tgtcatttct gagtcagttt gtgtataagg caagtgattt tatgtatggg   2640
tcctaccatc ctagttgttc ttttagacca gaaaccatta atagtggttt atggtttaat   2700
tccttgtcag tttctcttac ctatggaccc ctacaggggg ggtgtaagca atctgttttt   2760
agtggtaagg caacgtgttg ttacgcctac tcttatagag gcccaatggc atgtaaaggt   2820
gtttattcag gtgaattaag cacgaatttt gaatgtggat tgctggttta tgttactaag   2880
agtgatggct ctcgtataca gactagaaca gagcccttag tattaacgca atacaattat   2940
aataatatta ctttagataa gtgtgttgcc tataatatat atggcagagt gggccaaggt   3000
tttattacta atgtgactga ttctgctgct aattttagtt atttagcaga tggtgggtta   3060
gctattttag atacgtcggg tgccatagat gtttttgttg tacagggcat ctatggcctt   3120
aattattaca aggtcaatcc ttgtgaagat gttaaccaac aatttgtagt gtctggtggc   3180
aatatagttg gcattcttac ttctagaaat gaaacaggtt ctgaacaggt tgagaaccag   3240
ttttatgtta agttaaccaa tagctcacat cgtcgtaagc gttctattgg ccaaaacgta   3300
acaagttgtc cttatgttag ctatggcaga ttttgtattg aaccagatgg ttcgttaaag   3360
atgatagtgc cagaagaatt gaaacagttt gtggcacctt acttaatat tactgaaagt   3420
gtactcatac ctaacagttt taatcttact gttacagatg agtacataca aacacgtatg   3480
gataaggtcc aaatcaattg ccttcaatat gtttgcggca attctttgga gtgtagaaaa   3540
ttgtttcaac aatatggtcc ggtttgtgat aatatattgt ctgttgtaaa tagtgttagt   3600
caaaagaag atatgaact tttaagcttc tattcctcta ctaaaccaaa gggttatgat   3660
acaccagttc ttagtaatgt aagcactggt gaatttaata tttctcttct cttgaaaccc   3720
ccaagcagtc ctagtgggcg ttcttttcatt gaagagcttt tatttacaag tgttgaaaca   3780
gttggtttgc caactgatgc tgaatataaa aaatgcacag cgggaccttt gggtactctt   3840
aaagatctta tctgtgctag ggaatataat ggttattag tgttgcctcc aattattacg   3900
gcggatatgc aaacaatgta tactgcttct ttagtgggtg ctatggcctt tggtggtatt   3960
acatcagctg cagctatacc ttttgctact cagattcagg caagaattaa tcatcttgat   4020
attacacagt ctttgttaat gaaaaatcaa gaaaagattg ctgcttcctt taataaggcc   4080
attggtcata tgcaggaagg ttttagaagc acttctctag cattacaaca gattcaagat   4140
gttgttaata agcagagtgc tattcttact gaaactatga atctcttaa taagaatttt   4200
ggtgctatta catcagtcat tcaagatatt tacgcgcaac ttgacgcaat ccaagcagat   4260
gcacaagttg accgcctat tactggtaga ctttcatcac tctcagtgtt agcctctgct   4320
aaacagtctg agtatattag agtttcccag cagcgtgaat tagccactca aaaaattaat   4380
gagtgtgtta aatcacaatc taataggtac ggatttgtg gtagtggaag acatgttctt   4440
tcgataccac aaaatgcacc taatggtata gtgtttatac actttactta tacaccagag   4500
agttttgtta atgttactgc aatagtgggt ttttgtgtaa atcctgctaa tgctagtcag   4560
tatgctatag taccgctaa tggaagggt attttttaag cacgtactat   4620
atcactgcac gtgatatgta tatgccacga gacattactg caggagatat agttactctt   4680
acgtcttgtc aagcaaatta tgttaatgta aataaaaccg tcattactac atttgtagaa   4740
gatgacgatt tgattttga tgatgagttg tcaaaatggt ggaatgatac taagcatcag   4800
ctaccagact ttgacgactt caattacaca gtacccatac ttaatattag cggtgaaatt   4860
gattatattc aaggtgttat acagggtctt aatgactccc ttatagacct tgaagaactt   4920
```

```
tcaataatta aaacttatat taagtggcct tggtatgttt ggcttgccat attcttttgcc   4980
attattatct ttatccttat attaggatgg gttttcttca tgactggatg ttgtggttgt   5040
tgttgtgggt gctttggcat tattcctcta atgagtaagt gtggtaagaa atcttcttac   5100
tacactactt ttgataatga tgtggtaact taacaataca gacctaaaaa gtctgtttaa   5160
tgatccaaag tcccactagt ttcttaatag tattaatttt gctttggtgt aaacttgtac   5220
taagttgttt tagagagttt attattgccc ttcaacaact aacacaagtt ttactccaaa   5280
ttatcgatag taatttacag tctagactga cccttttggca cagtctagac taatgttaaa   5340
cttagaagca attattgaaa ccggtgatca agtgattcaa aaaatcagtt tcaatttaca   5400
gcatatttca agtgtattaa acacagaagt atttgacccc tttgactatt gttattacag   5460
aggaggtaat ttttgggaaa tagagtcagc tgaagattgt tcaggtgatg atgaatttat   5520
tgaataagtc gctagaggag aatggaagtt ttctaacggc actttacata tttgtaggat   5580
ttttagcatt ttatcttcta ggtagagcac ttcaagcatt tgtacaggct gctgatgctt   5640
gttgtttatt ttggtacacg tggttagtaa ttccaggagt taagggtaca gcctttgtat   5700
acaagtatac atatggtaga aaacttaaca attcggaatt agaagcagtt gttgttaacg   5760
agttcctaa gaacggttgg aataataaaa atccagcaaa ttttcaagat gtccaacgaa   5820
acaaattgta ctcttgactt tgaacagtca gttgagcttt ttaaagagta taatttattt   5880
ataactgcat tcttgttgtt cttaaccata atacttcagt atggttatgc aacgcgtagt   5940
aagtttattt atatacttaa aatgatagtg ttatggtgct tttggcccct taacattgca   6000
gtaggtgtaa tttcatgtat atacccacca aacacaggag gtcttgtcgc agcgataata   6060
cttactgtgt ttgcgtgtct ttcttttgta ggttattgga tccagagtat tagactcttt   6120
aagcggtgta gatcttggtg gtcatttaac ccagaatcta acgccgtagg ttcaatactc   6180
ctaactaatg gtcaacaatg taattttgct atagagagtg tgccgatggt gcttctcct   6240
attataaaga atggtgttct ttattgtgag ggtcagtggc ttgctaaatg tgaaccagac   6300
cacttgccta agacatatt tgtatgcaca ccagatagac gtaatatcta tcgtatggtg   6360
cagaaataca ctggtgacca aagcggaaat aagaaaggt ttgctacatt tgtctatgca   6420
aagcagtcag tagacactgg cgagctagaa agtgtagcaa caggtggaag tagccttttac   6480
acataaaatgt gtgtgtgtag agagtattta aaattattct tcaatagtgc ctctatttta   6540
agagcgcgga agagtatttg ttttgaggat attaatataa atcctctttg ttttgtactc   6600
tcttacaag agttattatt taagcaacag ttttttccttt cctttgtttg gaagaaagtt   6660
gttgttaatg gtgtagaatt ccaagtagaa aatggaaaag tccactacga aggaaacccc   6720
attttccaaa aaggttgttg taggttgtgg tcccattata agaaggatta aatggattaa   6780
accacctaca ctacttactt gtaataaggg cgtttggact tacaagcgct taacaaatac   6840
agacgatgaa atggctgact agttttggaa gagcagttat ttcttgttat aaagccctac   6900
tattaactca gttaagagta ttagataggt taattttaga tcacggacca aagcgagtct   6960
taacgtgtgg taggcgagtg cttttatctc aattagattt agtttatagg ttggcatata   7020
cgcccaccca atcgctggta tgaataatag taaagataat cctttttcgcg gagcaatagc   7080
aagaaaagcg cgaatttatc tgagagaagg attagagtgt gtttactttc ttaacaaagc   7140
aggaacacac gagccttgtc ccgcgtgtac ctccctagta tttcagggga aaacttgtga   7200
ggaacacaca gataataata atcttttgtc atggcgagcg gtaagacaac tgggaagaca   7260
gacgccccag cgccagtcat caaactagga gggccaaaac cacctaaagt tggttcttct   7320
ggaaatgcta gctggtttca agcactaaaa gccaagaagt taaattcacc tcctcctaag   7380
tttgaaggta gcggcgttcc tgataatgaa aatcttaaat taagccagca acatgggtac   7440
tggagacgtc aagccaggta caagccaggt tgatgtggta agggaagaaa atccagatgct   7500
tggtacttct attacactgg aacaggacca gccgctgacc tgaattgggg tgatagccaa   7560
gatggtatag tgtgggttc tgcaaagggt gctgatacta aatctagatc taaccagggt   7620
acaagggatc ctgataagtt tgaccaatac ccgctacgat tctcagatgg aggacctgat   7680
ggtaatttcc gttgggactt cattccaata aatcgtggta ggagtggaag atcaacagcg   7740
gcttcatcag cagcatctag tagagcaccg tcgcgtgatg gctcgcgtgg acgtagaagc   7800
ggagctgaag atgatcttat agctcgtgca gcaaagatca ttcaggatca gcagaagaag   7860
ggttctcgca ttactaaagc taaggccgat gaaatggctc atcgccggta ttgtaagcgt   7920
actatccac ctggttataa ggttgatcaa gtatttggct cccgtactaa aggtaaggag   7980
ggaaattttg gtgatgacaa gatgaatgag gagggtatta aggatgggcg cgttacagca   8040
atgctcaacc tagtccctag cagccatgct tgtctttttg gaagtagagt gacgcccaaa   8100
cttcaaccag atgggctgca cttgagattt gaattcactg ctgtggttc tagggatgat   8160
ccgcagtttg ataattatgt gaaaattgt gatcagtgtg tgatggtgat agggactcgg   8220
ccaaaagacg atgaaccgag accaaagtca cgcccaaatt caagacctgc tacaagaaca   8280
agttctccag cgccaagaca acagcgtcaa aagaaggaga agaagtcaaa gaagcaggat   8340
gatgaagtag ataaggcatt gacctcagat gaggagagga acaatgcaca gctggaattt   8400
gatgatgaac cgaaagtgat taactggggg gattcagcac ttggagagaa tgagttgtaa   8460
agctagattt ccaacttaac atcatgacg tgcgtatgct gttttccct actatagact   8520
ttttagcata ttatttttg ctatttgtat ggtttattac aggtgaagat tgtatgtatt   8580
tgttgtacac tcgtatgttc tatattatgt tttctgtagt tgttattagt gttgttcttg   8640
ttcttactct actgttctct tttctttatt ttagagtatc aataagaatc aaggaagata   8700
ggcatgtagt ttgattacct acatgtctat cgccagggaa atgtccaata tgtctactta   8760
gtagcctgga aacgaacggt agaccttag attttaattt agtttaattt ttagtttagt   8820
ttaagttagt ttagagtagg tataaagaag ccagtgccgg ggccacgcgg agtacgatcg   8880
agggtacagc actaggacgc ccactagggg aagagctaaa ttttagttta agttaagttt   8940
aattggctaa gtatagttaa aatttataag ctagtataga gttagagcaa aaaaaaaaaa   9000
aaaaaaaaaa aaaaaaaaaa aaaaaaaaaa aaaaaaaaaa aaaaaaaaaa aaaaaaaaaa   9060
aaaaaaaaaa aaaaaaaaaa aaaaaaaagt ttaaacttaa ttaagaattc ccttggctcg   9120
agttcgaaat cggatgccgg gaccgacgag tgcagaggcg tgcaagcgag cttggcgtaa   9180
tcatggtcat agctgtttcc tgtgtgaaat tgttatccgc tcacaattcc acacaacata   9240
cgagccggaa gcataaagtg taaagcctgg ggtgcctaat gagtgagcta actcacatta   9300
attgcgttgc gctcactgcc cgctttccag tcgggaaacc tgtcgtgcca gctgcattaa   9360
tgaatcggcc aacgcgcggg gagaggcggt ttgcgtattg ggcgctcttc cgcttcctcg   9420
ctcactgact cgctgcgctc ggtcgttcgg ctgcggcgag cggtatcagc tcactcaaag   9480
gcggtaatac ggttatccac agaatcaggg gataacgcag gaaagaacat gtgagcaaaa   9540
ggccagcaaa aggccaggaa ccgtaaaaag gccgcgttgc tggcgtttt ccataggctc   9600
cgcccccctg acgagcatca caaaaatcga cgctcaagtc agaggtggcg aaacccgaca   9660
```

```
ggactataaa gataccaggc gtttcccct ggaagctccc tcgtgcgctc tcctgttccg  9720
accctgccgc ttaccggata cctgtccgcc tttctccctt cgggaagcgt ggcgcttct  9780
catagctcac gctgtaggta tctcagttcg gtgtaggtcg ttcgctccaa gctgggctgt  9840
gtgcacgaac cccccgttca gcccgaccgc tgcgccttat ccggtaacta tcgtcttgag  9900
tccaacccgg taagacacga cttatcgcca ctggcagcca ccactggtaa caggattagc  9960
agagcgaggt atgtaggcgg tgctacagag ttcttgaagt ggtggcctaa ctacggctac 10020
actagaagaa cagtatttgg tatctgcgct ctgctgaagc cagttacctt cggaaaaaga 10080
gttggtagct cttgatccgg caaacaaacc accgctggta gcggtggttt ttttgtttgc 10140
aagcagcaga ttacgcgcag aaaaaaagga tctcaagaag atcctttgat cttttctacg 10200
gggtctgacg ctcagtggaa cgaaaactca cgttaaggga ttttggtcat gagattatca 10260
aaaaggatct tcacctagat cctttttaaat taaaaatgaa gttttaaatc aatctaaagt 10320
atatatgagt aaacttggtc tgacagttac caatgcttaa tcagtgaggc acctatctca 10380
gcgatctgtc tatttcgttc atccatagtt gcctgactcc ccgtcgtgta gataactacg 10440
atacgggagg gcttaccatc tggccccagt gctgcaatga taccgcgaga cccacgctca 10500
ccggctccag atttatcagc aataaaccag ccagccggaa gggccgagcg cagaagtggt 10560
cctgcaactt tatccgcctc catccagtct attaattgtt gccgggaagc tagagtaagt 10620
agttcgccag ttaatagttt gcgcaacgtt gttgccattg ctacaggcat cgtggtgtca 10680
cgctcgtcgt ttggtatggc ttcattcagc tccggttccc aacgatcaag gcgagttaca 10740
tgatccccca tgttgtgcaa aaaagcggtt agctccttcg gtcctccgat cgttgtcaga 10800
agtaagttgg ccgcagtgtt atcactcatg gttatggcag cactgcataa ttctcttact 10860
gtcatgccat ccgtaagatg cttttctgtg actggtgagt actcaaccaa gtcattctga 10920
gaatagtgta tgcggcgacc gagttgctct tgcccggcgt caatacggga taataccgcg 10980
ccacatagca gaactttaaa agtgctcatc attggaaaac gttcttcggg gcgaaaactc 11040
tcaaggatct taccgctgtt gagatccagt tcgatgtaac ccactcgtgc acccaactga 11100
tcttcagcat cttttacttt caccagcgtt tctgggtgag caaaaacagg aaggcaaaat 11160
gccgcaaaaa agggaataag ggcgacacgg aaatgttgaa tactcatact cttcctttc 11220
caatattatt gaagcattta tcagggttat tgtctcatga gcggatacat atttgaatgt 11280
atttagaaaa ataaacaaat aggggttccg cgcacattc cccgaaaagt gccacctgac 11340
gtctaagaaa ccattattat catgacatta acctataaaa ataggcgtat cacgaggccc 11400
tttcgtc                                                          11407
```

SEQ ID NO: 70           moltype = DNA   length = 52
FEATURE                 Location/Qualifiers
misc_feature            1..52
                        note = Primer
source                  1..52
                        mol_type = other DNA
                        organism = synthetic construct
SEQUENCE: 70
cagagcacaa gtttgatctt gtgatatctg atatgtatac agacaatgat tc             52

SEQ ID NO: 71           moltype = DNA   length = 32
FEATURE                 Location/Qualifiers
misc_feature            1..32
                        note = Primer
source                  1..32
                        mol_type = other DNA
                        organism = synthetic construct
SEQUENCE: 71
acttcaccaa catctcttac cagtaactta cc                                   32

SEQ ID NO: 72           moltype = DNA   length = 31
FEATURE                 Location/Qualifiers
misc_feature            1..31
                        note = Primer
source                  1..31
                        mol_type = other DNA
                        organism = synthetic construct
SEQUENCE: 72
ttactggtaa gagatgttgg tgaagtcact g                                    31

SEQ ID NO: 73           moltype = DNA   length = 35
FEATURE                 Location/Qualifiers
misc_feature            1..35
                        note = Primer
source                  1..35
                        mol_type = other DNA
                        organism = synthetic construct
SEQUENCE: 73
ggactttgga tcattaaaca gacttttag gtctg                                 35

SEQ ID NO: 74           moltype = DNA   length = 32
FEATURE                 Location/Qualifiers
misc_feature            1..32
                        note = Primer
source                  1..32
                        mol_type = other DNA
                        organism = synthetic construct
SEQUENCE: 74

```
aaagtctgtt taatgatcca aagtcccact ag                                     32

SEQ ID NO: 75           moltype = DNA  length = 48
FEATURE                 Location/Qualifiers
misc_feature            1..48
                        note = Primer
source                  1..48
                        mol_type = other DNA
                        organism = synthetic construct
SEQUENCE: 75
cttaactcct ggaattacta accacgtgta ccaaaataaa caacaagc                    48

SEQ ID NO: 76           moltype = AA  length = 1168
FEATURE                 Location/Qualifiers
source                  1..1168
                        mol_type = protein
                        organism = unidentified
                        note = Avian infectious bronchitis virus
SEQUENCE: 76
MLVKSLFLVT ILFALCSANL YDNESFVYYY QSAFRPGHGW HLHGGAYAVV NVSSENNNAG       60
TAPSCTAGAI GYSKNLSAAS VAMTAPLSGM SWSANSFCTA HCNFTSYIVF VTHCYKSGSN       120
SCPLTGLIPS GYIRIAAMKH GSAMPGHLFY NLTVSVTKYP KFRSLQCVNN YTSVYLNGDL       180
VFTSNYTEDV VAAGVHFKSG GPITYKVMRE VKALAYFVNG TAHDVILCDD TPRGLLACQY       240
NTGNFSDGFY PFTNTSIVKD KFIVYRESSV NTTLTLTNFT FSNESGAPPN TGGVDSFILY       300
QTQTAQSGYY NFNFSFLSSF VYRESNYMYG SYHPRCSFRP ETLNGLWFNS LSVSLTYGPI       360
QGGCKQSVFN GKATCCYAYS YGGPRGCKGV YRGELTQHFE CGLLVYVTKS DGSRIQTATQ       420
PPVLTQNFYN NINLGKCVDY NIYGRIGQGL ITNVTDLAVS YNYLSDAGLA ILDTSGAIDI       480
FVVQGEYGPN YYKVNPCEDV NQQFVVSGGK LVGILTSRNE TGSQLLENQF YIKITNGTRR       540
SRRSVTENVT NCPYVSYGKF CIKPDGSISV IVPKELDQFV APLLNVTEYV LIPNSFNLTV       600
TDEYIQTRMD KIQINCLQYV CGNSLACRKL FQQYGPVCDN ILSVVNSVGQ KEDMELLNFY       660
SSTKPARFNT PVFSNLSTGE FNISLLLTSP SSPRRRSFIE DLLFTSVESV GLPTDDAYKK       720
CTAGPLGFFK DLACAREYNG LLVLPPIITA EMQTLYTSSL VASMAFGGIT AAGAIPFATQ       780
LQARINHLGI TQSLLLKNQE KIAASFNKAI GHMQEGFRST SLALQQIQDV VNKQSAILTE       840
TMAALNKNFG AISSVIQDIY QQLDSIQADA QVDRLITGRL SSLSVLASAK QSEYIRVSQQ       900
RELATQKINE CVKSQSIRYS FCGNGRHVLT IPQNAPNGIV FIHFTYTPES FINVTAIVGF       960
CVSPANASQY AIVPANGRGI FIQVNGSYYI TARDMYMPRD ITAGDIVTLT SCQANYVSVN       1020
KTVITTFVDN DDFDFDDELS KWWNDTKHEL PDFDKFNYTV PILDIDSEID RIQGVIQGLN       1080
DSLIDLETLS ILKTYIKWPW YVWLAIAFAT IIFILILGWL FFMTGCCGCC CGCFGIIPLM       1140
SKCGKKSSYY TTFDNDVVTE QYRPKKSV                                          1168

SEQ ID NO: 77           moltype = AA  length = 1168
FEATURE                 Location/Qualifiers
source                  1..1168
                        mol_type = protein
                        organism = unidentified
                        note = Avian infectious bronchitis virus
SEQUENCE: 77
MLVKSLFLVT ILFALCSANL YDNESFVYYY QSAFRPGHGW HLHGGAYAVV NVSSENNNAG       60
TAPSCTAGAI GYSKNLSAAS VAMTAPLSGM SWSANSFCTA HCNFTSYIVF VTHCYKSGSN       120
SCPLTGLIPS GYIRIAAMKH GSAMPGHLFY NLTVSVTKYP KFRSLQCVNN YTSVYLNGDL       180
VFTSNYTEDV VAAGVHFKSG GPITYKVMRE VKALAYFVNG TAHDVILCDD TPRGLLACQY       240
NTGNFSDGFY PFTNTSIVKD KFIVYRESSV NTTCTLTNFT FSNESGAPPN TGGVDSFILY       300
QTQTAQSGYY NFNFSFLSSF VYRESNYMYG SYHPRCSFRP ETLNGLWFNS LSVSLTYGPI       360
QGGCKQSVFN GKATCCYAYS YGGPRGCKGV YRGELTQHFE CGLLVYVTKS DGSRIQTATQ       420
PPVLTQNFYN NINLGKCVDY NIYGRIGQGL ITNVTDLAVS YNYLSDAGLA ILDTSGAIDI       480
FVVQGEYGPN YYKVNPCEDV NQQFVVSGGK LVGILTSRNE TGSQLLENQF YIKITNGTRR       540
SRRSVTENVT NCPYVSYGKF CIKPDGSISV IVPKELDQFV APLLNVTEYV LIPNSFNLTV       600
TDEYIQTRMD KIQINCLQYV CGNSLACRKL FQQYGPVCDN ILSVVNSVGQ KEDMELLNFY       660
SSTKPARFNT PVFSNLSTGE FNISLLLTSP SSPRRRSFIE DLLFTSVESV GLPTDDAYKK       720
CTAGPLGFFK DLACAREYNG LLVLPPIITA EMQTLYTSSL VASMAFGGIT AAGAIPFATQ       780
LQARINHLGI TQSLLLKNQE KIAASFNKAI GHMQEGFRST SLALQQIQDV VNKQSAILTE       840
TMAALNKNFG AISSVIQDIY QQLDSIQADA QVDRLITGRL SSLSVLASAK QSEYIRVSQQ       900
RELATQKINE CVKSQSIRYS FCGNGRHVLT IPQNAPNGIV FIHFTYTPES FINVTAIVGF       960
CVSPANASQY AIVPANGRGI FIQVNGSYYI TARDMYMPRD ITAGDIVTLT SCQANYVSVN       1020
KTVITTFVDN DDFDFDDELS KWWNDTKHEL PDFDKFNYTV PILDIDSEID RIQGVIQGLN       1080
DSLIDLETLS ILKTYIKWPW YVWLAIAFAT IIFILILGWL FFMTGCCGCC CGCFGIIPLM       1140
SKCGKKSSYY TTFDNDVVTE QYRPKKSV                                          1168

SEQ ID NO: 78           moltype = DNA  length = 6217
FEATURE                 Location/Qualifiers
misc_feature            1..6217
                        note = Plasmid
source                  1..6217
                        mol_type = other DNA
                        organism = synthetic construct
SEQUENCE: 78
tcgcgcgttt cggtgatgac ggtgaaaacc tctgacacat gcagctcccg gagacggtca       60
cagcttgtct gtaagcggat gccgggagca gacaagcccg tcagggcgcg tcagcgggtg       120
ttggcgggtg tcgggctggc ttaactatg cggcatcaga gcagattgta ctgagagtgc       180
```

```
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgagctcggt acctcgcgaa    420
tgcatctaga tatgttggtg aagtcactgt ttctagtcac cattttgttt gcactatgta    480
gtgctaattt atatgacaac gaatcttttg tgtattacta ccagagtgct tttaggccaa    540
gacatggttg gcatttacat ggaggtgctt atgcagtagt taatgtgtct agtgaaaata    600
ataatgcagg tactgcccca agttgcactg ctggtgctat tggctacagt aagaatctca    660
gtgcggcctc agtagccatg actgcaccac taagtggtat gtcatggtct gccaactctt    720
tttgtacagc ccactgtaat tttacttctt atatagtgtt tgttacacat tgttataaga    780
gcggatctaa tagttgtcct ttgacaggtc ttattccaag cggttatatt cgtattgctg    840
ctatgaaaca tggaagtgct atgcctggtc acttatttta taatttaaca gtttctgtga    900
ctaaatatcc taagtttaga tcgctacaat gtgttaataa ttatacttct gtatatttaa    960
atggtgacct tgttttcaca tctaactata ctgaagatgt tgtagctgca ggtgtccatt   1020
ttaaaagtgg tggacctata acttataaag ttatgagaga ggttaaagcc ttggcttatt   1080
ttgtcaatgg tactgcacat gatgtcattc tatgtgatga cacacctaga ggtttgttag   1140
catgccaata taatactggc aatttttcag atggcttcta tccttttact aatactagta   1200
ttgttaagga taagttttatt gtttatcgtg aaagtagtgt caatactact tgtacattaa   1260
ctaatttcac gtttagtaat gaaagtggtg cccctcctaa tacaggtggt gttgacagtt   1320
ttatttata ccagacacaa acagctcaga gtgttatta taatttttaac ttttcatttc   1380
tgagtagttt tgtttatagg gaaagtaatt atatgtatgg atcttaccat ccacgttgta   1440
gttttagacc tgaaacccctt aatgggtttgt ggttaattc cctttctgtt tcattaacat   1500
acggtcccat tcaaggtggt tgtaagcaat ctgtatttaa tggtaaagca acttgttgtt   1560
atgcttattc atacggagga cctcgtggtt gtaaaggtgt ctatagaggt gagctaaacc   1620
agcatttga atgtggtttg ttagtttatg ttactaagag cgatggctcc cgtatacaaa   1680
ctgcaacaca accacctgta ttaacccaaa attttttataa taacatcaat ttaggtaagt   1740
gtgttgatta taatatatatat ggcagaattg gccaagtgct tattactaat gtaaccgact   1800
tagctgttag ttataattat ttatcagacg caggtttggc tatttttagat acatctggtg   1860
ccatagacat cttcgttgta caaggtgaat atggtcctaa ctattataag gttaatccat   1920
gtgaagatgt caaccaacag tttgtagttt ctggtggtaa attagtaggt attctcactt   1980
cacgtaatga aacaggttct cagcttcttg agaaccagtt ttatattaaa atcactaatg   2040
gaactcgtcg ttctagacgt tctgttactg aaaatgttac aaattgccct tatgttagtt   2100
atggcaagtt ttgtataaaa cctgatggtt caatttctgt aatagtacca aaagaactgg   2160
atcagtttgt ggcacctta cttaatgtta ctgaatatgt gctcataccct aacagttta   2220
atttaactgt tacagatgag tacatacaaa cgcgtatgga taagatccaa attaattgcc   2280
tgcagtatgt ttgtggcaat tctttggcct gtagaaaagct gtttcaacaa tatgggcctg   2340
tttgtgacaa catattgtct gtagtaaata gtgttggtca aaaagaagat atggaactttt  2400
taaatttcta ttcttctact aaaccagctc gttttaatac accagtttttt agtaatctta   2460
gcactggtga gtttaatatt tctctttttgt taacatcccc tagtagtcct aggaggcgtt   2520
cttttattga agatctttta tttacaagtg ttgaatctgt aggattacca acagatgacg   2580
catacaaaaa gtgcactgca ggaccttag gcttttttaa agaccttgca tgtgctcgtg   2640
aatataatgg tttgcttgtg ttgcctccta ttataacagc agaaatgcaa actttgtata   2700
ctagttcttt agtagcttct atggctttgt gtggttattac tgcagctggt gccatacctt   2760
ttgccacaca actgcaggct agaattaatc acttgggtat tacccagtca cttttgttga   2820
agaatcaaga aaaaattgct gcttccttta ataaggccat tggtcatatg caggaaggtt   2880
ttaggagtac atctctagca ttacaacaaa ttcaagatgt tgttaataag cagagtgcta   2940
ttcttactga gactatggca gcacttaata aaaattttgg tgctatttct tctgtgattc   3000
aagacattta ccagcaactt gattccatac aagcagatgc tcaagtggat cggctcataa   3060
ctggtagatt gtcatcactt tctgtcttag catctgctaa gcagtcggag tacattagag   3120
tgtcacaaca gcgtgagtta gctactcaga aaattaatga gtgtgttaaa tcacagtcta   3180
ttaggtattc cttttgtggt aatggacgac atgttttaac cataccacaa aatgccccta   3240
atggtatagt gtttatacac tttacttata caccagagag ctttattaat gttactgcaa   3300
tagtgggttt ttgtgtaagt cctgctaatg ctagtcagta tgcaatagtg cccgctaatg   3360
gtaggggtat ttttatacaa gttaatggta ttactacat cactgcacga gatatgtata   3420
tgccaagaga tattactgca ggagatatag ttacgcttac ttcttgtcaa gcaaattatg   3480
taagtgtaaa taagaccgtc attactacat ttgtagacaa tgatgatttt gattttgatg   3540
atgaattgtc aaaatggtgg aatgatacta agcatgagct accagacttt gacaaattca   3600
attacacagt acctatactt gacattgata gtgaaattga tcgtattcaa ggcgttatac   3660
agggtcttaa cgactctcta atagaccttg aaacactatc aatactcaaa acttatatta   3720
agtggcccttg gtatgtgtgg ttagccatag cttttgccac tattatcttc atccttaatac   3780
taggatggtt gttttttcatg actggttgtt gtggttgttg ttgtggatgc tttggcatta   3840
ttcctttaat gagtaagtgt ggtaagaaat cttcttatta cacgactttt gataatgatg   3900
tggtaactga acaatacaga cctaaaaagt ctgtttaaat cggatcccgg gccgtcgac   3960
tgcagaggcc tgcatgcaag cttggcgtaa tcatggtcat agctgtttcc tgtgtgaaat   4020
tgttatccgc tcacaattcc acacaacata cgagccggaa gcataaagtg taaagcctgg   4080
ggtgcctaat gagtgagcta actcacatta attgcgttgc gctcactgcc cgctttccag   4140
tcgggaaacc tgtcgtgcca gctgcattaa tgaatcggcc aacgcgcggg gagaggcggt   4200
ttgcgtattg ggcgctcttc cgcttcctcg ctcactgact cgctgcgctc ggtcgttcgg   4260
ctgcggcgag cggtatcagc tcactcaaag gcggtaatac ggttatccac agaatcaggg   4320
gataacgcag gaaagaacat gtgagcaaaa ggccagcaaa aggccaggaa ccgtaaaaag   4380
gccgcgttgc tggcgttttt ccataggctc cgcccccctg acgagcatca caaaaatcga   4440
cgctcaagtc agaggtggcg aaacccgaca ggactataaa gataccaggc gtttccccct   4500
ggaagctccc tcgtgcgctc tcctgttccg accctgccgc ttaccggata cctgtccgcc   4560
tttctccctt cgggaagcgt ggcgctttct catagctcac gctgtaggta tctcagttcg   4620
gtgtaggtcg ttcgctccaa gctgggctgt gtgcacgaac cccccgttca gcccgaccgc   4680
tgcgccttat ccggtaacta tcgtcttgag tccaacccgg taagacacga cttatcgcca   4740
ctggcagcag ccactggtaa caggattagc agagcgaggt atgtaggcgg tgctacagag   4800
ttcttgaagt ggtggcctaa ctacggctac actagaagaa cagtatttgg tatctgcgct   4860
ctgctgaagc cagttacctt cggaaaaaga gttggtagct cttgatccgg caaacaaacc   4920
```

```
accgctggta gcggtggttt ttttgtttgc aagcagcaga ttacgcgcag aaaaaaagga  4980
tctcaagaag atcctttgat cttttctacg gggtctgacg ctcagtggaa cgaaaactca  5040
cgttaaggga ttttggtcat gagattatca aaaaggatct tcacctagat ccttttaaat  5100
taaaaatgaa gttttaaatc aatctaaagt atatatgagt aaacttggtc tgacagttac  5160
caatgcttaa tcagtgaggc acctatctca gcgatctgtc tatttcgttc atccatagtt  5220
gcctgactcc ccgtcgtgta gataactacg atacgggagg cttaccatc tggccccagt  5280
gctgcaatga taccgcgaga cccacgctca ccggctccag atttatcagc aataaaccag  5340
ccagccggaa gggccgagcg cagaagtggt cctgcaactt tatccgcctc catccagtct  5400
attaattgtt gccgggaagc tagagtaagt agttcgccag ttaatagttt gcgcaacgtt  5460
gttgccattg ctacaggcat cgtggtgtca cgctcgtcgt ttggtatggc ttcattcagc  5520
tccggttccc aacgatcaag gcgagttaca tgatccccca tgttgtgcaa aaaagcggtt  5580
agctccttcg gtcctccgat cgttgtcaga gtaagttgg ccgcagtgtt atcactcatg  5640
gttatggcag cactgcataa ttctcttact gtcatgccat ccgtaagatg cttttctgtg  5700
actggtgagt actcaaccaa gtcattctga gaatagtgta tgcggcgacc gagttgctct  5760
tgcccggcgt caatacggga taataccgcg ccacatagca gaactttaaa agtgctcatc  5820
attggaaaac gttcttcggg gcgaaaactc tcaaggatct taccgctgtt gagatccagt  5880
tcgatgtaac ccactcgtgc acccaactga tcttcagcat cttttacttt caccagcgtt  5940
tctgggtgag caaaaacagg aaggcaaaat gccgcaaaaa agggaataag ggcgacacgg  6000
aaatgttgaa tactcatact cttcctttttt caatattatt gaagcattta tcagggttat  6060
tgtctcatga gcggatacat atttgaatgt atttagaaaa ataaacaaat aggggttccg  6120
cgcacatttc cccgaaaagt gccacctgac gtctaagaaa ccattattat catgacatta  6180
acctataaaa ataggcgtat cacgaggccc tttcgtc                           6217
```

```
SEQ ID NO: 79            moltype = DNA   length = 11416
FEATURE                  Location/Qualifiers
misc_feature             1..11416
                         note = Plasmid
source                   1..11416
                         mol_type = other DNA
                         organism = synthetic construct
SEQUENCE: 79
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcggggctgg cttaactatg cggcatcaga gcagattgta ctgagagtgc   180
accatatgcg gtgtgaaata ccgcacagat gcgtaaggag aaaataccgc atcaggcgcc   240
attcgccatt caggctgcgc aactgttggg aaggggcgatc ggtgcgggcc tcttcgctat   300
tacgccagct ggcgaaaggg ggatgtgctg caaggcgatt aagttgggta acgccagggt   360
ttttcccagt cacgacgttgt aaaacgacgg ccagtgaatt ggagatcggt acttcgcgaa   420
tgcgtcgaga tcggccgccc gggtaatacg actcactata gggacttaag atagatatta   480
atatatatct attgcactag ccttgcgcta gatttcaaac ttaacaaaac ggacttaaat   540
acctacagct ggtccccata ggtgttccat tgcagtgcac tttagtgccc tggatggcac   600
ctggccacct gtcaggtttt tgttgttaaa atatcattgt tgctggtatc actgcttgtt   660
ttgccgtgtc tcactttata catccgttgc ttgggctacc tagtatccag cgtcctacgg   720
gcgccgtggt cggttcgagt gcgaaggacc tctggttcat ctagcggtag gcgggtgtgt   780
ggaagtagcc cttcagacgt actggttctg ttgcgtgaaa cgcggggtca cctcccccca   840
catacctcta agggctttg agcctagcgt tgggctacgt tctcgcacaa ggtcggctat   900
acgacgtttg taggggtag tgccaaacaa cccctgggtt gacaggttct ggtggtgttt   960
cgaaaacaac aatgtgtgtg ccgcataata tgcgcgttat gcattttgga gcaggtagtg  1020
ataaaggagt ggcgcctggt agtactgttc ttaaacagtg gctccccgaa ggaacactcc  1080
ttgtcgataa tgatattgta gattatgttt ctgacgcaca cgtttctgtg cttttcagatt  1140
gcaataaata taagacagag cacaagtttg atcttgtgta atctgatatg tatacagaca  1200
atgattcaaa aagaaagcat gaaggcgtga tagccaataa tggcaatgat gacgtcttca  1260
tatacctttc aagttttcta cgcaataatt tggctctggg aggcagtttt gctgtaaaat  1320
taacagagac aagttggcat gagagtttat atgacattgc acaggattgt gcatggtgga  1380
caatgttttg tacagcagtg aatgcatctt cttcagaagc attcctgatt ggtgttaatt  1440
acttgggtgc aagtgcaaag gttaaagtta gtggaaaaac actgcacgca aattatatat  1500
tttggaggaa ttgtaattat ttacaaacct ctgcttatag tatatttgat gttgctaagt  1560
ttgatttgag attgaaagca cgccagttg ttaatcttaa gactgaacaa aagacagact  1620
tagtctttaa tttgataaag tgtggtaagt tactggtaag agatgttggt aacacctctt  1680
ttactagtga ctcttttgtg tgcactatgt agtgctaatt tatatgacaa cgaatctttt  1740
gtgtattact accagagtgc ttttaggcca ggacatggtt ggcatttaca tggaggtgct  1800
tatgcagtag ttaatgtgtc tagtgaaaat aataatgcag gtactgcccc aagttgcact  1860
gctggtgcta ttggctacag taagaatctc agtgcggcct cagtagccat gactgcacca  1920
ctaagtgta tgtcatggtc tgccaactct tttgtacag cccactgtaa ttttacttct  1980
tatatagtgt ttgttacaca ttgttataag agcggatcta atagttgtcc tttgacaggt  2040
cttattccaa gcggttatat tcgtattgct gctatgaaac atggaagtgc tatgcctggt  2100
cacttatttt ataatttaac agtttctgtg actaaatatc ctaagtttag atcgctacaa  2160
tgtgttaata attatactc tgtatattta aatggtaacc ttgttttcac atctaactat  2220
actgaagatg ttgtagctgc aggtgtccat tttaaaagtg gtgaccatat aacttataaa  2280
gttatgagag aggttaaagc cttgcttat tttgtcaatg gtactgcaca tgatgtcatt  2340
ctatgtgatg acacacctag aggtttgtta gcatgccaat ataatactgg caattttca  2400
gatgcttct atccttttac taatactagt attgttaagg ataagtttat tgtttatcgt  2460
gaaagtagtc tcaatactac ttgtacatta actaatttca cgtttagtaa tgaaagtggt  2520
gcccctccta atacaggtg gttgacagt tttatttta ccagacaca aacagctcag  2580
agtggttatt ataattttaa cttttcattt ctgagtagtt ttgtttatag ggaaagtaat  2640
tatatgtatg gatcttacca tccacgttgt agttttagac tgaaaccct taatggtttg  2700
tggtttaatt ccctttctgt ttcattaaca tacggtccca ttcaaggtgg ttgtaagcaa  2760
tctgtattta tggtaaagc aacttgttgt tatgcttatt catacggagg acctcgtggt  2820
tgtaaaggtg tctatagagg tgagctaaca cagcattttg aatgtggttt gttagtttat  2880
```

```
gttactaaga gcgatggctc ccgtatacaa actgcaacac aaccacctgt attaacccaa  2940
aatttttata ataacatcaa tttaggtaag tgtgttgatt ataatatata tggcagaatt  3000
ggccaaggtc ttattactaa tgtaaccgac ttagctgtta gttataatta tttatcagac  3060
gcaggtttgg ctattttaga tacatctggt gccatagaca tcttcgttgt acaaggtgaa  3120
tatggtccta actattataa ggttaatcca tgtgaagatg tcaaccaaca gtttgtagtt  3180
tctggtggta aattagtagg tattctcact tcacgtaatg aaacaggttc tcagcttctt  3240
gagaaccagt tttatattaa aatcactaat ggaactcgtc gttctagacg ttctgttact  3300
gaaaatgtta caaattgccc ttatgttagt tatggcaagt tttgtataaa acctgatggt  3360
tcaatttctg taatagtacc aaaagaactg gatcagtttg tggcacctt acttaatgtt  3420
actgaatatg tgctcatacc taacagtttt aatttaactg ttacagatga gtacatacaa  3480
acgcgtatgg ataagatcca aattaattgc ctgcagtatg tttgtggcaa ttctttggcc  3540
tgtagaaagc tgtttcaaca atatgggcct gtttgtgaca acatattgtc tgtagtaaat  3600
agtgttggtc aaaaagaaga tatggaactt ttaaatttct attcttctac taaaccagct  3660
cgttttaata caccagtttt tagtaatctt agcactggtg agtttaatat ttctcttttg  3720
ttaacatccc ctagtagtcc taggaggcgt tcttttattg aagatctttt atttacaagt  3780
gttgaatctg taggattacc aacagatgac gcatacaaaa agtgcactgc aggacccttta  3840
ggcttttta aagaccttgc atgtgctcgt gaatataatg gtttgcttgt gttgcctcct  3900
attataacag cagaaatgca aacttttgtat actagttctt tagtagctc tatggcttt  3960
ggtggtatta ctgcagctgg tgccatacct tttgccacac aactgcaggc tagaattaat  4020
cacttgggta ttacccagtc acttttgttg aagaatcaag aaaaaattgc tgcttccttt  4080
aataaggcca ttgtcatat gcaggaaggt tttaggagta catctctagc attacaacaa  4140
attcaagatg ttgttaataa gcagagtgct attcttactg agactaatgg agcacttaat  4200
aaaaattttg gtgctatttc ttctgtgatt caagacattt accagcaact tgattccata  4260
caagcagatg ctcaagtgga tcggctcata actggtagat tgtcatcact ttctgtctta  4320
gcatctgcta agcagtcgga gtacattaga gtgtcacaac agcgtgagtt agctactcag  4380
aaaattaatg agtgtgttaa atcacagtct attaggtatt ccttttgtgg taatggacga  4440
catgttttaa ccataccaca aaatgcccct aatggtatag tgtttataca ctttacttat  4500
acaccagaga gctttattaa tgttactgca atagtgggtt tttgtgtaag tcctgctaat  4560
gctagtcagt atgcaatagt gcccgctaat ggtaggggta tttttataca agttaatggt  4620
agttactaca tcactgcacg agatatgtat atgccaagaa atattactgc aggagatata  4680
gttacgctta cttcttgtca agcaaattat gtaagtgtaa ataagaccgt cattactaca  4740
tttgtagaca atgatgattt tgattttgat gatgaattgt caaatggtg gaatgatact  4800
aagcatgagc taccagactt tgacaaattc aattacacag tacctatact tgacattgat  4860
agtgaaattg atcgtattca aggcgttata cagggtctta acgactctct aatagaccct  4920
gaaacactat caatactcaa aacttatatt aagtggcctt ggtatgtgtg gctagccata  4980
gcttttgcca ctattatctt catcttaata ttaggatggg ttttcttcat gactgggtgt  5040
tgtggttgtt gttgtggatg ctttggcatt atgcctctaa tgagtaagtg tggtaagaaa  5100
tcttcttatt acacgacttt tgataacgat gtggtaactg aacaatacag acctaaaaag  5160
tctgtttaat gatccaaagt cccactagtt tcttaatagt attaattttg ctttggtgta  5220
aacttgtact aagttgtttt agagagttta ttattgccct tcaacaacta acacaagttt  5280
tactccaaat tatcgatagt aatttacagt ctagactgac cctttggcac agtctagact  5340
aatgttaaac ttagaagcaa ttattgaaac cggtgatcaa gtgattcaaa aaatcagttt  5400
caatttacag catatttcaa gtgtattaaa cacagaagta tttgacccct ttgactattg  5460
ttattacaga ggaggtaatt tttgggaaat agagtcagct gaagattgtt caggtgatga  5520
tgaatttatt gaataagtcg ctagaggaga atggaagttt tctaacggca ctttacatat  5580
ttgtaggatt tttagcattt tatcttctag gtagagcact tcaagcattt gtacaggctg  5640
ctgatgcttg ttgttttaatt tggtacacgt ggttagtaat tccaggagtt aagggtacag  5700
cctttgtata caagtataca tatggtagaa aacttaacaa ttcggaatta gaagcagttg  5760
ttgttaacga gttcctaag aacggttgga ataataaaaa tccagcaaat tttcaagatg  5820
tccaacgaaa caaattgtac tcttgactt gaacagtcag ttgagctttt taagagtat  5880
aatttattta taactgcatt cttgttgttc ttaaccataa tacttcagta tggttatgca  5940
acgcgtagta agtttatta tacttaaa atgatagtgt tatggtgctt ttggcccctt  6000
aacattgcag taggtgtaat ttcatgtata tacccaccaa acacaggagg tcttgtcgca  6060
gcgataatac ttactgtgtt tgcgtgtctt tcttttgtag gttattggat ccagagtatt  6120
agactcttta agcggtgtag atcttggtgg tcatttaacc agaatctaa cgccgtaggt  6180
tcaatactcc taactaatgg tcaacaatgt aatttgcta tagagagtgt gccgatggtg  6240
ctttctcctc ttataaagaa tggtgttctt tattgtgagg tcagtggct tgctaaatgt  6300
gaaccagacc acttgcctaa agacatattt gtatgcacac cagatagacg taatatctat  6360
cgtatggtgc agaaatacac tggtgaccaa agcggaaata agaaaggtt tgctcatttt  6420
gtctatgcaa agcagtcagt agacactggc gagctagaaa gtgtagcaac aggtggaagt  6480
agccttaca cataaatgtg tgtgtgtaga gagtatttaa aattattctt caatagtgcc  6540
tctatttaa gagcgcggaa gagtatttgt tttgaggata ttaatataaa tcctctttgt  6600
tttgtactct ctttacaaga gttattattt aagcaacagt ttttccttc ctttgtttgg  6660
aagaaagttg ttgttaatgg tgtagaattc caagtacgaa ccactacgaa  6720
ggaaacccca ttttccaaaa aggttgttgt aggttgtggt cccattataa gaaggattaa  6780
atggattaaa ccacctacac tacttacttg taataagggc gtttggactt acaagcgctt  6840
aacaaataca gacgatgaaa tggctgacta gtttggaag agcagttatt tcttgttata  6900
aagccctact attaactcag ttaagagtat tagataggtt aattttagat cacggaccaa  6960
agcgagtctt aacgtgtggt aggcgagtgc ttttatctca attagattta gtttataggt  7020
tggcatatac gcccacccaa tcgctggtat gaataatagt aaagataatc cttttcgcgg  7080
agcaatagca agaaaagcgc gaatttatct gagagaagga ttagagtgtg tttactttct  7140
taacaaagca ggacaagcag agccttgtcc cgcgtgtacc tccctagtat ttcagggaaa  7200
aacttgtgag gaacacacag ataataataa tcttttgtca tggcgagcgg taagacaact  7260
gggaagacag acgcccagc gccagtcatc aaactaggag gcaaaacc acctaaagtt  7320
ggttcttctg gaaatgctag ctggtttcaa gcactaaaag ccaagaagtt aaattccct  7380
cctcctaagt ttgaaggtag cggcgttcct gataatgaaa atcttaaatt aagccagcaa  7440
catgggtact ggaacgtca agccaggtac aagccaggta aaggcggaag aaaatcagtc  7500
ccagatgctt ggtacttcta ttacactgga acaggaccag ccgctgacct gaattgggt  7560
gatagccaag atggtatagt gtgggtttct gcaaagggtg ctgatactaa atctagatct  7620
```

```
aaccagggta caagggatcc tgataagttt gaccaatacc cgctacgatt ctcagatgga   7680
ggacctgatg gtaatttccg ttgggacttc attccaataa atcgtggtag gagtggaaga   7740
tcaacagcgg cttcatcagc agcatctagt agagcaccgt cgcgtgatgg ctcgcgtgga   7800
cgtagaagcg gagctgaaga tgatcttata gctcgtgcag caaagatcat tcaggatcag   7860
cagaagaagg gttctcgcat tactaaagct aaggccgatg aaatgctca tcgccggtat    7920
tgtaagcgta ctatcccacc tggttataag gttgatcaag tatttggtcc ccgtactaaa   7980
ggtaaggagg gaaattttgg tgatgacaag atgaatgagg agggtattaa ggatgggcgc   8040
gttacagcaa tgctcaacct agtccctagc agccatgctt gtcttttgg aagtagagtg     8100
acgcccaaac ttcaaccaga tgggctgcac ttgagatttg aatttactac tgtggtttct   8160
agggatgatc cgcagtttga taattatgtg aaaatttgtg atcagtgtgt cgatgtgta    8220
gggactcggc caaaagacga tgaaccgaga ccaaagtcac gcccaaattc aagacctgct   8280
acaagaacaa gttctccagc gccaagacaa cagcgtcaaa agaaggagaa gaagtcaaag   8340
aagcaggatg atgaagtaga taaggcattg acctcagatg aggagaggaa caatgcacag   8400
ctggaatttg atgatgaacc gaaagtgatt aactgggagg attcagcact tggagagaat   8460
gagttgtaaa gctagatttc caacttaaca tcatggacgt gcgtatgctg ttttcccta   8520
ctatagactt tttagcatat tattttttgc tatttgtatg gttattaca ggtgaagatt    8580
gtatgtattt gttgtacact cgtatgttct atattatgtt ttctgtagtt gttattagtg   8640
ttgttcttgt tcttactcta ctgttctctt ttctttattt tagagtatca ataagaatca   8700
aggaagatag gcatgtagtt tgattaccta catgtctatc gccagggaaa tgtctaatct   8760
gtctacttag tagcctggaa acgaacggta gacccttaga ttttaattta gtttaatttt   8820
tagtttagtt taagttagtt tagagtaggt ataagaagc cagtgccggg gccacgcgga    8880
gtacgatcga gggtacagca ctaggacgcc cactagggga agagctaaat tttagtttaa   8940
gttaagtta attggctaag tatagttaaa atttataggc tagtatagag ttagagcaaa    9000
aaaaaaaaaa aaaaaaaaaa aaaaaaaaaa aaaaaaaaaa aaaaaaaaaa aaaaaaaaaa   9060
aaaaaaaaaa aaaaaaaaaa aaaaaaaaaa aaaaagtt taaacttaat taagaattcc     9120
cttggctcga gttcgaaatc ggatgccggg accgacgagt gcagaggcgt gcaagcgagc   9180
ttggcgtaat catggtcata gctgtttcct gtgtgaaatt gttatccgct cacaattcca   9240
cacaacatac gagccggaag cataaagtgt aaagcctggg gtgcctaatg agtgagctaa   9300
ctcacattaa ttgcgttgcg ctcactgccc gctttccagt cgggaaacct gtcgtgccag   9360
ctgcattaat gaatcggcca acgcgcgggg agaggcggtt tgcgtattgg gcgctcttcc   9420
gcttcctcgc tcactgactc gctgcgctcg gtcgttcggc tgcggcgagc ggtatcagct   9480
cactcaaagg cggtaatacg gttatccaca gaatcagggg ataacgcagg aaagaacatg   9540
tgagcaaaag gccagcaaaa ggccaggaac cgtaaaaagg ccgcgttgct ggcgtttttc   9600
cataggctcc gcccccctga cgagcatcac aaaaatcgac gctcaagtca gaggtggcga   9660
aacccgacag gactataaag ataccaggcg tttccccctg gaagctccct cgtgcgctct   9720
cctgttccga ccctgccgct taccggatac ctgtccgcct ttctcccttc gggaagcgtg   9780
gcgctttctc atagctcacg ctgtaggtat ctcagttcgg tgtaggtcgt tcgctccaag   9840
ctgggctgtg tgcacgaacc ccccgttcag cccgaccgct gcgccttatc cggtaactat   9900
cgtcttgagt ccaacccggt aagacacga ttatcgccac tggcagcagc cactggtaac    9960
aggattagca gagcgaggta tgtaggcggt gctacagagt tcttgaagtg gtggcctaac   10020
tacggctaca ctagaagaac agtatttggt atctgcgctc tgctgaagcc agttaccttc   10080
ggaaaaagag ttggtagctc ttgatccggc aaacaaacca ccgctggtag cggtggtttt   10140
tttgtttgca agcagcagat tacgcgcaga aaaaaaggat ctcaagaaga tcctttgatc   10200
ttttctacgg ggtctgacgc tcagtggaac gaaaactcac gttaagggat tttggtcatg   10260
agattatcaa aaaggatctt cacctagatc cttttaaatt aaaaatgaag ttttaaatca   10320
atctaaagta tatatgagta aacttggtct gacagttacc aatgcttaat cagtgaggca   10380
cctatctcag cgatctgtct atttcgttca tccatagttg cctgactccc cgtcgtgtag   10440
ataactacga tacgggaggg cttaccatct ggccccagtg ctgcaatgat accgcgagac   10500
ccacgctcac cggctccaga tttatcagca ataaaccagc cagccggaag ggccgagcgc   10560
agaagtggtc ctgcaacttt atccgcctcc atccagtcta ttaattgttg ccgggaagct   10620
agagtaagta gttcgccagt taatagtttg cgcaacgttg ttgccattgc tacaggcatc   10680
gtggtgtcac gctcgtcgtt tggtatggct tcattcagct ccggttccca acgatcaagg   10740
cgagttacat gatcccccat gttgtgcaaa aaagcggtta gctccttcgg tcctccgatc   10800
gttgtcagaa gtaagttggc cgcagtgtta tcactcatgg ttatggcagc actgcataat   10860
tctcttactg tcatgccatc cgtaagatgc ttttctgtga ctggtgagta ctcaaccaag   10920
tcattctgag aatagtgtat gcggcgaccg agttgctctt gcccggcgtc aatacgggat   10980
aataccgcgc cacatagcag aactttaaaa gtgctcatca ttggaaaacg ttcttcgggg   11040
cgaaaactct caaggatctt accgctgttg agatccagtt cgatgtaacc cactcgtgca   11100
cccaactgat cttcagcatc ttttactttc accagcgttt ctgggtgagc aaaaacagga   11160
aggcaaaatg ccgcaaaaaa gggaataagg gcgacacgaa aatgttgaat actcatactc   11220
ttcctttttc aatattattg aagcatttat cagggttatt gtctcatgag cggatacata   11280
tttgaatgta tttagaaaaa taaacaaata ggggttccgc gcacatttcc ccgaaaagtg   11340
ccacctgacg tctaagaaac cattattatc atgacattaa cctataaaaa taggcgtatc   11400
acgaggccct ttcgtc                                                   11416

SEQ ID NO: 80           moltype = DNA  length = 29
FEATURE                 Location/Qualifiers
misc_feature            1..29
                        note = Primer
source                  1..29
                        mol_type = other DNA
                        organism = synthetic construct
SEQUENCE: 80
catataaatt agcactacat agtgcacac                                       29

SEQ ID NO: 81           moltype = DNA  length = 35
FEATURE                 Location/Qualifiers
misc_feature            1..35
                        note = Primer
```

```
source                  1..35
                        mol_type = other DNA
                        organism = synthetic construct
SEQUENCE: 81
atgtagtgct aatttatatg acaacgaatc ttttg                      35

SEQ ID NO: 82           moltype = DNA  length = 32
FEATURE                 Location/Qualifiers
misc_feature            1..32
                        note = Primer
source                  1..32
                        mol_type = other DNA
                        organism = synthetic construct
SEQUENCE: 82
acacatacca aggccactta atataagttt tg                         32

SEQ ID NO: 83           moltype = DNA  length = 28
FEATURE                 Location/Qualifiers
misc_feature            1..28
                        note = Primer
source                  1..28
                        mol_type = other DNA
                        organism = synthetic construct
SEQUENCE: 83
taagtggcct tggtatgtgt ggctagcc                              28

SEQ ID NO: 84           moltype = DNA  length = 21
FEATURE                 Location/Qualifiers
misc_feature            1..21
                        note = Primer
source                  1..21
                        mol_type = other DNA
                        organism = synthetic construct
SEQUENCE: 84
taatactggy aatttttcag a                                     21
```

MODIFIED S1 SUBUNIT OF THE CORONAVIRUS SPIKE PROTEIN

SEQUENCE LISTING

The Sequence Listing associated with this application is provided in xml format in lieu of a paper copy, and is hereby incorporated by reference into the specification. The name of the xml file containing the Sequence Listing is 01-3363-US-2_SL.xml. The xml file is 240,774 bytes; it was created on Jun. 1, 2023; and it is being submitted electronically via PatentCenter, concurrent with the filing of the specification.

BACKGROUND OF THE INVENTION

Avian coronavirus infectious bronchitis virus (IBV) is the prototype gammacoronavirus of the family Coronaviridae, order Nidovirales. Infectious bronchitis virus principally infects the upper respiratory epithelium of chickens, causing a respiratory disease, commonly complicated by secondary bacterial pathogens (Cook et al. 2012. Avian Pathol. 41:239-250). Some IBV strains additionally affect the renal tubuli, oviduct and parts of the gastrointestinal tract, leading to pathological lesions and clinical symptoms in these organ systems. The virus has a worldwide presence in both commercial and backyard chicken. Due to its high genomic variability IBV is discriminated in a wide variety of geno-, sero- and protectotypes. IBV is currently regarded as one of the economically most relevant viral pathogens in the poultry industry.

Infectious bronchitis virus is an enveloped virus with a positive sense single-stranded RNA genome of 27.6 kb (Cavanagh 2007. Vet. Res. 38:281-297). The first two-thirds of the viral genome comprise a large coding region (also designated as gene 1), divided into two open reading frames 1a and 1b, which encode for at least 15 nonstructural proteins involved in RNA replication, editing, and transcription. The last one-third of the viral genome codes for structural proteins: the spike protein (S, encoded by gene 2), the envelope protein (E, encoded by gene 3c), the membrane protein (M, encoded by gene 4), and the nucleocapsid protein (N, encoded by gene 6). Proteins S, E and M are part of the viral envelope while protein N forms the ribonucleoprotein core along with the viral RNA. The coronavirus spike protein determines the host species tropism (Kuo et al. 2000. J. Virol. 74:1393-1406). It is a dimeric or trimeric transmembrane protein, which is proteolytically cleaved into two subunits, S1 and S2. The glycosylated S1 domain forms the 'head' of the spike protein and contains the receptor binding domain that interacts with 2,3-linked sialic acids on the host cell surface (Promkuntod et al. 2014. Virology. 448:26-32). The S2 domain contains the remaining part of the ectodomain (the 'stalk'), the transmembrane domain and the endodomain located in the cytoplasm.

The to date widely used live-attenuated IBV vaccine strains H52 and H120 were developed in the 1960s in the Netherlands, by serial passaging of a Massachusetts IBV strain in embryonated chicken eggs (Bijlenga et al. 2004; Avian Pathol. 33:550-557). Said vaccine strains also have to be cultivated in embroynated chicken eggs for production. Today, IBV vaccines (both inactivated and live vaccines) are still propagated in emryonated chicken eggs which is cumbersome and expensive.

The only cell-line adapted IBV described so far is the IBV strain Beaudette, which efficiently replicates in Vero and BHK cells. Casais et al 2003 (J. Virol. 77; 9084-9089) show that the S protein of Beaudette is the determinant of cell line tropism by generating recombinant IBVs using ectodomain sequences of the Beaudette spike, which were able to transfer the extended cell line tropism to another IBV (M41). WO 2011/004146 discloses that the S2 subunit from Beaudette is responsible for the extended tissue tropism. A sequence within the S2 subunit, a heparan-sulphate binding site from Beaudette, has been identified to be responsible for the extended cell line tropism. Furthermore, Bickerton et al 2018 (Journal of Virology 92 (19)) disclose a Beaudette specific motif of eight amino acids. However, recombinant IBVs with a Beaudette spike S2 subunit are not suitable as vaccines. Ellis et al 2018 (J. Virol. 92(23)) describe that recombinant Beaudette with chimeric spikes with heterologous S1 subunits from M41 or QX in combination with Beaudette spike S2 subunit do not confer sufficient protection against S1 homologous challenges. Also, Beaudette wild type does not provide protection against homologous challenge like other licensed vaccines belonging to the Massachusetts serotype (Hodgson et al 2004: J Virol 78:13804-13811 or Geilhausen et al 1973: Archiv für die gesamte Virusforschung 40: 285-290).

Fang et al 2005 (Biochemical and Biophysical Research Communication 336; pages 417 to 423) disclose that the adaption of Beaudette for propagation in Vero cells resulted in 49 amino acid modifications, 26 located within the spike protein.

Taken together, providing IBV vaccines having an extended cell or tissue tropism by exchanging the spike protein to a heterologous Beaudette Spike protein would not result in IBV vaccines providing sufficient efficacy and with the Beaudette Spike sequence would be limited to protection against a Massachusetts serotype strain challenge and missing cross protection against further genotypes. Furthermore, the prior art motifs or sites identified in Beaudette have not been transferred into IBV vaccines showing both an extended cell culture or tissue tropism and efficacy in protection (no interference between extended tropism and vaccine efficacy has been shown).

Consequently, there is a need for single amino acids or short motifs that can be transferred into IBVs or IBV vaccines without influencing vaccine efficacy but enabling an extended cell or tissue tropism for production.

DETAILED DESCRIPTION OF THE INVENTION

Before the aspects of the present invention are described, it must be noted that as used herein and in the appended claims, the singular forms "a", "an", and "the" include plural reference unless the context clearly dictates otherwise. Thus, for example, reference to "an antigen" includes a plurality of antigens, reference to the "virus" is a reference to one or more viruses and equivalents thereof known to those skilled in the art, and so forth. Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies as reported in the publications which might be used in connection with the invention. Nothing herein is to be construed as an admission that the invention is not entitled to antedate such disclosure by virtue of prior invention.

Composition of Matter

The present invention solves the problems inherent in the prior art and provides a distinct advance in the state of the art.

Generally, the present invention provides an avian coronavirus Spike Protein or fragment thereof, wherein at least a part of the S1 subunit is from an avian coronavirus with a restricted cell or tissue tropism, and wherein at amino acid position 267 is a Cysteine.

Further, the present invention provides a recombinant avian coronavirus spike protein or fragment thereof comprising a mutation at amino acid position 267 to Cysteine.

Generally, the present invention also provides an IBV spike protein or fragment thereof, wherein at least a part of the S1 subunit is from an IBV with a restricted cell or tissue tropism, and wherein at amino acid position 267 is a Cysteine.

Further, the present invention provides a recombinant IBV spike protein or fragment thereof comprising a mutation at amino acid position 267 to Cysteine.

Advantageously, the experimental data show that coronavirus strains (strains such as exemplarily H52, QX SP2013-01478 and CR88 IBV strains) have an extended cell or tissue tropism after modifying a single position, position 267, into a Cystein within the spike protein.

The term "coronavirus" is well known to the person skilled in the art. In general coronaviruses are viruses of the subfamily Coronavirinae in the family Coronaviridae, in the order Nidovirales. Coronaviruses are enveloped viruses and have a positive-sense single-stranded RNA genome with a nucleocapsid of helical symmetry. The term "coronavirus" encompasses all strains, genotypes, protectotypes, and serotypes of infectious bronchitis virus. Examples of avian coronaviruses are infectious bronchitis virus (IBV); guinea fowl coronavirus (GfCoV) and turkey coronavirus (TCoV; turkey enteritis virus and bluecomb disease virus).

The term "IBV" refers to the infectious bronchitis virus which is well known to the person skilled in the art. The term "IBV" encompasses all strains, genotypes, protectotypes, and serotypes of infectious bronchitis virus.

The term "mutation" comprises modifications in the viral RNA encoding proteins leading to an alteration of said encoded protein. Further, the term "mutation" comprises genetically engineered mutations. The term mutation relates to, but is not limited to, substitutions (replacement of one or several nucleotides/base pairs), deletions (removal of one, several or all nucleotides/base pairs), and/or insertions (addition of one or several nucleotides/base pairs). As used herein, a mutation may be a single mutation or several mutations, therefore, often the term "mutation(s)" used and relates to both a single mutation and several mutations. However, the term mutation is well known to the person skilled in the art and the person skilled in the art can generate mutations without further ado.

The term "spike" refers to a specific protein of the avian coronavirus or IBV that is well known by the person skilled in the art. The spike protein is the major inducer of antibodies and a protective immune response. Further, the spike (S) protein facilitates cell entry of the avian coronavirus or IBV by binding cellular receptors on the host cell and also by mediating virus-cell membrane fusion with the host cell membranes. In addition, it determines the tissue and cell tropism of the virus strain.

The term "protein", "amino acid" and "polypeptide" are used interchangeably. The term "protein" refers to a sequence of amino acids composed of the naturally occurring amino acids as well as derivatives thereof. The naturally occurring amino acids are well known in the art and are described in standard text books of biochemistry. Within the amino acid sequence the amino acids are connected by peptide bonds. Further, the two ends of the amino acid sequence are referred to as the carboxyl terminus (C-terminus) and the amino terminus (N-terminus). The term "protein" encompasses essentially purified proteins or protein preparations comprising other proteins in addition. Further, the term also relates to protein fragments. Moreover, it includes chemically modified proteins. Such modifications may be artificial modifications or naturally occurring modifications such as phosphorylation, glycosylation, myristylation and the like.

Mutation 267

In one aspect of the avian coronavirus or IBV spike protein or fragment thereof according to the present invention the Cysteine at amino acid position 267 is introduced by a mutation. The wording "introduced" means that the mutation has been introduced by genetic engineering (artificially, e.g., by human intervention).

In another specific aspect of the avian coronavirus or IBV spike protein or fragment thereof according to the present invention the mutation is an amino acid substitution, deletion or insertion.

In another specific aspect of the avian coronavirus or IBV spike protein or fragment thereof according to the present invention a hydrophobic amino acid at amino acid position 267 is mutated into a Cysteine; or a Phenylalanine or Leucine at amino acid position 267 is mutated into a Cysteine.

Extended Cell or Tissue Tropism

In another specific aspect of the avian coronavirus or IBV spike protein or fragment thereof according to the present invention the Cysteine at amino acid position 267 or said mutation at amino acid position 267 to Cysteine leads to an extended cell or tissue tropism of the avian coronavirus or IBV.

The term "cell or tissue" is known by the person skilled in the art. The term cell encompasses cell lines such as the cell lines listed elsewhere herein as well as primary cells. The term tissue encompasses cells from tissues such as the ones listed elsewhere herein, exemplarily such as primary chicken embryo cells from lung or liver or primary chicken fibroblasts. The term encompasses the propagation of cells or tissue (cells) in culture outside the organism. The term "culture" relates to the propagation of cells (such as cell line cells or primary cells or tissue cells) outside the organism under defined culture conditions known by the person skilled in the art.

The term "extended tropism" means that the avian coronavirus or IBV of the invention can be propagated in cells (such as cell lines) or tissue cells (in addition to primary chicken embryo cells from kidney). In contrast, coronavirus vaccines (such as IBV vaccines) or non-cell culture adapted wildtype coronaviruses or IBV's (cell line adapted IBV Beaudette strains are described) can only be propagated in embryonated chicken eggs or primary chicken embryo cells from kidney (after adaption). Accordingly, a coronavirus (such as IBV) of the invention with extended cell or tissue tropism has the capacity to infect and/or replicate in one or more cell lines or tissue cells other than primary chicken embryo cells from kidney. Preferably, the coronavirus (such as IBV) of the invention with extended cell or tissue tropism has the capacity to infect and/or replicate in one or more cell lines as listed herein. Accordingly, a coronavirus or IBV with extended cell or tissue tropism may, for example, have the capacity to infect and/or replicate in PBS-12SF, EB66 or HEK 293T cells.

The term "restricted tropism" means that the avian coronavirus or IBV can be grown if at all only on primary chicken embryo cells from kidney. Accordingly, a coronavirus or IBV with restricted cell or tissue tropism does not have the capacity to infect and/or replicate in e.g. PBS-12SF, EB66 or HEK 293T cells.

Advantageously, the experimental data show that IBV strains such as exemplarily H52 and CR88 have an extended cell or tissue tropism after modifying a single position, position 267, into a Cystein within the spike protein. Further, it has been shown that the modification to a Cystein at Position 267 is genetically stable.

In another specific aspect of the avian coronavirus or IBV spike protein or fragment thereof according to the present invention the avian coronavirus or IBV is infecting and/or replicating in at least one cell line or cell selected from the list consisting of: primary chicken embryo cells from lung or liver or primary chicken fibroblasts, a chicken embryo fibroblast cell line, a duck embryonic stem cell line, a human embryonic kidney cell line, a baby hamster kidney cell line, an african green monkey kidney cell line, a rabbit kidney cell line, a canine kidney cell line, a chicken liver cell line, a bovine kidney cell line, a porcine kidney cell line and an insect cell line.

In another specific aspect of the avian coronavirus or IBV spike protein or fragment thereof according to the present invention the avian coronavirus is infecting and/or replicating in at least one cell line selected from the list consisting of: DF-1 (Douglas Foster), EB66 (duck embryonic stem cell line), PBS-12, PBS-12SF (PBS-12 serum free), BHK21 (baby hamster kidney), HEK 293T (human embryonic kidney), Vero (Verda Reno), MA104, RK13 (rabbit kidney), LMH (leghorn male hepatoma), MDCK (Madin-Darby canine kidney), MDBK (Madin-Darby bovine kidney), PK15 (porcine kidney), PK2A (porcine kidney), SF9, SF21 and SF+(*Spodoptera frugiperda*).

In another specific aspect of the avian coronavirus or IBV spike protein or fragment thereof according to the present invention the avian coronavirus or IBV is infecting and/or replicating in at least one cell line selected from the list consisting of: DF-1, EB66, PBS-12, PBS-12SF, BHK, HEK 293T, Vero, MA104 and RK13.

Preferably, the IBV is infecting and/or replicating in the EB66, PBS-12SF or HEK 293T cell line.

All mentioned cell lines are well known to the person skilled in the art and are commercially and/or publicly available. MDCK cells are exemplarily deposited at the American Tissue Culture Collection under accession number ATCC CCL-34 or ATCC CRL-2285. DF-1 cells are exemplarily deposited at the American Tissue Culture Collection under accession number ATCC CRL-12203). PBS-12SF cells are exemplarily deposited at the American Tissue Culture Collection under accession number ATCC PTA-8565 or deposited at RRID under CVCL_1K17. BHK-21 cells are exemplarily deposited at the American Tissue Culture Collection under accession number ATCC CCL-10. HEK 293T cells are exemplarily deposited at the American Tissue Culture Collection under accession number ATCC CRL-3216. Vero cells are exemplarily deposited at the American Tissue Culture Collection under accession number ATCC CCL-81. MA104 and cells are exemplarily deposited at the American Tissue Culture Collection under accession number ATCC CRL-2378. RK13 cells are exemplarily deposited at the American Tissue Culture Collection under accession number ATCC CCL-37.

Numbering of Amino Acid Position 267

In another specific aspect of the avian coronavirus or IBV spike protein or fragment thereof according to the present invention the numbering of amino acid position 267 refers to the amino acid position 267 in the spike protein of an IBV H52, an IBV H120 or an M41.

In another specific aspect of the avian coronavirus or IBV spike protein or fragment thereof according to the present invention the numbering of amino acid position 267 refers to the amino acid position 267 in the spike protein of an IBV H52.

In another specific aspect of the avian coronavirus or IBV spike protein or fragment thereof according to the present invention the numbering of amino acid position 267 refers to the amino acid position 267 in the spike protein as exemplarily given in SEQ ID NO:1.

In another specific aspect of the avian coronavirus or IBV spike protein or fragment thereof according to the present invention the amino acid sequence of SEQ ID NO:1 is used for determining the position numbering in the spike protein.

In another specific aspect of the avian coronavirus or IBV spike protein or fragment thereof according to the present invention for determining the amino position 267 in a spike protein the amino acid sequence is aligned to the amino acid sequence of SEQ ID NO:1.

In another specific aspect of the avian coronavirus or IBV spike protein or fragment thereof according to the present invention the amino acid position 267 is within the S1 subunit of the spike protein.

In another specific aspect of the avian coronavirus or IBV spike protein or fragment thereof according to the present invention the amino acid position 267 corresponds to amino acid position 269 of the spike sequence of IBV CR88.

In another specific aspect of the avian coronavirus or IBV spike protein or fragment thereof according to the present invention the amino acid position 267 corresponds to amino acid position 270 of the spike sequence of IBV QX.

In another specific aspect of the avian coronavirus or IBV spike protein or fragment thereof according to the present invention the amino acid position 267 corresponds to amino acid position 271 of the spike sequence of IBV Q1.

In another specific aspect of the avian coronavirus or IBV spike protein or fragment thereof according to the present invention the amino acid position 267 corresponds to amino acid position 270 of the spike sequence of IBV Var2.

In another specific aspect of the avian coronavirus or IBV spike protein or fragment thereof according to the present invention the amino acid position 267 corresponds to amino acid position 274 of the spike sequence of IBV Brazil.

In another specific aspect of the avian coronavirus or IBV spike protein or fragment thereof according to the present invention the amino acid position 267 corresponds to amino acid position 274 of the spike sequence of IBV Ark99.

In another specific aspect of the avian coronavirus or IBV spike protein or fragment thereof according to the present invention the spike protein has one or more of the following amino acids selected from the group consisting of:

264 is an asparagine, and/or
265 is a threonine, and/or
269 is a leucine, and/or
271 is an asparagine, and/or
272 is a phenylalanine.

The numbering of said amino acid positions refer to the amino acid positions within the spike protein as exemplarily given in SEQ ID NO:1.

Spike

The present invention also provides a spike protein or fragment thereof as described above, wherein the spike protein or fragment thereof is selected from the group consisting of: infectious bronchitis virus (IBV); guinea fowl coronavirus (GfCoV), turkey coronavirus (TCoV; turkey enteritis virus and bluecomb disease virus), feline infectious peritonitis virus (FIPV), feline enteric coronavirus (FECV); Transmissible gastro-enteritis virus (TGEV), porcine respiratory coronavirus (PRCoV), porcine epidemic diarrhea virus (PEDV), porcine hemagglutinating encephalomyelitis virus (PHEV); Severe acute respiratory syndrome coronavirus (SARS-CoV), Middle east respiratory syndrome coronavirus (MERS-CoV) Human Coronavirus 229E (HCoV-229E), human coronavirus NL63 (HCoV-NL63), human coronavirus HKU1 (HCoV-HKU1), human coronavirus OC43 (HCoV-OC43); canine coronavirus (CCoV), canine respiratory coronavirus (CRCoV), Mouse Hepatitis Virus (MHV), Bovine coronavirus (BCV). Thus, the present invention also provides a coronavirus spike protein or fragment thereof, wherein at least a part of the S1 subunit is from a coronavirus with a restricted cell or tissue tropism, and wherein at amino acid position 267 is a Cysteine and wherein the spike protein is selected from the group consisting of: infectious bronchitis virus (IBV); guinea fowl coronavirus (GfCoV), turkey coronavirus (TCoV; turkey enteritis virus and bluecomb disease virus), feline infectious peritonitis virus (FIPV), feline enteric coronavirus (FECV); Transmissible gastro-enteritis virus (TGEV), porcine respiratory coronavirus (PRCoV), porcine epidemic diarrhea virus (PEDV), porcine hemagglutinating encephalomyelitis virus (PHEV); Severe acute respiratory syndrome coronavirus (SARS-CoV), Middle east respiratory syndrome coronavirus (MERS-CoV) Human Coronavirus 229E (HCoV-229E), human coronavirus NL63 (HCoV-NL63), human coronavirus HKU1 (HCoV-HKU1), human coronavirus OC43 (HCoV-OC43); canine coronavirus (CCoV), canine respiratory coronavirus (CRCoV), Mouse Hepatitis Virus (MHV), Bovine coronavirus (BCV). Further, the present invention also provides a recombinant coronavirus spike protein or fragment thereof comprising a mutation at amino acid position 267 to Cysteine, wherein the spike protein is selected from the group consisting of: infectious bronchitis virus (IBV); guinea fowl coronavirus (GfCoV), turkey coronavirus (TCoV; turkey enteritis virus and bluecomb disease virus), feline infectious peritonitis virus (FIPV), feline enteric coronavirus (FECV); Transmissible gastro-enteritis virus (TGEV), porcine respiratory coronavirus (PRCoV), porcine epidemic diarrhea virus (PEDV), porcine hemagglutinating encephalomyelitis virus (PHEV); Severe acute respiratory syndrome coronavirus (SARS-CoV), Middle east respiratory syndrome coronavirus (MERS-CoV) Human Coronavirus 229E (HCoV-229E), human coronavirus NL63 (HCoV-NL63), human coronavirus HKU1 (HCoV-HKU1), human coronavirus OC43 (HCoV-OC43); canine coronavirus (CCoV), canine respiratory coronavirus (CRCoV), Mouse Hepatitis Virus (MHV), Bovine coronavirus (BCV).

In another specific aspect of the avian coronavirus spike protein or fragment thereof according to the present invention the avian coronavirus spike protein or fragment thereof is selected from the group consisting of: infectious bronchitis virus (IBV); guinea fowl coronavirus (GfCoV) and turkey coronavirus (TCoV; turkey enteritis virus and bluecomb disease virus).

In another specific aspect of the avian coronavirus spike protein or fragment thereof according to the present invention the avian coronavirus is IBV (infectious bronchitis virus).

IBV strains can be classified by serotype and genotype. Serotype classification involves treatment of the virus with neutralizing antibodies, whereas genotype classification generally involves examining the sequence of the S1 (spike) protein. However, the different IBV strains are well known to the person skilled in the art. Infectious bronchitis virus was first discovered in the United States in the 1930s.

The first IBV serotype identified was Massachusetts and remained the only serotype until the discovery of a different IBV serotype in 1956. Nowadays, several additional serotypes, including Arkansas and Delaware have been identified in the United States of America in addition to the originally identified Massachusetts type. Today, IBV Mass viruses can be identified in many countries of the world.

The IBV strain Beaudette is of Massachusetts type and was derived following at least 150 passages in chick embryos. The IBV strain Beaudette was originally isolated by Beaudette and Hudson (J. Am. Vet. Med. A. 90, 51-60, 1937) and passaged in chicken embryos. Other Massachusetts type IBV strains besides Beaudette are H120, H52, and M41. The H120 strain was passaged 120 times in embryonated chickens eggs.

IBV QX is described as virulent field isolate of IBV which was originally isolated in China. However, the virus has spread towards Europe and has been identified in parts of Western Europe, predominantly in the Netherlands, but also in Germany, France, Belgium, Denmark and in the UK. In addition, the QX genotype or serotype has been described in several countries in Asia and Africa.

The strains designated "Italian-02" or "Italy-02" was isolated in the late 1990's in Italy. The sequence analysis of one of these isolates was published in 2002 (NCBI-BLAST, number AJ457137). However, studies have shown that this Italian-02 strain is widespread in Europe and that, apart from IBV variant strain 4/91 it has become one of the most predominant genotypes in the UK, Spain, France and The Netherlands.

Since 1996 a new Infectious Bronchitis virus (IBV) genotype, referred to as Q1, has circulated in China and was reported for the first time in Italy in 2011. Q1 is associated with an increase of mortality, kidney lesions and proventriculitis.

Furthermore, strains D274, B1648/D8880, D1466, V1397 and Arkansas have been identified in Europe as well.

It is in the general knowledge of a person skilled in the art where to obtain any IBV strains. IBV strains can be commercially purchased, obtained from scientific Institutes or the genomes can be synthetical synthesized as complementary DNA as IBV strains have been sequenced and the sequences have been published and are, thus, available. Furthermore, IBV strains can be isolated from the field. The methods to isolate IBV strains and to characterize the IBV strains are well known to the person skilled in the art. Valter Leonardo de Quadros 2011 (Dissertation, Das Infektiöse Bronchitis Virus (IBV): Molekularbiologische Untersuchungen zur Diagnostik und zum Vorkommen sowie zur Pathogenität des Genotyps IBV QX in spezifisch pathogenfreien (SPF) Broilern, Freie Universität Berlin), Worthington et al. 2009 (Avian Pathology 37(3), 247-257), Liu et al. 2009 (Virus Genes 38: 56-65), Dolz et al. 2006 (Avian Pathology 35 (2): 77-85), Farsang et al. 2002 (Avian Pathology 31: 229-236) and Feng et al. 2014 (Virus Genes 49: 292-303) describe how to isolate and differentiate different IBV strains.

IBV strains are typically differentiated by the coding sequence of the S1 subunit of the spike protein (Valastro et al. 2016. Infect Genet Evol. 39:349-364) but can also be differentiated by their complete nucleotide sequence or the sequences of specific proteins such as the spike protein, nucleocapsid protein, envelope (E) protein or membrane (M) glycoprotein. Because the spike protein determines host tropism and antigenicity of IBV, the IBV genotypes are classified by the coding sequence of the subunit 1 of the spike proteins. Alternatively, IBV strains can be differentiated by their serotype. Serotype classification involves serological assays of the virus involving serotype-specific antibodies.

In another specific aspect of the IBV spike protein or fragment thereof according to the present invention the spike protein or fragment thereof is from an IBV with a genotype or serotype or strain selected from a list consisting of: Arkansas (such as Arkansas 99), Brazil (such as BR-1, BR-2, 23/2013, IBV/Brasil/351/1984), California (such as California 1734/04, California 99), Connecticut, Delaware (such as Delaware 98), Dutch (such as D207, D212, D274, D3128, D3896, D8880, D1466), Florida, Georgia (such as Georgia GA-07, GA-08, GA-12, GA-13), Gray, Holte, Iowa (such as Iowa 97 and Iowa 69), Italy02), JMK, LDT3, Maine (such as Maine 209), Massachusetts (such as M41, H52, H120; excluding Beaudette), Pennsylvania (such as Pennsylvania 1220/98, Pennsylvania Wolg/98), PL84084, Qu (such as Qu-mv), QX (such as GB341/96), Q1, SE 17, Variant 2 (such as IS/1494/06, IBV/Ck/EG/CU/4/2014, gammaCoV/Ck/Poland/G052/2016) and 4/91 (793B, CR88).

In another specific aspect of the IBV spike protein or fragment thereof according to the present invention the spike protein or fragment thereof is not from a Beaudette strain.

In another specific aspect of the IBV spike protein or fragment thereof according to the present invention the Spike protein or fragment thereof is from an IBV selected from a list of genotypes or serotypes or strains consisting of: Massachusetts (not Beaudette), 4/91, QX, Q1, Italy 02, Arkansas, Connecticut, Georgia, LDT3, PL84084, Variant 2 and Brazil.

The wording "not Beaudette" is used equivalent to excluding Beaudette. Thus, the wording "Massachusetts (not Beaudette)" means that spike proteins or fragments thereof from Massachusetts strains such as M41, H52 and H120 are comprised, but spike proteins or fragments thereof from Beaudette strains are excluded.

In another specific aspect of the IBV spike protein or fragment thereof according to the present invention the Spike protein or fragment thereof is from an IBV selected from a list of genotypes or serotypes consisting of: Massachusetts (not Beaudette), 4/91, QX, Q1, Arkansas, Variant 2 and Brazil.

In another specific aspect of the IBV spike protein or fragment thereof according to the present invention the Spike protein or fragment thereof is from an IBV selected from a list of genotypes or serotypes consisting of Massachusetts (not Beaudette) and 4/91.

In another specific aspect of the IBV spike protein or fragment thereof according to the present invention the Massachusetts strain is selected from a list consisting of: H120, H52, Spain/98/308, IBMA5-1, SD/97/01, Spain/96/334 and M41-M21883.

In another specific aspect of the IBV spike protein or fragment thereof according to the present invention the 4/91 strain is selected from a list consisting of: Spain/98/328, Spain/92/35, IR-3654-VM, FR-CR88061-88, FR-85131-85, UK-1233-95, UK/3/91, Spain/00/336, UK/7/91, 4/91-pathogenic, 4/91 attenuated and IB4-91.

In another specific aspect of the IBV spike protein or fragment thereof according to the present invention the QX strain is selected from a list consisting of: FR-L1450T-05, FR-L1450L-05, NL-L1449T-04, NL-L1449K-04, IBV/Ck/SP/170/09, IBV/Ck/SP/79/08, IBV/Ck/SP/248/09, HBN, IBVQX, LX4, BJQ, CK/CH/LGD/03, SP2013-01470, SP2013-014171, SP2013-01478 and GB341/96.

In another specific aspect of the IBV spike protein or fragment thereof according to the present invention the Q1 strain is selected from a list consisting of: CK/CH/LDL/98I, CK/CH/LSD/08-10, J2, Q1, AR08ER22, AR08BA21, 12.185, 12.124, 12.216 and Chile-295-10.

In another specific aspect of the IBV spike protein or fragment thereof according to the present invention the Italy 02 strain is selected from a list consisting of: Spain/99/316, Italy-02, UK-L633-04, It-497-02, Spain/05/866, Spain/04/221, Spain/00/337, Spain/155/09 and Spain/03/08.

In another specific aspect of the IBV spike protein or fragment thereof according to the present invention the Arkansas strain is selected from a list consisting of: Ark99, ArkGA, ArkDPI, AL/5364/00, ARKDPI11, AL/0803/01, AL/7149/00, ArkDPI101, AL/1221/01, AL/1793/01 and AL/4614/98.

In another specific aspect of the IBV spike protein or fragment thereof according to the present invention the Variant 2 strain is selected from a list consisting of: IS/1494/06, IBV/Ck/EG/CU/4/2014, gammaCoV/Ck/Poland/G052/2016, Eg/CLEVB-2/IBV/012, D1344/2/4/10_EG, TR8 and IB VAR2-06.

In another specific aspect of the IBV spike protein or fragment thereof according to the present invention the Brazil strain is selected from a list consisting of: BR-1, BR-2, 23/2013, and IBV/Brasil/351/1984.

In another specific aspect of the IBV spike protein or fragment thereof according to the present invention the Spike protein or fragment thereof is from an IBV of Massachusetts (not Beaudette), QX or 4/91 genotype or serotype.

In another specific aspect of the IBV spike protein or fragment thereof according to the present invention the Spike protein or fragment thereof is from an IBV of Massachusetts (not Beaudette) genotype or serotype.

In another specific aspect of the IBV spike protein or fragment thereof according to the present invention the Spike protein or fragment thereof is from an IBV of QX genotype or serotype.

In another specific aspect of the IBV spike protein or fragment thereof according to the present invention the Spike protein or fragment thereof is from an IBV of 4/91 genotype or serotype.

In another specific aspect of the IBV spike protein or fragment thereof according to the present invention the IBV strain is H52, H120, QX SP2013-01478 or CR88.

In another specific aspect of the IBV spike protein or fragment thereof according to the present invention the IBV spike protein or fragment thereof consists of or comprises an amino acid sequence as shown in SEQ ID NO: 2, 3, 4, 5, 6, 7, 8, 77 or a sequence having at least 80%, 85%, 90%, 93%, 95%, 96%, 97%, 98%, 99%, 99.5%, 99.6%, 99.7%, 99.8%, 99.9%, 99.95%, 99.98% or 99.99% sequence identity thereto.

The term "identity" or "sequence identity" is known in the art and refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, MD 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

The terms "identity", "sequence identity" and "percent identity" are used interchangeably herein. For the purpose of this invention, it is defined here that in order to determine the percent identity of two amino acid sequences or two nucleic acid sequences, the sequences are aligned for optimal comparison purposes (e.g., gaps can be introduced in the sequence of a first amino acid or nucleic acid for optimal alignment with a second amino or nucleic acid sequence). The amino acid or nucleotide residues at corresponding amino acid or nucleotide positions are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are of the same length.

A sequence comparison may be carried out over the entire lengths of the two sequences being compared or over fragments of the two sequences. Typically, the comparison will be carried out over the full length of the two sequences being compared. However, sequence identity may be carried out over a region of, for example, twenty, fifty, one hundred or more contiguous amino acid residues.

The skilled person will be aware of the fact that different computer programs are available to determine the homology between two sequences. For instance, a comparison of sequences and determination of percent identity between two sequences can be accomplished using a mathematical algorithm. In a preferred embodiment, the percent identity between two amino acid or nucleic acid sequences is determined using the Needleman and Wunsch (J. Mol. Biol. (48): 444-453 (1970)) algorithm which has been incorporated into the GAP program in the Accelrys GCG software package (available at http://www.accelrys.com/products/gcg/), using either a Blosum 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

The protein sequences or nucleic acid sequences of the present invention can further be used as a "query sequence" to perform a search against public databases to, for example, to identify other family members or related sequences. Such searches can be performed using the BLASTN and BLASTP programs (version 2.0) of Altschul, et al. (1990) J. Mol. Biol. 215:403-10. BLAST protein searches can be performed with the BLASTP program, score=50, wordlength=3 to obtain amino acid sequences homologous to protein molecules of the invention. To obtain gapped alignments for comparison purposes, Gapped BLAST can be utilized as described in Altschul et al. (1997) Nucleic Acids Res. 25(17): 3389-3402. When utilizing BLAST and Gapped BLAST programs, the default parameters of the respective programs (e.g., BLASTP and BLASTN) can be used. See the homepage of the National Center for Biotechnology Information at http://www.ncbi.nlm.nih.gov/.

As used herein, it is in particular understood that the term "identical to the sequence of SEQ ID NO: X" is equivalent to the term "identical to the sequence of SEQ ID NO: X over the length of SEQ ID NO: X" or to the term "identical to the sequence of SEQ ID NO: X over the whole length of SEQ ID NO: X", respectively. In this context, "X" is any integer selected from 1 to 84 so that "SEQ ID NO: X" represents any of the SEQ ID NOs mentioned herein.

In another specific aspect of the IBV spike protein or fragment thereof according to the present invention the IBV spike protein or fragment thereof consists of or comprises an amino acid sequence as shown in SEQ ID NO: 2 or a sequence having at least 80%, 85%, 90%, 93%, 95%, 96%, 97%, 98%, 99%, 99.5%, 99.6%, 99.7%, 99.8%, 99.9%, 99.95%, 99.98% or 99.99% sequence identity thereto.

In another specific aspect of the IBV spike protein or fragment thereof according to the present invention the IBV spike protein or fragment thereof consists of or comprises an amino acid sequence as shown in SEQ ID NO: 3 or a sequence having at least 80%, 85%, 90%, 93%, 95%, 96%, 97%, 98%, 99%, 99.5%, 99.6%, 99.7%, 99.8%, 99.9%, 99.95%, 99.98% or 99.99% sequence identity thereto.

In another specific aspect of the IBV spike protein or fragment thereof according to the present invention the IBV spike protein or fragment thereof consists of or comprises an amino acid sequence as shown in SEQ ID NO: 4 or a sequence having at least 80%, 85%, 90%, 93%, 95%, 96%, 97%, 98%, 99%, 99.5%, 99.6%, 99.7%, 99.8%, 99.9%, 99.95%, 99.98% or 99.99% sequence identity thereto.

In another specific aspect of the IBV spike protein or fragment thereof according to the present invention the IBV spike protein or fragment thereof consists of or comprises an amino acid sequence as shown in SEQ ID NO: 5 or a sequence having at least 80%, 85%, 90%, 93%, 95%, 96%, 97%, 98%, 99%, 99.5%, 99.6%, 99.7%, 99.8%, 99.9%, 99.95%, 99.98% or 99.99% sequence identity thereto.

In another specific aspect of the IBV spike protein or fragment thereof according to the present invention the IBV spike protein or fragment thereof consists of or comprises an amino acid sequence as shown in SEQ ID NO: 6 or a sequence having at least 80%, 85%, 90%, 93%, 95%, 96%, 97%, 98%, 99%, 99.5%, 99.6%, 99.7%, 99.8%, 99.9%, 99.95%, 99.98% or 99.99% sequence identity thereto.

In another specific aspect of the IBV spike protein or fragment thereof according to the present invention the IBV spike protein or fragment thereof consists of or comprises an amino acid sequence as shown in SEQ ID NO: 7 or a sequence having at least 80%, 85%, 90%, 93%, 95%, 96%, 97%, 98%, 99%, 99.5%, 99.6%, 99.7%, 99.8%, 99.9%, 99.95%, 99.98% or 99.99% sequence identity thereto.

In another specific aspect of the IBV spike protein or fragment thereof according to the present invention the IBV spike protein or fragment thereof consists of or comprises an amino acid sequence as shown in SEQ ID NO: 8 or 77 or a sequence having at least 80%, 85%, 90%, 93%, 95%, 96%, 97%, 98%, 99%, 99.5%, 99.6%, 99.7%, 99.8%, 99.9%, 99.95%, 99.98% or 99.99% sequence identity thereto.

In another specific aspect of the IBV spike protein or fragment thereof according to the present invention the IBV spike protein or fragment thereof is selected from a list of genotypes consisting of: GI-2 to 27, GII-1, GIII-1, GIV-1, GV-1, GVI-1.

Valastro et al 2016 (Infection, Genetics and Evolution 39; 349-364) describe a phylogeny-based classification system combined with a lineage nomenclature for the assignment of IBV strains. 6 genotypes (GI to GVI) are defined that together comprise 32 distinct viral lineages.

In another specific aspect of the IBV spike protein or fragment thereof according to the present invention the spike protein or fragment thereof is not from the GI-1 genotype. The GI-1 genotype relates to the Massachusetts genotype/serotype.

In another specific aspect of the avian coronavirus spike protein or fragment thereof according to the present invention said at least a part of the S1 subunit from an avian coronavirus with a restricted cell or tissue tropism is selected from the group consisting of: Infectious bronchitis virus (IBV); guinea fowl coronavirus (GfCoV) and turkey coronavirus (TCoV; turkey enteritis virus and bluecomb disease virus).

In another specific aspect of the avian coronavirus spike protein or fragment thereof according to the present invention said at least a part of the S1 subunit from an avian coronavirus with a restricted cell or tissue tropism is from IBV (infectious bronchitis virus).

In another specific aspect of the IBV spike protein or fragment thereof according to the present invention said at least a part of the S1 subunit is from an IBV selected from a list of genotypes or serotypes or strains consisting of: Arkansas (such as Arkansas 99), Brazil (such as BR-1, BR-2, 23/2013, IBV/Brasil/351/1984), California (such as California 1734/04, California 99), Connecticut, Delaware (such as Delaware 98), Dutch (such as D207, D212, D274, D3128, D3896, D8880, D1466), Florida, Georgia (such as Georgia GA-07, GA-08, GA-12, GA-13), Gray, Holte, Iowa (such as Iowa 97 and Iowa 69), Italy02, JMK, LDT3, Maine (such as Maine 209), Massachusetts (such as M41, H52, H120; excluding Beaudette), Pennsylvania (such as Pennsylvania 1220/98, Pennsylvania Wolg/98), PL84084, Qu (such as Qu-mv), QX (such as GB341/96), Q1, SE 17, Variant 2 (such as IS/1494/06, IBV/Ck/EG/CU/4/2014, gammaCoV/Ck/Poland/G052/2016) and 4/91 (793B, CR88).

In another specific aspect of the IBV spike protein or fragment thereof according to the present invention said at least a part of the S1 subunit is from an IBV selected from a list of genotypes or serotypes or strains consisting of Massachusetts (not Beaudette), 4/91, QX, Q1, Italy 02, Arkansas, Connecticut, Georgia, LDT3, PL84084, Variant 2 and Brazil.

In another specific aspect of the IBV spike protein or fragment thereof according to the present invention said at least a part of the S1 subunit is from an IBV selected from a list of genotypes or serotypes consisting of Massachusetts (not Beaudette), 4/91, QX, Q1, Arkansas, Variant 2 and Brazil.

In another specific aspect of the IBV spike protein or fragment thereof according to the present invention the Massachusetts strain is selected from a list consisting of: H120, H52, Spain/98/308, IBMA5-1, SD/97/01, Spain/96/334 and M41-M21883.

In another specific aspect of the IBV spike protein or fragment thereof according to the present invention the 4/91 strain is selected from a list consisting of: Spain/98/328, Spain/92/35, IR-3654-VM, FR-CR88061-88, FR-85131-85, UK-1233-95, UK/3/91, Spain/00/336, UK/7/91, 4/91-pathogenic, 4/91 attenuated and IB4-91.

In another specific aspect of the IBV spike protein or fragment thereof according to the present invention the QX strain is selected from a list consisting of: FR-L1450T-05, FR-L1450L-05, NL-L1449T-04, NL-L1449K-04, IBV/Ck/SP/170/09, IBV/Ck/SP/79/08, IBV/Ck/SP/248/09, HBN, IBVQX, LX4, BJQ, CK/CH/LGD/03 and GB341/96.

In another specific aspect of the IBV spike protein or fragment thereof according to the present invention the Q1 strain is selected from a list consisting of: CK/CH/LDL/98I, CK/CH/LSD/08-10, J2, Q1, AR08ER22, AR08BA21 and Chile-295-10.

In another specific aspect of the IBV spike protein or fragment thereof according to the present invention the Italy 02 strain is selected from a list consisting of: Spain/99/316, Italy-02, UK-L633-04, It-497-02, Spain/05/866, Spain/04/221, Spain/00/337, Spain/155/09 and Spain/03/08.

In another specific aspect of the IBV spike protein or fragment thereof according to the present invention the Arkansas strain is selected from a list consisting of: Ark99, ArkGA, ArkDPI, AL/5364/00, ARKDPI11, AL/0803/01, AL/7149/00, ArkDPI101, AL/1221/01, AL/1793/01 and AL/4614/98.

In another specific aspect of the IBV spike protein or fragment thereof according to the present invention the Variant 2 strain is selected from a list consisting of: IS/1494/06, IBV/Ck/EG/CU/4/2014, gammaCoV/Ck/Poland/G052/2016, Eg/CLEVB-2/IBV/012, D1344/2/4/10_EG, TR8 and IB VAR2-06.

In another specific aspect of the IBV spike protein or fragment thereof according to the present invention the Brazil strain is selected from a list consisting of: BR-1, BR-2, 23/2013 and IBV/Brasil/351/1984.

In another specific aspect of the IBV spike protein or fragment thereof according to the present invention said at least a part of the S1 subunit is from an IBV selected from a list of genotypes or serotypes consisting of Massachusetts (not Beaudette), QX and 4/91.

In another specific aspect of the IBV spike protein or fragment thereof according to the present invention said at least a part of the S1 subunit is from an Massachusetts (not Beaudette) IBV genotype or serotype.

In another specific aspect of the IBV spike protein or fragment thereof according to the present invention said at least a part of the S1 subunit is from an QX IBV genotype or serotype.

In another specific aspect of the IBV spike protein or fragment thereof according to the present invention said at least a part of the S1 subunit is from an 4/91 IBV genotype or serotype.

In another specific aspect of the IBV spike protein or fragment thereof according to the present invention said at least a part of the S1 subunit is from an IBV strain H120, H52, QX SP2013-01478 or CR88.

In another specific aspect of the IBV spike protein or fragment thereof according to the present invention said at least a part of the S1 subunit is from an IBV strain H120 or H52.

In another specific aspect of the avian coronavirus spike protein or fragment thereof according to the present invention the at least a part of the S1 subunit is at least 1, 5, 10, 15, 20, 25, 50, 100, 150, 200, 250, 300, 350, 400 or 500 contiguous amino acids from a S1 subunit sequence of an avian coronavirus or IBV with a restricted cell or tissue tropism or a sequence having at least 90%, 95%, 96%, 97%, 98%, 99% sequence identity thereto.

In another specific aspect of the avian coronavirus or IBV spike protein or fragment thereof according to the present invention the at least a part of the S1 subunit is at least 1, 5, 10, 15, 20, 25, 50, 100, 150, 200, 250, 300, 350, 400 or 500 contiguous amino acids from a S1 subunit sequence of an avian coronavirus or IBV as described herein or a sequence having at least 90%, 95%, 96%, 97%, 98%, 99% sequence identity thereto.

In another specific aspect of the IBV spike protein or fragment thereof according to the present invention said at least a part of the S1 subunit from an IBV with a restricted cell or tissue tropism has at least 1, 5, 10, 15, 20, 25, 50, 100, 150, 200, 250, 300, 350, 400 or 500 contiguous amino acids of the amino acid sequence as shown in SEQ ID NO: 2, 3, 4, 5, 6, 7, 8, 77 or a sequence having at least 90%, 95%, 96%, 97%, 98%, 99% sequence identity thereto.

In another specific aspect of the avian coronavirus or IBV spike protein or fragment thereof according to the present invention the coronavirus or IBV with restricted cell or tissue tropism is restricted to infection and/or replication in emryonated chicken eggs and/or primary chicken kidney cells.

In another specific aspect of the avian coronavirus or IBV spike protein or fragment thereof according to the present invention the coronavirus or IBV with restricted cell or tissue tropism is not infecting and/or replicating in EB66 cells.

In another specific aspect of the avian coronavirus or IBV spike protein or fragment thereof according to the present invention the coronavirus or IBV with restricted cell or tissue tropism is not infecting and/or replicating in PBS-12SF and/or HEK 293T cells.

Fragment

In another specific aspect of the avian coronavirus or IBV spike protein or fragment thereof according to the present invention the fragment of the avian coronavirus or IBV spike protein has a length of at least 500, 750, 1000 or 1077 amino acids.

In another specific aspect of the avian coronavirus or IBV spike protein or fragment thereof according to the present invention the fragment of the avian coronavirus or IBV spike protein has a length of at least 1000 amino acids.

In another specific aspect of the avian coronavirus or IBV spike protein or fragment thereof according to the present invention the fragment of the avian coronavirus or IBV spike protein has a length of at least 500, 750, 1000 or 1075 amino acids from the N-Terminus.

The term "N-terminus" is well known to the person skilled in the art. The N-terminus is also termed amino-terminus, NH2-terminus, N-terminal end or amine-terminus. When the protein is translated from messenger RNA, it is created from N-terminus to C-terminus. Thus, the N-terminus is the start of an amino acid chain (protein or polypeptide) comprising said amine group (—NH2).

In another specific aspect of the avian coronavirus or IBV spike protein or fragment thereof according to the present invention the fragment of the avian coronavirus or IBV spike protein is the ectodomain of the spike protein.

The term "ectodomain" is well known to a person skilled in the art. The spike protein comprises different functional parts, the signal sequence, the ectodomain, the transmembrane domain and the endodomain (from N-terminus to C-terminus). Thus, after cleavage of the signal sequence, the N-terminus of the spike protein starts with the ectodomain. The IBV spike ectodomains has a length of about 1075 amino acids and differs by a few amino acids in length dependent on the IBV strain.

In another specific aspect of the avian coronavirus or IBV spike protein according to the present invention the Cysteine at amino acid position 267 or the mutation at amino acid position 267 to Cysteine is genetically stable. Advantageously, the experimental data show that the Cysteine at amino acid position 267 or the mutation at amino acid position 267 to Cysteine is genetically stable and remains stable over time (over passage).

The term "genetically stable" means that the Cysteine at amino acid position 267 or the mutation at amino acid position 267 to Cysteine remains stable over time (over passage). Preferably, said Cysteine at amino acid position 267 or the mutation at amino acid position 267 to Cysteine is still present after at least 3 passages, more preferably after at least 6 passages, even more preferably after at least 9 passages, even more preferably after at least 12 passages, most preferred after 15 passages in cell culture or tissue culture of an IBV having said avian coronavirus or IBV spike protein according to the present invention.

Nucleotide Sequence and Plasmids

Further, the present invention provides a nucleotide sequence encoding the spike protein or fragment thereof as described herein.

Further, the present invention provides a plasmid comprising a nucleotide sequence as described herein.

The term "nucleic acid" or "nucleic acid sequence" or "nucleotide sequence" refers to polynucleotides including DNA molecules, RNA molecules, cDNA molecules or derivatives. The term encompasses single as well as double stranded polynucleotides. The nucleic acid of the present invention encompasses isolated polynucleotides (i.e. isolated from its natural context) and genetically modified forms. Moreover, comprised are also chemically modified polynucleotides including naturally occurring modified polynucleotides such as glycosylated or methylated polynucleotides or artificially modified ones such as biotinylated polynucleotides. Further, the terms "nucleic acid" and "polynucleotide" are interchangeable and refer to any nucleic acid. The terms "nucleic acid" and "polynucleotide" also specifically include nucleic acids composed of nucleotides with the nucleobases other than the five biologically occurring bases (adenine, guanine, thymine, cytosine and uracil).

The term "plasmid" refers to cytoplasmic DNA that replicates independently of the bacterial chromosome within a bacterial host cell. In a specific aspect of the present invention the term "plasmid" and/or "transfer plasmid" and/or "donor plasmid" refers to an element of recombinant DNA technology useful for construction of e.g. recombinant viruses or an expression cassette for insertion into a viral vector. In another specific aspect the term "plasmid" may be used to specify a plasmid useful for DNA vaccination purposes.

Cell

Further, the present invention provides a cell comprising a plasmid as described herein. The cell can be an eukaryotic or prokaryotic cell.

Viral Particle, Avian Coronavirus and IBV

Further, the present invention provides a viral particle comprising a spike protein or fragment thereof as described herein.

Further, the present invention provides an avian coronavirus comprising the spike protein or fragment thereof as described herein.

Further, the present invention provides an IBV (infectious bronchitis virus) comprising the spike protein as described herein.

In another specific aspect of the avian coronavirus or IBV according to the present invention the avian coronavirus or IBV is attenuated.

The term "attenuated" refers to a pathogen having a reduced virulence in comparison to the wildtype isolate. In the present invention, an attenuated IBV is one in which the virulence has been reduced so that it does not cause clinical signs of an IBV infection but is capable of inducing an immune response in the target animal, but may also mean that the clinical signs are reduced in incidence or severity in animals infected with the attenuated IBV in comparison with a "control group" of animals infected with non-attenuated IBV and not receiving the attenuated virus. In this context, the term "reduce/reduced" means a reduction of at least 10%, preferably 25%, even more preferably 50%, still more preferably 60%, even more preferably 70%, still more preferably 80%, still more preferably 90%, even more preferably 95% and most preferably of 100% as compared to the control group infected with non-attenuated IBV as defined above. Thus, an attenuated, IBV strain is one that is suitable for incorporation into an immunogenic composition comprising a modified live IBV.

In another specific aspect of the avian coronavirus or IBV according to the present invention the avian coronavirus or IBV is inactivated.

Any conventional inactivation method can be used for purposes of the present invention. Thus, inactivation can be performed by chemical and/or physical treatments which are known to the person skilled in the art. Preferred inactivation methods include the addition of cyclized binary ethylenimine (BEI) including the addition of a solution of 2-bromoethyleneamine hydrobromide (BEA), which has been cyclized to binary ethylenimine (BEI). Preferred further chemical inactivation agents comprise but are not limited to Triton X-100, Sodium deoxycholate, Cetyltrimethylammonium bromide, β-Propiolactone, Thimerosal, Phenol and Formaldehyde (Formalin). However, the inactivation may also comprise a neutralization step. Preferred neutralization agents include but are not limited to sodium thiosulfate, sodium bisulfite and the alike.

Preferred formalin inactivation conditions include formalin concentration between from about 0.02% (v/v)-2.0% (v/v), more preferably from about 0.1% (v/v)-1.0% (v/v), still more preferably from about 0.15% (v/v)-0.8% (v/v), even more preferably from about 0.16% (v/v)-0.6% (v/v), and most preferably about 0.2% (v/v)-0.4% (v/v). Incubation time depends on the resistance of the IBV. In general, the inaction process is performed until no growth of the IBV can be detected in a suitable cultivation system.

Preferably, the inactivated IBV of the present invention is formalin inactivated, preferably using the concentrations as described hereinabove.

The inactivated IBV of the invention may be incorporated into liposomes using known technology such as that described in Nature, 1974, 252, 252-254 or Journal of Immunology, 1978, 120, 1109-13. In another embodiment of the invention, the inactivated IBV of the invention may be conjugated to suitable biological compounds such as polysaccharides, peptides, proteins, or the like, or a combination thereof.

In another specific aspect of the avian coronavirus or IBV according to the present invention the avian coronavirus or IBV is genetically engineered.

The term "genetically engineered" refers to an avian coronavirus or IBV which has been mutated by using "reverse genetics" approaches. Preferably, the avian coronavirus or IBV according to the present invention has been genetically engineered. The reverse genetics technique involves the preparation of synthetic recombinant viral RNAs. However, "reverse genetics" techniques are well known to the person skilled in the art.

In another specific aspect of the avian coronavirus or IBV according to the present invention the avian coronavirus or IBV is a recombinant.

The term "recombinant" as used herein relates to a RNA genome (or RNA sequence, cDNA sequence or protein) having any modifications that do not naturally occur to the corresponding RNA genome (or RNA sequence, cDNA sequence or protein). For instance, a RNA genome (or RNA sequence, cDNA sequence or protein) is considered "recombinant" if it contains an insertion, deletion, inversion, relocation or a point mutation introduced artificially, e.g., by human intervention. Therefore, the RNA genomic sequence (or RNA sequence, cDNA sequence or protein) is not associated with all or a portion of the sequences (or RNA sequence, cDNA sequence or protein) with which it is associated in nature. The term "recombinant" as used with respect to a virus, means a virus produced by artificial manipulation of the viral genome. The term "recombinant virus" encompasses genetically modified viruses.

In another specific aspect of the avian coronavirus or IBV according to the present invention the avian coronavirus or IBV is chimeric.

The term "chimeric" refers to an avian coronavirus or IBV comprising one or more nucleotide sequences from another coronavirus or IBV. Preferably, the term refers to an IBV virus comprising one or more nucleotide sequences from another IBV strain.

In another specific aspect of the IBV according to the present invention the IBV is from an IBV with a genotype or serotype or strain selected from a list consisting of: Arkansas (such as Arkansas 99), Brazil (such as BR-1, BR-2, 23/2013, IBV/Brasil/351/1984), California (such as California 1734/04, California 99), Connecticut, Delaware (such as Delaware 98), Dutch (such as D207, D212, D274, D3128, D3896, D8880, D1466), Florida, Georgia (such as Georgia GA-07, GA-08, GA-12, GA-13), Gray, Holte, Iowa (such as Iowa 97 and Iowa 69), Italy 02, JMK, LDT3, Maine (such as Maine 209), Massachusetts (M41, H52, H120, Beaudette), Pennsylvania (such as Pennsylvania 1220/98, Pennsylvania Wolg/98), PL84084, Qu (such as Qu-mv), QX (such as GB341/96), Q1, SE 17, Variant 2 (such as IS/1494/06, IBV/Ck/EG/CU/4/2014, gammaCoV/Ck/Poland/G052/2016) and 4/91 (793B, CR88).

In another specific aspect of the IBV according to the present invention the IBV is selected from a list of genotypes or serotypes or strains consisting of: Massachusetts, 4/91, QX, Q1, Italy 02, Arkansas, Connecticut, Georgia, LDT3, PL84084, Variant 2 and Brazil.

In another specific aspect of the IBV according to the present invention the IBV is selected from a list of genotypes or serotypes consisting of: Massachusetts, 4/91, QX, Q1, Arkansas, Variant 2 and Brazil.

In another specific aspect of the IBV according to the present invention the Massachusetts strain is selected from a list consisting of: H120, H52, Spain/98/308, IBMA5-1, SD/97/01, Beaudette, Spain/96/334 and M41-M21883.

In another specific aspect of the IBV according to the present invention the 4/91 strain is selected from a list consisting of: Spain/98/328, Spain/92/35, IR-3654-VM, FR-CR88061-88, FR-85131-85, UK-1233-95, UK/3/91, Spain/00/336, UK/7/91, 4/91-pathogenic, 4/91 attenuated and IB4-91.

In another specific aspect of the IBV according to the present invention the QX strain is selected from a list consisting of: FR-L1450T-05, FR-L1450L-05, NL-L1449T-04, NL-L1449K-04, IBV/Ck/SP/170/09, IBV/Ck/SP/79/08, IBV/Ck/SP/248/09, HBN, IBVQX, LX4, BJQ, CK/CH/LGD/03 and GB341/96.

In another specific aspect of the IBV according to the present invention the Q1 strain is selected from a list consisting of: CK/CH/LDL/98I, CK/CH/LSD/08-10, J2, Q1, AR08ER22, AR08BA21 and Chile-295-10.

In another specific aspect of the IBV according to the present invention the Italy 02 strain is selected from a list consisting of: Spain/99/316, Italy-02, UK-L633-04, It-497-02, Spain/05/866, Spain/04/221, Spain/00/337, Spain/155/09 and Spain/03/08.

In another specific aspect of the IBV according to the present invention the Arkansas strain is selected from a list consisting of: Ark99, ArkGA, ArkDPI, AL/5364/00, ARKDPI11, AL/0803/01, AL/7149/00, ArkDPI101, AL/1221/01, AL/1793/01 and AL/4614/98.

In another specific aspect of the IBV according to the present invention the Variant 2 strain is selected from a list consisting of: IS/1494/06, IBV/Ck/EG/CU/4/2014, gammaCoV/Ck/Poland/G052/2016, Eg/CLEVB-2/IBV/012, D1344/2/4/10_EG, TR8 and IB VAR2-06.

In another specific aspect of the IBV according to the present invention the Brazil strain is selected from a list consisting of: BR-1, BR-2, 23/2013 and IBV/Brasil/351/1984.

In another specific aspect of the IBV according to the present invention the spike protein or fragment thereof is from an IBV of Massachusetts or 4/91 genotype or serotype.

In another specific aspect of the IBV according to the present invention the spike protein or fragment thereof is from an IBV of Massachusetts genotype or serotype.

In another specific aspect of the IBV according to the present invention the spike protein or fragment thereof is from an IBV of 4/91 genotype or serotype.

In another specific aspect of the IBV according to the present invention the IBV strain is H120, H52 or CR88.

In another specific aspect of the IBV according to the present invention the IBV strain is H120 or H52.

In another specific aspect of the IBV according to the present invention the IBV has a IBV spike protein or fragment thereof consisting of or comprising an amino acid sequence as shown in SEQ ID NO: 2, 3, 4, 5, 6, 7, 8, 77 or a sequence having at least 80%, 85%, 90%, 93%, 95%, 96%, 97%, 98%, 99%, 99.5%, 99.6%, 99.7%, 99.8%, 99.9%, 99.95%, 99.98% or 99.99% sequence identity thereto.

In another specific aspect of the IBV according to the present invention the IBV has an extended cell or tissue tropism.

In another specific aspect of the IBV according to the present invention the IBV is infecting and/or replicating in at least one cell line or cell as described herein. Preferably, the IBV is infecting and/or replicating in at least one cell line as described herein.

Further, the present invention provides a cell comprising:
the viral particle as described herein, or
the avian coronavirus or IBV as described herein.

In another specific aspect of the cell according to the present invention the cell is a cell line or cell selected from the list consisting of: primary chicken embryo cells, a chicken embryo fibroblast cell line, a duck embryonic stem cell line, a human embryonic kidney cell line, a baby hamster kidney cell line, an african green monkey kidney cell line, a rabbit kidney cell line, a canine kidney cell line, a chicken liver cell line, a bovine kidney cell line, a porcine kidney cell line and an insect cell line.

In another specific aspect of the cell according to the present invention the cell is a cell line selected from the list consisting of: DF-1 (Douglas Foster), EB66 (duck embryonic stem cell line), PBS-12, PBS-12SF (PBS-12 serum free), BHK21 (baby hamster kidney), HEK 293T (human embryonic kidney), Vero (Verda Reno), MA104, RK13 (rabbit kidney), LMH (leghorn male hepatoma), MDCK (Madin-Darby canine kidney), MDBK (Madin-Darby bovine kidney), PK15 (porcine kidney), PK2A (porcine kidney), SF9, SF21 and SF+(*Spodoptera frugiperda*).

In another specific aspect of the cell according to the present invention the cell is a cell line selected from the list consisting of: DF-1, EB66, PBS-12, PBS-12SF, BHK, HEK 293T, Vero, MA104 and RK13.

In another specific aspect of the cell according to the present invention the primary chicken embryo cell is a fibroblast or a cell derived from liver or lung tissue.

Further, the present invention provides an immunogenic composition comprising:
the spike protein as described herein, or
the viral particle as described herein, or
the avian coronavirus or IBV as described herein.

Thus, the present invention also provides an immunogenic composition comprising an avian coronavirus or IBV comprising an avian coronavirus or IBV spike protein or fragment thereof, wherein at least a part of the S1 subunit is from an avian coronavirus or IBV with a restricted cell or tissue tropism, and wherein at amino acid position 267 is a Cysteine. Further, the present invention also provides an immunogenic composition comprising an avian coronavirus or IBV comprising a recombinant avian coronavirus or IBV spike protein or fragment thereof comprising a mutation at amino acid position 267 to Cysteine. Further, the amino acid sequence of SEQ ID NO:1 is used for determining the position numbering in the spike protein. Preferably, the amino acid sequence of the spike protein is aligned to the amino acid sequence of SEQ ID NO:1

Further, the present invention provides a vaccine comprising:
the spike protein as described herein, or
the viral particle as described herein, or
the coronavirus or IBV as described herein.

Further, the present invention provides a modified live vaccine with an extended cell or tissue tropism comprising:
the spike protein as described herein, or
the viral particle as described herein, or
the coronavirus or IBV as described herein.

The term "immunogenic composition" refers to a composition that comprises at least one antigen, which elicits an immunological response in the host to which the immunogenic composition is administered. Such immunological response may be a cellular and/or antibody-mediated immune response to the immunogenic composition of the invention. Preferably, the immunogenic composition induces an immune response and, more preferably, confers protective immunity against one or more of the clinical signs of a IBV infection. The host is also described as "subject". Preferably, any of the hosts or subjects described or mentioned herein is an avian or poultry.

Usually, an "immunological response" includes but is not limited to one or more of the following effects: the production or activation of antibodies, B cells, helper T cells, suppressor T cells, and/or cytotoxic T cells and/or gamma-delta T cells, directed specifically to an antigen or antigens included in the immunogenic composition of the invention. Preferably, the host will display either a protective immunological response or a therapeutically response.

A "protective immunological response" or "protective immunity" will be demonstrated by either a reduction or lack of clinical signs normally displayed by an infected host, a quicker recovery time and/or a lowered duration of infectivity or lowered pathogen titer in the tissues or body fluids or excretions of the infected host.

In case where the host displays a protective immunological response such that resistance to new infection will be enhanced and/or the clinical severity of the disease reduced, the immunogenic composition is described as a "vaccine".

The term "modified live" and "attenuated" are used interchangeable herein.

In another specific aspect of the immunogenic composition or vaccine according to the present invention the immunogenic composition or vaccine comprises a pharmaceutically acceptable carrier.

The term "pharmaceutical-acceptable carrier" includes any and all solvents, dispersion media, coatings, stabilizing agents, diluents, preservatives, antibacterial and antifungal agents, isotonic agents, adsorption delaying agents, adjuvants, immune stimulants, and combinations thereof.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

In another specific aspect of the immunogenic composition or vaccine according to the present invention the pharmaceutically acceptable carrier is phosphate buffered saline.

Preferably, the immunogenic composition further comprises sucrose gelatin stabilizer.

Preferably, the pharmaceutically acceptable carrier is chitosan.

Chitosan is a natural deacetylated polysaccharide from chitin in crustaceans (e.g., shrimp, crab), insects, and other invertebrates. Recently, Rauw et al. 2009 (Vet Immunol Immunop 134:249-258) demonstrated that chitosan enhanced the cellular immune response of live Newcastle disease vaccine and promoted its protective effect. Further, Wang et al., 2012 (Arch Virol (2012) 157:1451-1461) have shown results revealing the potential of chitosan as an adjuvant for use in a live attenuated influenza vaccine.

Preferably, the immunogenic composition can further include one or more other immunomodulatory agents such as, e.g. interleukins, interferons, or other cytokines. The amounts and concentrations of adjuvants and additives useful in the context of the present invention can readily be determined by the skilled artisan.

In some aspects, the immunogenic composition of the present invention contains an adjuvant. "Adjuvants" as used herein, can include aluminum hydroxide and aluminum phosphate, saponins e.g., Quil A, QS-21 (Cambridge Biotech Inc., Cambridge MA), GPI-0100 (Galenica Pharmaceuticals, Inc., Birmingham, AL), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.), John Wiley and Sons, NY, pp 51-94 (1995) and Todd et al., Vaccine 15:564-570 (1997). Exemplary adjuvants are the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol; (BF Goodrich, Ohio, USA) are particularly appropriate. They are cross-linked with an allyl sucrose or with allyl pentaerythritol. Among then, there may be mentioned Carbopol 974P, 934P and 971P. Most preferred is the use of Carbopol 971P. Among the copolymers of maleic anhydride and alkenyl derivative, are the copolymers EMA (Monsanto), which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta GA), SAF-M (Chiron, Emeryville CA), monophosphoryl lipid A, Avridine lipid-amine adjuvant, heat-labile enterotoxin from E. coli (recombinant or otherwise), cholera toxin, IMS 1314 or muramyl dipeptide, or naturally occurring or recombinant cytokines or analogs thereof or stimulants of endogenous cytokine release, among many others.

It is expected that an adjuvant can be added in an amount of about 100 µg to about 10 mg per dose, preferably in an amount of about 100 µg to about 10 mg per dose, more preferably in an amount of about 500 µg to about 5 mg per dose, even more preferably in an amount of about 750 µg to about 2.5 mg per dose, and most preferably in an amount of about 1 mg per dose. Alternatively, the adjuvant may be at a concentration of about 0.01 to 50%, preferably at a concentration of about 2% to 30%, more preferably at a concentration of about 5% to 25%, still more preferably at a concentration of about 7% to 22%, and most preferably at a concentration of 10% to 20% by volume of the final product.

In another specific aspect of the immunogenic composition or vaccine according to the present invention the immunogenic composition or vaccine is effective in the treatment and/or prophylaxis of clinical signs caused by IBV in a subject of need. The terms "treatment and/or prophylaxis", "clinical signs" and "of need" have been defined elsewhere.

In another specific aspect of the immunogenic composition or vaccine according to the present invention said immunogenic composition or vaccine is formulated for a single-dose administration.

The volume for a single-dose has been defined elsewhere herein.

It has furthermore been shown that one dose of the immunogenic composition of the present invention is effective after the administration of such single dose of such immunogenic composition or vaccine.

In another specific aspect of the immunogenic composition or vaccine according to the present invention the immunogenic composition or vaccine is administered subcutaneously, intramuscularly, oral, in ovo, via spray, via drinking water or by eye drop.

In another specific aspect of the immunogenic composition or vaccine according to the present invention the immunogenic composition or vaccine comprises 1 to 10 $\log_{10}$ EID50 per dose of the IBV.

In another specific aspect of the immunogenic composition or vaccine according to the present invention the immunogenic composition or vaccine comprises 2 to 5 $\log_{10}$ EID50 per dose of the IBV.

In another specific aspect of the immunogenic composition or vaccine according to the present invention the immunogenic composition or vaccine comprises 2 to 4 $\log_{10}$ EID50 per dose of the IBV.

Method for Manufacture, Culturing and Modification

Further, the present invention provides a method for altering the cell or tissue tropism of an avian coronavirus comprising the use of the avian coronavirus spike protein or fragment thereof as described herein.

Further, the present invention provides a method for extending the cell or tissue tropism of an avian coronavirus comprising the use of the avian coronavirus spike protein or fragment thereof as described herein.

Further, the present invention provides a method for the production or manufacture of an avian coronavirus with an extended cell or tissue tropism comprising the use of the avian coronavirus spike protein or fragment thereof as described herein.

Further, the present invention provides a method for culturing an avian coronavirus in a cell or tissue culture comprising the use of the avian coronavirus spike protein or fragment thereof as described herein.

Further, the present invention provides a method for modifying an avian coronavirus comprising modifying the amino acid position 267 in the spike protein of said avian coronavirus.

Further, the present invention provides a method for mutating the amino acid position 267 in an avian coronavirus spike protein comprising:
a) providing an avian coronavirus spike nucleotide or protein sequence,
b) identifying position 267 in the spike protein by alignment with a reference sequence,
c) mutating the position 267 of the spike protein of step b) into a cysteine,
d) obtaining the mutated spike protein of step c).

Furthermore, the present invention provides a method for mutating the amino acid position 267 in an avian coronavirus spike protein of an avian coronavirus comprising:
a) providing an avian coronavirus,
b) identifying position 267 in the spike protein by alignment with a reference sequence,
c) mutating the position 267 of the spike protein of step b) into a cysteine,
d) obtaining the mutated avian coronavirus of step c).

The term "obtaining" comprises the harvest, isolation, purification and/or formulation (e.g. finishing, inactivation and/or blending) of said spike protein or fragment thereof. The term "harvest" refers to collecting or recovering said avian coronavirus or IBV with the modified spike protein from the transfected or infected cell or cell line. Any conventional method known in the art can be used, e.g. any separation method. Well known methods in the art comprise centrifugation or filtration, such as using a semi-permeable membrane having a certain pore size. The term "isolation" comprises an isolation step of said avian coronavirus or IBV with the modified spike protein. Methods for the isolation from the transfected or infected cell or cell line are known to a person skilled in the art. Those methods comprise physical and/or chemical methods, including but are not limited to freeze thaw cycles, treatment with ultrasound and the alike. Methods for the "purification" of said avian coronavirus or IBV with the modified spike protein from the isolate are known to a person skilled in the art, for example by those methods described in Protein purification methods—a practical approach (E. L. V. Harris and S. Angel, eds., IRL Press at Oxford University Press). Those methods include, but are not limited to, separation by centrifugation and/or filtration, precipitation, size exclusion (gel filtration) chromatography, affinity chromatography, metal chelate chromatography, ion-exchange chromatography covalent chromatography, hydrophobic interaction chromatography, and the alike. The vector can be obtained in a purified pure form, or free or substantially free of other cellular materials or culture medium etc. After said isolation and/or purification the antigen exhibits a purity of at least 80%, preferably 80%-90%, more preferably 90%-97%, most preferred more than 97% up to an absolute pure form without any contamination.

According to a further aspect, "obtaining" as used herein may also include further finishing steps as part of the final formulation process, like the addition of buffer, inactivation, neutralization steps and the alike.

In another specific aspect of the method according to the present invention the spike protein or fragment thereof has at amino acid position 267 a Cysteine.

In another specific aspect of the method according to the present invention the Cysteine at amino acid position 267 is introduced by a mutation.

In another specific aspect of the method according to the present invention the mutation is an amino acid substitution, deletion or insertion.

In another specific aspect of the method according to the present invention a Phenylalanine or Leucine is modified or mutated into a Cysteine at amino acid at position 267.

In another specific aspect of the method according to the present invention the avian coronavirus is an IBV as described herein.

Thus, the present invention provides a method for altering the cell or tissue tropism of an IBV comprising the use of the avian coronavirus spike protein or fragment thereof as described herein.

Thus, the present invention provides a method for extending the cell or tissue tropism of an IBV comprising the use of the IBV spike protein or fragment thereof as described herein.

Thus, the present invention provides a method for the production or manufacture of an IBV with an extended cell or tissue tropism comprising the use of the IBV spike protein or fragment thereof as described herein.

Thus, the present invention provides a method for culturing an IBV in a cell or tissue culture comprising the use of the IBV spike protein or fragment thereof as described herein.

Thus, the present invention provides a method for modifying an IBV comprising modifying the amino acid position 267 in the spike protein of said IBV.

Thus, the present invention provides a method for mutating the amino acid position 267 in an IBV spike protein comprising:
a) providing an IBV spike nucleotide or protein sequence,
b) identifying position 267 in the spike protein by alignment with a reference sequence,
c) mutating the position 267 of the spike protein of step b) into a cysteine,
d) obtaining the mutated spike protein of step c).

Thus, the present invention provides a method for mutating the amino acid position 267 in an IBV spike protein of an IBV comprising:
a) providing an IBV,
b) identifying position 267 in the spike protein by alignment with a reference sequence,
c) mutating the position 267 of the spike protein of step b) into a cysteine,
d) obtaining the mutated IBV of step c).

In another specific aspect of the method according to the present invention the coronavirus spike protein is an IBV (infectious bronchitis virus) spike protein as described herein.

In another specific aspect of the method according to the present invention the Cysteine at amino acid position 267 or said mutation at amino acid position 267 to Cysteine leads to an extended cell or tissue tropism.

In another specific aspect of the method according to the present invention the avian coronavirus or IBV is infecting and/or replicating in a cell line or cell as described herein.

In another specific aspect of the method according to the present invention the numbering of amino acid position 267 is done as described herein.

Kits

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration preferably for administration to subjects, especially poultry. Associated with such container(s) can be a notice in the form prescribed by a governmental agency regulating the manufacture, use or sale of pharmaceuticals or biological products, which notice reflects approval by the agency of manufacture, use or sale for administration.

The present invention provides a kit comprising the viral particle, avian coronavirus, IBV, the immunogenic composition or vaccine as described herein.

In one specific aspect of the kit according to the present invention the kit further comprises an instruction letter for the treatment and/or prophylaxis of diseases of avians or an instruction letter for the treatment and/or prophylaxis of diseases of poultry or an instruction letter for the treatment and/or prophylaxis of IB.

In one specific aspect of the kit according to the present invention the kit further comprises a dispenser capable of administering a vaccine to said animal.

Method of Treatment

Further, the present invention provides a method for immunizing a subject comprising administering to such subject an immunogenic composition as described herein.

The term "immunizing" relates to an active immunization by the administration of an immunogenic composition to a subject to be immunized, thereby causing an immunological response against the antigen included in such immunogenic composition.

Preferably, immunization results in lessening of the incidence of the particular avian coronavirus or IBV infection in a flock or in the reduction in the severity of clinical signs caused by or associated with the particular avian coronavirus or IBV infection.

Further, the immunization of a subject in need with the immunogenic compositions as provided herewith, results in preventing infection of a subject by avian coronavirus or IBV infection. Even more preferably, immunization results in an effective, long-lasting, immunological-response against IBV infection. It will be understood that the said period of time will last more than 1 month, preferably more than 2 months, preferably more than 3 months, more preferably more than 4 months, more preferably more than 5 months, more preferably more than 6 months. It is to be understood that immunization may not be effective in all subjects immunized. However, the term requires that a significant portion of subjects of a flock are effectively immunized.

Preferably, a flock of subjects is envisaged in this context which normally, i.e. without immunization, would develop clinical signs normally caused by or associated with an avian coronavirus or IBV infection. Whether the subjects of a flock are effectively immunized can be determined without further ado by the person skilled in the art. Preferably, the immunization shall be effective if clinical signs in at least 33%, at least 50%, at least 60%, at least 70%, at least 80%, at least 90%, still more preferably in at least 95% and most preferably in 100% of the subjects of a given flock are lessened in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, still more preferably by at least 95% and most preferably by 100% in comparison to subjects that are either not immunized or immunized with an immunogenic composition that was available prior to the present invention but subsequently infected by the particular avian coronavirus or IBV.

Further, the present invention provides a method of treating or preventing clinical signs caused by IBV in a subject of need, the method comprises administering to the subject a therapeutically effective amount of an immunogenic composition or vaccine as described herein.

As shown in the Examples, the immunogenic composition or vaccine as provided herein has been proven to be efficacious in treating or preventing clinical signs caused by IBV in a subject. Therefore, the experimental data show that the modification of the amino acid at amino acid position 267 into a Cystein does not have any impact on the efficacy of the vaccine.

The term "treating or preventing" refers to the lessening of the incidence of the particular IBV infection in a flock or the reduction in the severity of clinical signs caused by or associated with the particular IBV infection. Thus, the term "treating or preventing" also refers to the reduction of the number of subjects in a flock that become infected with the particular IBV (=lessening of the incidence of the particular IBV infection) or to the reduction of the severity of clinical signs normally associated with or caused by a IBV infection or the reduction of virus shedding after infection with the particular IBV or preventing or lessening egg drop in laying hens after infection with the particular IBV in a group of subjects which subjects have received an effective amount of the immunogenic composition as provided herein in comparison to a group of subjects which subjects have not received such immunogenic composition.

The "treating or preventing" generally involves the administration of an effective amount of the immunogenic composition of the present invention to a subject or flock of subjects in need of or that could benefit from such a treatment/prophylaxis. The term "treatment" refers to the administration of the effective amount of the immunogenic composition once the subject or at least some subjects of the flock is/are already infected with such IBV and wherein such subjects already show some clinical signs caused by or associated with such IBV infection. The term "prophylaxis" refers to the administration of a subject prior to any infection of such subject with IBV or at least where such subject or none of the subjects in a group of subjects do not show any clinical signs caused by or associated with the infection by such IBV. The terms "prophylaxis" and "preventing" are used interchangeable in this application.

The term "an effective amount" as used herein means, but is not limited to an amount of antigen, that elicits or is able to elicit an immune response in a subject. Such effective amount is able to lessen the incidence of the particular IBV infection in a flock or to reduce the severity of clinical signs of the particular IBV infection.

Preferably, clinical signs are lessened in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, still more preferably by at least 95% and most preferably by 100% in comparison to subjects that are either not treated or treated with an immunogenic composition that was available prior to the present invention but subsequently infected by the particular IBV.

The term "clinical signs" as used herein refers to signs of infection of a subject from IBV. The clinical signs of infection depend on the pathogen selected. Examples for such clinical signs include but are not limited to respiratory distress, nephritis, salpingitis, abnormal egg production, ruffled feathers, depression, reduced growth rates and reduced appetite. Signs of respiratory distress encompass respiratory signs including gasping, coughing, sneezing, tracheal rales, nasal and ocular discharge, tracheal lesions and ciliostasis in the trachea. Signs of nephritis encompass kidney lesions and watery diarrhea. Signs of abnormal egg production encompass egg drop, eggs of smaller size, inferior shell, reduced internal egg quality, eggs with thin albumen and ciliostasis in the oviduct. However, the clinical signs also include but are not limited to clinical signs that are directly observable from a live animal. Examples for clinical signs that are directly observable from a live animal include nasal and ocular discharge, coughing, gasping, sneezing, tracheal rales, ruffled feathers, conjunctivitis, weight loss, reduced growth rates, reduced appetite, dehydration, watery diarrhea, lameness, lethargy, wasting and unthriftiness and the like.

Preferably, the clinical signs lessened in incidence or severity in a treated subject compared to subjects that are either not treated or treated with an immunogenic composition that was available prior to the present invention but subsequently infected by the particular IBV refer to a reduction of ciliostasis, a reduction of rales, a reduction of egg drop, a reduction of kidney lesions, a reduction of watery diarrhea, a reduction in weight loss, a lower virus load, a reduced viral shedding, or combinations thereof.

The term "in need" or "of need", as used herein means that the administration/treatment is associated with the boosting or improvement in health or clinical signs or any other positive medicinal effect on health of the subjects which receive the immunogenic composition in accordance with the present invention.

Further, the present invention provides a method of reducing the ciliostasis in a subject of need, in comparison to a subject of a non-immunized control group of the same species, the method comprises administering to the subject a therapeutically effective amount of an immunogenic composition or vaccine as described herein.

As shown in the Examples, the immunogenic composition or vaccine as provided herein has been proven to be efficacious in reducing ciliostasis.

The term "ciliostasis" refers to a reduced movement of the cilia in the trachea. Thus, ciliostasis may be determined by examining the inner lining of the tracheal rings for the movement of the cilia. It is in the general knowledge of a person skilled in the art how to determine the movement of the cilia in the trachea.

Preferably, the movement of the cilia is not reduced from day 10 after challenge or infection, more preferably from day 5 after challenge or infection, more preferably from day 4 after challenge or infection, more preferably from day 3 after challenge or infection and most preferably from day 1 or 2 after challenge or infection with the IBV as compared to a subject of a non-immunized control group of the same species.

The term "reduction of ciliostasis" means, that the ciliostasis is reduced by at least 10%, preferably by at least 20%, more preferably by at least 30%, even more preferably by at least 40%, even more preferably by at least 50%, even more preferably by at least 60%, even more preferably by at least 70%, even more preferably by at least 80%, even more preferably by at least 90%, even more preferably by at least 95% and most preferably by 100% as compared to a subject of a non-immunized control group of the same species. It is in the general knowledge of a person skilled in the art how to measure the reduction of the ciliostasis.

Further, the present invention provides the immunogenic composition or vaccine as described herein for use in a method for immunizing a subject, the method comprises administering to the subject a therapeutically effective amount of said immunogenic composition or vaccine.

Further, the present invention provides the immunogenic composition or vaccine as described herein for use in a method of treating or preventing clinical signs caused by IBV in a subject of need, the method comprises administering to the subject a therapeutically effective amount of said immunogenic composition or vaccine.

Further, the present invention provides the immunogenic composition or vaccine as described herein for use in a method of reducing the ciliostasis in a subject of need, in comparison to a subject of a non-immunized control group of the same species, the method comprises administering to the subject a therapeutically effective amount of said immunogenic composition or vaccine.

In one specific aspect of the method or use according to the present invention said subject is avian.

The term "avian" is well known to the person skilled in the art. The term "avian" encompasses all birds including poultry.

In one specific aspect of the method or use according to the present invention said subject is poultry.

The term "poultry" is well known to the person skilled in the art. The term "poultry" encompasses chickens, turkeys, quails, pheasants, guineafowl, geese, and ducks. Further, the term "chicken" includes broiler, laying hens, and reproductive stocks for both also referred as breeders.

In one specific aspect of the method or use according to the present invention said subject is selected from the list consisting of chicken, turkey, quail, or pheasant.

In one specific aspect of the method or use according to the present invention said subject is chicken.

In one specific aspect of the method or use according to the present invention the immunogenic composition or vaccine is administered once.

It is understood, that a single-dose is administered only once. As shown in the Examples the immunogenic composition as provided herein has been proven to be efficacious after the administration of a single dose to a subject of need.

The dose volume per poultry depends on the route of vaccination and the age of the poultry.

Typically, eye drop vaccines are administered in a volume of 1 to 100 µl per dose at any age. Preferably, the single-dose for eye drop vaccines has a total volume between about 5 µl and 70 µl and more preferably between about 20 µl and 50 µl with a single 20 µl, 25 µl, 30 µl, 35 µl, 40 µl, 45 µl or 50 µl dose being preferred. Most preferred, the single-dose for eye drop vaccines has a total volume between about 30 µl and 50 µl with a single 30 µl, 35 µl, 40 µl, 45 µl or 50 µl dose being preferred.

Spray vaccines may contain the dose in a volume of 25 to 1000 µl for day-old poultry. Preferably, the single-dose for spray vaccines has a total volume between about 50 µl and 5000 µl, more preferably between about 75 µl and 2000 µl, more preferably between about 100 µl and 1000 µl, even more preferably between about 200 µl and 900 µl, even more preferably between about 300 µl and 800 µl and even more preferably between about 400 µl and 700 µl with a single 400 µl, 425 µl, 450 µl, 475 µl, 500 µl, 525 µl, 550 µl, 575 µl, 600 µl, 625 µl, 650 µl, 675 µl or 700 µl dose being preferred. Most preferred the single-dose has a total volume of 400 µl, 450 µl 500 µl, 550 µl, 600 µl, 650 µl or 700 µl.

The vaccine for in ovo vaccination may contain the dose in a volume of 50 to 100 µl, preferably 50 µl. Preferably, the single-dose for in ovo vaccines has a total volume between about 10 µl and 250 µl, more preferably between about 15 µl and 200 µl, even more preferably between about 20 µl and 150 µl, even more preferably between about 30 µl and 100 µl, even more preferably between about 30 µl and 75 µl and with a single 30 µl, 35 µl, 40 µl, 45 µl, 50 µl, 55 µl, 60 µl, 65 µl, 70 µl or 75 µl dose being preferred. Most preferred the single-dose has a total volume of 40 µl, 45 µl, 50 µl, 55 µl or 60 µl.

The vaccine for intramuscular or subcutaneous vaccination or one dose of a drinking water vaccine may contain the dose in a volume of 30 µl to 1000 µl. Preferably, the single-dose has a total volume between about 30 µl and 1000 µl, more preferably between about 50 µl and 500 µl, more preferably between about 75 µl and 250 µl and even more preferably between about 100 µl and 200 µl with a single 100 µl, 110 µl, 120 µl, 125 µl, 130 µl, 135 µl, 140 µl, 145 µl, 150 µl, 160 µl, 170 µl, 175 µl, 180 µl, 190 µl, 155 µl, or 200 µl dose being the most preferred.

In one specific aspect of the method or use according to the present invention the immunogenic composition or vaccine is administered at two or more doses.

However, the immunogenic composition can be administered at two or more doses, with a first dose being administered prior to the administration of a second (booster) dose.

In a preferred aspect of the two-time administration regimen, both the first and second doses of the immunogenic composition are administered in the same amount. Preferably, each dose is in the preferred amounts specified above. In addition to the first and second dose regimen, an alternate embodiment comprises further subsequent doses. For example, a third, fourth, or fifth dose could be administered in these aspects. Preferably, subsequent third, fourth, and fifth dose regimens are administered in the same amount as the first dose, with the time frame between the doses being consistent with the timing between the first and second doses mentioned above.

Preferably, the first administration of the vaccine is performed within the first three weeks of age, more preferably within the first week of age and most preferred at one day-of-age by methods as described below. A second administration can be performed within the first 20 weeks of age, preferably within 16-18 weeks of age, more preferably between 6-12 weeks of age. Exemplary, the initial (first) vaccination is performed at 1-10 days of age and the second vaccination (booster) is performed with a live or inactivated vaccine at 6-12 or 16-18 weeks of age. More preferably, the initial (first) vaccination is performed at one day-of-age and the second vaccination (booster) is performed with a live or inactivated vaccine at 6-12 or 16-18 weeks of age.

In case in ovo vaccination is used, preferably the first admiration is performed when embryos are between 15 to 19 days old, preferably at day 17, 18 or 19, most preferably at day 18 of age. A second administration can be performed within the first three weeks of age, preferably within the first 10 days of age.

In one specific aspect of the method or use according to the present invention said immunogenic composition or vaccine is administered subcutaneously, intramuscularly, oral, in ovo, via spray, via drinking water or by eye drop.

The immunogenic composition is, preferably, administered topically or systemically. Suitable routes of administration conventionally used are oral or parenteral administration, such as intranasal, intravenous, intradermal, transdermal, intramuscular, intraperitoneal, subcutaneous, as well as inhalation, in ovo, via spray, via drinking water or by eye drop. However, depending on the nature and mode of action of a compound, the immunogenic composition may be administered by other routes as well. For example, such other routes include intracutaneously, intravenously, intravascularly, intraarterially, intraperitoneally, intrathecally, intratracheally, intracutaneously, intracardially, intralobally, intralobarly, intramedullary, intrapulmonarily, intrarectally, and intravaginally. However, most preferred the immunogenic composition is administered subcutaneously, intramuscularly, oral, in ovo, via spray, via drinking water or by eye drop.

Live IBV vaccines are preferably administered individually by eye drop, intranasal, intramuscular or subcutaneous.

More preferably, mass application methods, including drinking water and aerosol spray vaccination, are used. Also preferred is the use of vaccines as embryo vaccines (so-called in ovo vaccines) as described further below.

For example, broilers may be vaccinated at one-day of age or at 1-3 weeks of age, particularly for broilers with high levels of MDA. Laying stock or reproduction stock may be vaccinated initially at 1-10 days of age and boosted with the vaccine at 7-12 or 16-18 weeks of age.

In Ovo Administration

As outlined above, the present invention also provides an IBV vaccine that can be safely administered via the in ovo route and at the same time is able to induce a protective immune response. The in ovo administration is well known to the person skilled in the art and the person skilled in the art can perform in ovo administration without further ado. The in ovo administration of the vaccine involves the administration of the vaccine to an avian embryo while contained in the egg (for a review on in ovo vaccination see: Ricks et al., Advances in Vet. Med. 495-515, 1999). The vaccine may be administered to any suitable compartment of the egg (e. g. allantois fluid, yolk sac, amnion, air cell or into the embryo) as described in the art (Sharma; Am. J. Vet. Res. 45 1619-1623, 1984). Preferably the vaccine is administered below the shell (aircell) membrane and chorioallantoic membrane.

Preferably, the vaccine is injected into embryonated eggs during late stages of the embryonation, generally during the final quarter of the incubation period, preferably 3-4 days prior to hatch. Preferably, the admiration is performed when embryos are between 15 to 19 days old, preferably at day 17, 18 or 19, most preferably at day 18 of age. Subsequently, the vaccinated embryonated eggs are transferred to an incubator for hatch. The process of in ovo administration can be automated using a robotic injection process as described in the prior art.

Usually conventional vaccines for post-hatch vaccination of poultry cannot be used for in ovo vaccination, because late stage embryos are highly susceptible to infection with most vaccine viruses examined. However, International patent application WO 01/64244 discloses that IBV vaccines can be used for in ovo administration provided it is applied at a very low doses. Further, Wakenell et al. 1986 (Am. J. Vet. Res., 47 933-938) discloses that passaging an IB vaccine virus in tissue culture rendered the virus apathogenic for embryos.

In one specific aspect of the method or use according to the present invention said immunogenic composition or vaccine is administered via eye drop.

Typically, the live vaccine for post-hatch administration comprises the attenuated IBV in a concentration of $10^1$ to $10^8$ $EID_{50}$ (50% Egg Infective Dose) per dose, preferably in a concentration of $10^2$ to $10^5$ $EID_{50}$ per dose and, more preferably, in a concentration of $10^2$ to $10^4$ $EID_{50}$ per unit dose and, even more preferably, in a concentration of $10^2$ to $10^3$ $EID_{50}$ per dose.

The live vaccine for in ovo administration typically comprises an amount of the attenuated IBV of $10^2$ to $10^7$ $EID_{50}$/embryo, preferably $10^2$ to $10^3$ $EID_{50}$/embryo in a volume of 50 to 100 μl, preferably 50 μl.

Preferably, the immunogenic composition of the present invention comprises the IBV of the present invention in amounts of about 1 to about 10 $log_{10}$ EID (egg infective dose)$_{50}$/ml per dose, preferably about 2 to about 8 $log_{10}$ $EID_{50}$ per dose, preferably in an amount of about 2 to about 7 $log_{10}$ $EID_{50}$ per dose, more preferably in an amount of about 2 to about 6 $log_{10}$ $EID_{50}$ per dose, even more preferably in an amount of about 2 to about 5 $log_{10}$ $EID_{50}$ per dose, even more preferably in an amount of about 2 to about 4 $log_{10}$ $EID_{50}$ per dose, most preferably in an amount of about 2 to about 3 $log_{10}$ $EID_{50}$ per dose. More preferably, the immunogenic composition of the present invention comprises the IBV of the present invention in amounts of about 1, 1.5, 2, 2.5, 3, 3.5, 4, 4.5, 5, 5.5, 6, 6.5, 7, 7.5 or $log_{10}$ $EID_{50}$ per dose.

In one specific aspect of the method or use according to the present invention the immunogenic composition or vaccine comprises 1 to 10 $log_{10}$ $EID_{50}$ per dose of the IBV.

In one specific aspect of the method or use according to the present invention the immunogenic composition or vaccine comprises 2 to 5 $log_{10}$ $EID_{50}$ per dose of the IBV.

In one specific aspect of the method or use according to the present invention the immunogenic composition or vaccine comprises 2 to 4 $log_{10}$ $EID_{50}$ per dose of the IBV.

In one specific aspect of the method or use according to the present invention the immunogenic composition or vaccine is administered to subjects within the first week of age, within the first three days of age, within the first two days of age, or within the first day of age.

Preferably, the subject to be immunized is 1, 2, 3, 4, 5, 6, 7, 8, 9, 10, 11, 12, 13, 14, 15, 16, 17, 18, 19, 20 or 21 days of age. More preferably, said subject to be immunized is 1, 2, 3, 4, 5, 6, 7, 8, 9, 10, 11, 12, 13 or 14 days of age. Most preferably, said subject to be immunized is 1, 2, 3, 4, 5, 6 or 7 days of age.

However, it has to be understood that after vaccination of the subject being a few days of age, it does need several days for the immune system of the poultry to build up immunity against an IBV infection. Therefore, preferably, the subjects are immunized within the first 24 h of age.

In one specific aspect of the method or use according to the present invention the immunogenic composition or vaccine is administered to subjects within the first day of age. As shown in the Examples the immunogenic composition as provided herein has been proven to be safe and efficacious when administered to 1-day old poultry.

In one specific aspect of the method or use according to the present invention said method results in an improvement in an efficacy parameter selected from the group consisting of: prevention or reduction of ciliostasis, prevention or reduction of rales, prevention or reduction of egg drop, prevention or reduction of kidney lesions, prevention or reduction of watery diarrhea, prevention or reduction in weight loss, a lower virus load, a reduced viral shedding or combinations thereof, in comparison to a subject of a non-treated control group of the same species.

The terms "treatment and/or prophylaxis" have been defined elsewhere, wherein the terms "prophylaxis" and "preventing" or "prevention" are used interchangeable in this application. Further, the terms "shedding" has been defined elsewhere, too.

The term "reducing", "reduced", "reduction" or "lower" means, that the efficacy parameter (ciliostasis, rales, egg drop, kidney lesions, watery diarrhea, weight loss, virus load, viral shedding) is reduced by at least 10%, preferably by at least 20%, more preferably by at least 30%, even more preferably by at least 40%, even more preferably by at least 50%, even more preferably by at least 60%, even more preferably by at least 70%, even more preferably by at least 80%, even more preferably by at least 90%, even more preferably by at least 95% and most preferably by 100% as compared to a subject of a non-immunized control group of the same species. It is in the general knowledge of a person skilled in the art how to measure the improvement in the efficacy parameters.

The term "virus load" or "virus titer" is a measure of the severity of an active viral infection, and can be determined by methods known to the person skilled in the art. The term "viral titre" is a measure of infectious units per volume of a virus preparation. Viral titre is an endpoint in a biological procedure and is defined as the dilution at which a certain proportion of tests carried out in parallel show an effect (Reed and Muench, 1938). The determination can be based on the detection of viral proteins such as by antibody binding to the viral proteins and further detection or, alternatively, by detection of viral RNA by amplification methods such as RT-PCR. Monitoring of virion associated viral RNA in plasma by nucleic acid amplification methods is a widely used parameter to assess the status and progression of retroviral disease, and to evaluate the effectiveness of prophylactic and therapeutic interventions. Exemplary, the virus load or virus titer can be calculated by estimating the live amount of virus in an involved body fluid such as a number of RNA copies per milliliter of blood plasma.

The term "ciliostasis" is well known to the person skilled in that art. The surface of the trachea is covered with specialised epithelial cells, which are lined with numerous, motile, hair-like structures called cilia. The term "ciliostasis" encompasses the reduction or loss of cilia and/or loss or partial loss of ciliary activity. Ciliostasis can be determined without further ado by the person skilled in the art.

The term "rales" is well known to the person skilled in that art. However, the term "rales" encompasses tracheal rales and refers to sounds emanating from the bronchi. Rales can be determined without further ado by the person skilled in the art.

The term "egg drop" is well known to the person skilled in that art. The term "egg drop" encompasses a decreased egg production.

In one specific aspect of the method or use according to the present invention the treatment or prevention results in a prevention or reduction of ciliostasis as compared to subjects of a non-treated control group of the same species.

In one specific aspect of the method or use according to the present invention the treatment or prevention results in a prevention or reduction of kidney lesions as compared to subjects of a non-treated control group of the same species.

In one specific aspect of the method or use according to the present invention the treatment or prevention results in a prevention or reduction of egg drop as compared to subjects of a non-treated control group of the same species.

The present invention further provides the viral particle, avian coronavirus, IBV, immunogenic composition or vaccine as described herein for therapeutic use.

The present invention further provides the viral particle, avian coronavirus, IBV, immunogenic composition or vaccine as described herein for use as an immunogen or vaccine.

The present invention further provides the viral particle, avian coronavirus, IBV, immunogenic composition or vaccine as described herein for use as a medicament.

The present invention further provides the use of the viral particle, avian coronavirus, IBV, immunogenic composition or vaccine as described herein for the manufacture of a medicament.

The present invention further provides the use of the viral particle, avian coronavirus, IBV, immunogenic composition or vaccine as described herein for the treatment and/or prophylaxis of IBV infections in a subject.

Clauses

The following clauses are also described herein:
1. An avian coronavirus spike protein or fragment thereof, wherein at least a part of the S1 subunit is from an avian coronavirus with a restricted cell or tissue tropism, and wherein at amino acid position 267 is a Cysteine.
2. A recombinant avian coronavirus spike protein or fragment thereof comprising a mutation at amino acid position 267 to Cysteine.
3. An IBV spike protein or fragment thereof, wherein at least a part of the S1 subunit is from an IBV with a restricted cell or tissue tropism, and wherein at amino acid position 267 is a Cysteine.
4. A recombinant IBV spike protein or fragment thereof comprising a mutation at amino acid position 267 to Cysteine.

Mutation 267
5. The avian coronavirus or IBV spike protein or fragment thereof of clause 1 or 3, wherein the Cysteine at amino acid position 267 is introduced by a mutation.
6. The avian coronavirus or IBV spike protein or fragment thereof of clause 2, 4 or 5, wherein the mutation is an amino acid substitution, deletion or insertion.
7. The avian coronavirus or IBV spike protein or fragment thereof of any one of clauses 2 and 4 to 6, wherein a hydrophobic amino acid at amino acid position 267 is mutated into a Cysteine; or a Phenylalanine or Leucine at amino acid position 267 is mutated into a Cysteine.

Extended Cell or Tissue Tropism
8. The avian coronavirus or IBV spike protein or fragment thereof of any one of clauses 1 to 7, wherein the Cysteine at amino acid position 267 or said mutation at amino acid position 267 to Cysteine leads to an extended cell or tissue tropism of the avian coronavirus or IBV.
9. The avian coronavirus or IBV spike protein or fragment thereof of any one of clauses 1 to 8, wherein the avian coronavirus or IBV is infecting and/or replicating in at least one cell line or cell selected from the list consisting of: primary chicken embryo cells from lung or liver or primary chicken fibroblasts, a chicken embryo fibroblast cell line, a duck embryonic stem cell line, a human embryonic kidney cell line, a baby hamster kidney cell line, an African green monkey kidney cell line, a rabbit kidney cell line, a canine kidney cell line, a chicken liver cell line, a bovine kidney cell line, a porcine kidney cell line and an insect cell line.
10. The avian coronavirus or IBV spike protein or fragment thereof of any one of clauses 1 to 9, wherein the avian coronavirus or IBV is infecting and/or replicating in at least one cell line selected from the list consisting of: DF-1 (Douglas Foster), EB66 (duck embryonic stem cell line), PBS-12, PBS-12SF (PBS-12 serum free), BHK21 (baby hamster kidney), HEK 293T (human embryonic kidney), Vero (Verda Reno), MA104, RK13 (rabbit kidney), LMH (leghorn male hepatoma), MDCK (Madin-Darby canine kidney), MDBK (Madin-Darby bovine kidney), PK15 (porcine kidney), PK2A (porcine kidney), SF9, SF21 and SF+ (*Spodoptera frugiperda*).
11. The avian coronavirus or IBV spike protein or fragment thereof of any one of clauses 1 to 10, wherein the avian coronavirus or IBV is infecting and/or replicating in at least one cell line selected from the list consisting of: DF-1, EB66, PBS-12, PBS-12SF, BHK, HEK 293T, Vero, MA104 and RK13.

Numbering of Amino Acid Position 267
12. The avian coronavirus or IBV spike protein or fragment thereof of any one of clauses 1 to 11, wherein the numbering of amino acid position 267 refers to the amino acid position 267 in the spike protein of an IBV H52, an IBV H120 or an M41.
13. The avian coronavirus or IBV spike protein or fragment thereof of any one of clauses 1 to 12, wherein the numbering of amino acid position 267 refers to the amino acid position 267 in the spike protein of an IBV H52.
14. The avian coronavirus or IBV spike protein or fragment thereof of any one of clauses 1 to 12, wherein the numbering of amino acid position 267 refers to the amino acid position 267 in the spike protein as exemplarily given in SEQ ID NO:1.
15. The avian coronavirus or IBV spike protein or fragment thereof of any one of clauses 1 to 12, wherein the amino acid sequence of SEQ ID NO:1 is used for determining the position numbering in the spike protein.
16. The avian coronavirus or IBV spike protein or fragment thereof of any one of clauses 1 to 12, wherein for determining the amino position 267 in a spike protein the amino acid sequence is aligned to the amino acid sequence of SEQ ID NO:1.
17. The avian coronavirus or IBV spike protein or fragment thereof of any one of clauses 1 to 16, wherein the amino acid position 267 is within the S1 subunit of the spike protein.
18. The avian coronavirus or IBV spike protein or fragment thereof of any one of clauses 1 to 17, wherein the spike protein has one or more of the following amino acids selected from the group consisting of:
  264 is an asparagine, and/or
  265 is a threonine, and/or
  269 is a leucine, and/or
  271 is an asparagine, and/or
  272 is a phenylalanine.

Spike
19. The avian coronavirus spike protein or fragment thereof of any one of clauses 1 and 2 and 5 to 18, wherein the avian coronavirus spike protein or fragment thereof is selected from the group consisting of: infectious bronchitis virus (IBV); guinea fowl coronavirus (GfCoV) and turkey coronavirus (TCoV; turkey enteritis virus and bluecomb disease virus).
20. The avian coronavirus spike protein or fragment thereof of any one of clauses 1 and 2 and 5 to 19, wherein the avian coronavirus is IBV (infectious bronchitis virus).
21. The IBV spike protein or fragment thereof of any one of clauses 3 to 20, wherein the spike protein is from an IBV with a genotype or serotype or strain selected from a list consisting of: Arkansas (such as Arkansas 99), Brazil (such as BR-1, BR-2, 23/2013, IBV/Brasil/351/1984), California (such as California 1734/04, California 99), Connecticut, Delaware (such as Delaware 98), Dutch (such as D207, D212, D274, D3128, D3896, D8880, D1466), Florida, Georgia (such as Georgia GA-07, GA-08, GA-12, GA-13), Gray, Holte, Iowa (such as Iowa 97 and Iowa 69), Italy 02, JMK, LDT3, Maine (such as Maine 209), Massachusetts (such as M41, H52, H120; excluding Beaudette), Pennsylvania (such as Pennsylvania 1220/98, Pennsylvania Wolg/98), PL84084, Qu (such as Qu-mv), QX (such as GB341/96), Q1, SE 17, Variant 2 (such as IS/1494/06, IBV/Ck/EG/CU/4/2014, gammaCoV/Ck/Poland/G052/2016) and 4/91 (793B, CR88).

22. The IBV spike protein or fragment thereof of any one of clauses 3 to 21, wherein the spike protein is not from a Beaudette strain.

23. The IBV spike protein or fragment thereof of any one of clauses 3 to 22, wherein the Spike protein or fragment thereof is from an IBV selected from a list of genotypes or serotypes or strains consisting of Massachusetts (not Beaudette), 4/91, QX, Q1, Italy 02, Arkansas, Connecticut, Georgia, LDT3, PL84084, Variant 2 and Brazil.

24. The IBV spike protein or fragment thereof of any one of clauses 3 to 23, wherein the Spike protein or fragment thereof is from an IBV selected from a list of genotypes or serotypes consisting of Massachusetts (not Beaudette), 4/91, QX, Q1, Arkansas, Variant 2 and Brazil.

25. The IBV spike protein or fragment thereof of any one of clauses 3 to 24, wherein the Spike protein or fragment thereof is from an IBV selected from a list of genotypes or serotypes consisting of Massachusetts (not Beaudette) and 4/91.

26. The IBV spike protein or fragment thereof of clause 24, wherein the Massachusetts strain is selected from a list consisting of: H120, H52, Spain/98/308, IBMA5-1, SD/97/01, Spain/96/334 and M41-M21883.

27. The IBV spike protein or fragment thereof of clause 24, wherein the 4/91 strain is selected from a list consisting of: Spain/98/328, Spain/92/35, IR-3654-VM, FR-CR88061-88, FR-85131-85, UK-1233-95, UK/3/91, Spain/00/336, UK/7/91, 4/91-pathogenic, 4/91 attenuated and IB4-91.

28. The IBV spike protein or fragment thereof of clause 24, wherein the QX strain is selected from a list consisting of: FR-L1450T-05, FR-L1450L-05, NL-L1449T-04, NL-L1449K-04, IBV/Ck/SP/170/09, IBV/Ck/SP/79/08, IBV/Ck/SP/248/09, HBN, IBVQX, LX4, BJQ, CK/CH/LGD/03, SP2013-01470, SP2013-014171, SP2013-01478 and GB341/96.

29. The IBV spike protein or fragment thereof of clause 24, wherein the Q1 strain is selected from a list consisting of: CK/CH/LDL/98I, CK/CH/LSD/08-10, J2, Q1, AR08ER22, AR08BA21, 12.185, 12.124, 12.216 and Chile-295-10.

30. The IBV spike protein or fragment thereof of clause 24, wherein the Arkansas strain is selected from a list consisting of: Ark99, ArkGA, ArkDPI, AL/5364/00, ARKDPI11, AL/0803/01, AL/7149/00, ArkDPI101, AL/1221/01, AL/1793/01 and AL/4614/98.

31. The IBV spike protein or fragment thereof of clause 24, wherein the Italy 02 strain is selected from a list containing of: Spain/99/316, Italy-02, UK-L633-04, It-497-02, Spain/05/866, Spain/04/221, Spain/00/337, Spain/155/09 and Spain/03/08.

32. The IBV spike protein or fragment thereof of clause 24, wherein the Variant 2 strain is selected from a list consisting of: IS/1494/06, IBV/Ck/EG/CU/4/2014, gammaCoV/Ck/Poland/G052/2016, Eg/CLEVB-2/IBV/012, D1344/2/4/10_EG, TR8 and IB VAR2-06.

33. The IBV spike protein or fragment thereof of clause 24, wherein the Brazil strain is selected from a list consisting of: BR-1, BR-2, 23/2013, and IBV/Brasil/351/1984.

34. The IBV spike protein or fragment thereof of any one of clauses 3 to 24, wherein the Spike protein or fragment thereof is from an IBV of Massachusetts (not Beaudette), 4/91 or QX genotype or serotype.

35. The IBV spike protein or fragment thereof of any one of clauses 3 to 24, wherein the IBV strain is H52, H120, QX SP2013-01478 or CR88.

36. The IBV spike protein or fragment thereof of any one of clauses 3 to 35, wherein the IBV spike protein or fragment thereof consists of or comprises an amino acid sequence as shown in SEQ ID NO: 2, 3, 4, 5, 6, 7, 8, 77 or a sequence having at least 80%, 85%, 90%, 93%, 95%, 96%, 97%, 98%, 99%, 99.5%, 99.6%, 99.7%, 99.8%, 99.9%, 99.95%, 99.98% or 99.99% sequence identity thereto.

37. The IBV spike protein or fragment thereof of any one of clauses 3 to 36, wherein the IBV spike protein or fragment thereof is selected from a list of genotypes consisting of: GI-2 to 27, GII-1, GIII-1, GIV-1, GV-1, GVI-1.

38. The IBV spike protein or fragment thereof of any one of clauses 3 to 37, wherein the spike protein or fragment thereof is not from the GI-1 genotype.

39. The avian coronavirus spike protein or fragment thereof of any one of clauses 1 and 5 to 38, wherein said at least a part of the S1 subunit from an avian coronavirus with a restricted cell or tissue tropism is selected from the group consisting of: Infectious bronchitis virus (IBV); guinea fowl coronavirus (GfCoV) and turkey coronavirus (TCoV; turkey enteritis virus and bluecomb disease virus).

40. The avian coronavirus spike protein or fragment thereof of any one of clauses 1 and 5 to 38, wherein said at least a part of the S1 subunit from an avian coronavirus with a restricted cell or tissue tropism is from IBV (infectious bronchitis virus).

41. The IBV spike protein or fragment thereof of any one of clauses 3 and 5 to 40, wherein said at least a part of the S1 subunit is from an IBV selected from a list of genotypes or serotypes or strains consisting of: Arkansas (such as Arkansas 99), Brazil (such as BR-1, BR-2, 23/2013, IBV/Brasil/351/1984), California (such as California 1734/04, California 99), Connecticut, Delaware (such as Delaware 98), Dutch (such as D207, D212, D274, D3128, D3896, D8880, D1466), Florida, Georgia (such as Georgia GA-07, GA-08, GA-12, GA-13), Gray, Holte, Iowa (such as Iowa 97 and Iowa 69), Italy 02, JMK, LDT3, Maine (such as Maine 209), Massachusetts (such as M41, H52, H120; excluding Beaudette), Pennsylvania (such as Pennsylvania 1220/98, Pennsylvania Wolg/98), PL84084, Qu (such as Qu-mv), QX (such as GB341/96), Q1, SE 17, Variant 2 (such as IS/1494/06, IBV/Ck/EG/CU/4/2014, gammaCoV/Ck/Poland/G052/2016) and 4/91 (793B, CR88).

42. The IBV spike protein or fragment thereof of any one of clauses 3 and 5 to 41, wherein said at least a part of the S1 subunit is from an IBV selected from a list of genotypes or serotypes or strains consisting of Massachusetts (not Beaudette), 4/91, QX, Q1, Italy 02, Arkansas, Connecticut, Georgia, LDT3, PL84084, Variant 2 and Brazil.

43. The IBV spike protein or fragment thereof of any one of clauses 3 and 5 to 41, wherein said at least a part of the S1 subunit is from an IBV selected from a list of genotypes or serotypes consisting of Massachusetts, 4/91, QX, Q1, Arkansas, Variant 2 and Brazil.

44. The IBV spike protein or fragment thereof of clause 43, wherein the Massachusetts strain is selected from a list consisting of: H120, H52, Spain/98/308, IBMA5-1, SD/97/01, Spain/96/334 and M41-M21883.

45. The IBV spike protein or fragment thereof of clause 43, wherein the 4/91 strain is selected from a list consisting of:

Spain/98/328, Spain/92/35, IR-3654-VM, FR-CR88061-88, FR-85131-85, UK-1233-95, UK/3/91, Spain/00/336, UK/7/91, 4/91-pathogenic, 4/91 attenuated and IB4-91.

46. The IBV spike protein or fragment thereof of clause 43, wherein the QX strain is selected from a list consisting of: FR-L1450T-05, FR-L1450L-05, NL-L1449T-04, NL-L1449K-04, IBV/Ck/SP/170/09, IBV/Ck/SP/79/08, IBV/Ck/SP/248/09, HBN, IBVQX, LX4, BJQ, CK/CH/LGD/03 and GB341/96.

47. The IBV spike protein or fragment thereof of clause 43, wherein the Q1 strain is selected from a list consisting of: CK/CH/LDL/98I, CK/CH/LSD/08-10, J2, Q1, AR08ER22, AR08BA21 and Chile-295-10.

48. The IBV spike protein or fragment thereof of clause 43, wherein the Arkansas strain is selected from a list consisting of: Ark99, ArkGA, ArkDPI, AL/5364/00, ARKDPI11, AL/0803/01, AL/7149/00, ArkDPI101, AL/1221/01, AL/1793/01 and AL/4614/98.

49. The IBV spike protein or fragment thereof of clause 43, wherein the Variant 2 strain is selected from a list consisting of: IS/1494/06, IBV/Ck/EG/CU/4/2014, gammaCoV/Ck/Poland/G052/2016, Eg/CLEVB-2/IBV/012, D1344/2/4/10_EG, TR8 and IB VAR2-06.

50. The IBV spike protein or fragment thereof of clause 43, wherein the Brazil strain is selected from a list consisting of: BR-1, BR-2, 23/2013 and IBV/Brasil/351/1984.

51. The IBV spike protein or fragment thereof of any one of clauses 3 and 5 to 43, wherein said at least a part of the S1 subunit is from an IBV selected from a list of genotypes or serotypes consisting of Massachusetts (not Beaudette), QX and 4/91.

52. The IBV spike protein or fragment thereof of any one of clauses 3 and 5 to 43, wherein said at least a part of the S1 subunit is from an IBV strain H120, H52, QX SP2013-01478 or CR88.

53. The avian coronavirus spike protein or fragment thereof of any one of clauses 1 and 3 and 5 to 52, wherein the at least a part of the S1 subunit is at least 1, 5, 10, 15, 20, 25, 50, 100, 150, 200, 250, 300, 350, 400 or 500 contiguous amino acids from a S1 subunit sequence of an avian coronavirus or IBV with a restricted cell or tissue tropism or a sequence having at least 90%, 95%, 96%, 97%, 98%, 99% sequence identity thereto.

54. The avian coronavirus or IBV spike protein or fragment thereof of any one of clauses 1 and 3 and 5 to 52, wherein the at least a part of the S1 subunit is at least 1, 5, 10, 15, 20, 25, 50, 100, 150, 200, 250, 300, 350, 400 or 500 contiguous amino acids from a S1 subunit sequence of an avian coronavirus or IBV of any one of clauses 36 to 50 or a sequence having at least 90%, 95%, 96%, 97%, 98%, 99% sequence identity thereto.

55. The IBV spike protein or fragment thereof of any one of clauses 3 and 5 to 52, wherein said at least a part of the S1 subunit from an IBV with a restricted cell or tissue tropism has at least 1, 5, 10, 15, 20, 25, 50, 100, 150, 200, 250, 300, 350, 400 or 500 contiguous amino acids of the amino acid sequence as shown in SEQ ID NO: 2, 3, 4, 5, 6, 7, 8, 77 or a sequence having at least 90%, 95%, 96%, 97%, 98%, 99% sequence identity thereto.

56. The avian coronavirus or IBV spike protein or fragment thereof of any one of clauses 1 and 3 and 5 to 55, wherein the avian coronavirus or IBV with restricted cell or tissue tropism is restricted to infection and/or replication in emryonated chicken eggs and/or primary chicken kidney cells.

57. The avian coronavirus or IBV spike protein or fragment thereof of any one of clauses 1 and 3 and 5 to 56, wherein the avian coronavirus or IBV with restricted cell or tissue tropism is not infecting and/or replicating in EB66 cells.

58. The avian coronavirus or IBV spike protein or fragment thereof of any one of clauses 1 and 3 and 5 to 56, wherein the avian coronavirus or IBV with restricted cell or tissue tropism is not infecting and/or replicating in PBS-12 and/or HEK 293T cells.

Fragment

59. The avian coronavirus or IBV spike protein or fragment thereof of any one of clauses 1 to 58, wherein the fragment of the avian coronavirus or IBV spike protein has a length of at least 500, 750, 1000 or 1077 amino acids.

60. The avian coronavirus or IBV spike protein or fragment thereof of any one of clauses 1 to 59, wherein the fragment of the avian coronavirus or IBV spike protein has a length of at least 1000 amino acids.

61. The avian coronavirus or IBV spike protein of any one of clauses 1 to 60, wherein the Cysteine at amino acid position 267 or the mutation at amino acid position 267 to Cysteine is genetically stable.

62. A nucleotide sequence encoding the spike protein or fragment thereof of any one of clauses 1 to 61.

63. A plasmid comprising a nucleotide sequence of clause 62.

64. A cell comprising a plasmid of clause 63.

65. A viral particle comprising a spike protein or fragment thereof of any one of clauses 1 to 61.

66. An avian coronavirus comprising the spike protein or fragment thereof of any one of clauses 1 to 61.

67. An IBV (infectious bronchitis virus) comprising the spike protein of any one of clauses 3 to 61.

68. The avian coronavirus or IBV of clauses 66 or 67, wherein the avian coronavirus or IBV is attenuated.

69. The avian coronavirus or IBV of any one of clauses 66 to 68, wherein the avian coronavirus or IBV is genetically engineered.

70. The avian coronavirus or IBV of any one of clauses 66 to 69, wherein the avian coronavirus or IBV is recombinant.

71. The avian coronavirus or IBV of any one of clauses 66 to 70, wherein the avian coronavirus or IBV is chimeric.

72. The IBV of any one of clauses 67 to 71, wherein the IBV is from an IBV with a genotype selected from a list of strains consisting of: Arkansas (such as Arkansas 99), Brazil (such as BR-1, BR-2, 23/2013, IBV/Brasil/351/1984), California (such as California 1734/04, California 99), Connecticut, Delaware (such as Delaware 98), Dutch (such as D207, D212, D274, D3128, D3896, D8880, D1466), Florida, Georgia (such as Georgia GA-07, GA-08, GA-12, GA-13), Gray, Holte, Iowa (such as Iowa 97 and Iowa 69), Italy 02, JMK, LDT3, Maine (such as Maine 209), Massachusetts (M41, H52, H120, Beaudette), Pennsylvania (such as Pennsylvania 1220/98, Pennsylvania Wolg/98), PL84084, Qu (such as Qu-mv), QX (such as GB341/96), Q1, SE 17, Variant 2 (such as IS/1494/06, IBV/Ck/EG/CU/4/2014, gammaCoV/Ck/Poland/G052/2016) and 4/91 (793B, CR88).

73. The IBV of any one of clauses 67 to 72, wherein the IBV is selected from a list of genotypes or serotypes consisting of Massachusetts, 4/91, QX, Q1, Italy 02, Arkansas, Connecticut, Georgia, LDT3, PL84084, Variant 2 and Brazil.

74. The IBV of any one of clauses 67 to 73, wherein the IBV is selected from a list of genotypes or serotypes consisting of Massachusetts, 4/91, QX, Q1, Arkansas, Variant 2 and Brazil.

75. The IBV of clause 74, wherein the Massachusetts strain is selected from a list consisting of: H120, H52, Spain/98/308, IBMA5-1, SD/97/01, Beaudette, Spain/96/334 and M41-M21883.

76. The IBV of clause 74, wherein the 4/91 strain is selected from a list consisting of: Spain/98/328, Spain/92/35, IR-3654-VM, FR-CR88061-88, FR-85131-85, UK-1233-95, UK/3/91, Spain/00/336, UK/7/91, 4/91-pathogenic, 4/91 attenuated and IB4-91.

77. The IBV of clause 74, wherein the QX strain is selected from a list consisting of: FR-L1450T-05, FR-L1450L-05, NL-L1449T-04, NL-L1449K-04, IBV/Ck/SP/170/09, IBV/Ck/SP/79/08, IBV/Ck/SP/248/09, HBN, IBVQX, LX4, BJQ, CK/CH/LGD/03 and GB341/96.

78. The IBV of clause 74, wherein the Q1 strain is selected from a list consisting of: CK/CH/LDL/98I, CK/CH/LSD/08-10, J2, Q1, AR08ER22, AR08BA21 and Chile-295-10.

79. The IBV of clause 74, wherein the Italy 02 strain is selected from a list consisting of: Spain/99/316, Italy-02, UK-L633-04, It-497-02, Spain/05/866, Spain/04/221, Spain/00/337, Spain/155/09 and Spain/03/08.

80. The IBV of clause 74, wherein the Arkansas strain is selected from a list consisting of: Ark99, ArkGA, ArkDPI, AL/5364/00, ARKDPI11, AL/0803/01, AL/7149/00, ArkDPI101, AL/1221/01, AL/1793/01 and AL/4614/98.

81. The IBV of clause 74, wherein the Variant 2 strain is selected from a list consisting of: IS/1494/06, IBV/Ck/EG/CU/4/2014, gammaCoV/Ck/Poland/G052/2016, Eg/CLEVB-2/IBV/012, D1344/2/4/10_EG, TR8 and IB VAR2-06.

82. The IBV of clause 74, wherein the Brazil strain is selected from a list consisting of: BR-1, BR-2, 23/2013 and IBV/Brasil/351/1984.

83. The IBV of any one of clauses 67 to 74, wherein the Spike protein or fragment thereof is from an IBV of Massachusetts or 4/91 genotype or serotype.

84. The IBV of any one of clauses 67 to 74, wherein the IBV strain is H120, H52 or CR88.

85. The IBV of any one of clauses 67 to 84, wherein the IBV has an IBV Spike Protein or fragment thereof consisting of or comprising an amino acid sequence as shown in SEQ ID NO: 2, 3, 4, 5, 6, 7, 8, 77 or a sequence having at least 80%, 85%, 90%, 93%, 95%, 96%, 97%, 98%, 99%, 99.5%, 99.6%, 99.7%, 99.8%, 99.9%, 99.95%, 99.98% or 99.99% sequence identity thereto.

86. The IBV of any one of clauses 67 to 85, wherein the IBV has an extended cell or tissue tropism.

87. The IBV of any one of clauses 67 to 86, wherein the IBV is infecting and/or replicating in at least one cell line or cell of any one of clauses 9 to 11.

88. A cell comprising:
the viral particle of clause 65, or
the avian coronavirus or IBV of any one of clauses 66 to 87.

89. The cell of clause 88, wherein the cell is a cell line or cell selected from the list consisting of: primary chicken embryo cells, a chicken embryo fibroblast cell line, a duck embryonic stem cell line, a human embryonic kidney cell line, a baby hamster kidney cell line, an African green monkey kidney cell line, a rabbit kidney cell line, a canine kidney cell line, a chicken liver cell line, a bovine kidney cell line, a porcine kidney cell line and an insect cell line.

90. The cell of clauses 88 or 89, wherein the cell is a cell line selected from the list consisting of: DF-1 (Douglas Foster), EB66 (duck embryonic stem cell line), PBS-12, PBS-12SF (PBS-12 serum free), BHK21 (baby hamster kidney), HEK 293T (human embryonic kidney), Vero (Verda Reno), MA104, RK13 (rabbit kidney), LMH (leghorn male hepatoma), MDCK (Madin-Darby canine kidney), MDBK (Madin-Darby bovine kidney), PK15 (porcine kidney), PK2A (porcine kidney), SF9, SF21 and SF+(*Spodoptera frugiperda*).

91. The cell of any one of clauses 88 to 89, wherein the cell is a cell line selected from the list consisting of: DF-1, EB66, PBS-12, PBS-12SF, BHK, HEK 293T, Vero, MA104 and RK13.

92. The cell of clause 89, wherein the primary chicken embryo cell is a fibroblast or a cell derived from liver or lung tissue.

93. An immunogenic composition comprising:
the spike protein of any one of clauses 1 to 61, or
the viral particle of clause 65, or
the avian coronavirus or IBV of any one of clauses 66 to 87.

94. A vaccine comprising:
the spike protein of any one of clauses 1 to 61, or
the viral particle of clause 65, or
the coronavirus or IBV of any one of clauses 66 to 87.

95. A modified live vaccine with an extended cell or tissue tropism comprising:
the spike protein of any one of clauses 1 to 61, or
the viral particle of clause 65, or
the coronavirus or IBV of any one of clauses 66 to 87.

96. The immunogenic composition or vaccine of any one of clauses 93 to 95, wherein the immunogenic composition or vaccine comprises a pharmaceutically acceptable carrier.

97. The immunogenic composition or vaccine of clause 96, wherein the pharmaceutically acceptable carrier is phosphate buffered saline.

98. The immunogenic composition or vaccine of any one of clauses 93 to 97, wherein the immunogenic composition or vaccine is effective in the treatment and/or prophylaxis of clinical signs caused by IBV in a subject of need.

99. The immunogenic composition or vaccine of any one of clauses 93 to 98, wherein the immunogenic composition or vaccine comprises 1 to 10 $\log_{10}$ $EID_{50}$ of the IBV.

100. The immunogenic composition or vaccine of any one of clauses 93 to 99, wherein the immunogenic composition or vaccine comprises 2 to 5 $\log_{10}$ $EID_{50}$ of the IBV.

101. The immunogenic composition or vaccine of any one of clauses 93 to 100, wherein the immunogenic composition or vaccine comprises 2 to 4 $\log_{10}$ $EID_{50}$ of the IBV.

102. A method for altering the cell or tissue tropism of an avian coronavirus comprising the use of the avian coronavirus spike protein or fragment thereof of any one of clauses 1 to 61.

103. A method for extending the cell or tissue tropism of an avian coronavirus comprising the use of the avian coronavirus spike protein or fragment thereof of any one of clauses 1 to 61.

104. A method for the production or manufacture of an avian coronavirus with an extended cell or tissue tropism comprising the use of the avian coronavirus spike protein or fragment thereof of any one of clauses 1 to 61.

105. A method for culturing an avian coronavirus in a cell or tissue culture comprising the use of the avian coronavirus spike protein or fragment thereof of any one of clauses 1 to 61.

106. A method for modifying an avian coronavirus comprising modifying the amino acid position 267 in the spike protein of said avian coronavirus.

107. A method for mutating the amino acid position 267 in an avian coronavirus spike protein comprising:

a) providing an avian coronavirus spike nucleotide or protein sequence,
b) identifying position 267 in the spike protein by alignment with a reference sequence,
c) mutating the position 267 of the spike protein of step b) into a cysteine,
d) obtaining the mutated spike protein of step c).

108. The method of any one of clauses 102 to 106, wherein the spike protein or fragment thereof has at amino acid position 267 a Cysteine.

109. The method of any one of clause 106 to 108, wherein the Cysteine at amino acid position 267 is introduced by a mutation.

110. The method of clause 109, wherein the mutation is an amino acid substitution, deletion or insertion.

111. The method of any one of clause 106 to 111, wherein a Phenylalanine or Leucine is modified or mutated into a Cysteine at amino acid at position 267.

112. The method of any one of clauses 102 to 111, wherein the avian coronavirus is an IBV of any one of clauses 67 to 87.

113. The method of any one of clauses 102 to 112, wherein the coronavirus spike protein is an IBV (infectious bronchitis virus) spike protein of any one of clauses 3 to 61.

114. The method of any one of clauses 102 to 113, wherein the Cysteine at amino acid position 267 or said mutation at amino acid position 267 to Cysteine leads to an extended cell or tissue tropism.

115. The method of any one of clauses 102 to 114, wherein the avian coronavirus or IBV is infecting and/or replicating in at least one cell line or cell of any one of clauses 9 to 11.

116. The method of to any one of clause 106 to 115, wherein the numbering of amino acid position 267 is done according to any one of clauses 12 to 18.

Kit Clauses

117. A kit comprising the viral particle, avian coronavirus, IBV, the immunogenic composition or vaccine of any one of clauses 65 to 88 and 93 to 101.

118. The kit of clause 117, wherein the kit further comprises an instruction letter for the treatment and/or prophylaxis of diseases of avians or an instruction letter for the treatment and/or prophylaxis of diseases of poultry or an instruction letter for the treatment and/or prophylaxis of IB.

119. The kit of clauses 117 or 118, wherein the kit further comprises a dispenser capable of administering a vaccine to said animal.

Method of Treatment Clauses

120. A method for immunizing a subject comprising administering to such subject an immunogenic composition or vaccine of any one of clauses 93 to 101.

121. A method of treating or preventing clinical signs caused by IBV in a subject of need, the method comprises administering to the subject a therapeutically effective amount of an immunogenic composition or vaccine of any one of clauses 93 to 101.

122. A method of reducing the ciliostasis in a subject of need, in comparison to a subject of a non-immunized control group of the same species, the method comprises administering to the subject a therapeutically effective amount of an immunogenic composition or vaccine of any one of clauses 93 to 101.

123. The immunogenic composition or vaccine of any one of clauses 93 to 101 for use in a method for immunizing a subject, the method comprises administering to the subject a therapeutically effective amount of said immunogenic composition or vaccine.

124. The immunogenic composition or vaccine of any one of clauses 93 to 101 for use in a method of treating or preventing clinical signs caused by IBV in a subject of need, the method comprises administering to the subject a therapeutically effective amount of said immunogenic composition or vaccine.

125. The immunogenic composition or vaccine of any one of clauses 93 to 101 for use in a method of reducing the ciliostasis in a subject of need, in comparison to a subject of a non-immunized control group of the same species, the method comprises administering to the subject a therapeutically effective amount of said immunogenic composition or vaccine.

126. The method or use of any one of clauses 120 to 125, wherein said subject is avian.

127. The method or use of any one of clauses 120 to 126, wherein said subject is poultry.

128. The method or use of any one of clauses 120 to 127, wherein said subject is selected from the list consisting of chicken, turkey, quail, or pheasant.

129. The method or use of any one of clauses 120 to 128, wherein said subject is chicken.

130. The method or use of any one of clauses 120 to 129, wherein the immunogenic composition or vaccine is administered once.

131. The method or use of any one of clauses 120 to 129, wherein the immunogenic composition or vaccine is administered at two or more doses.

132. The method or use of any one of clauses 120 to 131, wherein said immunogenic composition or vaccine is administered subcutaneously, intramuscularly, oral, in ovo, via spray, via drinking water or by eye drop.

133. The method or use of any one of clauses 120 to 132, wherein said immunogenic composition or vaccine is administered via eye drop.

134. The method or use of any one of clauses 120 to 133, wherein the immunogenic composition or vaccine comprises 1 to 10 $\log_{10}$ $EID_{50}$ per dose of the IBV.

135. The method or use of any one of clauses 120 to 134, wherein the immunogenic composition or vaccine comprises 2 to 5 $\log_{10}$ $EID_{50}$ per dose of the IBV.

136. The method or use of any one of clauses 120 to 135, wherein the immunogenic composition or vaccine comprises 2 to 4 $\log_{10}$ $EID_{50}$ per dose of the IBV.

137. The method or use of any one of clauses 120 to 136, wherein the immunogenic composition or vaccine is administered to subjects within the first week of age, within the first three days of age, within the first two days of age, or within the first day of age.

138. The method or use of any one of clauses 120 to 137, wherein the immunogenic composition or vaccine is administered to subjects within the first day of age.

139. The method or use of any one of clauses 120 to 138, wherein said method results in an improvement in an efficacy parameter selected from the group consisting of: prevention or reduction of ciliostasis, prevention or reduction of rales, prevention or reduction of egg drop, prevention or reduction of kidney lesions, prevention or reduction of watery diarrhea, prevention or reduction in weight loss, a lower virus load, a reduced viral shedding or combinations thereof, in comparison to a subject of a non-treated control group of the same species.

140. The method or use of any one of clauses 120 to 139, wherein the treatment or prevention results in a prevention or reduction of ciliostasis as compared to subjects of a non-treated control group of the same species.

141. The method or use of any one of clauses 120 to 140, wherein the treatment or prevention results in a prevention or reduction of kidney lesions as compared to subjects of a non-treated control group of the same species.

142. The method or use of any one of clauses 120 to 141, wherein the treatment or prevention results in a prevention or reduction of egg drop as compared to subjects of a non-treated control group of the same species.

143. The viral particle, avian coronavirus, IBV, immunogenic composition or vaccine of any one of clauses 65 to 87 and 93 to 101 for therapeutic use.

144. The viral particle, avian coronavirus, IBV, immunogenic composition or vaccine of any one of clauses 65 to 87 and 93 to 101 for use as an immunogen or vaccine.

145. The viral particle, avian coronavirus, IBV, immunogenic composition or vaccine of any one of clauses 65 to 87 and 93 to 101 for use as a medicament.

146. Use of the viral particle, avian coronavirus, IBV, immunogenic composition or vaccine of any one of clauses 65 to 87 and 93 to 101 for the manufacture of a medicament.

147. Use of the viral particle, avian coronavirus, IBV, immunogenic composition or vaccine of any one of clauses 65 to 87 and 93 to 101 for the treatment and/or prophylaxis of IBV infections in a subject.

BRIEF DESCRIPTION OF THE DRAWINGS

FIG. 1. In ovo kinetics for H52 rIBV S F267C in comparison to H52 rIBV wild type virus assessed by detection of viral load via RT-qPCR. Data point represent the mean of 5 samples per time point. Error bars indicate the standard deviation.

FIG. 2. Passaging of H52 rIBV S F267C in Eb66® cells. RT-qPCR CT values are determined at the time point of infection (t=0) and harvest (t=72) of each passage. P1 to P5 are generated by infection with a 1/10 dilution of the virus stock of the previous passage. P6 and P7 are generated by inoculation with a 1/1000 dilution of the previous passage. The experiment is repeated with an MOI of 0.001 for the first passage and similar results are obtained.

FIG. 7. Replication of H52 rIBV S F267C in PBS-12SF cells determined via immunofluorescence analysis. One of three independent experiments is shown.

FIG. 8: Relocation of H52 rIBV S F267C in PBS-12SF cells determined via nucleic acid extraction from the supernatant and subsequent RT-qPCR analysis. One of two independent experiments is shown.

FIG. 9. Replication of H52 rIBV S F267C in HEK 293T cells determined via immunofluorescence analysis. One of three independent experiments is shown.

FIG. 10. In ovo kinetics for CR88 rIBV S L269C in comparison to CR88 rIBV wild type virus assessed by detection of viral load via RT-qPCR. Data point represent the mean of 5 samples per time point. Error bars indicate the standard deviation.

FIG. 11. Passaging of CR88 rIBV S L269C in Eb66® cells. RT-qPCR CT values are determined at the time point of infection (t=0) and harvest (t=72) of the respective passage. CR88 rIBV wild type is included as negative control. For CR88 rIBV S L269C data for P2, P5 and P8 are shown. The CR88 rIBV included in the same passaging experiment has one passage less in the initial passage (P1) and the last passage (P7). Each passage is generated by infection with a 1/100 dilution of the previous passage.

FIG. 16. In ovo kinetics for H52 rIBV QX S L270C and CR88 rIBV QX S L270C compared to IBV QX, H52 rIBV and CR88 rIBV, assessed by detection of viral load via RT-qPCR. Data point represent the mean of 5 samples per time point. Error bars indicate the standard deviation.

FIG. 17. Passaging of CR88 rIBV QX S L270C in Eb66® cells. RT-qPCR CT values are determined at the time point of infection (t=0) and harvest (t=72) of the respective passage.

FIG. 18. Passaging of H52 rIBV QX S L270C in Eb66® cells. RT-qPCR CT values are determined at the time point of infection (t=0) and harvest (t=72) of the respective passage.

FIG. 19. Replication kinetics of H52 rIBV QX S L270C and CR88 rIBV QX S L270C in EB66® cells. Cells are infected with rIBV at an MOI of 0.001 based on TCID$_{50}$ titers from the third EB66®-propagated passage of the viruses. Nucleic acids are isolated at 0, 8, 24 and 48 hpi and analyzed via IBV-specific RT-qPCR. Each data point represents the mean ct value of three independent experiments, each performed in triplicates. Error bars indicate the standard error of the mean (SEM).

SEQUENCES OVERVIEW

Figure 3:
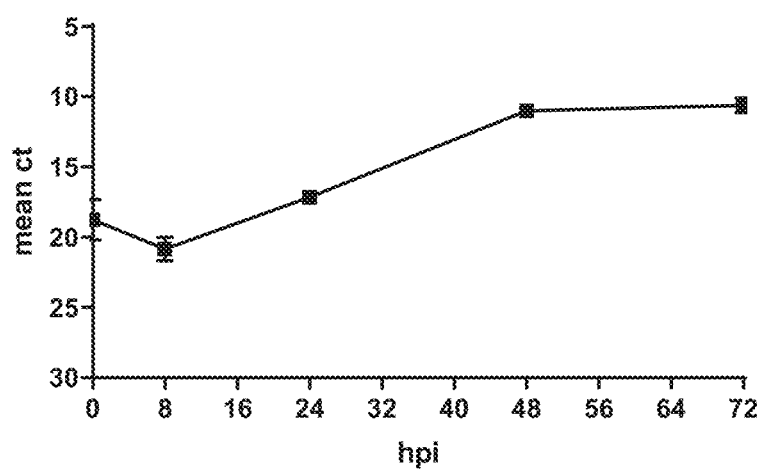
FIG. 3. Replication kinetics of H52 rIBV S F267C in EB66® cells. Cells are infected with rIBV at an MOI of 0.001 based on TCID50 titers from the third EB66®-propagated passage of the viruses. Nucleic acids are isolated at 0, 8, 24, 48 and 72 hpi and analyzed via IBV-specific RT-qPCR. Each data point represents the mean ct value of three independent experiments. Error bars indicate the standard error of the mean (SEM).

SEQ ID NO:1 IBV H52 spike protein
SEQ ID NO:2 IBV H52 spike protein with F267C mutation
SEQ ID NO:3 IBV CR88 spike with L269C mutation
SEQ ID NO:4 IBV QX spike protein with L270C mutation
SEQ ID NO:5 IBV Q1 spike protein with L271C mutation
SEQ ID NO:6 IBV Var 2 spike protein with L270C mutation
SEQ ID NO:7 IBV BR-I spike protein with L274C mutation
SEQ ID NO:8 IBV Ark spike protein with L274C mutation
SEQ ID NO:9 pUC57-s H52 rIBV donor plasmid
SEQ ID NO:10 pUC57-s H52 rIBV S F267C donor plasmid
SEQ ID NO:11 IBV CR88 spike sequence
SEQ ID NO:12 pUC57-s CR88 mIBV donor plasmid
SEQ ID NO:13 pGEM-T IBV CR88 spike plasmid
SEQ ID NO:14 pUC57-s CR88 rIBV S L269C donor plasmid
SEQ ID NO:15 pGEM-T IBV CR88 spike with L269C mutation
SEQ ID NO:16 to 64 primers
SEQ ID NO:65 IBV QX spike protein
SEQ ID NO:66 pGEM-T IBV QX S L270C plasmid
SEQ ID NO:67 pUC57-s CR88 rIBV donor plasmid
SEQ ID NO:68 pUC57-s CR88 rIBV QX S L270C donor plasmid
SEQ ID NO:69 pUC57-s H52 rIBV QX S L270C donor plasmid
SEQ ID NO:70 to 75 primers
SEQ ID NO:76 IBV ArkDPI spike protein
SEQ ID NO:77 IBV ArkDPI spike protein with L274C mutation
SEQ ID NO:78 pUC57-s IBV ArkDPI S L274C
SEQ ID NO:79 pUC57-s H52 rIBV ArkDPI S Ecto L274C donor plasmid
SEQ ID NO:80 to 84 primers

EXAMPLES

The following examples are set forth below to illustrate specific embodiments of the present invention. These examples are merely illustrative and are understood not to limit the scope or the underlying principles of the present invention.

Example 1

Generation of Recombinant IBV H52 in which the Amino Acid 267 of the Spike Protein is Mutated to a Cysteine For the generation of recombinant IBV the method of targeted RNA recombination as described by van Beurden et al. (Virol J. 2017; 14(1):109) is applied.

Donor Plasmid Construction

The pUC57-s IBV-5-1b-S-SIR-3T donor plasmid, hereafter referred to as pUC57-s H52 rIBV donor plasmid (SEQ ID NO:9), is used as template for the construction of the H52 rIBV donor plasmid with a H52 spike in which the amino acid 267 of the H52 spike (SEQ ID NO:1) S1 subunit is mutated from a phenylalanine to a cysteine (SEQ ID NO:2) which is called pUC57-s H52 rIBV S F267C (SEQ ID NO:10). Mutation of the wild type sequence is achieved by using the Q5® Site-Directed Mutagenesis Kit (NEB) with the primers PO1942 and PO1943 (table 1) and according to the kit protocol, with an annealing temperature of 58° C. and an elongation time of 5 minutes and 30 seconds. Positive clones are identified by EcoRV and XhoI restriction digest, flowed by Sanger sequencing with primers P0618 and P0633 (table 1). Afterwards, the integrity of the spike and donor region sequence is confirmed by sequencing with primers SEQ ID NO:19 to SEQ ID NO: 40 in table 1.

TABLE 1

Primers for SDM and sequencing

| SEQ ID NO: | Name | Sequence |
|---|---|---|
| 64 | M13-24F | ccagggttttcccagtcacg |
| 16 | M13-24R | cggataacaatttcacacagg |
| 17 | PO1942 | aacactattttcacgatagac |
| 18 | PO1943 | aatactacttgtacgttacacaatttc |
| 19 | P0618 | taaatggtgatcttgttt |
| 20 | P0632 | gcattcactgctgtacaa |
| 21 | P0633 | cgctcttagtaacataaac |
| 22 | P0636 | ctgaggtcaatgctttatc |
| 23 | P0706 | gacagagcacaagtttgatc |
| 24 | P0709 | acttcaagcatttgtacagg |
| 25 | P0710 | ggtcaacaatgtaattttgct |
| 26 | P0713 | gcagatgctaaaacagaaag |
| 27 | P0714 | tcacctgaacaatcttcagc |
| 28 | P0715 | ggtcaccagtatatttctgc |
| 29 | P0718 | aaagaagcaggatgatgaag |
| 30 | P0726 | aagagatgttggtaacacct |
| 31 | P0728 | ctaaaccggctggttttaat |

TABLE 1-continued

Primers for SDM and sequencing

| SEQ ID NO: | Name | Sequence |
|---|---|---|
| 32 | PO729 | ccatagcttttgccactatt |
| 33 | PO731 | cgcttgtaaatagaaggtct |
| 34 | PO732 | acataccaaggccacttaat |
| 35 | PO733 | ggtcctgttccagtatagta |
| 36 | PO734 | cttgtcctgctttgttaaga |
| 37 | PO756 | gtggatcgtcttataactgg |
| 38 | PO759 | ctcgcattacaaaggctaag |
| 39 | PO766 | ccagttataggacacccatc |
| 40 | PO767 | gttggttcttctggaaatgt |

Targeted RNA Recombination and Rescue of Recombinant IBV

The H52 murinized (m)IBV helper virus and recombinant IBV are generated as described by van Beurden et al. (Virol J. 2017; 14(1):109). Briefly, for the generation of H52 rIBV S F267C, LR7 cells are infected with H52 mIBV and electroporated with in vitro transcript generated from the pUC57-s H52 S F267C donor plasmid (SEQ ID NO:10) and subsequently injected into 8 day old embryonated SPF chicken eggs (VALO BioMedia). After up to 8 days of incubation, the allantoic fluids of all eggs are analyzed separately for the rescue of recombinant IBV after RNA isolation with the MagMAX™ Core Nucleic Acid Purification Kit (ThermoFisher) and the KingFisher™ Duo Prime Purification System (ThermoFisher) and by using SuperScript™ III One-Step RT-PCR System with Platinum™ Taq DNA Polymerase (ThermoFisher). Primers P01323 and P01324 (table 2) binding in H52 IBV lab and H52 IBV S spike are used to distinguish the recombinant IBV from mIBV. Positive samples are further analyzed to confirm the presence of the intended spike F267C mutation using the SuperScript™ III One-Step RT-PCR System with Platinum™ Taq DNA Polymerase with primers P0618 and P0633 (table 2) followed by QIAquick PCR purification and Sanger sequencing with the same primers. The positive allantoic fluid of the egg inoculated with the highest dilution of LR7 cells is used for an end-point dilution in 8-day old SPF eggs. Nucleic acids isolation and sample analysis is conducted as described above. The same procedure is applied for a second end-point dilution. Afterwards, one positive-tested allantoic fluid is used for propagation in 10-day old embryonated SPF chicken eggs. The allantoic fluid is diluted 1:1000 in 1×PBS and 100 µl are injected per egg, which are subsequently incubated at 37.5° C. and 60% humidity. Allantoic fluid is harvested 48 hours post inoculation, pooled, cleared from debris and stored at −80° C.

TABLE 2

PCR and sequencing primers used to identify rescued H52 rIBV and to confirm the targeted S F267C mutation.

| SEQ ID NO: | Name | Sequence |
|---|---|---|
| 41 | PO1323 | tcagcatggacgtgtggtta |
| 42 | PO1324 | ccccatgtaaatgccaacca |
| 19 | PO618 | taaatggtgatcttgttt |
| 21 | PO633 | cgctcttagtaacataaac |

In Vitro and in Ovo Characterization of Recombinant IBV
Determination of Embryo Infectious Dose 50% ($EID_{50}$)

An aliquot of the virus stock is thawed and 10-fold diluted in 1×PBS to determine the 50% embryo infectious dose ($EID_{50}$) by inoculation of 100 µl into the allantoic cavity of five 8-day old embryonated chicken eggs per dilution. Eggs are incubated at 36.5° C., 60% humidity until 7 days post inoculation. Eggs with dead embryos after 24 hours are excluded from the experiment. All other eggs with dead embryos at 7 days post inoculation are considered positive. All eggs with living embryos are candled from the bottom at 7 days post inoculation to identify dwarfs, which are considered positive. The $EID_{50}$/ml is calculated with the formula of Reed and Muench (Am J Epidemiol, 1938; 27(3): 493-497).

Tissue Culture Infectious Dose 50% ($TCID_{50}$)

Eb66® cell viability is analyzed with BioRad TC20 and trypan blue with the gate set to 6-13 µm. Per 96 well $2×10^6$ living Eb66® cells/ml in EX-CELL® EBx™ GRO-I Serum-Free Media+2.5 mM L-Glutamine are seeded 1 day prior to inoculation and incubated at 37° C. and 7.5% $CO_2$. A 10-fold serial dilution of the virus in Eb66® cell medium is performed and 100 µl per dilution (at least 4 replicates per dilution) are added to Eb66® cells after removing the culture medium. If allantoic fluid is used for infection it is passed though a 0.45 µm pore sized filter prior to dilution. Infected cells are incubated for 72 hours followed by immunofluorescence staining to identify positive wells. Medium is aspirated from all wells, which are subsequently washed with 1×PBS before the addition of 100 µl ethanol per well for cell fixation for 10 min at RT and subsequent air drying of the cells. The cells are incubated with 100 µl of primary chicken anti-IBV Mass serum (Boehringer Ingelheim), diluted 1:250 in 1×PBS, for 45 min at room temperature. After removal of the primary antibody each well is washed three times with 1×PBS. 100 µl of secondary Alexa Fluor 488 goat anti-chicken IgG antibody (ThermoFisher Scientific, 1:500 dilution in 1×PBS) are added and incubated for 45 min at room temperature in the dark. After removal of the secondary antibody, each well is washed three times with 1×PBS, leaving the final wash on the cells. Positive wells are identified by fluorescence microscopy and recorded to calculate the $TCID_{50}$/ml with the formula of Reed and Muench (Am J Epidemiol, 1938; 27(3):493-497).

In Ovo Replication Kinetics

Eight day-old embryonated chicken eggs are inoculated with $10^2$ $EID_{50}$ of rIBV and the respective controls. Eggs are candled daily after 0, 8, 24, 34, 48 and 72 hours of incubation and embryo mortality is recorded. Five preselected eggs per sample and time point are removed and transferred to 4° C. for at least 2 hours. Subsequently, the allantoic fluid is harvested and stored at −80° C. For analysis, samples are thawed and diluted 1:10 in 1×PBS without Ca and Mg and nucleic acids are extracted with the QIAamp DNA Blood Mini kit (Qiagen) with addition of carrier RNA using the Hamilton Starlet pipet robot. Extracted nucleic acids are analyzed by RT-qPCR for the relative amount of IBV RNA with a protocol adapted from Callison et al. (J Virol Methods. 2006; 138(1-2):60-5). Briefly, the same primers and probe are used and the thermoprofile is adapted for the use of TaqMan® Fast Virus 1-Step Master Mix (ThermoFisher) and the ABI™ 7900HT Fast Real-Time PCR System (Thermo Fisher Scientific). All nucleic acid samples are analyzed in triplicates using a 10-fold dilution series of IBV H52 as reference.

Figures 1, 2:
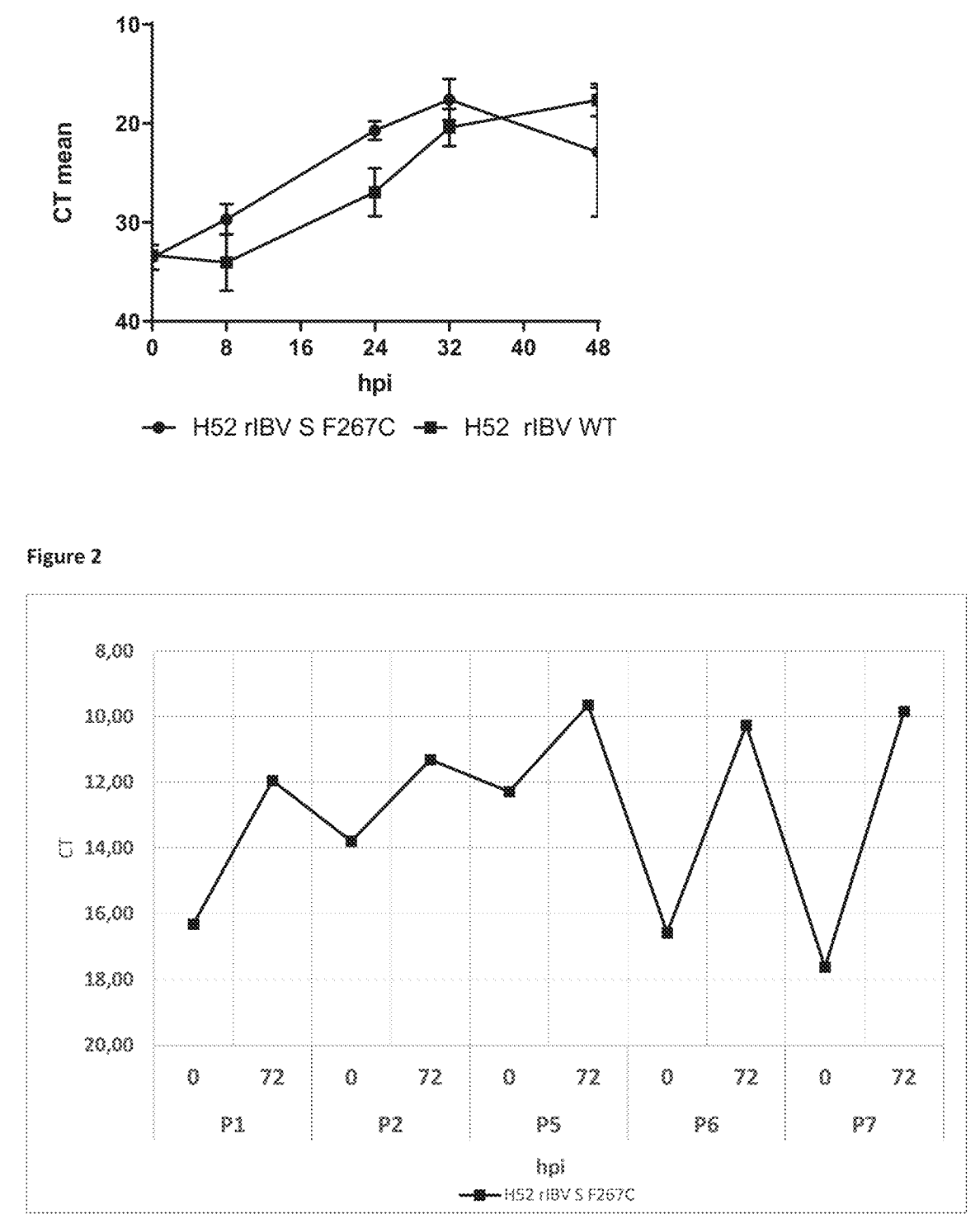

Similar in ovo replication kinetics are observed for H52 rIBV wild type and H52 rIBV S F267C (FIG. 1). This suggests no disadvantage by the mutation of Phenylalanine to Cysteine at the position 267 of the spike for in ovo replication efficiency of the mutated rIBV compared to the wild type rIBV.

Passaging of rIBV in Eb66® Cells

Eb66® cells are seeded at a density of $4 \times 10^5$ cells/ml in EX-CELL® EBx™ GRO-I Serum-Free Media+2.5 mM L-Glutamine into T25 flasks with a total volume of 5 ml and are infected with rIBV and controls. The cultures are incubated for 72 hours at 37° C. and 7.5% $CO_2$ and shaking at 100 rpm. The culture is harvested and stored at −80° C. For passages 1, 2, 5, 6 and 7 virus replication is assessed via RT-qPCR. For this, 250 μl of the suspension are removed directly after inoculation (time point 0 h) and after harvest (time point 72 h) for nucleic acid isolation. Nucleic acids are isolated with the MagMAX™ Core Nucleic Acid Purification Kit (ThermoFisher) and the KingFisher™ Duo Prime Purification System (ThermoFisher). The RT-qPCR is performed as described above.

To analyze if H52 rIBV S F267C is able to replicate in cells, Eb66® cells were inoculated with a 1/10 dilution of the allantoic fluid stock. Propagation of the virus is detected by a decreased ct value after 72 hours in the first and following passages. Due to dilution of the virus for the next passage the ct value increases compared to the ct value measured at harvest of the inoculum before decreasing again during the 72 h culture due to virus replication. Replication becomes even more obvious in higher passages 6 and 7 for which the inoculation is conducted with a 1/1000 dilution of the previous passage (FIG. 2). The results clearly show replication of H52 rIBV F267C over 7 passages in Eb66® cells. Thus, it is apparent that the modification to a Cystein at Position 267 is genetically stable since the IBV still has the extended cell culture/tissue tropism after 7 passages.

In addition, the infectious titers for the allantoic fluid stock ($10^{6.33}$ TCID$_{50}$/ml, $10^{7.22}$ EID$_{50}$/ml) and Eb66® passages P1 ($10^{4.67}$ TCID$_{50}$/ml), P5 ($10^{5.33}$ TCID$_{50}$/ml) and P7 ($10^6$ TCID$_{50}$/ml, $10^{5.84}$ EID$_{50}$/ml) are determined. They confirm efficient replication of H52 rIBV S F267C during the Eb66® passaging process and sustained infectivity in SPF eggs. The F267C mutation therefore enables replication in cell lines without disturbing the ability to replicate in ovo.

Eb66® Cell Replication Kinetics

Figure 4:
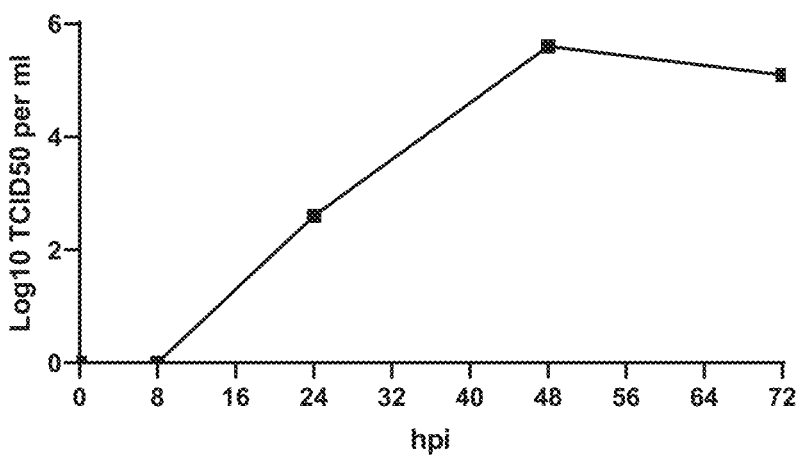
FIG. 4. Replication kinetics of H52 rIBV S F267C in EB66® cells. Samples of time points 0, 8, 24, 48 and 72 hpi are analyzed by TCID50 titration. Results of one experiment are shown.

Passage 3 harvested from Eb66® cells is used to perform replication kinetics in Eb66® cells. Eb66® cells are seeded and incubated as described for passaging and infected with an MOI of 0.001 based on the TCID$_{50}$ titer. Samples are taken directly after inoculation, as well as 8, 24, 48 and 72 hpi (hours post infection). Samples are analyzed for viral RNA content as described for the passaging experiment (FIG. 3). In addition, samples are analyzed for their infectivity via TCID$_{50}$ assay (FIG. 4). Efficient replication is detected with both methods and a plateau phase for replication is reached as early as 48 hours post infection. Conclusively, the replication cycle in Eb66® cells is equally efficient as in embryonated chicken eggs.

Determination of Vaccine Efficacy

Fertilized SPF eggs are incubated for 18 days in an egg setter at 99.7° F. and 50% humidity with 1 turn per hour. At day 18 of incubation the eggs are candled and fertile eggs are transferred to the hatcher and incubated at 99° F. and 70% humidity until hatch. Chicks without clinical signs or deformation are randomly distributed into respective treatment groups and transferred into separate isolators. Three chicks serve as strict negative control (SNC) group, five chicks are enrolled in the challenge control (CC) group and at least 10 in groups which are vaccinated with the Eb66®-adapted recombinant IBV and are subsequently challenged. Animals are kept under housing conditions in compliance to local and national requirements for animal welfare recommendations. The light regime is adjusted to 16 hours light per day. Feed and water are provided ad libitum. After transfer to the isolator, chicks are vaccinated (1-day old) with $10^3$ EID$_{50}$ per chicken via eye drop (total volume 50 μl, 25 μl per eye) while the SNC and CC groups remain untreated. At 21 days post vaccination chickens of the CC and vaccinated groups are challenged with $10^3$ to $10^4$ EID$_{50}$ per chicken of the homologous challenge strain via eye drop (total volume 50 μl, 25 μl per eye). At 7 days post challenge all chickens are euthanized, kidneys are removed and stored in RNAlater Stabilization Solution (ThermoFisher) at 4° C. for IBV-specific RT-qPCR analysis. In addition, tracheas are removed and transferred into 50 ml tubes with warm cell culture medium. Afterwards, tracheas are cleaned from connective tissues and flushed with cell culture medium. The tracheas are cut into tracheal rings using the McIlwain tissue chopper set to 0.6-0.8 mm slice thickness. Per trachea three rings of the upper part, four rings of the middle part and three rings of the lower part are analyzed for ciliar beating by light microscopy and scored for ciliostasis (see table 3). A ring is recorded as normal if more than 50% of the internal ring shows vigorous ciliar movement (Score 2 and lower). A ring is recorded as positive for ciliostasis if less than 50% of the cilia are beating (Score 3 and 4). An animal is considered protected if not fewer than 9 out of 10 rings show normal ciliar activity.

For IBV-specific RT-qPCR analysis kidney tissue pieces are warmed up to room temperature and transferred to separate 2 ml Precellys tubes, which are filled with medium and PBS, respectively. Kidneys are homogenized with the Precellys® tissue homogenizer (Bertin Instruments) for 1×20 sec at 6800 rpm. Choanal wabs are eluted in 2 ml 1×PBS. Nucleic acids are isolated from 200 μl eluate and tissue homogenate respectively using the MagMAX™ Core Nucleic Acid Purification Kit (ThermoFisher) and the KingFisher™ Duo Prime Purification System (ThermoFisher). RT-qPCR is performed as described for the in ovo kinetics above, except for using a StepOnePlus™ Real-Time PCR System (ThermoFisher).

TABLE 3

| Scoring of ciliostasis in tracheal rings | |
|---|---|
| Ciliar activity [%] | Ciliostasis score |
| 100 | 0 |
| 75-99 | 1 |
| 50-74 | 2 |
| 25-49 | 3 |
| 0-25 | 4 |

Figure 5:
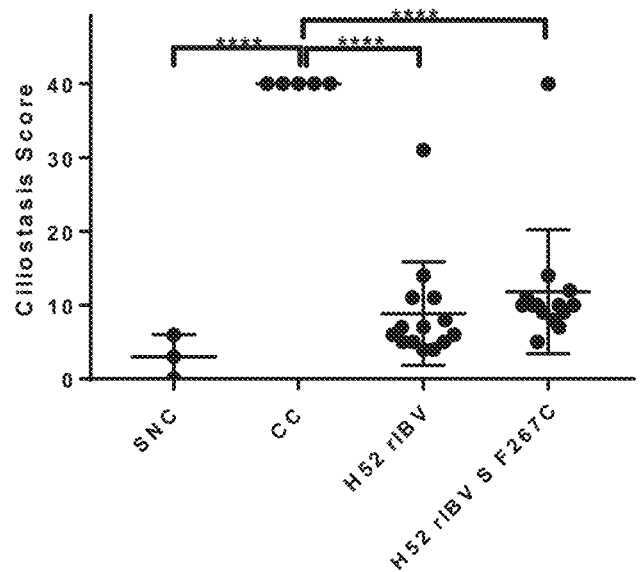
FIG. 5. Summary of ciliostasis scoring for protection by H52 rIBV S F267C against M41 challenge. The sum of the 10 individual scores for the 10 rings of one animal is calculated and is represented by one dot in the graph. Maximum ciliostasis corresponds to a score of 40, while no ciliostasis is represented by a score of 0. Mean and significance are calculated using GraphPad Prism and an ordinary one-way ANOVA test (p<0,0001).

The objective of the study is to demonstrate that the cell culture adapted H52 rIBV S F267C passaged eight times in Eb66® cells is able to confer protection against challenge with virulent M41 strain. All chickens are observed daily for clinical signs and no clinical signs are recorded after vaccination or challenge. Back titrations for the vaccination with H52 rIBV and H52 rIBV S F267C at 1-day of age determine a titer of $10^{3.2}$ $EID_{50}$/animal and $10^{2.87}$ $EID_{50}$/animal (target $10^3$ $EID_{50}$/animal), respectively, and $10^3$ $EID_{50}$/animal (target $10^3$ $EID_{50}$/animal) for challenge with IBV M41 at 21 days post vaccination. Ciliostasis is scored as described in table 3 and results are depicted in FIG. 5.

The average ciliostasis value of the sum of the 10 individual scores for each animal and the protection rates are summarized in table 4. All animals of the strict negative control show normal ciliar movement (100% protection) while all animals of the challenge control group are positive for ciliostasis (0% protection). In contrast, 93% of the animals vaccinated with H52 rIBV are protected and equally well protected are the animals vaccinated with the Eb66®-passaged H52 rIBV S F267C.

TABLE 4

Summary of ciliostasis scoring for protection at 28 days post vaccination and 7 days post challenge. The mean ciliostasis score per group is calculated by adding up the sum score of the individual chickens per group and dividing the group sum by the number of animals (highest possible score 40, lowest possible score 0). For not affected animals, at least 9 of the 10 tracheal explants show normal ciliar activity.

| Vaccine | Challenge | #animals/ not affected | Mean Ciliostasis Score | Not affected [%] |
|---|---|---|---|---|
| — | — | 3/3 | 3 | 100 |
| — | M41 | 5/0 | 40 | 0 |
| H52 rIBV | M41 | 14/13 | 8.9 | 93 |
| H52 rIBV S F267C | M41 | 14/13 | 11.8 | 93 |

Figure 6:
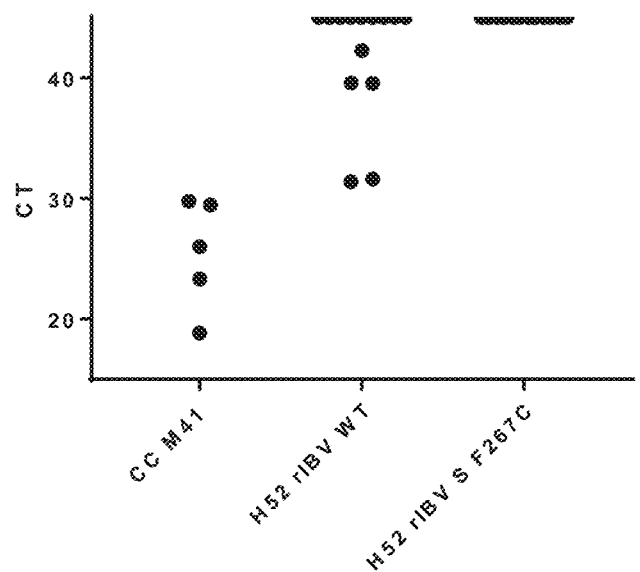
FIG. 6. Summary of RT-qPCR results of kidneys tissues 7 days after challenge for the efficacy study of H52 rIBV S F267C. Each individual bird is indicated by one dot.

In addition, the viral load in the kidneys of animals vaccinated with H52 rIBV S F267C is as efficiently reduced as for H52 rIBV and compared to the M41 challenge control (FIG. 6). In summary, the H52 rIBV S F267C propagated in Eb66® cells protects as efficient against virulent M41 challenge as the H52 rIBV wild type. Further, the modification to a Cystein at Position 267 is genetically stable.

Infection of PBS-12SF Cells with rIBV

The ability to infect PBS-12SF cells is analyzed for the allantoic fluid stocks of H52 rIBV S F267C and H52 rIBV as negative control. PBS-12SF cells are seeded in OptiPRO SFM (ThermoFisher Scientific)+10% GlutaMAX (ThermoFisher Scientific) medium into 12-well plates to reach 80 to 90% confluence on the next day. The cells are incubated at 37° C. and 5% $CO_2$. Before infection the allantoic fluid virus stocks are passed through a 0.45 µm pore sized filter. PBS-12SF cells are infected with $10^{5.74}$ $EID_{50}$ of each virus per well for 4 hours at 37° C. and 5% $CO_2$ before the supernatant is taken off and fresh medium is added for further incubation. After 72 hours the supernatant is taken off and the cells are washed with 1×PBS and 50 µl TrypLE Select (ThermoFisher Scientific) are added to detach cells. Cells are resuspended in supernatant and transferred to a T25 flask with 80-90% confluent PBS-12SF cells (P2), which is incubated for 72 hours. Again, the supernatant and cells are collected and transferred to a T75 flask with 80-90% confluent PBS-12SF cells, which is incubated for 72 hours (P3). The supernatant is harvested. The cells are detached by trypsin treatment and seeded into 12 well plates at a ratio of 1 to 3 in fresh medium and incubated until the next day. Medium is aspirated, cells are washed with 1×PBS, fixed with ice-cold 100% ethanol and air dried. Subsequently cells are rehydrated with 1×PBS and afterwards the primary chicken anti-IBV Mass serum (Boehringer Ingelheim) is added at a dilution of 1 to 200 and incubated for 45 minutes at room temperature. After removal of the antibody, cells are washed and the secondary Alexa Fluor 488 goat anti-chicken IgG antibody (ThermoFisher Scientific, 1:500 dilution in 1×PBS) is added for 45 minutes at room temperature in the dark. Finally, the cells are washed three times with 1×PBS and analyzed by fluorescence microscopy (FIG. 7). Infected cells are detected for H52 rIBV S F267C, while cells infected with H52 rIBV wild type and the uninfected negative control remain negative as expected. Furthermore, 250 µl of supernatant were stored after each of the passages 1, 2 and 3 for nucleic acid extraction and RT-qPCR as described above. A continuous decrease in the ct value (corresponding to replication and propagation of the virus) can be observed for H52 rIBV S F267C over the passaging process while the ct value for H52 rIBV wild type increases as expected. (FIG. 8).

In summary, these data confirm that the single mutation of Phenylalanine to Cysteine at position 267 of the H52 spike renders the virus capable to replicate in PBS12-SF cells, while the H52 wild type virus lacks this ability.

Infection of HEK-293T Cells with rIBV

The ability to infect HEK 293T cells is analyzed for the allantoic fluid stocks of H52 rIBV S F267C and H52 rIBV as negative control. 293T cells are seeded in DMEM (Lonza)+10% FCS (SAFC)+L-Glutamine (Lonza)+1% P/S (Gibco) medium into 12-well plates to reach 80 to 90% confluence on the next day. The cells are incubated at 37° C. and 5% $CO_2$. Before infection the allantoic fluid virus stocks are passed through a 0.45 µm pore sized filter. HEK 293T cells are infected with roughly $10^6$ $EID_{50}$ of each virus per well. After 72 hours the supernatant is taken off and the cells are washed with 1×PBS and 50 µl TrypLE Select (ThermoFisher Scientific) are added to detach cells. Cells are resuspended in supernatant and transferred to a T25 flask with 80-90% confluent HEK 293T cells and 5 ml fresh medium (P2), which is incubated for 72 hours. Again, the supernatant and cells are collected and transferred to a T75 flask with 80-90% confluent HEK 293T cells and 10 ml fresh medium, which is incubated for 72 hours (P3). The supernatant is harvested. The cells are detached by trypsin treatment and seeded into 12 well plates at a ratio of 1 to 3 in fresh medium and incubated until the next day. Medium is aspirated, cells are washed with 1×PBS, fixed with ice-cold 100% ethanol and air dried. Subsequently cells are rehydrated with 1×PBS and afterwards the primary chicken anti-IBV Mass serum (Boehringer Ingelheim) is added at a dilution of 1 to 200 and incubated for 45 minutes at room temperature. After removal of the antibody, cells are washed and the secondary Alexa Fluor 488 goat anti-chicken IgG antibody (ThermoFisher Scientific, 1:500 dilution in 1×PBS) is added for 45 minutes at room temperature in the dark. Finally, the cells are washed three times with 1×PBS and analyzed by fluorescence microscopy (FIG. 9). Infected cells are detected for the positive control as well as H52 rIBV S F267C, while cells infected with H52 rIBV wild type and the uninfected negative control remain negative as expected.

In summary, these data confirm that the single mutation of Phenylalanine to Cysteine at position 267 of the H52 spike renders the virus capable to replicate in HEK 293T cells, while the H52 wild type virus lacks this ability.

Conclusion Example 1: The data show that the mutation to Cysteine at the position 267 of the spike sequence (reference sequence for the numbering is SEQ ID NO:1) in an IBV leads to an extended cell culture and tissue tropism. An H52 recombinant IBV having the F267C mutation in the spike protein can be efficiently cultured in different cell lines such as EB66, PBS-12SF and HEK 293T cells. It is assumed that said IBV can be cultured in other cell lines as well. Further, said mutation has no impact on in ovo replication of the virus and the replication kinetics in ovo and in vitro are similar. Finally, vaccine efficacy is sustained even after passaging in a cell line, laying the basis for successful IBV vaccine development without a need for in ovo culture but using cell lines instead.

Example 2

Generation of Recombinant IBV CR88 in which the Amino Acid 269 of the Spike Protein is Mutated to a Cysteine In order to determine if the change to a Cysteine at position 267 in the IBV spike can also be applied to other genotypes or serotypes, the spike amino acid sequence (SEQ ID NO:11) of the CR88 IBV strain was aligned to the H52 Spike amino acid sequence (SEQ ID NO:1) to determine the position equivalent to amino acid position 267 of H52 spike for IBV CR88 spike, which was determined as the Leucine at position 269 of the CR88 spike.

Construction of an IBV CR88 Murinized Donor Plasmid

To generate the CR88 murinized (m)IBV donor plasmid the donor sequence is synthesized by a commercial supplier: 497 bases of the 5' UTR of the CR88 genome are fused to the 3' part of the lab region (752 bases) and the first 72 bases coding for the CR88 IBV spike, followed by 3753 bases of the MHV spike ectodomain, continuing with the terminal 210 bases of the CR88 IBV spike and the following sequence until the 3' end of the genome. In addition, a SacI restriction site and the sequence of the T7 promoter are added to the 5' end of the donor region, as well as a 100× polyA sequence, followed by a Not I restriction site for linearization at the 3' end, respectively. A silent A to C mutation at position 5634 of the assembled sequence is introduced to generate an XhoI restriction site. The synthesized sequence is inserted into pUC57-simple to yield the pUC57-s CR88 mIBV donor plasmid (SEQ ID NO:12).

Rescue of CR88 mIBV

CR88 mIBV is rescued in analogy to H52 mIBV (van Beurden et al. Virol J. 2017; 14(1):109) with some alterations: The virus allantoic fluid stock is concentrated via ultracentrifugation before isolation of the viral RNA for electroporation. 18 ml of viral allantoic fluid are centrifuged at 50,000×g for 2 hours through a 2 ml 20% Sucrose cushion in TNE (Tris, NaCl, EDTA) buffer. The supernatant is discarded and the pellet resuspended in 150p TNE buffer followed by RNA isolation with QIAamp viral RNA mini kit (Qiagen). Further, chicken embryo fibroblasts (CEFs) instead of BHK cells are used for electroporation (2 pulses 250V/300 µF, 10 sec break) and 1.25% DMSO is added to the electroporation mixture.

Donor Plasmid Construction

The CR88 spike nucleic acid sequence with flanking sequences is synthesized by a commercial supplier and cloned into pGEM-T (SEQ ID NO:13). It is used as a template for site directed mutagenesis to change the leucine at amino acid position 269 of the IBV CR88 spike (SEQ ID NO:11) into a cysteine (SEQ ID NO:3). For this, the QuikChangeMulti Site-Directed Mutagenesis Kit (Agilent Technologies) according to the manufacturer's protocol and the primer PO1886 (table 5) designed by the corresponding online tool are used. Positive clones are identified by restriction digest and analyzed for the presence of the desired mutation by Sanger sequencing with primer P0618 and P01410 (table 5). For the generation of the pUC57-s CR88 rIBV S L269C donor plasmid (SEQ ID NO:14), the pGEM-T CR88 S L269C plasmid containing the mutated CR88 spike sequence (SEQ ID NO:15) is digested with PacI, XhoI and PvuI. The band corresponding to the spike is cut from the gel and purified with the QIAquick gel extraction kit (Qiagen). Further, the CR88 mIBV donor plasmid (SEQ ID NO:12) is digested with PacI, XhoI and KpnI to obtain the donor plasmid backbone. The band with the highest molecular weight is cut from the gel and purified via QIAquick Gel Extraction Kit (Qiagen). The purified spike insert and CR88 donor plasmid backbone are ligated using T4 DNA ligase (ThermoFisher Scientific) at 16° C. over night. The ligation mixture is transformed into NEB 5-α competent E. coli (NEB) by heat shock. After GeneJET Plasmid Miniprep Kit (ThermoFisher Scientific), positive clones are identified by restriction digest and characterized for the targeted mutation by Sanger sequencing with primers P0618, P01014 (table 5).

Targeted RNA Recombination and Rescue of Recombinant IBV

For rescue of CR88 rIBV S L269C, LR7 cells are infected with CR88 mIBV and electroporated with in vitro transcript generated from the NotI linearized pUC57-s CR88 S L269C donor plasmid, and subsequently injected into 8-day old embryonated SPF chicken eggs (VALO BioMedia). After up to 8 days of incubation, the allantoic fluids of all eggs are analyzed separately for the rescue of recombinant IBV after RNA isolation with the MagMAX™ Core Nucleic Acid Purification Kit (ThermoFisher) and the KingFisher™ Duo Prime Purification System (ThermoFisher) and by using SuperScript™ III One-Step RT-PCR System with Platinum™ Taq DNA Polymerase (ThermoFisher). Primers P01728 and P01729 (Table 5) binding in CR88 IBV lab and CR88 IBV S spike are used to distinguish the recombinant IBV from mIBV. The positive allantoic fluid of the egg inoculated with the highest dilution of LR7 cells is used for an end-point dilution in 8-day old embryonated SPF eggs. Nucleic acid isolation is conducted as described above. Samples are analyzed via RT-qPCR conducted according to the protocol adapted from Callison et al. (J Virol Methods. 2006; 138(1-2):60-5). Briefly, the same primers and probe are used and the thermoprofile is adapted for the use of TaqMan® Fast Virus 1-Step Master Mix (ThermoFisher) and the StepOnePlus or the ABI7900 HT Fast Real-Time PCR Systems (ThermoFisher Scientific). Afterwards, one positive-tested allantoic fluid of a high dilution is used for propagation in 8-day old embryonated SPF chicken eggs. The allantoic fluid is diluted 1:100 in 1×PBS and 100 µl is injected per egg which are subsequently incubated at 37.5° C. and 60% humidity. Allantoic fluid is harvested at 48 hours post inoculation, cleared from debris and stored at −80° C.

TABLE 5

SDM primer to obtain the CR88 S L269C mutation and sequencing primers for confirmation of the targeted mutation and confirmation of CR88 rIBV rescue.

| SEQ ID NO: | Name | Sequence |
|---|---|---|
| 43 | PO1886 | gtatatcgagaaagtagcactaacactactt gtaagttaactaatttcagttttactaatg |
| 19 | PO618 | taaatggtgatcttgttt |
| 44 | PO1410 | tttgtatacgagagccatca |
| 45 | PO1728 | tcagcgtggacatgtggtta |
| 46 | PO1729 | ccccatataggtgccaacct |

In Vitro and in Ovo Characterization of Recombinant IBV

The Embryo infectious dose 50% ($EID_{50}$) and the tissue culture infectious dose 50% ($TCID_{50}$) for CR88 rIBV S L269C are determined as described for H52 rIBV S F267C. Further, the in ovo and in vitro replication kinetics and the passaging was conducted as described for H52 rIBV S F267C.

Similar in ovo replication kinetics are observed for CR88 rIBV wild type and CR88 rIBV S L269C (FIG. 10). This suggests no disadvantage of the Cysteine mutation in the spike of CR88 rIBV S L269C for the in ovo replication efficiency of the mutated rIBV compared to the wild type rIBV CR88 as it was shown for H52 rIBV S F267C and H52 rIBV wild type.

Figure 12:
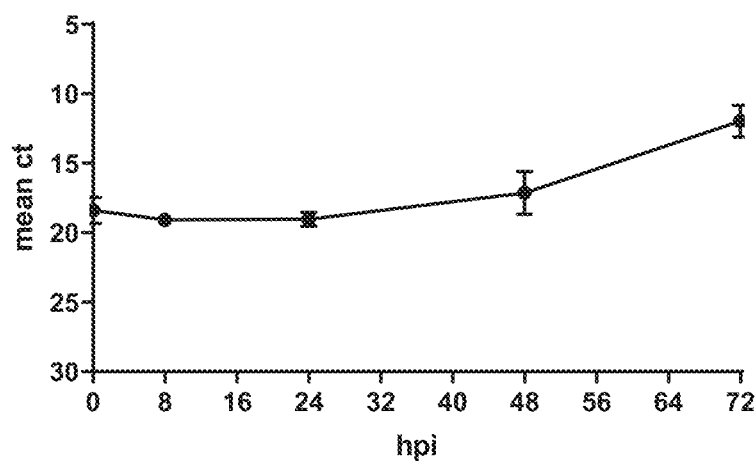
FIG. 12. Replication kinetics of CR88 rIBV S L269C in EB66® cells. Cells are infected with rIBV at an MOI of 0.001 based on TCID$_{50}$ titers from the third EB66®-propagated passage of the viruses. Nucleic acids are isolated at 0, 8, 24, 48 and 72 hpi and analyzed via IBV-specific RT-qPCR. Each data point represents the mean ct value of three independent experiments. Error bars indicate the standard error of the mean (SEM).
Figure 13:
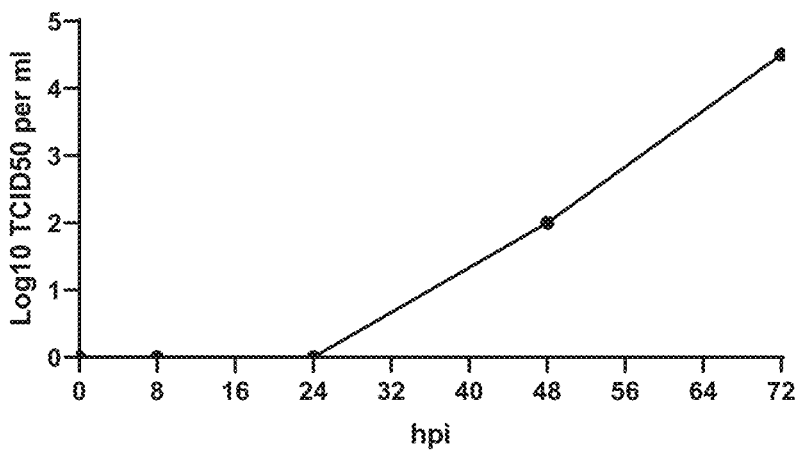
FIG. 13. Replication kinetics of CR88 rIBV S L269C in EB66® cells. Samples of time points 0, 8, 24, 48 and 72 hpi are analyzed by TCID50 titration. Results of one experiment are shown.

To analyze if CR88 rIBV S L269C is able to replicate in cells, Eb66® cells are inoculated with a 1/100 dilution of the allantoic fluid stock. Propagation of the virus is detected by a decreased ct value after 72 hours in the first and following passages. Due to dilution of the virus for the next passage the ct value increases compared to the ct value measured at harvest of the inoculum before decreasing again during the 72 h culture due to virus replication. Replication of CR88 rIBV S L269C is clearly visible over the passaging process by a decreasing ct value for the 72 h time point compared to the 0 h time point directly after infection. In contrast, the ct values of the CR88 rIBV wild type negative control confirm no replication for this virus in any of the analyzed passages and dilution of the initial inoculum during the passaging process (FIG. 11). The results clearly show replication of CR88 rIBV L269C over 7 passages in Eb66® cells while wild type virus is not able to replicate, highlighting that the L269C mutation in the spike is crucial for the extended cell or tissue tropism. Efficient replication for CR88 rIBV S L269C is also detected via RT-qPCR (FIG. 12) and $TCID_{50}$ determination (FIG. 13) in a replication kinetic experiment in Eb66® cells.

In addition, the infectious titers for the allantoic fluid stock ($10^3$ $TCID_{50}$/ml, $10^8$ $EID_{50}$/ml) and Eb66® passages P1 ($10^{3.5}$ $TCID_{50}$/ml, $10^{5.84}$ $EID_{50}$/ml), P5 ($10^{5.3}$ $TCID_{50}$/ml) and P8 ($10^6$ $TCID_{50}$/ml, $10^6$ $EID_{50}$/ml) are determined. They confirm efficient replication of CR88 rIBV S L269C during the Eb66® passaging process and sustained infectivity in SPF eggs. The L269C mutation therefore enables replication in cell lines without disturbing the ability to replicate in ovo.

Determination of Vaccine Efficacy

Figure 14:
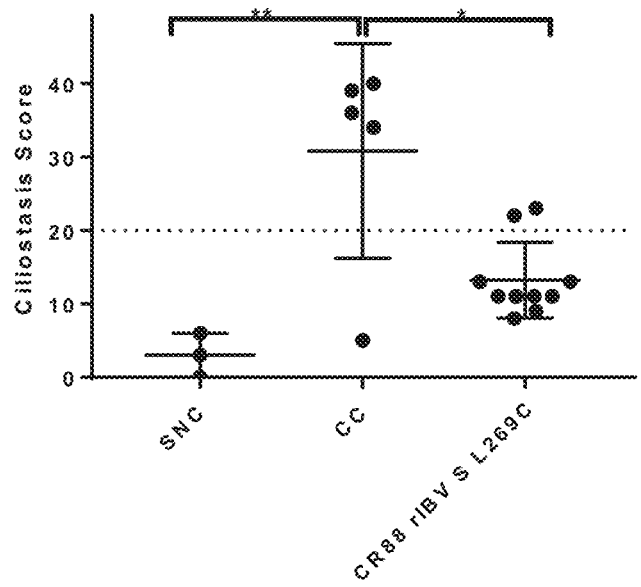
FIG. 14. Summary of ciliostasis scoring for protection by CR88 rIBV S L269C against 793B challenge. The sum of the 10 individual scores for the 10 rings of one animal is calculated and is represented by one dot in the graph. Maximum ciliostasis corresponds to a score of 40, while no ciliostasis is represented by a score of 0. Mean and significance are calculated using GraphPad Prism and an ordinary one-way ANOVA test (*p<0.02, **p<0.007).

Testing for the efficacy of CR88 rIBV S L269C against challenge with IBV 793B was conducted as described for H52 rIBV S F269C above. The objective of the study is to demonstrate that the cell culture adapted CR88 rIBV S L269C passaged one time in Eb66® cells is able to confer protection against a virulent 793B strain. All chickens are observed daily for clinical signs. No clinical signs are recorded after vaccination or challenge. Back titrations for the vaccination with CR88 rIBV S L269C at 1-day of age determine a titer of $10^{3.6}$ $EID_{50}$/animal (target $10^3$ $EID_{50}$/animal), respectively, and $10^{4.1}$ $EID_{50}$/animal (target $10^4$ $EID_{50}$/animal) for challenge with IBV 793B at 21 days post vaccination. Ciliostasis is scored as described in table 3 and results are depicted in FIG. 14 and summarized in table 6. All animals of the strict negative control show normal ciliar movement while 4 of the 5 animals of the challenge control group are positive for ciliostasis. In contrast, 80% of the animals vaccinated with CR88 rIBV S L269C are protected.

TABLE 6

Summary of ciliostasis scoring for protection at 28 days post vaccination and 7 days post challenge. The mean ciliostasis score per group is calculated by adding up the sum score of the individual chickens per group and dividing the group sum by the number of animals (highest possible score 40, lowest possible score 0). For not affected animals, at least 9 of the 10 tracheal explants show normal ciliar activity.

| Vaccine | Challenge | #animals/ not affected | Mean Ciliostasis Score | Not affected [%] |
|---|---|---|---|---|
| — | — | 3/3 | 3 | 100 |
| — | 793B | 5/1 | 30.8 | 20 |
| CR88 rIBV S L269C | 793B | 10/8 | 13.2 | 80 |

Figure 15:
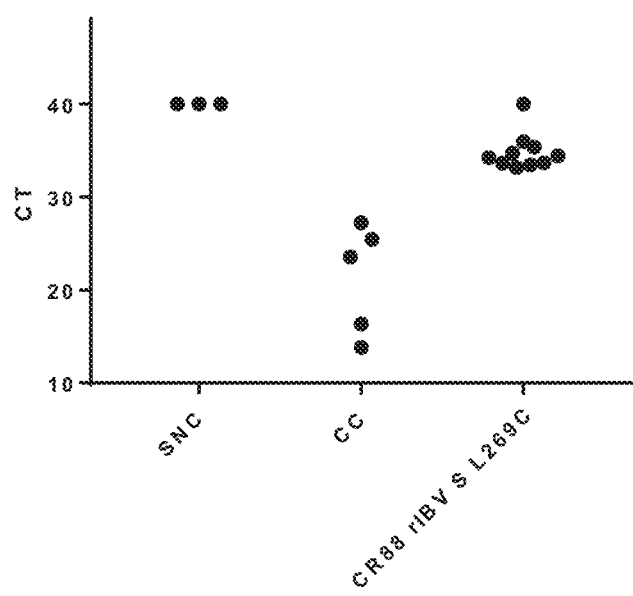
FIG. 15. Summary of RT-qPCR results of kidneys tissues 7 days after challenge for the efficacy study of CR88 rIBV S L269C. Each individual bird is indicated by one dot.

In addition, the viral RNA load is significantly reduced in kidneys of animals vaccinated with CR88 rIBV S L269C compared to the challenge control (FIG. 15). In summary, the CR88 rIBV S L269C propagated in Eb66® cells efficiently protects against virulent 793B challenge. The spike mutation L269C adapts the virus to propagation in cells while the in vivo efficacy is sustained.

Conclusion Example 2: The data show that the mutation to Cysteine at position 267 of the spike (reference sequence for the numbering is SEQ ID NO:1) corresponding to position 269 in CR88 spike leads to an extended cell or tissue tropism in a recombinant IBV CR88, too. Further, said mutation has no impact on in ovo replication of the virus. Finally, vaccine efficacy is sustained even after propagation in a cell line, laying the basis for successful IBV vaccine development without a need for in ovo culture but using cell lines instead.

Example 3

Generation of Chimeric Recombinant IBV CR88 or H52 in which the CR88 or H52 Spike Gene is Replaced by a QX Spike Gene in which the Amino Acid 270 of the Spike Protein is Mutated to a Cysteine In order to further elaborate if the change to a Cysteine at position 267 of the spike to achieve cell culture tropism can be transferred to additional IBV genotypes, the QX spike amino acid (SEQ ID NO:65) sequence was aligned to the H52 spike amino acid sequence (SEQ ID NO:1) to determine the position equivalent to amino acid position 267 of H52 spike for IBV QX spike, which was determined as the Leucine at position 270 of the QX spike.

In order to analyze the potential of a QX spike with a mutation at amino acid position 270 to Cysteine to infect cells, a recombinant IBV CR88 and a recombinant IBV H52 are generated in which the sequence encoding the CR88 spike or H52 spike respectively is replaced by the sequence encoding a QX spike with a Cysteine at position 270 of the spike protein (SEQ ID NO:4). For this the steps for the construction and rescue of an H52 mIBV and CR88 mIBV are conducted as described in example 1 and 2.

Cloning and Mutation of the QX Spike Gene

The QX spike sequence is amplified from IBV QX viral RNA via one step RT-PCR (SuperScript® III One-Step RT-PCR, Platinum® Taq) using the primers P01367 and P01347 (table 7) and cloned using the pGEM-T vector System (Promega). It serves as template for site directed mutagenesis using the primers P02163 and P02164 (table 7) designed with the NEBaseChanger to generate the a plasmid pGEM-T IBV QX S L270C (SEQ ID NO:66). To identify clones with plasmids carrying the desired mutation Sanger sequencing with the primers P01398 and P0633 located in the region flanking the mutation is performed after a positive restriction digest (table 7).

TABLE 7

Primers for cloning and site-directed mutagenesis of the QX spike sequence

| SEQ ID NO | Name | Sequence |
|---|---|---|
| 47 | P01367 | cgcggatccgccaccatgttggtgaagtcactg |
| 48 | P01347 | gcggcggccgcttaaacagactttttaggtctg |
| 49 | P02163 | taatactacttgtgcgttaactaattttactttagtaatg |
| 50 | P02164 | acactactttcacgatag |
| 51 | P01398 | aatttaacagttagcgtatc |
| 21 | P0633 | cgctcttagtaacataaac |

Donor Plasmid Construction

The pUC57-s H52 rIBV QX S L270C donor plasmid (SEQ ID NO:69) is constructed using the NEBuilder® HiFi DNA Assembly Cloning Kit (NEB) and online tool for primer design. For this, the pUC57-s H52 rIBV donor plasmid (SEQ ID NO:9) is digested using the restriction sites EcoRV, PmlI and BlpI close to the H52 spike coding sequence to linearize the plasmid and remove the H52 spike and flanking sequences. The QIAquick gel extraction kit (Qiagen) is used to purify the band corresponding to the pUC57-s IBV H52 backbone without the H52 spike coding sequence. The QX S L270C nucleic acid coding sequence and the flanking 5' and 3' IBV H52 sequences are amplified in three separate PCR reactions with Q5® High-Fidelity DNA Polymerase (NEB; see table 8 for primers). The PCR products are purified by QIAquick gel extraction (Qiagen) and are used for Gibson assembly with the NEBuilder® HiFi DNA Assembly Cloning Kit (NEB) according to the kit protocol to generate the pUC57-s H52 rIBV QX S L270C (SEQ ID NO:69) donor plasmid.

The pUC57-s CR88 rIBV QX S L270C donor plasmid (SEQ ID NO:68) is constructed using the NEBuilder® HiFi DNA Assembly Cloning Kit (NEB) and online tool for primer design. Two PCR fragments are generated: One for the CR88 backbone using pUC57-s CR88 rIBV (SEQ ID NO:67) as template and one for the mutated QX spike L270C using pGEM-T IBV CR88 S L270C (SEQ ID NO:66) as template for Q5 PCR with the primers in table 8. The PCR products are gel purified with the QIAquick gel extraction kit (Qiagen) before they were used for Gibson assembly according to the kit protocol to generate the pUC57-s CR88 rIBV QX S L270C donor plasmid (SEQ ID NO:68).

TABLE 8

Primers designed with the NEBuilder online tool for Gibson assembly of pUC57-s CR88 rIBV QX L270C donor plasmid (PCR 1, 2) and the pUC57-s H52 rIBV QX L270C (PCR 3, 4, 5)

| PCR | SEQ ID NO | Primer name | product | Sequence |
|---|---|---|---|---|
| 1 | 52 | P02207 | QX spike | aagtgtggtaagttactggtaagaga tgttggtgaagtcactg |
|  | 53 | P02208 |  | agaaaagatgtgggactttaatcat taaacagactttttaggtctg |
| 2 | 54 | P02209 | CR88 backbone | tgattaaaagtcccacatcttttcta atattattaattcttctttgg |
|  | 55 | P02210 |  | ctcttaccagtaacttaccacactta attaaattaaagactaagtc |
| 3 | 70 | P01783 | H52 5' flank | cagagcacaagtttgatcttgtgatA TCTGATATGTATACAGACAATGATTC |
|  | 71 | P02062 |  | acttcaccaacatCTCTTACCAGTAA CTTACC |
| 4 | 72 | P02063 | QX S L270C | ttactggtaagagATGTTGGTGAAGT CACTG |
|  | 73 | P02064 |  | ggactttggatcaTTAAACAGACTTT TTAGGTCTG |
| 5 | 74 | P02065 | H52 3' flank | aaagtctgtttaaTGATCCAAAGTCC CACTAG |
|  | 75 | P01788 |  | cttaactcctggaattactaaccacG TGTACCAAAATAAACAACAAGC |

Successful assembly of the pUC57-s CR88 rIBV QX S L270C and the pUC57-s H52 rIBV QX S L270C is identified by plasmid restriction digest with NheI and NotI or EcoRV, BlpI and PmlI respectively and characterized by sequencing with the primers in table 9.

TABLE 9 primers for sequencing of the pUC57-s CR88 rIBV QX S L270C and pUC57-s H52 rIBV QX S L270C donor plasmids.

| SEQ ID NO | Primer name | Sequence |
|---|---|---|
| 56 | P01565 | caggattgtgcatggtggac |
| 51 | P01398 | aatttaacagttagcgtatc |
| 57 | P02090 | gaagtgaayacaagatcaccattt |
| 58 | P01420 | tgactgattctgctgctaaa |
| 44 | P01410 | tttgtatacgagagccatca |
| 59 | P01421 | tcttgaaaccccccaagtag |
| 60 | P01425 | tatattcagcatcagttggc |
| 61 | P01422 | ggattttgtggtagtggaag |
| 62 | P01575 | ccactattgcagtaacattaaca |
| 63 | P01567 | ctagactgtaagttactattg |

Targeted RNA Recombination and Rescue of Recombinant IBV

For rescue of CR88 rIBV QX S L270C and H52 rIBV QX S L270C, LR7 cells are infected with CR88 mIBV or H52 mIBV respectively and electroporated with in vitro transcript generated from the NotI or MssI linearized pUC57-s CR88 rIBV QX S L270C or pUC57-s H52 rIBV QX S L270C donor plasmid respectively, and subsequently injected into 8-day old embryonated SPF chicken eggs (VALO BioMedia). After up to 8 days of incubation, the allantoic fluids of some eggs are analyzed separately for the rescue of recombinant IBV after RNA isolation with the MagMAX™ Core Nucleic Acid Purification Kit (ThermoFisher) and the KingFisher™ Duo Prime Purification System (ThermoFisher) and by using SuperScript™ III One-Step RT-PCR System with Platinum™ Taq DNA Polymerase (ThermoFisher). Primers PO1398 and P0633 (Table 7) binding in the QX spike sequence are used to identify the rescue of recombinant virus. The positive (defined by embryonic death or by a positive RT-PCR result) allantoic fluid of the egg inoculated with the highest dilution of LR7 cells is used for an end-point dilution in 8-day old embryonated SPF eggs. Nucleic acid isolation is conducted as described above. Samples are analyzed via RT-qPCR conducted according to the protocol adapted from Callison et al. (J Virol Methods. 2006; 138(1-2):60-5). Briefly, the same primers and probe are used and the thermoprofile is adapted for the use of TaqMan® Fast Virus 1-Step Master Mix (ThermoFisher) and the StepOnePlus or the ABI7900 HT Fast Real-Time PCR Systems (ThermoFisher Scientific). Afterwards, one positive-tested allantoic fluid of a preferably high dilution is used for propagation in 8-day old embryonated SPF chicken eggs. The allantoic fluid is diluted 1:100 in 1×PBS and 100 µl is injected per egg, which are subsequently incubated at 37.5° C. and 60% humidity. Allantoic fluid is harvested at 48 hours post inoculation, cleared from debris and stored at −80° C.

In Vitro and in Ovo Characterization of Recombinant IBV

The Embryo infectious dose 50% (EID50) and the tissue culture infectious dose 50% (TCID50) for CR88 rIBV QX S L270C and H52 rIBV QX S L270C is determined as described for H52 rIBV S F267C. Further, the in ovo and in vitro replication kinetics and the passaging was conducted as described for H52 rIBV S F267C.

Figures 16, 17:
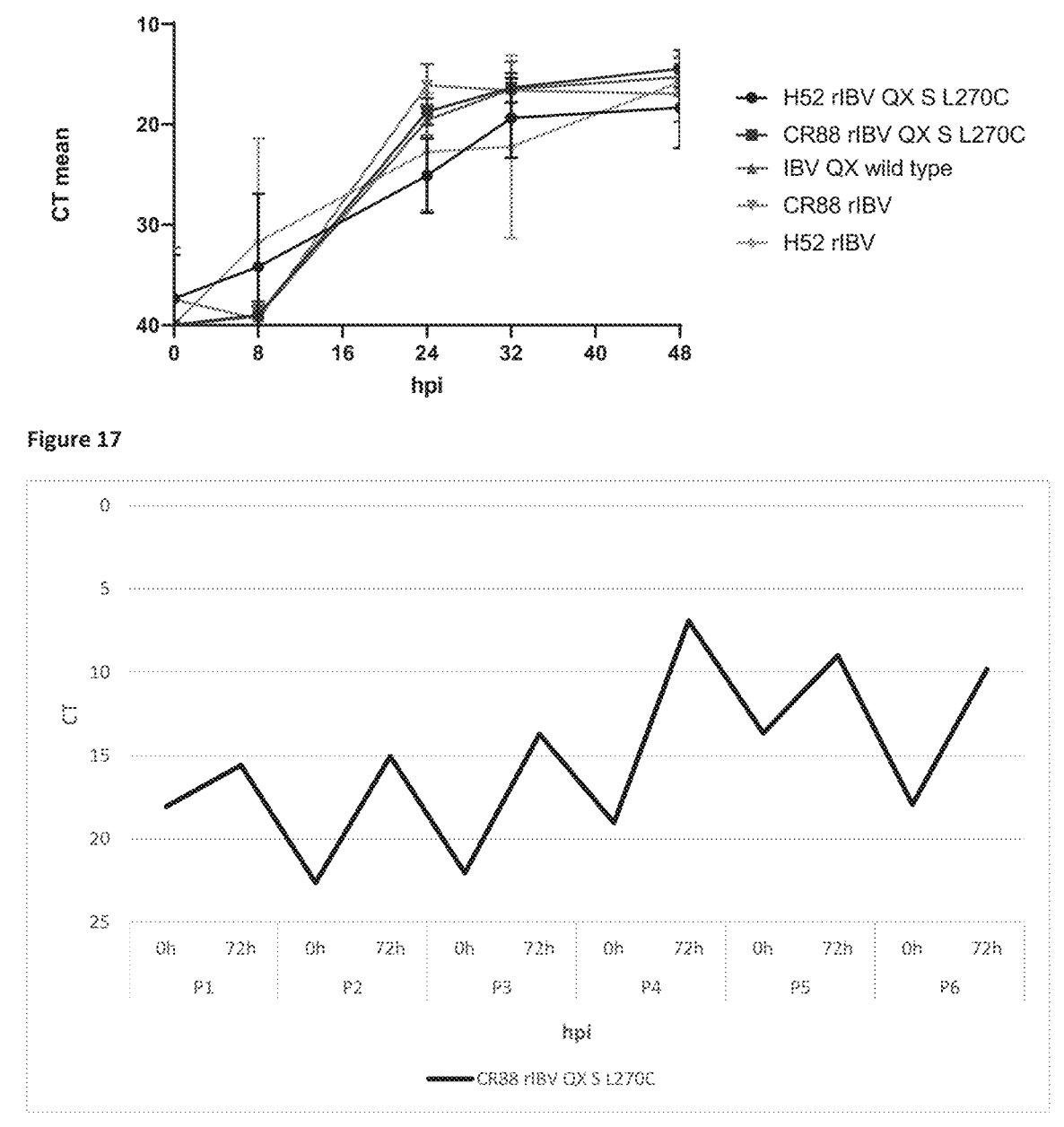

Similar peak ct values after 48 hours with slightly different in ovo replication kinetics are observed for CR88 rIBV QX S L270C and H52 rIBV QX S L270C (FIG. 16). While CR88 rIBV QC L270C replicates very similar to CR88 rIBV and IBV QX wild type, H52 rIBV QX s L270C replicates more similar to H52 rIBV. This suggests no disadvantage of the Cysteine mutation in the spike of CR88 rIBV QX S L270C and H52 rIBV QX S L270C for the in ovo replication efficiency of the mutated rIBV compared to other rIBV or wild type IBV.

Figures 18, 19:
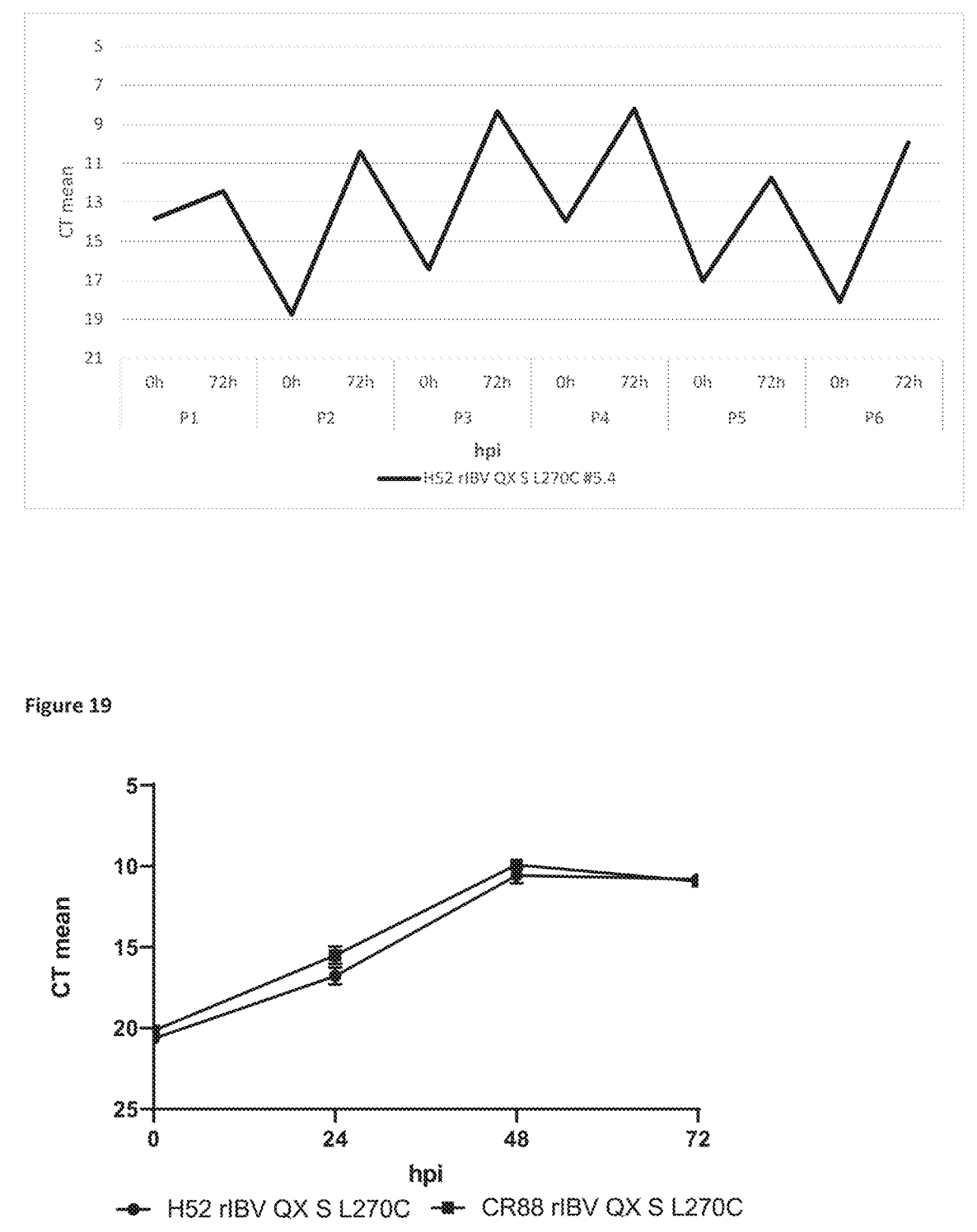

To analyze if CR88 rIBV QX S L270C and H52 rIBV QX S L270C are able to replicate in cells, EB66® cells are inoculated with a 1/100 dilution of the allantoic fluid stock. Propagation of the viruses is analyzed by isolation of viral RNA and subsequent RT-qPCR analysis. Replication of CR88 rIBV QX S L270C and H52 rIBV QX S L270C is clearly visible over the passaging process by a decreasing mean ct value for the 72 h time point compared to the 0 h time point directly after infection (FIGS. 17 and 18). Due to dilution of the virus for the next passage the ct value increases compared to the ct value measured at harvest of the inoculum before decreasing again during the 72 h culture due to virus replication. Efficient replication for of CR88 rIBV QX S L270C and H52 rIBV QX S L270C is also detected via RT-qPCR (FIG. 19) in a replication kinetic experiment in Eb66® cells. Both viruses display similar replication patterns with peak CT values after 48 hours.

In addition, the infectious titers for the allantoic fluid stock of CR88 rIBV QX S L270C ($10^8$ $EID_{50}$/ml) and Eb66® passages P2 ($10^6$ $TCID_{50}$/ml, $10^{8.17}$ $EID_{50}$/ml), P6 ($10^6$ $TCID_{50}$/ml, $10^{7.83}$ $EID_{50}$/ml) and P9 ($10^6$ $TCID_{50}$/ml, $10^{8.5}$ $EID_{50}$/ml) are determined. Further, the infectious titers for the allantoic fluid stock of H52 rIBV QX S L270C ($10^8$ $EID_{50}$/ml) and Eb66® passages P3 ($10^{4.5}$ $TCID_{50}$/ml, $10^{8.13}$ $EID_{50}$/ml) and P6 ($10^{5.5}$ $TCID_{50}$/ml, $10^{8.13}$ $EID_{50}$/ml) are determined. They confirm efficient replication of CR88 rIBV QX S L270C during the Eb66® passaging process and sustained infectivity in SPF eggs. The L270C mutation therefore enables replication in cell lines without disturbing the ability to replicate in ovo.

Determination of Vaccine Efficacy

Figure 20:
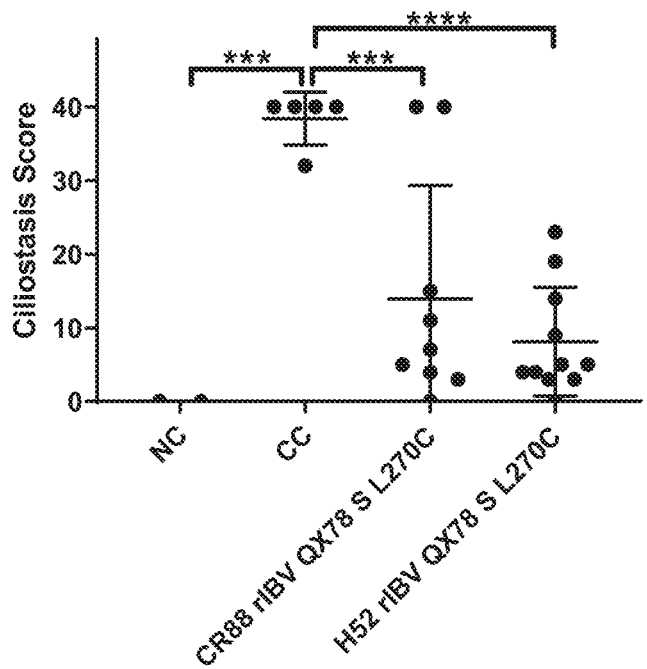
FIG. 20. Summary of ciliostasis scoring for protection by CR88 rIBV QX S L270C and H52 rIBV QX S L270C against D388 QX challenge. The sum of the 10 individual scores for the 10 rings of one animal is calculated and is represented by one dot in the graph. Maximum ciliostasis corresponds to a score of 40, while no ciliostasis is represented by a score of 0. Mean and significance are calculated using GraphPad Prism and an ordinary one-way ANOVA test (*p<0.001, **p<0.0001).

Testing for the efficacy of CR88 rIBV QX S L270C and H52 rIBV QX S L270C against challenge with IBV D388 QX was conducted as described for H52 rIBV S F269C above. The objective of the study is to demonstrate that the cell culture adapted CR88 rIBV QX S L270C and H52 rIBV QX S L270C passaged six times in EB66® cells is able to confer protection against a virulent D388 QX strain. All chickens are observed daily for clinical signs. No clinical signs are recorded after vaccination or challenge. Back titrations for the vaccination with CR88 rIBV QX S L270C and H52 rIBV QX S L270C at 1-day of age determine a titer of $10^{4.2}$ $EID_{50}$/animal and $10^{3.3}$ $EID_{50}$/animal (target $10^3$ $EID_{50}$/animal), respectively, and $10^{3.5}$ $EID_{50}$/animal (target $10^3$ $EID_{50}$/animal) for challenge with IBV D388 QX at 21 days post vaccination. Ciliostasis is scored as described in table 3 and results are depicted in FIG. 20 and summarized in table 10. All animals of the strict negative control show normal ciliar movement while all animals of the challenge control group are positive for ciliostasis. In contrast, 78% and 91% animals vaccinated with CR88 rIBV QX S L270C or H52 rIBV QX S L270C are protected.

TABLE 10

Summary of ciliostasis scoring for protection at 28 days post vaccination and 7 days post challenge. The mean ciliostasis score per group is calculated by adding up the sum score of the individual chickens per group and dividing the group sum by the number of animals (highest possible score 40, lowest possible score 0). For not affected animals, at least 9 of the 10 tracheal explants show normal ciliar activity.

| Vaccine | Challenge | #animals/ not affected | Mean Ciliostasis Score | Not affected [%] |
| --- | --- | --- | --- | --- |
| — | — | 3/2* | 0 | 100 |
| — | D388 QX | 5/0 | 38.4 | 0 |
| CR88 rIBV QX S L270C | D388 QX | 9/7 | 13.9 | 78 |
| H52 rIBV QX S L270C | D388 QX | 11/10 | 8.1 | 91 |

*one animal of the strict negative control died, death was not associated to IBV clinical signs or lesions.

Figure 21:
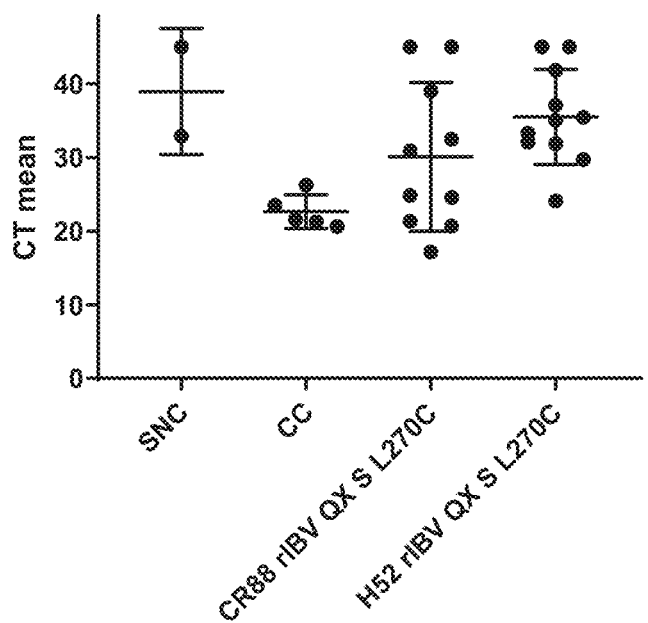
FIG. 21. Summary of RT-qPCR results of kidneys tissues 7 days after challenge for the efficacy study of CR88 rIBV QX S L270C and H52 rIBV QX S L270C. Each individual bird is indicated by one dot.

In addition, the viral RNA load is significantly reduced in kidneys of animals vaccinated with CR88 rIBV QX S L270C or H52 rIBV QX L270C compared to the challenge control animals (FIG. 21). In summary, CR88 rIBV QX S L270C and H52 rIBV QX S L270C propagated in EB66® cells efficiently protects against virulent D388 QX challenge. The spike mutation L270C adapts the virus to propagation in cells while the in vivo efficacy is sustained.

Conclusion Example 3: The data show that the mutation to Cysteine at position 267 of the spike (reference sequence for the numbering is SEQ ID NO:1) corresponding to position 270 in IBV QX spike leads to an extended cell or tissue tropism, too. In addition, the tissue culture tropism of a spike with the Cysteine mutation is not restricted to the homologous genetic background, as the QX L270C spike is inserted into the CR88 and H52 genetic backbone and the CR88 rIBV QX S L270C and H52 rIBV QX S L270C efficiently replicate in cells and efficiently protect against virulent IBV D388 QX challenge.

Example 4

Generation of Chimeric Recombinant IBV H52 in which the H52 Spike Ectodomain Coding Sequence is Replaced by an ARKDPI Spike Ectodomain Coding Sequence in which the Amino Acid 274 of the Spike Protein is Mutated to a Cysteine In order to further elaborate if the change to a Cysteine at position 267 of the spike to achieve cell culture tropism can be transferred to additional IBV genotypes, the ArkDPI spike amino acid (SEQ ID NO:76) sequence was aligned to the H52 spike amino acid sequence (SEQ ID NO:1) to determine the position equivalent to amino acid position 267 of H52 spike for IBV ArkDPI spike, which was determined as the Leucine at position 274 of the ArkDPI spike.

In order to analyze the potential of a ArkDPI spike with a mutation at amino acid position 274 to Cysteine to infect cells, a recombinant IBV H52 is generated in which the sequence encoding the H52 spike is replaced by the sequence encoding an ArkDPI spike with a Cysteine at position 274 of the ArkDPI spike protein (SEQ ID NO:77). For this the steps for the construction and rescue of an H52 mIBV are conducted as described in example 1.

Donor Plasmid Construction

The pUC57-s ArkDPI spike L274C plasmid (SEQ ID NO:78) is synthesized by a commercial supplier. The pUC57-s H52 rIBV ArkDPI S Ecto L274C donor plasmid (SEQ ID NO:79) is constructed using the NEBuilder® HiFi DNA Assembly Cloning Kit (NEB) and online tool for primer design. For this, the pUC57-s H52 rIBV donor plasmid (SEQ ID NO:9) is digested using the restriction sites EcoRV, PmlI and BlpI close to the H52 spike coding sequence to linearize the plasmid and remove the H52 spike and flanking sequences. The QIAquick gel extraction kit (Qiagen) is used to purify the band corresponding to the pUC57-s IBV H52 backbone without the H52 spike coding sequence. The ArkDPI S Ecto L274C nucleic acid coding sequence and the flanking 5' and 3' IBV H52 sequences are amplified in three separate PCR reactions with Q5® High-Fidelity DNA Polymerase (NEB; see table 11 for primers). The PCR products are purified by QIAquick gel extraction (Qiagen) and are used for Gibson assembly with the NEBuilder® HiFi DNA Assembly Cloning Kit (NEB) according to the kit protocol to generate the pUC57-s H52 rIBV ArkDPI S Ecto L274C (SEQ ID NO:79) donor plasmid.

TABLE 11

Primers designed with the NEBuilder online tool for Gibson assembly of the pUC57-s H52 rIBV ArkDPI S Ecto L274C.

| PCR | SEQ ID NO | Primer name | product | Sequence |
|---|---|---|---|---|
| 1 | 70 | P01783 | H52 5' flank | cagagcacaagtttgatcttg tgatatctgatatgtatacag acaatgattc |
|   | 80 | PO2424 |  | catataaattagcactacata gtgcacac |
| 2 | 81 | PO2425 | ArkDPI S Ecto | atgtagtgctaatttatatga caacgaatcttttg |
|   | 82 | PO2426 |  | acacataccaaggccacttaa tataagttttg |
| 3 | 83 | PO2427 | H52 3' flank | taagtggccttggtatgtgtg gctagcc |
|   | 75 | P01788 |  | cttaactcctggaattactaa ccacgtgtaccaaaataaaca acaagc |

Successful assembly of the pUC57-s H52 rIBV ArkDPI S Ecto L274C is identified by plasmid restriction digest with BlpI and XhoI.

Targeted RNA Recombination and Rescue of Recombinant IBV

For rescue of H52 rIBV ArkDPI S Ecto L274C, LR7 cells are infected with H52 mIBV respectively and electroporated with in vitro transcript generated from the MssI linearized pUC57-s H52 rIBV ArkDPI S Ecto L274C donor plasmid, and subsequently injected into 8-day old embryonated SPF chicken eggs (VALO BioMedia). After up to 8 days of incubation, the allantoic fluids of some eggs are analyzed separately for the rescue of recombinant IBV after RNA isolation with the MagMAX™ Core Nucleic Acid Purification Kit (ThermoFisher) and the KingFisher™ Duo Prime Purification System (ThermoFisher) and by using SuperScript™ III One-Step RT-PCR System with Platinum™ Taq DNA Polymerase (ThermoFisher). Primers P01317 and P0633 (Table 12) binding in the ArkDPI spike sequence are used to identify the rescue of recombinant virus. The positive (defined by embryonic death or by a positive RT-PCR result) allantoic fluid of the egg inoculated with the highest dilution of LR7 cells is used for an end-point dilution in 8-day old embryonated SPF eggs. Nucleic acid isolation is conducted as described above. Samples are analyzed via RT-qPCR conducted according to the protocol adapted from Callison et al. (J Virol Methods. 2006; 138(1-2):60-5). Briefly, the same primers and probe are used and the thermoprofile is adapted for the use of TaqMan® Fast Virus 1-Step Master Mix (ThermoFisher) and the StepOnePlus or the ABI7900 HT Fast Real-Time PCR Systems (ThermoFisher Scientific). Afterwards, one positive-tested allantoic fluid preferably of a high dilution is used for propagation in 8-day old embryonated SPF chicken eggs. The allantoic fluid is diluted 1:100 in 1×PBS and 100 μl is injected per egg, which are subsequently incubated at 37.5° C. and 60% humidity. Allantoic fluid is harvested at 48 hours post inoculation, cleared from debris and stored at −80° C.

TABLE 12

Primers for detection of
H52 rIBV ArkDPI S Ecto L274C.

| SEQ ID NO | Primer name | Sequence |
|---|---|---|
| 84 | PO1317 | taatactggyaatttttcaga |
| 21 | PO633 | cgctcttagtaacataaac |

In Vitro Characterization of Recombinant IBV

The Embryo infectious dose 50% (EID50) and the tissue culture infectious dose 50% (TCID50) for H52 rIBV ArkDPI S Ecto L274C is determined as described for H52 rIBV S F267C. Further, the in vitro replication kinetics and the passaging was conducted as described for H52 rIBV S F267C.

To analyze if H52 rIBV ArkDPI S Ecto L274C is able to replicate in cells, EB66® cells are inoculated with a 1/10 dilution of the allantoic fluid stock for the first passage and with a 1/10 or 1/100 dilution for the subsequent passages. Propagation of the viruses is analyzed by isolation of viral RNA and subsequent RT-qPCR analysis. Replication of H52 rIBV ArkDPI S Ecto L274C is clearly visible after three passages by a decreasing mean ct value for the 72 h time point (11.59) compared to the 0 h time point (21.09) directly after infection.

Conclusion Example 4: The data show that the mutation to Cysteine at position 267 of the spike (reference sequence for the numbering is SEQ ID NO:1) corresponding to position 274 in IBV ArkDPI spike leads to an extended cell or tissue tropism, too. In addition, the tissue culture tropism of a spike with the Cysteine mutation is not restricted to the homologous genetic background, as the ArkDPI L274C spike ectodomain is inserted into the H52 genetic backbone and the H52 rIBV ArkDPI S Ecto L274C efficiently replicates in cells.

The invention claimed is:

1. A method for the production or manufacture of an avian coronavirus having extended cell or tissue tropism comprising mutating amino acid position 267 of an avian coronavirus spike protein or fragment of an avian coronavirus having restricted cell or tissue tropism to Cysteine, wherein the amino acid sequence of SEQ ID NO:1 is used for determining the position numbering in the spike protein, and wherein the mutation at amino acid position 267 to Cysteine leads to extended cell or tissue tropism of the avian coronavirus.

2. A method for the production or manufacture of an avian coronavirus having extended cell or tissue tropism comprising mutating amino acid position 267 of an avian coronavirus spike protein or fragment, wherein at least a part of the 51 subunit is from an avian coronavirus having restricted cell or tissue tropism, to Cysteine, wherein the amino acid sequence of SEQ ID NO:1 is used for determining the position numbering in the spike protein, and wherein the mutation at amino acid position 267 to Cysteine leads to extended cell or tissue tropism of the avian coronavirus.

3. The method of claim 1 or 2, wherein the avian coronavirus is IBV (infectious bronchitis virus).

4. The method of claim 1 or 2, wherein the avian coronavirus is cultured by infecting and/or replicating in at least one cell line selected from the list consisting of: DF-1 (Douglas Foster), PBS-12, PBS-12SF (PBS-12 serum free), BHK21 (baby hamster kidney), HEK 293T (human embryonic kidney), Vero (Verda Reno), MA104, RK13 (rabbit kidney), LMH (leghorn male hepatoma), MDCK (Madin-Darby canine kidney), MDBK (Madin-Darby bovine kidney), PK15 (porcine kidney), PK2A (porcine kidney), SF9, SF21 and SF+(*Spodoptera frugiperda*).

5. The method of claim 1 or 2, wherein the amino acid position 267 is within the S1 subunit of the spike protein.

6. The method of claim 3, wherein the spike protein is not from an IBV Beaudette strain.

7. The method of claim 3, wherein the spike protein is from an IBV with a genotype or serotype or a strain selected from a list consisting of: Arkansas, Brazil, California, Connecticut, Delaware, Dutch, Florida, Georgia, Gray, Holte, Iowa, Italy-02, JMK, LDT3, Maine, H52, H120, M41, Pennsylvania, PL84084, Qu, QX, Q1, SE 17, Variant 2 and 4/91.

8. The method of claim 3, wherein the IBV spike protein or fragment thereof is selected from a list of genotypes consisting of: GI-2 to 27, GILL GIII-1, GIV-1, GV-1, GVI-1.

9. The method of claim 3, wherein the IBV spike protein or fragment thereof consists of or comprises an amino acid sequence as shown in SEQ ID NO: 2, 3, 4, 5, 6, 7, 8, 77 or a sequence having at least 80%, 85%, 90%, 93%, 95%, 96%, 97%, 98%, 99%, 99.5%, 99.6%, 99.7%, 99.8%, 99.9%, 99.95%, 99.98% or 99.99% sequence identity thereto.

10. The method of claim 3, wherein said at least a part of the 51 subunit is from an IBV selected from a list of genotypes or serotypes or strains consisting of: Arkansas, Brazil, California, Connecticut, Delaware, Dutch, Florida, Georgia, Gray, Holte, Iowa, Italy-02, JMK, LDT3, Maine, H52, H120, M41, Pennsylvania, Pennsylvania, PL84084, Qu, QX, Ql, SE 17, Variant 2 and 4/91.

11. The method of claim 3, wherein the avian coronavirus or IBV with restricted cell or tissue tropism is restricted to infection and/or replication in embryonated chicken eggs and/or in primary chicken kidney cells.

12. A method for mutating the amino acid position 267 in an avian coronavirus spike protein comprising:

a) providing an avian coronavirus or an avian coronavirus spike nucleotide or protein sequence,
b) identifying position 267 in the spike protein by alignment with a reference sequence,
c) mutating the position 267 of the spike protein of step b) into a cysteine,
d) obtaining the mutated spike protein of step c).

13. The method of claim 12, wherein a Phenylalanine or Leucine is modified or mutated into a Cysteine at amino acid at position 267.

14. The method of claim 12, wherein the avian coronavirus is IBV.

15. The method of claim 12, wherein said mutation at amino acid position 267 to Cysteine leads to an extended cell or tissue tropism.

16. The method of claim 12, wherein the avian coronavirus or IBV is cultured by infecting and/or replicating in at least one cell line selected from the list consisting of: DF-1 (Douglas Foster), PBS-12, PBS-12SF (PBS-12 serum free), BHK21 (baby hamster kidney), HEK 293T (human embryonic kidney), Vero (Verda Reno), MA104, RK13 (rabbit kidney), LMH (leghorn male hepatoma), MDCK (Madin-Darby canine kidney), MDBK (Madin-Darby bovine kidney), PK15 (porcine kidney), PK2A (porcine kidney), SF9, SF21 and SF+(*Spodoptera frugiperda*).

17. The method of claim 1, wherein the avian coronavirus with restricted cell or tissue tropism is restricted to infection and/or replication in embryonated chicken eggs and/or in primary chicken kidney cells.

18. The method of claim 2, wherein the avian coronavirus with restricted cell or tissue tropism is restricted to infection and/or replication in embryonated chicken eggs and/or in primary chicken kidney cells.

* * * * *